United States Patent
Wang et al.

(10) Patent No.: US 9,957,270 B2
(45) Date of Patent: May 1, 2018

(54) FUSED PYRIMIDINE-BASED HYDROXAMATE DERIVATIVES

(71) Applicant: Agency for Science, Technology and Research, Singapore (SG)

(72) Inventors: Haishan Wang, Singapore (SG); Dizhong Chen, Singapore (SG); Chang Kai Soh, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days. days.

(21) Appl. No.: 15/124,654

(22) PCT Filed: Mar. 13, 2015

(86) PCT No.: PCT/SG2015/050038
§ 371 (c)(1),
(2) Date: Sep. 8, 2016

(87) PCT Pub. No.: WO2015/137887
PCT Pub. Date: Sep. 17, 2015

(65) Prior Publication Data
US 2017/0044162 A1    Feb. 16, 2017

(30) Foreign Application Priority Data
Mar. 13, 2014 (SG) .............. 10201400634Q

(51) Int. Cl.
| | | |
|---|---|---|
| *A01N 43/90* | (2006.01) | |
| *A61K 31/52* | (2006.01) | |
| *A61K 31/519* | (2006.01) | |
| *C07D 473/00* | (2006.01) | |
| *C07D 487/00* | (2006.01) | |
| *C07D 473/34* | (2006.01) | |
| *C07D 473/32* | (2006.01) | |
| *A61K 45/06* | (2006.01) | |
| *A61K 31/5377* | (2006.01) | |
| *C07D 473/16* | (2006.01) | |
| *C07D 473/40* | (2006.01) | |

(52) U.S. Cl.
CPC .......... *C07D 473/34* (2013.01); *A61K 31/52* (2013.01); *A61K 31/5377* (2013.01); *A61K 45/06* (2013.01); *C07D 473/16* (2013.01); *C07D 473/32* (2013.01); *C07D 473/40* (2013.01)

(58) Field of Classification Search
None
See application file for complete search history.

(56) References Cited

FOREIGN PATENT DOCUMENTS

| | | |
|---|---|---|
| WO | WO-93/020078 A1 | 10/1993 |
| WO | WO-99/038877 A2 | 8/1999 |
| WO | WO-03/099820 A1 | 12/2003 |
| WO | WO-2008/115974 A2 | 9/2008 |
| WO | WO-2009/020990 A1 | 2/2009 |
| WO | WO-2010/117425 A1 | 10/2010 |
| WO | WO-2012/172043 A1 | 12/2012 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
CAS Registry No. 1062163-20-5, 5 pages.
CAS Registry No. 1062163-21-6, 5 pages.
CAS Registry No. 1062163-32-9, 5 pages.
CAS Registry No. 1062163-36-3, 5 pages.
CAS Registry No. 1062163-37-4, 5 pages.
CAS Registry No. 1062163-52-3, 5 pages.
CAS Registry No. 1062163-59-0, 5 pages.
CAS Registry No. 1062163-63-6, 5 pages.
CAS Registry No. 1062163-77-2, 5 pages.
CAS Registry No. 1062163-80-7, 5 pages.
CAS Registry No. 157013-04-2, 2 pages.
CAS Registry No. 235744-83-9, 2 pages.
CAS Registry No. 235744-92-0, 2 pages.
International Search Report for PCT/SG2015/050038, 6 pages (dated Jun. 15, 2015).
Liao, J. et al., Inhibition of PTEN tumor suppressor promotes the generation of induced pluripotent stem cells, The American Society of Gene & Cell Therapy, 21(6):1242-1250 (2013).
Melman, A. et al., Selective A3 adenosine receptor antagonists derived from nucleosides containing a bicyclo[3.1.0]hexane ring system, Bioorganic & Medicinal Chemistry, 16(18):8546-8556 (2008).
Written Opinion for PCT/SG2015/050038, 8 pages (dated Jun. 15, 2015).

* cited by examiner

*Primary Examiner* — Jeffrey H Murray
(74) *Attorney, Agent, or Firm* — Choate, Hall & Stewart LLP

(57) ABSTRACT

The present invention relates to fused pyrimidine-based hydroxamate compounds of formula (I), comprising a hydroxamate group, that are inhibitors of histone deacetylase (HDAC) and kinases. More particularly, the present invention relates to hydroxamate substituted purine or 5H-pyrrolo[3,2-d]pyrimidine derivatives, methods for their preparation, pharmaceutical compositions containing these compounds and uses of these compounds in the treatment of disorders/conditions/diseases involving, relating to or associated with enzymes having histone deacetylase, non-histone deacetylase and kinase activities/functions and/or via unspecified/multi-targeted mechanisms.

13 Claims, 34 Drawing Sheets

GDC-0980

BEZ235

GDC-0941

ZSTK474

Wortmannin

PI103

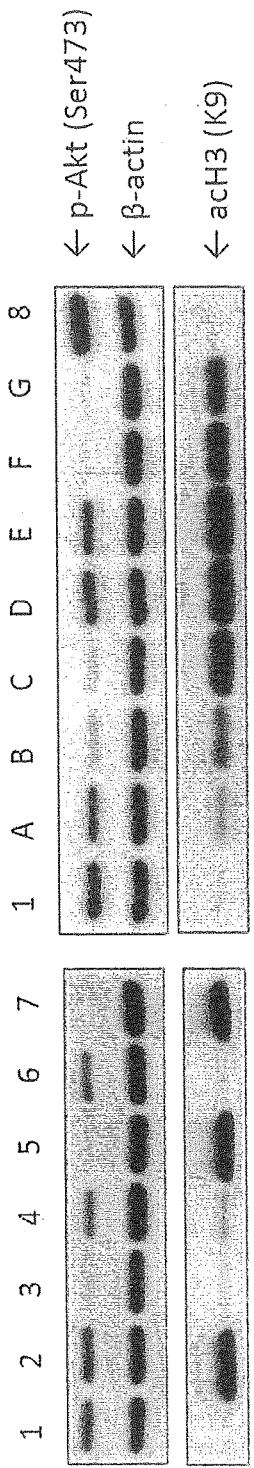
Fig. 15A
Fig. 15B
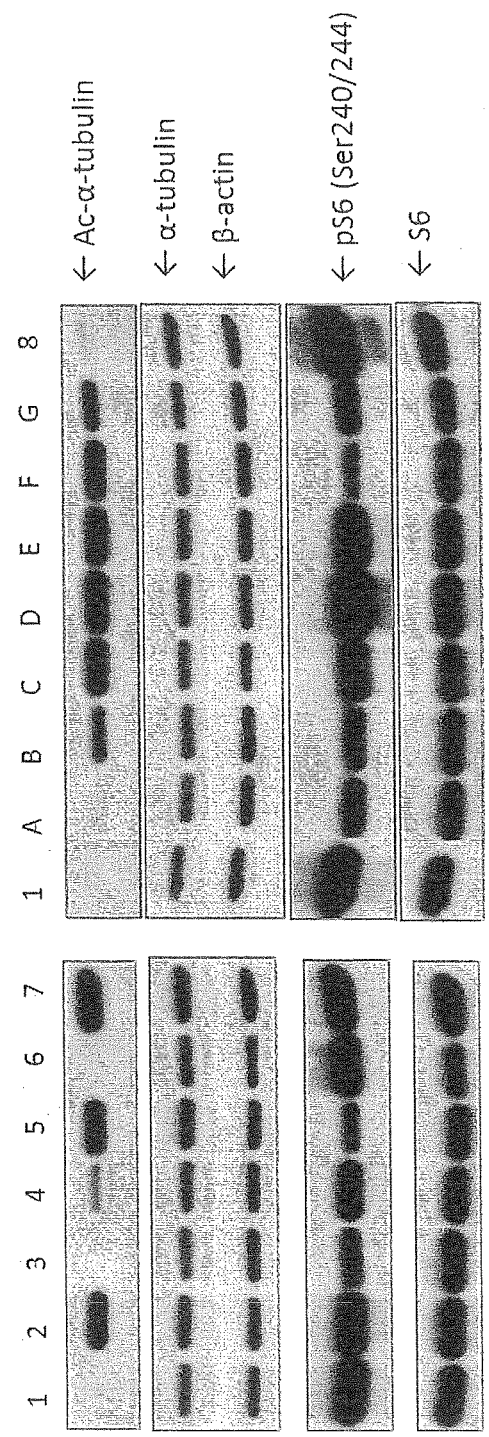
Fig. 15C
Fig. 15D

FUSED PYRIMIDINE-BASED HYDROXAMATE DERIVATIVES

CROSS-REFERENCE TO RELATED APPLICATIONS

This patent application is a National Stage Entry of International Patent Application No. PCT/SG2015/050038, filed on Mar. 13, 2015, which claims priority to SG 10201400634Q, filed on Mar. 13, 2014, the entire contents of each of which are hereby incorporated by reference herein.

TECHNICAL FIELD

The present invention generally relates to fused pyrimidine-based hydroxamate compounds that are inhibitors of histone deacetylase (HDAC) and kinases. More particularly, the present invention relates to hydroxamate substituted purine or 5H-pyrrolo[3,2-d]pyrimidine derivatives, methods for their preparation, pharmaceutical compositions containing these compounds and uses of these compounds in the treatment of disorders/conditions/diseases involving, relating to or associated with enzymes having histone deacetylase, non-histone deacetylase and kinase activities.

BACKGROUND ART

There is a general interest in the design, synthesis and development of hybrid-drugs or multi-target drugs which can increase the probability of the treatment or efficacy by acting on two or more proven pathways of validated targets. For example, cancer cell survival relies on many key pathways, thus, the blockade or inhibition of one pathway may only have a small probability of killing the cancer cells or inhibiting the growth of cancer cells. Cancer cells can compensate or bypass the blocked function or pathway and even synergize their functions. This principle has been validated and is already in use, for example, in combination chemotherapy for cancer treatment, where a combination of drugs such as histone deacetylase (HDAC) inhibitors vorinostat and a variety of known drugs in clinical trials, cocktail drugs for HIV treatment, and augmentin (a mixture of amoxicillin and clavulanic acid) for antibacterial treatment are administered together. There are also successful multi-target drugs in the market, such as multi-kinase inhibitors sunitinib and sorafenib. Both combination therapy and multi-target drugs are aimed to enhance efficacy and/or overcome drug resistance by modulating or inhibiting multiple targets, pathways or networks involved in disease progression. Combination therapy or polytherapy uses more than one drug, thus its advantage is that there are a number of single agents that are available for combination and there are options for testing a variety of combinations of drugs for research and development. However, combination therapy has disadvantages. For example, single agents in general are developed for single agent therapy only and are not necessarily optimized for combination therapy. Further, not all single agents are suitable for or compatible with combination therapy. Defining the dosage regime for two or more agents in combination is a very complex process which requires consideration for dosage level, sequence of administration and potential drug-drug interaction in clinical settings. Further, in addition to the cost of having to use multiple drugs, combination therapy can often lead to unwanted adverse effects or dangerous drug-drug interactions. For example, everolimus was combined with sorafenib in a phase I clinical trials for treatment of advanced hepatocellular carcinoma cancer (HCC), but its dose could not be escalated to a biologically effective concentration due to adverse events.

In contrast, a multi-target drug molecule, as a single agent, works on at least two targets. The advantage of multi-target drugs is that a single agent can achieve modulation of multiple (kinase) targets simultaneously. However, the number of drugs that can do this is still limited. As multi-target drugs typically encompass the chemical features of the scaffolds of both parent drugs, the molecular weight or size of the drug is usually larger, and this often leads to the drug not receiving sufficient exposure either due to toxicity or drug metabolism. It is not a trivial task to design new molecules based on two scaffolds of the parent drugs. Usually the desired efficacy is not obtained or there are new undesired side effects. It is therefore not predictable how to combine two scaffolds to achieve a new multi-target drug. Therefore an observed good activity without undesired side effects is a surprising finding.

There is therefore a need to provide a compound that overcomes, or at least ameliorates, one or more of the disadvantages described above. There is also a need to provide a pharmaceutical composition comprising the compound, methods for treating diseases using the compound and a method for synthesizing the compound.

SUMMARY

A series of fused pyrimidine-based small molecules to target histone deacetylases (HDACs) and phosphatidylinositide 3-kinases (PI3K)-AKT-mammalian target of rapamycin (mTOR) pathway have been designed and synthesised. These molecules contain a zinc-binding group (hydroxamic acid) to inhibit histone deacetylase and other deacetylase activities as well as a fused pyrimidine core decorated with substitutes to modulate PI3K-AKT-mTOR pathway. Each molecule has a unique potency profile against each targets and the entire series covers most of possible combinations of the broad range of potency required for each target for a variety of indications or applications. These molecules work as multi-target drugs for treatment of cancer and non-oncology applications.

In a first aspect, there is provided a compound of formula (I);

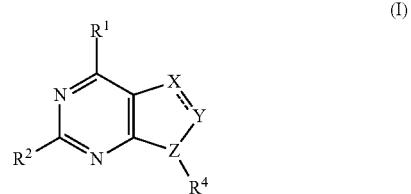

wherein X, Y and Z are independently selected from N, $CHR^3$ or $CR^3$, wherein at least one of X, Y or Z is N; ----- is a single or double bond, as valency allows; $R^1$ and $R^2$ are independently selected from the group consisting of a bond, halogen, optionally substituted alkyl, optionally substituted amino, optionally substituted alkyloxy, optionally substituted cycloalkyl, optionally substituted heterocycloalkyl, optionally substituted aryl and optionally substituted heteroaryl; $R^3$ and $R^4$ are independently selected from the group consisting of a bond, hydrogen, halogen, optionally substituted alkyl, optionally substituted amino, optionally substituted alkyloxy, optionally substituted cycloalkyl, optionally substituted heterocycloalkyl, optionally substituted aryl and optionally substituted heteroaryl; at least one of $R^1$, $R^2$, $R^3$ or $R^4$ is further independently substituted by an hydroxamate group -L-$R^5$-$L^2$-$R^6$-$L^3$-CON($R^a$)O$R^b$, wherein; $R^a$ and $R^b$ are independently selected from the group consisting of a bond, hydrogen, optionally substituted alkyl, optionally substituted acyl and optionally substituted amino acid residue; $L^1$, $L^2$ and $L^3$ are independently selected from the group consisting of a bond, optionally substituted alkyl, optionally substituted alkenyl and optionally substituted alkynyl; $R^5$ and $R^6$ are independently selected from the group consisting of a bond, O, S, $NR^c$, $S(O)_n$, optionally substituted amide, optionally substituted urea, optionally substituted carbonylurea, optionally substituted thiourea, optionally substituted sulfonamide, optionally substituted aminosulfonamide, optionally substituted sulfonylurea, optionally substituted oxime, optionally substituted cycloalkyl, optionally substituted heterocycloalkyl, optionally substituted aryl and optionally substituted heteroaryl; wherein; $R^c$ is independently selected from the group consisting of a bond, hydrogen, optionally substituted alkyl, optionally substituted alkenyl, optionally substituted alkynyl and optionally substituted acyl; and n is an integer from 0 to 2; or a pharmaceutically acceptable form or prodrug thereof.

In a second aspect, there is provided a pharmaceutical composition comprising a compound as defined above, or a pharmaceutically acceptable form or prodrug thereof, and a pharmaceutically acceptable excipient.

In further embodiments of the disclosure, a method of inhibiting a deacetylase and/or kinase selected from the group consisting of a lipid kinase/protein kinase or a fragment or a complex thereof or a functional equivalent thereof and a PI3K or Akt kinase or mTOR kinase or a fragment or a complex thereof or a functional equivalent thereof, the method including exposing the protein kinase or a fragment or complex thereof or a functional equivalent thereof and/or co-factor(s) thereof to an effective amount of a compound as defined above, is disclosed.

In some embodiments, the deacetylase is a histone deacetylase or a fragment or a complex thereof or a functional equivalent thereof. In some embodiments the histone deacetylase or a fragment or complex thereof is HDAC1 or HDAC2 or HDAC3 or HDAC6 or HDAC8 or a fragment thereof, or a complex thereof or a functional equivalent thereof. In some embodiments the HDACs is HDAC1 or HDAC6 a fragment or complex thereof or a functional equivalent thereof.

In some embodiments, the lipid kinase/protein kinase is a PI3K kinase or a fragment thereof or a complex thereof or a functional equivalent thereof. In some embodiments the PI3K kinase or a fragment or a complex thereof or a functional equivalent thereof, is a class I PI3K or a fragment thereof or a complex thereof or a functional equivalent thereof.

In some embodiments, the protein kinase is a serine/threonine protein kinase or a lipid kinase or a fragment or a complex thereof or a functional equivalent thereof. In some embodiments the serine/threonine protein kinase or a fragment or complex thereof is an mTOR protein kinase or a fragment thereof, or a complex thereof or a functional equivalent thereof. In some embodiments the serine/threonine protein kinase is mTORC1 or a fragment or complex thereof or a functional equivalent thereof.

Advantageously, the compound may contain a zinc-binding group (hydroxamic acid) to inhibit histone deacetylase and other deacetylase activities as well as a fused pyrimidine core decorated with substitutes to modulate PI3K-AKT-mTOR pathway. Advantageously, the compound may contain both a zinc-binding group and a fused pyrimidine core so that it may simultaneously inhibit histone deacetylase and other deacetylase activity and modulate the PI3K-AKT-mTOR pathway. Further advantageously, since the compound contains a zinc-binding group, it may inhibit any enzyme containing zinc in its active site. More advantageously, the compound may be used as an inhibitor of histone deacetylase and other deacetylase activities. The compound may be used as a modulator for PI3K-AKT-mTOR pathway.

More advantageously, the components for each of the target; that is, for HDAC or kinase, are within the same molecule, rendering them compatible with each other. This overcomes the issue of adverse drug-drug interactions. Further, each of the components for each of the target may be separately optimized in terms of position at which they are incorporated and substituents which they may have. This may in turn result in the modulation of the activity and physico-chemical properties of the drug. Further advantageously, the compound may work in an additive or synergistic manner by targeting two separate targets. It is therefore possible to put the most potent groups for each of the targets within the same molecule. In addition, the optimization for compatibility of physico-chemical properties, structure-activity relationships and testing of the efficacy of the compound may be done on a single agent without having to test for multiple agents.

Further advantageously, the compound is designed and created in such a way that each molecule has a unique potency profile against each target (ranging from low to high). This suggests that the compounds may be tweaked so that it can be tailored to have different efficacy towards different targets for a variety of indications or applications. For example, the combination of potency for HDAC/PI3K inhibition can be described to be: high/high, high/medium, high/low, medium/high, medium/medium, medium/low, low/high, low/medium and low/low. Depending on the potency combination, any combination of target enzyme may be targeted. Further, by having a wide range of compounds that have a variety of potency combinations, it may be possible to mimic a combinatorial library for combination therapy. Further advantageously, for a specific cancer or condition, best compounds may be selected by evaluating it in vitro and/or in vivo.

More advantageously, the compounds are small. It has been found that these small size molecules are less toxic and have less occurrences of adverse drug effects while maintaining a high level of activity.

In practice, design and synthesis of a working multi-target molecule by hybridising or merging or de novo design is not a simple task to achieve.

In some embodiments, the method exposing the one or more protein kinase(s) to the compound includes administering the compound to a mammal containing the one or more protein kinase(s).

In a further embodiments, there is provided a method of treating or preventing a condition in a mammal in which inhibition of one or more protein kinase(s) selected from the group consisting of a serine/threonine protein kinase or a fragment or a complex thereof or a functional equivalent thereof and a PI3K kinase or a fragment or a complex thereof or a functional equivalent thereof, prevents, inhibits or ameliorates a pathology or a symptomology of the condition, the method including administration of a therapeutically effective amount of a compound as defined above.

In some embodiments, the conditions are cancer, angiogenic disorder or pathological angiogenesis, fibrosis, inflammatory conditions, asthma, neurological disorders, neurodegenerative disorders, muscle degenerative disorders, autoimmune disorders, disorders of the blood or disorders of the bone marrow. In some embodiments the cancer is selected from the group consisting of hematologic cancer and solid tumor such as myeloproliferative disorders (idiopathic myelofibrosis, polycythemia vera, essential thrombocythemia, chronic myeloid leukemia), myeloid metaplasia, chronic myelomonocytic leukemia, acute lymphocytic leukemia, acute erythroblastic leukemia, Hodgkin's and Non Hodgkin's disease, B-cell lymphoma, diffuse large B cell lymphoma, acute T-cell leukemia, myelodysplastic syndromes, plasma cell disorder, hairy cell leukemia, kaposi's sarcoma, lymphoma; gynaecologic cancer such as breast carcinoma, ovarian cancer, cervical cancer, vaginal and vulva cancer, endometrial hyperplasia; gastrointestinal tract cancer such as colorectal carcinoma, polyps, liver cancer, gastric cancer, pancreatic cancer, gall bladder cancer; urinary tract cancer such as prostate cancer, kidney and renal cancer; urinary bladder cancer, urethral cancer, penile cancer; skin cancer such as melanoma; brain tumour such as glioblastoma, neuroblastoma, astrocytoma, ependymona, brain-stem gliomas, medulloblastoma, menigiomas, astrocytoma, oligodendroglioma; head and neck cancer such as nasopharyngeal carcinoma, laryngeal carcinoma; respiratory tract cancer such as lung carcinoma (NSCLC and SCLC), mesothelioma; eye disease such as retinoblastoma; musculoskeleton diseases such as osteosarcoma, musculoskeleletal neoplasm; Squamous cell carcinoma and fibroid tumour.

In further embodiments, there is provided a use of the compound as defined above to inhibit one or more deacetylase(s) selected from the group consisting of HDACs and non-histone deacetylase or a fragment or a complex thereof or a functional equivalent thereof.

In even further embodiments, there is provided a use of the compound as defined above to inhibit one or more protein kinase(s) selected from the group consisting of a serine/threonine protein kinase or a fragment or a complex thereof or a functional equivalent thereof and a Akt or mTOR kinase or a fragment or a complex thereof or a functional equivalent thereof.

In some embodiments, the protein kinase is a PI3K kinase or a fragment thereof or a complex thereof or a functional equivalent thereof. In some embodiments the PI3K kinase or a fragment thereof or a complex thereof or a functional equivalent thereof, is a class I PI3K or a fragment thereof or a complex thereof or a functional equivalent thereof.

In a third aspect, there is provided a method of inhibiting HDAC and/or PI3K in a cell comprising administering to a cell a compound as defined above, or a pharmaceutically acceptable form or prodrug thereof.

In some embodiments, there is provided a method of prevention or treatment of a proliferative condition in a subject, the method including administration of a therapeutically effective amount of a compound as defined above.

In a fourth aspect, there is provided a method of treating a HDAC- or PI3K-related disorder comprising administering to a subject in need of treatment a compound as defined above, or a pharmaceutically acceptable form or prodrug thereof, or a composition as defined above.

In a fifth aspect, there is provided a method of treating a HDAC- and PI3K-related disorder comprising administering to a subject in need of treatment a compound as defined above, or a pharmaceutically acceptable form or prodrug thereof, or a composition as defined above.

In an sixth aspect, there is provided a method of modulating the self-renewal or differentiation of stem-cells comprising administering to a subject in need of treatment a compound as defined above, or a pharmaceutically acceptable form or prodrug thereof, or a composition as defined above.

In further embodiments, there is provided a use of the compound as defined above in the preparation of a medicament for treating a condition in an animal in which inhibition one or more deacetylase(s) selected from the group consisting of HDACs and non-histone deacetylase or a fragment or a complex thereof or a functional equivalent thereof, prevents, inhibits or ameliorates a pathology or a symptomology of the condition.

In further embodiments there is provided a use of the compound as defined above in the preparation of a medicament for treating a condition in an animal in which inhibition of one or more protein kinase(s) selected from the group consisting of a serine/threonine protein kinase or a fragment or a complex thereof or a functional equivalent thereof and a PI3K kinase or a fragment or a complex thereof or a functional equivalent thereof, prevents, inhibits or ameliorates a pathology or a symptomology of the condition.

In a seventh aspect, there is provided a use of the compound as defined above, or a pharmaceutically acceptable form or prodrug thereof, or the composition as defined above, in the manufacture of a medicament for treatment of a HDAC- or PI3K-related disorder.

In an eighth aspect, there is provided a use of the compound as defined above, or a pharmaceutically acceptable form or prodrug thereof, or the composition as defined above in the manufacture of a medicament for treatment of a HDAC- and PI3K-related disorder.

In a ninth aspect, there is provided a use of the compound as defined above, or a pharmaceutically acceptable form or prodrug thereof, or the composition as defined above, in the manufacture of a medicament for modulating the self-renewal or differentiation of stem-cells.

In further embodiments, there is provided a use of the compound as defined above or a pharmaceutically acceptable salt, N-oxide or prodrug thereof in the treatment of a condition in which inhibition of one or more protein kinase(s) selected from the group consisting of a serine/threonine protein kinase or a fragment or a complex thereof or a functional equivalent thereof and a PI3K kinase or a fragment or a complex thereof or a functional equivalent thereof, prevents, inhibits or ameliorates a pathology or a symptomology of the condition.

In some embodiments the protein kinase is a serine/threonine protein kinase or a fragment or a complex thereof or a functional equivalent thereof. In some embodiments the serine/threonine protein kinase or a fragment or complex thereof is an mTOR protein kinase or a fragment thereof, or a complex thereof or a functional equivalent thereof. In some embodiments the serine/threonine protein kinase is mTORC1 or a fragment or complex thereof or a functional equivalent thereof.

In some embodiments, the protein kinase is a PI3K kinase or a fragment thereof or a complex thereof or a functional equivalent thereof. In some embodiments the PI3K kinase or a fragment thereof or a complex thereof or a functional equivalent thereof, is a class I PI3K or a fragment thereof or a complex thereof or a functional equivalent thereof.

In some embodiments, the serine/threonine protein kinase or a fragment or complex thereof is an Akt protein kinase or a fragment thereof, or a complex thereof or a functional equivalent thereof.

In further embodiments, there is provided a method of reprogramming cells to induced pluripotent stem cells (iPS cells). The method comprises administration of a therapeutically effective amount of a compound as defined above to cells isolated from a subject.

In further embodiments, there is provided a use of the compound as defined above in the preparation of a medicament for treating a proliferative condition in a subject.

In some embodiments the conditions are cancer, angiogenic disorder or pathological angiogenesis, fibrosis, inflammatory conditions, asthma, neurological disorders, neurodegenerative disorders, muscle degenerative disorders, autoimmune disorders, disorders of the blood or disorders of the bone marrow. In some embodiments the cancer is selected from the group consisting of hematologic cancer and solid tumor such as myeloproliferative disorders (idiopathic myelofibrosis, polycythemia vera, essential thrombocythemia, chronic myeloid leukemia), myeloid metaplasia, chronic myelomonocytic leukemia, acute lymphocytic leukemia, acute erythroblastic leukemia, Hodgkin's and Non Hodgkin's disease, B-cell lymphoma, diffuse large B cell lymphoma, acute T-cell leukemia, myelodysplastic syndromes, plasma cell disorder, hairy cell leukemia, kaposi's sarcoma, lymphoma; gynaecologic cancer such as breast carcinoma, ovarian cancer, cervical cancer, vaginal and vulva cancer, endometrial hyperplasia; gastrointestinal tract cancer such as colorectal carcinoma, polyps, liver cancer, gastric cancer, pancreatic cancer, gall bladder cancer; urinary tract cancer such as prostate cancer, kidney and renal cancer; urinary bladder cancer, urethral cancer, penile cancer; skin cancer such as melanoma; brain tumour such as glioblastoma, neuroblastoma, astrocytoma, ependynoma, brain-stem gliomas, medulloblastoma, menigiomas, astrocytoma, oligodendroglioma; head and neck cancer such as nasopharyngeal carcinoma, laryngeal carcinoma; respiratory tract cancer such as lung carcinoma (NSCLC and SCLC), mesothelioma; eye disease such as retinoblastoma; musculoskeleton diseases such as osteosarcoma, musculoskeleletal neoplasm; Squamous cell carcinoma and fibroid tumour.

Advantageously, the compounds as defined above demonstrated inhibitory activities against HDAC enzymes and PI3K kinases and anti-proliferative activities against a variety of human tumour cell lines. Most of the compound as defined above demonstrated good drug-like properties, that is, in vitro metabolic stability, solubility and desirable lipophilicity. Further advantageously, the compounds also showed activity against multi-targets in tumor cells, i.e., hyperacetylation of histones and α-tubulin due to inhibition of HDACs; PI3K-AKT-mTOR pathway: reduction of phosphor-Akt (Ser473) or inhibition the activity of mTORC2, and reduction of phospho-P7056K (Thr389)/phospho-P8556K (Thr412), phospho-S6 (Ser240/244) and phospho-4E-BP1 (Thr37/46) or inhibition of the activity of mTOCR1. More advantageously, these compounds also induced cell apoptosis in PC-3 cells and MV-4-11 cells, cell death in MV-4-11 cells, much more efficiently than PI3k inhibitor GDC-0941.

Advantageously, these compounds also modulated biological drug targets in tumor models. The compounds induced histone hyperacetylation in PC-3 prostate tumors when orally dosed in tumor-bearing mice and induced histone hyperacetylation in MV4-11 xenograft tumors via different routes of administration. The compound also demonstrated excellent antitumor activity in HCC models such as NCr nude mice HepG2 xenograft model and CB17 scid mice HepG2 xenograft model as well as HuH-7 HCC xenograft model. The compound was also demonstrated to have broad antitumor activity in a number of xenograft models when dosed orally in 4T1 mouse metastatic breast cancer model, NCI-H460 lung cancer xenograft model and MV4-11 leukaemia xenograft model.

The disclosure further relates to a process for synthesizing the compound of formula (I) and its precursors.

In a tenth aspect, there is provided a process for synthesizing the compound of formula (I) comprising the steps of; (a) providing a halogen-disubstituted purine-based or halogen di-substituted fused pyrimidine-based compound; (b) alkylating the amine (—NH— group) in the compound of step (a); (c) selectively or sequentially displacing the halide atoms of the intermediary compound of step (b) with an optionally substituted boronic ester or an optionally substituted amine to form a substituted aromatic or a substituted amine, respectively; (d) selectively coupling the intermediary compound of step (c) with a protected hydroxamic acid group having the structure -L$^1$-R$^5$-L$^2$-R$^6$-L$^3$-CON(R$^a$)OR$^b$ or an ester (hydroxamic acid precursor); and (e) converting the protected hydroxamate or the ester of the intermediary compound of step (d) to a hydroxamic acid under reaction conditions to form the compound of formula (I).

In an eleventh aspect, there is provided a process for synthesizing the compound of formula (I), comprising the steps of; (a) providing a halogen-disubstituted purine-based or halogen di-substituted fused pyrimidine-based compound; (b) selectively displacing one of the halide atoms of said compound with an optionally substituted boronic ester or an optionally substituted amine to form a substituted aromatic or a substituted amine, respectively; (c) alkylating the amine (—NH— group) in the intermediary compound of step (b); (d) selectively displacing the remaining halide atom of the intermediary compound of step (c) with an optionally substituted boronic ester or an optionally substituted amine to form a substituted aromatic or a substituted amine, respectively; (e) selectively coupling the intermediary compound of step (d) with a protected hydroxamic acid group having the structure -L$^1$-R$^5$-L$^2$-R$^6$-L$^3$-CON(R$^a$)OR$^b$ or an ester (hydroxamic acid precursor); and (f) converting the protected hydroxamate or the ester of the intermediary compound of step (e) to a hydroxamic acid under reaction conditions to form the compound of formula (I).

In a twelfth aspect, there is provided a process for synthesizing the compound of formula (I);

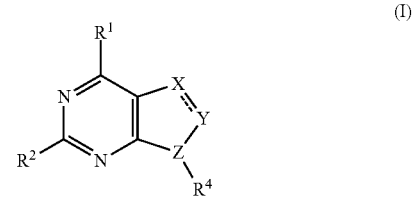

comprising the steps of; (a) providing a halogen-disubstituted purine-based or halogen di-substituted fused pyrimidine-based compound; (b) alkylating the amine in the compound of step (a); (c) selectively or sequentially displacing the halide atoms of the intermediary compound of step (b) with an optionally substituted boronic ester or an optionally substituted amine to form a substituted aromatic or a substituted amine, respectively; (d) alkylating, in the intermediary compound of step (c), the carbon atom that corresponds to the Y-position of formula (I); (e) selectively coupling the intermediary compound of step (d) with a protected hydroxamic acid group having the structure -L$^1$-

$R^5$-$L^2$-$R^6$-$L^3$-CON($R^a$)O$R^b$ or an ester (hydroxamic ester precursor); and (f) converting the protected hydroxamate or the ester of the intermediary compound of step (e) to a hydroxamic acid under reaction conditions to form the compound of formula (I).

In a thirteenth aspect, there is provided a process for synthesizing the compound of formula (I), comprising the steps of; (a) providing a halogen-disubstituted purine-based or halogen di-substituted fused pyrimidine-based compound; (b) selectively displacing one of the halide atoms of said compound with an optionally substituted boronic ester or an optionally substituted amine to form a substituted aromatic or a substituted amine, respectively; (c) alkylating the amine (—NH— group) in the intermediary compound of step (b); (d) alkylating, in the intermediary compound of step (c), the carbon atom that corresponds to the Y-position of formula (I); (e) selectively displacing the remaining halide atom of the intermediary compound of step (d) with an optionally substituted boronic ester or an optionally substituted amine to form a substituted aromatic or a substituted amine, respectively; (f) selectively coupling the compound of step (e) with a protected hydroxamic acid group having the structure -$L^1$-$R^5$-$L^2$-$R^6$—CON($R^a$)O$R^b$ or an ester (hydroxamic acid precursor); and (g) converting the protected hydroxamate or the ester of the intermediary compound of step (f) to a hydroxamic acid under reaction conditions to form the compound of formula (I).

These and other features of the present teachings are set forth herein.

DEFINITIONS

In this specification a number of terms are used which are well known to a skilled addressee. Nevertheless for the purposes of clarity a number of terms will be defined. The following words and terms used herein shall have the meaning indicated:

In the definitions of a number of substituents below it is stated that "the group may be a terminal group or a bridging group". This is intended to signify that the use of the term is intended to encompass the situation where the group is a linker between two other portions of the molecule as well as where it is a terminal moiety. Using the term alkyl as an example, some publications would use the term "alkylene" for a bridging group and hence in these other publications there is a distinction between the terms "alkyl" (terminal group) and "alkylene" (bridging group). In the present application no such distinction is made and most groups may be either a bridging group or a terminal group.

"Acyl" means an R—C(=O)-group in which the R group may be an optionally substituted alkyl, optionally substituted cycloalkyl, optionally substituted heterocycloalkyl, optionally substituted aryl or optionally substituted heteroaryl group as defined herein. Examples of acyl include acetyl, benzoyl and amino acid derived aminoacyl. The group may be a terminal group or a bridging group. If the group is a terminal group it is bonded to the remainder of the molecule through the carbonyl carbon.

"Acylamino" means an R—C(=O)—NH— group in which the R group may be an alkyl, cycloalkyl, heterocycloalkyl; aryl or heteroaryl group as defined herein. The group may be a terminal group or a bridging group. If the group is a terminal group it is bonded to the remainder of the molecule through the nitrogen atom.

"Alkenyl" as a group or part of a group denotes an aliphatic hydrocarbon group containing at least one carbon-carbon double bond and which may be straight or branched preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkenyloxy" refers to an alkenyl-O— group in which alkenyl is as defined herein. Preferred alkenyloxy groups are $C_1$-$C_6$ alkenyloxy groups. The group may be a terminal group or a bridging group. If the group is a terminal group it is bonded to the remainder of the molecule through the oxygen atom.

"Alkyl" as a group or part of a group refers to a straight or branched aliphatic hydrocarbon group, preferably a $C_1$-$C_{12}$ alkyl, more preferably a $C_1$-$C_{10}$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Alkylamino" includes both mono-alkylamino and dialkylamino, unless specified. "Mono-alkylamino" means a Alkyl-NH— group, in which alkyl is as defined herein. "Dialkylamino" means a (alkyl)$_2$N— group, in which each alkyl may be the same or different and are each as defined herein for alkyl. The alkyl group is preferably a $C_1$-$C_6$ alkyl group. The group may be a terminal group or a bridging group. If the group is a terminal group it is bonded to the remainder of the molecule through the nitrogen atom.

"Alkylaminocarbonyl" refers to a group of the formula (Alkyl)$_x$(H)$_y$NC(=O)— in which alkyl is as defined herein, x is 1 or 2, and the sum of X+Y=2. The group may be a terminal group or a bridging group. If the group is a terminal group it is bonded to the remainder of the molecule through the carbonyl carbon.

"Alkyloxy" refers to an alkyl-O— group in which alkyl is as defined herein. Preferably the alkyloxy is a $C_1$-$C_6$alkyloxy. Examples include, but are not limited to, methoxy and ethoxy. The group may be a terminal group or a bridging group.

"Alkyloxyalkyl" refers to an alkyloxy-alkyl-group in which the alkyloxy and alkyl moieties are as defined herein. The group may be a terminal group or a bridging group. If the group is a terminal group it is bonded to the remainder of the molecule through the alkyl group.

"Alkyloxyary" refers to an alkyloxy-aryl-group in which the alkyloxy and aryl moieties are as defined herein. The group may be a terminal group or a bridging group. If the group is a terminal group it is bonded to the remainder of the molecule through the aryl group.

"Alkyloxycarbonyl" refers to an alkyl-O—C(=O)— group in which alkyl is as defined herein. The alkyl group is preferably a $C_1$-$C_6$ alkyl group. Examples include, but are not limited to, methoxycarbonyl and ethoxycarbonyl. The group may be a terminal group or a bridging group. If the group is a terminal group it is bonded to the remainder of the molecule through the carbonyl carbon.

"Alkyloxycycloalkyl" refers to an alkyloxy-cycloalkyl-group in which the alkyloxy and cycloalkyl moieties are as defined herein. The group may be a terminal group or a bridging group. If the group is a terminal group it is bonded to the remainder of the molecule through the cycloalkyl group.

"Alkyloxyheteroaryl" refers to an alkyloxy-heteroaryl-group in which the alkyloxy and heteroaryl moieties are as defined herein. The group may be a terminal group or a bridging group. If the group is a terminal group it is bonded to the remainder of the molecule through the heteroaryl group.

"Alkyloxyheterocycloalkyl" refers to an alkyloxy-heterocycloalkyl-group in which the alkyloxy and heterocycloalkyl moieties are as defined herein. The group may be a terminal group or a bridging group. If the group is a terminal group it is bonded to the remainder of the molecule through the heterocycloalkyl group.

"Alkylsulfinyl" means an alkyl-S—(=O)— group in which alkyl is as defined herein. The alkyl group is preferably a $C_1$-$C_6$ alkyl group. Exemplary alkylsulfinyl groups include, but not limited to, methylsulfinyl and ethylsulfinyl. The group may be a terminal group or a bridging group. If the group is a terminal group it is bonded to the remainder of the molecule through the sulfur atom.

"Alkylsulfonyl" refers to an alkyl-S(=O)$_2$— group in which alkyl is as defined above. The alkyl group is preferably a $C_1$-$C_6$ alkyl group. Examples include, but not limited to methylsulfonyl and ethylsulfonyl. The group may be a terminal group or a bridging group. If the group is a terminal group it is bonded to the remainder of the molecule through the sulfur atom.

"Alkynyl" as a group or part of a group means an aliphatic hydrocarbon group containing a carbon-carbon triple bond and which may be straight or branched preferably having from 2-12 carbon atoms, more preferably 2-10 carbon atoms, more preferably 2-6 carbon atoms in the normal chain. Exemplary structures include, but are not limited to, ethynyl and propynyl. The group may be a terminal group or a bridging group.

"Alkynyloxy" refers to an alkynyl-O— group in which alkynyl is as defined herein. Preferred alkynyloxy groups are $C_1$-$C_6$ alkynyloxy groups. The group may be a terminal group or a bridging group. If the group is a terminal group it is bonded to the remainder of the molecule through the oxygen atom.

"Amino acid" as a group or part of a group means having at least one primary, secondary, tertiary or quaternary amino group, and at least one acid group, wherein the acid group may be a carboxylic, sulfonic, or phosphonic acid, or mixtures thereof. The amino groups may be "alpha", "beta", "gamma" . . . to "omega" with respect to the acid group(s). The amino acid may be natural or synthetic, and may include their derivatives. The backbone of the "amino acid" may be substituted with one or more groups selected from halogen, hydroxy, guanido, heterocyclic groups. Thus the term "amino acids" also includes within its scope glycine, alanine, valine, leucine, isoleucine, methionine, proline, phenylalanine, tryptophane, serine, threonine, cysteine, tyrosine, asparagine, glutamine, asparte, glutamine, lysine, arginine and histidine, taurine, betaine, N-methylalanine etc. (L) and (D) forms of amino acids are included in the scope of this disclosure. Additionally, the amino acids suitable for use in the present disclosure may be derivatized to include amino acids that are hydroxylated, phosphorylated, sulfonated, acylated, and glycosylated, to name a few. "Amino acid residue" refers to amino acid structures that lack a hydrogen atom of the amino group (—NH—CHR—COOH), or the hydroxy moiety of the carboxygroup (NH2-CHR—O—), or both (—NH—CHR—O—).

"Amino" refers to groups of the form —NR$_a$R$_b$ wherein R$_a$ and R$_b$ are individually selected from the group including but not limited to hydrogen, optionally substituted alkyl, optionally substituted alkenyl, optionally substituted alkynyl, and optionally substituted aryl groups.

"Aminoalkyl" means an NH$_2$-alkyl-group in which the alkyl group is as defined herein. The group may be a terminal group or a bridging group. If the group is a terminal group it is bonded to the remainder of the molecule through the alkyl group.

"Aminosulfonyl" means an NH$_2$—S(=O)$_2$— group. The group may be a terminal group or a bridging group. If the group is a terminal group it is bonded to the remainder of the molecule through the sulfur atom.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group.

"Arylalkenyl" means an aryl-alkenyl-group in which the aryl and alkenyl are as defined herein. Exemplary arylalkenyl groups include phenylallyl. The group may be a terminal group or a bridging group. If the group is a terminal group it is bonded to the remainder of the molecule through the alkenyl group.

"Arylalkyl" means an aryl-alkyl-group in which the aryl and alkyl moieties are as defined herein. Preferred arylalkyl groups contain a $C_{1-5}$ alkyl moiety. Exemplary arylalkyl groups include benzyl, phenethyl, 1-naphthalenemethyl and 2-naphthalenemethyl. The group may be a terminal group or a bridging group. If the group is a terminal group it is bonded to the remainder of the molecule through the alkyl group.

"Arylalkyloxy" refers to an aryl-alkyl-O— group in which the alkyl and aryl are as defined herein. The group may be a terminal group or a bridging group. If the group is a terminal group it is bonded to the remainder of the molecule through the oxygen atom.

"Arylamino" includes both mono-arylamino and di-arylamino unless specified. Mono-arylamino means a group of formula arylNH—, in which aryl is as defined herein. di-arylamino means a group of formula (aryl)$_2$N— where each aryl may be the same or different and are each as defined herein for aryl. The group may be a terminal group or a bridging group. If the group is a terminal group it is bonded to the remainder of the molecule through the nitrogen atom.

"Arylheteroalkyl" means an aryl-heteroalkyl-group in which the aryl and heteroalkyl moieties are as defined herein. The group may be a terminal group or a bridging group. If the group is a terminal group it is bonded to the remainder of the molecule through the heteroalkyl group.

"Aryloxy" refers to an aryl—O— group in which the aryl is as defined herein. Preferably the aryloxy is a $C_6$-$C_{18}$aryloxy, more preferably a $C_6$-$C_{10}$aryloxy. The group may be a terminal group or a bridging group. If the group is a terminal group it is bonded to the remainder of the molecule through the oxygen atom.

"Arylsulfonyl" means an aryl-S(=O)$_2$— group in which the aryl group is as defined herein. The group may be a terminal group or a bridging group. If the group is a terminal group it is bonded to the remainder of the molecule through the sulfur atom.

A "bond" is a linkage between atoms in a compound or molecule. The bond may be a single bond, a double bond, or a triple bond.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. A cycloalkenyl group typically is a $C_3$-$C_{12}$ alkenyl group. The group may be a terminal group or a bridging group.

"Cycloalkyl" refers to a saturated monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_{12}$ alkyl group. The group may be a terminal group or a bridging group.

"Cycloalkylalkyl" means a cycloalkyl-alkyl-group in which the cycloalkyl and alkyl moieties are as defined herein. Exemplary monocycloalkylalkyl groups include cyclopropylmethyl, cyclopentylmethyl, cyclohexylmethyl and cycloheptylmethyl. The group may be a terminal group or a bridging group. If the group is a terminal group it is bonded to the remainder of the molecule through the alkyl group.

"Cycloalkylalkenyl" means a cycloalkyl-alkenyl-group in which the cycloalkyl and alkenyl moieties are as defined herein. The group may be a terminal group or a bridging group. If the group is a terminal group it is bonded to the remainder of the molecule through the alkenyl group.

"Cycloalkylheteroalkyl" means a cycloalkyl-heteroalkyl-group in which the cycloalkyl and heteroalkyl moieties are as defined herein. The group may be a terminal group or a bridging group. If the group is a terminal group it is bonded to the remainder of the molecule through the heteroalkyl group.

"Cycloalkyloxy" refers to a cycloalkyl-O— group in which cycloalkyl is as defined herein. Preferably the cycloalkyloxy is a $C_1$-$C_6$cycloalkyloxy. Examples include, but are not limited to, cyclopropanoxy and cyclobutanoxy. The group may be a terminal group or a bridging group. If the group is a terminal group it is bonded to the remainder of the molecule through the oxygen atom.

"Cycloalkenyloxy" refers to a cycloalkenyl-O— group in which the cycloalkenyl is as defined herein. Preferably the cycloalkenyloxy is a $C_1$-$C_6$cycloalkenyloxy. The group may be a terminal group or a bridging group. If the group is a terminal group it is bonded to the remainder of the molecule through the oxygen atom.

"Cycloamino" refers to a saturated monocyclic, bicyclic, or polycyclic ring containing at least one nitrogen in at least one ring. Each ring is preferably from 3 to 10 membered, more preferably 4 to 7 membered. The group may be a terminal group or a bridging group. If the group is a terminal group it is bonded to the remainder of the molecule through the nitrogen atom.

"Haloalkyl" refers to an alkyl group as defined herein in which one or more of the hydrogen atoms has been replaced with a halogen atom selected from the group consisting of fluorine, chlorine, bromine and iodine. A haloalkyl group typically has the formula $C_nH_{(2n+1-m)}X_m$ wherein each X is independently selected from the group consisting of F, Cl, Br and I. In groups of this type n is typically from 1 to 10, more preferably from 1 to 6, most preferably 1 to 3. m is typically 1 to 6, more preferably 1 to 3. Examples of haloalkyl include fluoromethyl, difluoromethyl and trifluoromethyl.

"Haloalkenyl" refers to an alkenyl group as defined herein in which one or more of the hydrogen atoms has been replaced with a halogen atom independently selected from the group consisting of F, Cl, Br and I.

"Haloalkynyl" refers to an alkynyl group as defined herein in which one or more of the hydrogen atoms has been replaced with a halogen atom independently selected from the group consisting of F, Cl, Br and I.

"Halogen" represents chlorine, fluorine, bromine or iodine.

"Heteroalkyl" refers to a straight- or branched-chain alkyl group preferably having from 2 to 12 carbons, more preferably 2 to 6 carbons in the chain, one or more of which has been replaced by a heteroatom selected from S, O, P and N. Exemplary heteroalkyls include alkyl ethers, secondary and tertiary alkyl amines, amides, alkyl sulfides, and the like. Examples of heteroalkyl also include hydroxy$C_1$-$C_6$alkyl, $C_1$-$C_6$alkyloxy$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl. The group may be a terminal group or a bridging group.

"Heteroalkyloxy" refers to an heteroalkyl-O— group in which heteroalkyl is as defined herein. Preferably the heteroalkyloxy is a $C_1$-$C_6$heteroalkyloxy. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. A heteroaryl group is typically a $C_1$-$C_{18}$ heteroaryl group. A heteroaryl group may comprise 3 to 8 ring atoms. A heteroaryl group may comprise 1 to 3 heteroatoms independently selected from the group consisting of N, O and S. The group may be a terminal group or a bridging group.

"Heteroarylalkyl" means a heteroaryl-alkyl group in which the heteroaryl and alkyl moieties are as defined herein. Preferred heteroarylalkyl groups contain a lower alkyl moiety. Exemplary heteroarylalkyl groups include pyridylmethyl. The group may be a terminal group or a bridging group. If the group is a terminal group it is bonded to the remainder of the molecule through the alkyl group.

"Heteroarylalkenyl" means a heteroaryl-alkenyl-group in which the heteroaryl and alkenyl moieties are as defined herein. The group may be a terminal group or a bridging group. If the group is a terminal group it is bonded to the remainder of the molecule through the alkenyl group.

"Heteroarylheteroalkyl" means a heteroaryl-heteroalkyl-group in which the heteroaryl and heteroalkyl moieties are as defined herein. The group may be a terminal group or a bridging group. If the group is a terminal group it is bonded to the remainder of the molecule through the heteroalkyl group.

"Heteroarylamino" refers to groups containing an aromatic ring (preferably 5 or 6 membered aromatic ring)

having at least one nitrogen and at least another heteroatom as ring atoms in the aromatic ring, preferably from 1 to 3 heteroatoms in at least one ring. Suitable heteroatoms include nitrogen, oxygen and sulphur. Arylamino and aryl is as defined herein. The group may be a terminal group or a bridging group. If the group is a terminal group it is bonded to the remainder of the molecule through the nitrogen atom.

"Heteroaryloxy" refers to a heteroaryl-O— group in which the heteroaryl is as defined herein. Preferably the heteroaryloxy is a $C_1$-$C_{18}$heteroaryloxy. The group may be a terminal group or a bridging group. If the group is a terminal group it is bonded to the remainder of the molecule through the oxygen atom.

"Heterocyclic" refers to saturated, partially unsaturated or fully unsaturated monocyclic, bicyclic or polycyclic ring system containing at least one heteroatom selected from the group consisting of nitrogen, sulfur and oxygen as a ring atom. Examples of heterocyclic moieties include heterocycloalkyl, heterocycloalkenyl and heteroaryl.

"Heterocycloalkenyl" refers to a heterocycloalkyl as defined herein but containing at least one double bond. A heterocycloalkenyl group typically is a $C_2$-$C_{12}$ heterocycloalkenyl group. The group may be a terminal group or a bridging group.

"Heterocycloalkyl" refers to a saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane. A heterocycloalkyl group typically is a $C_2$-$C_{12}$ heterocycloalkyl group. A heterocycloalkyl group may comprise 3 to 8 ring atoms. A heterocycloalkyl group may comprise 1 to 3 heteroatoms independently selected from the group consisting of N, O and S. The group may be a terminal group or a bridging group.

"Heterocycloalkylalkyl" refers to a heterocycloalkyl-alkyl-group in which the heterocycloalkyl and alkyl moieties are as defined herein. Exemplary heterocycloalkylalkyl groups include (2-tetrahydrofuryl)methyl, (2-tetrahydrothiofuranyl) methyl. The group may be a terminal group or a bridging group. If the group is a terminal group it is bonded to the remainder of the molecule through the alkyl group.

"Heterocycloalkylalkenyl" refers to a heterocycloalkyl-alkenyl-group in which the heterocycloalkyl and alkenyl moieties are as defined herein. The group may be a terminal group or a bridging group. If the group is a terminal group it is bonded to the remainder of the molecule through the alkenyl group.

"Heterocycloalkylheteroalkyl" means a heterocycloalkyl-heteroalkyl-group in which the heterocycloalkyl and heteroalkyl moieties are as defined herein. The group may be a terminal group or a bridging group. If the group is a terminal group it is bonded to the remainder of the molecule through the heteroalkyl group.

"Heterocycloalkyloxy" refers to a heterocycloalkyl-O— group in which the heterocycloalkyl is as defined herein. Preferably the heterocycloalkyloxy is a $C_1$-$C_6$heterocycloalkyloxy. The group may be a terminal group or a bridging group. If the group is a terminal group it is bonded to the remainder of the molecule through the oxygen atom.

"Heterocycloalkenyloxy" refers to a heterocycloalkenyl-O— group in which heterocycloalkenyl is as defined herein. Preferably the Heterocycloalkenyloxy is a $C_1$-$C_6$ Heterocycloalkenyloxy. The group may be a terminal group or a bridging group. If the group is a terminal group it is bonded to the remainder of the molecule through the oxygen atom.

"Heterocycloamino" refers to a saturated monocyclic, bicyclic, or polycyclic ring containing at least one nitrogen and at least another heteroatom selected from nitrogen, sulfur, oxygen, preferably from 1 to 3 heteroatoms in at least one ring. Each ring is preferably from 3 to 10 membered, more preferably 4 to 7 membered. The group may be a terminal group or a bridging group. If the group is a terminal group it is bonded to the remainder of the molecule through the nitrogen atom.

"Hydroxyalkyl" refers to an alkyl group as defined herein in which one or more of the hydrogen atoms has been replaced with an OH group. A hydroxyalkyl group typically has the formula $C_nH_{(2n+1-x)}(OH)_x$. In groups of this type n is typically from 1 to 10, more preferably from 1 to 6, most preferably from 1 to 3. x is typically from 1 to 6, more preferably from 1 to 4.

"Lower alkyl" as a group means unless otherwise specified, an aliphatic hydrocarbon group which may be straight or branched having 1 to 6 carbon atoms in the chain, more preferably 1 to 4 carbons such as methyl, ethyl, propyl (n-propyl or isopropyl) or butyl (n-butyl, isobutyl or tertiary-butyl). The group may be a terminal group or a bridging group.

"Subject" refers to a human or an animal.

"Sulfinyl" means an R—S(=O)— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfinylamino" means an R—S(=O)—NH— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the nitrogen atom.

"Sulfonyl" means an R—S(=O)$_2$— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfonylamino" means an R—S(=O)$_2$—NH— group. The group may be a terminal group or a bridging group. If the group is a terminal group it is bonded to the remainder of the molecule through the nitrogen atom.

It is understood that included in the family of compounds of Formula (I) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Additionally, Formula (I) is intended to cover, where applicable, solvated as well as unsolvated forms of the compounds. Thus, each formula includes compounds having the indicated structure, including the hydrated as well as the non-hydrated forms.

Further, it is possible that compounds of the invention may contain more than one asymmetric carbon atom. In those compounds, the use of a solid line to depict bonds to asymmetric carbon atoms is meant to indicate that all possible stereoisomers are meant to be included. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

The term "optionally substituted" as used herein means the group to which this term refers may be unsubstituted, or may be substituted with one or more groups independently selected from alkyl, alkenyl, alkynyl, thioalkyl, cycloalkyl, cycloalkylalkyl, cycloalkenyl, cycloalkylalkenyl, heterocycloalkyl, cycloalkylheteroalkyl, cycloalkyloxy, cycloalkenyloxy, cycloamino, halo, carboxyl, haloalkyl, haloalkynyl, alkynyloxy, heteroalkyl, heteroalkyloxy, hydroxyl, hydroxyalkyl, alkoxy, thioalkoxy, alkenyloxy, haloalkoxy, haloalkenyl, haloalkynyl, haloalkenyloxy, nitro, amino, nitroalkyl, nitroalkenyl, nitroalkynyl, nitroheterocyclyl, alkylamino, dialkylamino, alkenylamine, aminoalkyl, alkynylamino, acyl, alkyloxy, alkyloxyalkyl, alkyloxyaryl, alkyloxycarbonyl, alkyloxycycloalkyl, alkyloxyheteroaryl, alkyloxyheterocycloalkyl, alkenoyl, alkynoyl, acylamino, diacylamino, acyloxy, alkylsulfonyloxy, heterocyclic, heterocycloalkenyl, heterocycloalkyl, heterocycloalkylalkyl, heterocycloalkylalkenyl, heterocycloalkylheteroalkyl, heterocycloalkyloxy, heterocycloalkenyloxy, heterocycloxy, heterocycloamino, haloheterocycloalkyl, alkylsulfinyl, alkylsulfonyl, alkylsulfenyl, alkylcarbonyloxy, alkylthio, acylthio, aminosulfonyl, phosphorus-containing groups such as phosphono and phosphinyl, sulfinyl, sulfinylamino, sulfonyl, sulfonylamino, aryl, heteroaryl, heteroarylalkyl, heteroarylalkenyl, heteroarylheteroalkyl, heteroarylamino, heteroaryloxy, arylalkenyl, arylalkyl, alkylaryl, alkylheteroaryl, aryloxy, arylsulfonyl, cyano, cyanate, isocyanate, —C(O)NH(alkyl), and —C(O)N(alkyl)$_2$.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present disclosure and specified formulae.

"Prodrug" means a compound that undergoes conversion to a compound of formula (I) within a biological system, usually by metabolic means (e.g. by hydrolysis, reduction or oxidation). For example an ester prodrug of a compound of formula (I) containing a hydroxyl group may be convertible by hydrolysis in vivo to the parent molecule. Suitable esters of compounds of formula (I) containing a hydroxyl group, are for example formates, acetates, citrates, lactates, tartrates, malonates, oxalates, salicylates, propionates, succinates, fumarates, maleates, methylene-bis-β-hydroxynaphthoates, gestisates, isethionates, di-p-toluoyltartrates, methane sulphonates, ethanesulphonates, benzenesulphonates, p-toluenesulphonates, cyclohexylsulphamates and quinates. As another example an ester prodrug of a compound of formula (I) containing a carboxy group may be convertible by hydrolysis in vivo to the parent molecule. (Examples of ester prodrugs are those described by F. J. Leinweber, Drug Metab. Res., 18:379, 1987). Similarly, an acyl prodrug of a compound of formula (I) containing an amino group may be convertible by hydrolysis in vivo to the parent molecule (Many examples of prodrugs for these and other functional groups, including amines, are described in Prodrugs: Challenges and Rewards (Parts 1 and 2); Ed V. Stella, R. Borchardt, M. Hageman, R. Oliyai, H. Maag and J Tilley; Springer, 2007)

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The term "functional equivalent" is intended to include variants of the specific protein kinase species described herein. It will be understood that kinases may have isoforms, such that while the primary, secondary, tertiary or quaternary structure of a given kinase isoform is different to the protoypical kinase, the molecule maintains biological activity as a protein kinase. Isoforms may arise from normal allelic variation within a population and include mutations such as amino acid substitution, deletion, addition, truncation, or duplication. Also included within the term "functional equivalent" are variants generated at the level of transcription. Enzymes (including HDACs and PI3Ks) have isoforms that arise from transcript variation. Other functional equivalents include kinases having altered post-translational modification such as glycosylation.

The term "reprogramming cells" is intended to include erasure and remodeling of epigenetic marks, such as DNA methylation, during mammalian development.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means ±10% of the stated value, more typically ±7.5% of the stated value, more typically ±5% of the stated value, more typically ±4% of the stated value, more typically ±3% of the stated value, more typically, ±2% of the stated value, even more typically ±1% of the stated value, and even more typically ±0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 15 shows the inhibition of HDACs and modulation of PI3k-Akt-mTOR pathway in PC-3 cells treated with the compounds.

DETAILED DESCRIPTION OF EMBODIMENTS

Hybrid-drug or multi-target drugs can increase the probability of treatment or efficacy of treatment by acting on two or more proven pathways or validated targets. For example, cancer cell survival relies on many key pathways, thus, the blocking or inhibition of one pathway may only have a small probability of killing or inhibiting the growth of target cells. To illustrate, if the probability of success is assumed to be 0.4 or 40% for each pathway, the probability of failure is 1−0.4=0.6. If two pathways (or targets) are targeted, the probability of failure will become 0.6×0.6=0.36, whilst the probability of success increased drastically (1−0.36=0.64). If three pathways are targeted, the chance of success will be 0.784 and increase so on and so forth.

Biological systems are not simple, as they can compensate each other and also synergize their functions. However, the principle of targeting multiple pathways has been validated and is already in use, such as in combination chemotherapy for cancer treatment. Examples include combination of drugs such as histone deacetylase (HDAC) inhibitors vorinostat and a variety of known drugs in clinical trials, cocktail drugs for HIV treatment, and augmentin (a mixture of amoxicillin and clavulanic acid) for antibacterial treatment. There are also successful multi-target drugs in the market, such as multi-kinase inhibitors sunitinib and sorafenib. However, instead of using of two or more drugs for combination or discovering some multi-target drug by chance, novel multi-target drug molecules can be designed to target a combination of validated and/or novel drug targets which work additively or synergistically by incorporating the key chemical structure motifs needed for each target and global modifying target profile and drug like properties. The design and development of this type of drug may be more challenging, but the advantage is that the molecules are new chemical entities rather than physical mixtures or chemical conjugates of two or more drugs, thus they are patentable and more importantly, they have new pharmacological properties.

Figure 1:
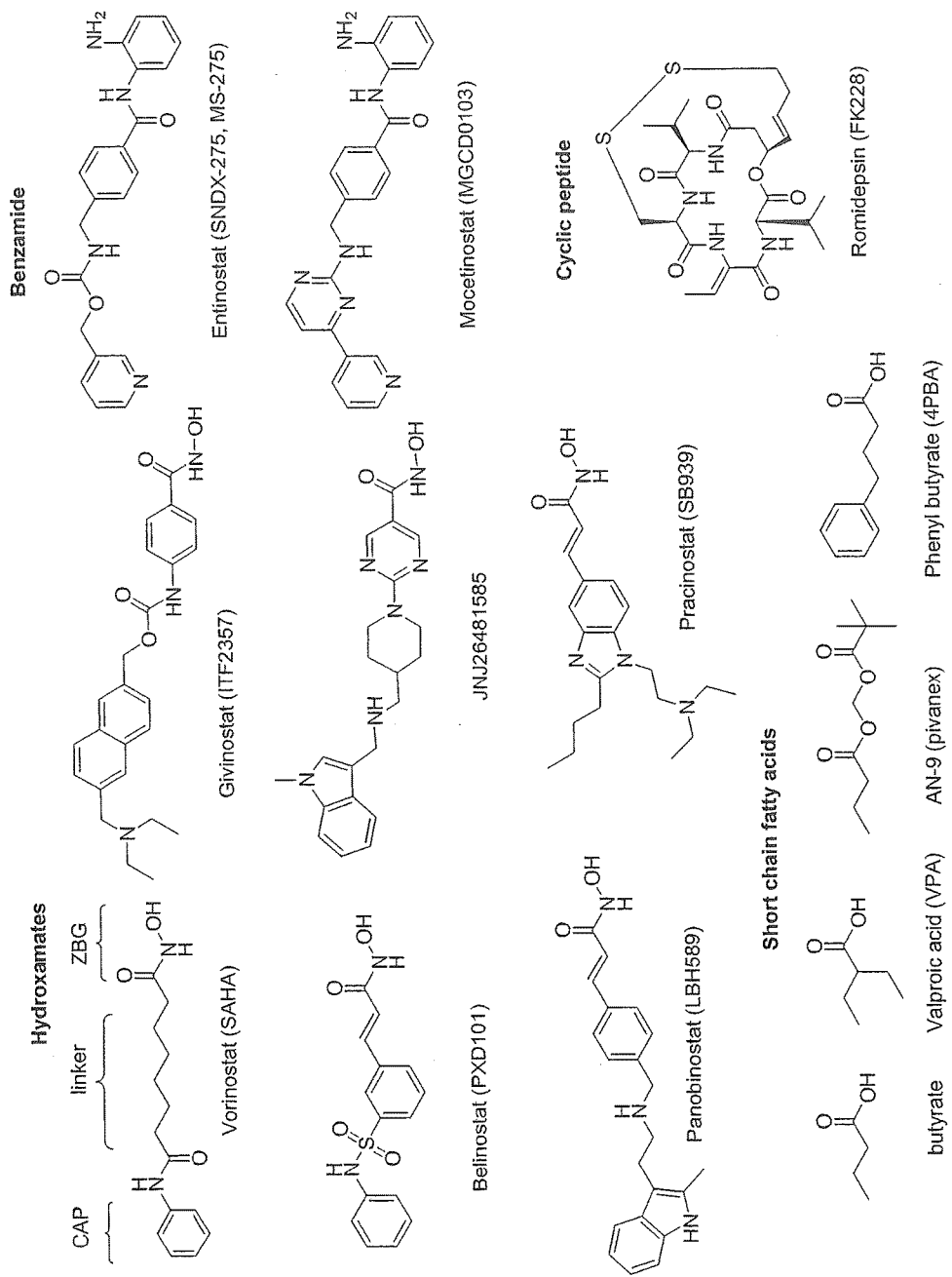
FIG. 1 is a scheme showing typical classes of known HDAC inhibitors and that a typical HDAC inhibitor (vorinostat) comprises of three parts: zinc-binding group (ZBG), linker, and a lipophilic and surface recognition "CAP" group. The CAP is sitting outside of the binding pocket of HDAC enzymes, thus CAP group can be replaced with a kinase inhibitor scaffold to afford a novel HDAC-kinase dual inhibitor.

Epigenetics can be considered to be chemical modifications to DNA which controls gene usage Amino-acid residues of histone molecules—especially those located at their amino (N)-terminal tails—are subject to various post-translational modifications, including methylation, acetylation, phosphorylation, ubiquitination, sumoylation, citrullination and ADP ribosylation. Several types of covalent modifications (such as acetylation and lysine methylation) are reversible, whereas acetylation at various residues is believed to have a more structural role, making the nucleosome structure 'looser' and more accessible to transcription factors. Histone deacetylase (HDAC) has been a validated anticancer drug target (FIG. 1) and research on HDAC inhibitors is ongoing. In addition, HDAC inhibitors have potential use in autoimmune and inflammatory disorders such as rheumatoid arthritis and diabetes mellitus due to their ability to inhibit the expression of pro-inflammatory cytokines such as TNFα. HDAC inhibitors may also have non-oncology indications such as in self-renewal and differentiation of stem cells.

HDAC inhibitors (HDACi) have been approved to be used additively or synergistically with many chemotherapeutic agents and kinase inhibitors. For example, treatment with HDACi panobinostat combined with sorafenib demonstrated the highest preclinical efficacy in treatment of hepatocellular carcinoma cancer (HCC) models, providing the rationale for clinical studies with this novel combination. mTOR inhibitors significantly enhanced HDACi-induced apoptosis in HCC cells. The inhibition of both mTORC1/2 not only efficiently blocked mTORC1 signalling, but also abrogated AKT-feedback activation caused by selective mTORC1 inhibition. In vivo studies indicated that the combination of mTOR inhibitor AZD8055 and HDACi vorinostat almost completely inhibited tumor-growth, without obvious adverse effects, which suggested that a combining-regimen of mTOR inhibitor and HDACi may be an effective therapeutic strategy for treatment of HCC. Furthermore, the dual PI3K/mTOR inhibitor PKI-587 (PF-05212384) and sorafenib targeting PI3K/AKT/mTOR and Ras/Raf/MAPK pathways has been shown to synergistically inhibit HCC cell proliferation. Thus the HDAC-kinase inhibitor, particularly an inhibitor that multiply inhibits the HDAC/PI3K-Akt-mTOR pathway would serve the purpose of the two or three individual agents for the treatment of HCC and other applicable diseases, provided that both the HDAC motif and kinase scaffold are selected appropriately.

Figure 2:
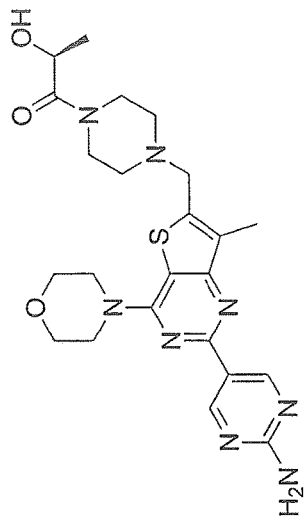
FIG. 2 shows examples of PI3K/mTOR inhibitors.
Figure 2:
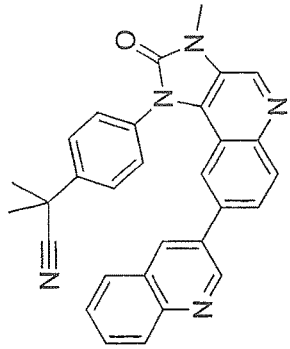
Figure 2:
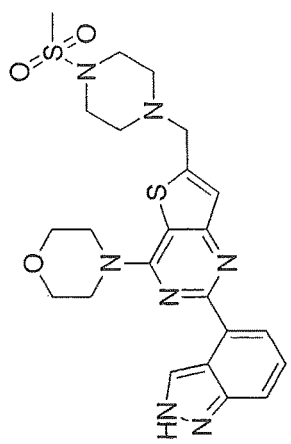
Figure 2:
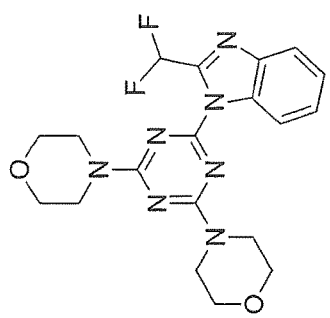
Figure 2:
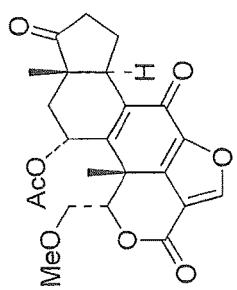
Figure 2:
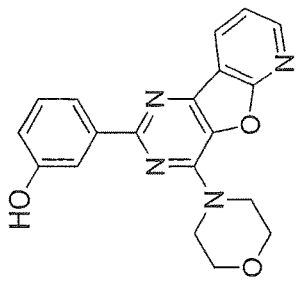

Imatinib is the first kinase that enjoyed great success in both the field of science and sales. Since then, the study of kinase inhibitors has become a very attractive field, and many kinase drug candidates are now in clinical trials. The phosphatidylinositide 3-kinase-AKT-mammalian target of the rapamycin (PI3K-Akt-mTOR) signalling pathway widely regulates divergent physiological processes and is crucial to many aspects of cell growth and survival, including cell cycle progression, differentiation, transcription, translation and apoptosis. Dysregulation, either through amplification or as a direct result of mutations, has been closely linked to the development and progression of a wide range of cancers, prompting intense interest in the development of small molecule modulators of key proteins in this cascade. PI3K, Akt and other kinases, such as 3-phosphoinositide dependent protein kinase-1 (PDK1), mTOR, have been directly targeted with varying degrees of clinical success to date (FIG. 2).

PI3K-mTOR pathway also plays an import role in cell migration and angiogenesis. The unique function of p110α in regulating endothelial cell motility supports the importance of this protein over p110β and p110δ in vascular remodeling and angiogenesis. Class II PI3K isoform, PI3K-C2α has a crucial role in vascular formation and barrier integrity and represents a new therapeutic target for vascular disease. Temsirolimus, an mTOR inhibitor approved for the treatment of renal cell carcinoma (RCC), inhibits proliferation and migration in retinal pigment epithelial and endothelial cells via mTOR Inhibition and decreases VEGF and PDGF Expression. CCI-779 Inhibits rhabdomyosarcoma xenograft growth by an antiangiogenic mechanism linked to the targeting of mTOR/Hif-1α/NEGF Signaling. A HDAC/PI3K-Akt-mTOR pathway multi-target inhibitor would be beneficial for the treatment of hypervascular tumors such as HCC, RCC and thyroid carcinomas as well as retinal angiogenesis diseases.

Angiogenesis inhibitors have been successfully used in the treatment of cancers. HDAC inhibitors are used to target tumor angiogenesis, as they can alter vascular endothelial growth factor signalling. Class IIb HDAC6 can regulate endothelial cell migration and angiogenesis by deacetylation of cortactin and regulate cell migration in an EB1-dependent manner HDAC6 is therefore a target for inhibiting endothelial cell migration and angiogenesis.

Both liver and kidney fibrosis have high unmet medical needs. HDAC inhibitors have been studied in experimental liver and kidney fibrosis. Histone deacetylase 2 is upregulated in normal and keloid scars. Class II HDAC Inhibition hampers hepatic stellate sell activation by induction of microRNA-29 and microRNA-29b prevents liver fibrosis by attenuating hepatic stellate cell activation and inducing apoptosis through targeting PI3K/AKT pathway. Furthermore, HS-173, a novel PI3K inhibitor, attenuates the activation of hepatic stellate cells in liver fibrosis. All these growing evidences support development of a HDAC/PI3K-Akt-mTOR pathway multi-target inhibitor for treatment of pathological fibrosis.

A compound of Formula (I);

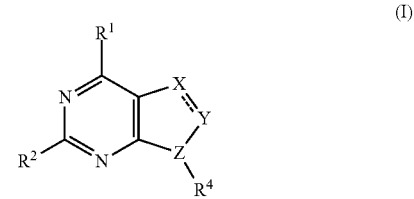

wherein X, Y and Z may be independently selected from N, CHR³ or CR³, wherein at least one of X, Y or Z is N;

----- may be a single or double bond, as valency allows;

R¹ and R² may be independently selected from the group consisting of a bond, halogen, optionally substituted alkyl, optionally substituted amino, optionally substituted alkyloxy, optionally substituted cycloalkyl, optionally substituted heterocycloalkyl, optionally substituted aryl and optionally substituted heteroaryl;

R³ and R⁴ may be independently selected from the group consisting of a bond, hydrogen, halogen, optionally substituted alkyl, optionally substituted amino, optionally substituted alkyloxy, optionally substituted cycloalkyl, optionally substituted heterocycloalkyl, optionally substituted aryl and optionally substituted heteroaryl;

at least one of R¹, R², R³ or R⁴ may be further independently substituted by an hydroxamate group -L¹-R⁵-L²-R⁶-L³-CON(Rᵃ)ORᵇ, wherein;

Rᵃ and Rᵇ may be independently selected from the group consisting of a bond, hydrogen, optionally substituted alkyl, optionally substituted acyl and optionally substituted amino acid residue;

L¹, L² and L³ may be independently selected from the group consisting of a bond, optionally substituted alkyl, optionally substituted alkenyl and optionally substituted alkynyl;

R⁵ and R⁶ may be independently selected from the group consisting of a bond, O, S, NRᶜ, S(O)ₙ, optionally substituted amide, optionally substituted urea, optionally substituted carbonylurea, optionally substituted thiourea, optionally substituted sulfonamide, optionally substituted aminosulfonamide, optionally substituted sulfonylurea, optionally substituted oxime, optionally substituted cycloalkyl, optionally substituted heterocycloalkyl, optionally substituted aryl and optionally substituted heteroaryl; wherein;

Rᶜ may be independently selected from the group consisting of a bond, hydrogen, optionally substituted alkyl, optionally substituted alkenyl, optionally substituted alkynyl and optionally substituted acyl; and n may be an integer from 0 to 2;

or a pharmaceutically acceptable form or prodrug thereof, is provided.

X, Y and Z may be independently selected from N, CHR³ or CR³, wherein at least one of X, Y or Z is N. X may be N, CHR³ or CR³. Y may be N, CHR³ or CR³. Z may be N, CHR³ or CR³. X, Y and Z may all be N. X and Z may both be N and Y may be CR³. X may be CR³, Y may be CR³ and Z may be N. X may be CH, Y may be CR³ and Z may be N. X may be N, Y may be CR³ and Z may be CR³. X may be N, Y may be CR³ and Z may be CH.

X may be CH₂, Y may be CHR³ and Z may be N. X and Z may both be N and Y may be CHR³. X may be CHR³, Y may be CHR³ and Z may be N. X may be CH₂, Y may be CHR³ and Z may be N. X may be N, Y may be CHR³ and Z may be CHR³. X may be N, Y may be CHR³ and Z may be CH₂.

----- may be a single or double bond, as valency allows. X and Y may be connected by a double bond. X and Y may be connected by a single bond.

The compound may have any one of the following Formulae (Ib), (Ic) or (Id);

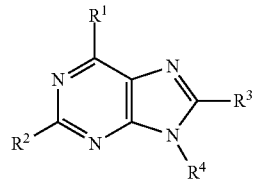

(Ib)

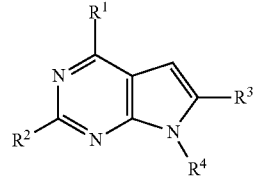

(Ic)

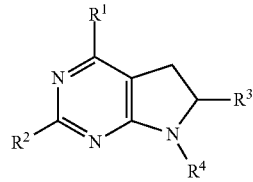

(Id)

R¹ and R² may be independently selected from the group consisting of a bond, halogen, optionally substituted alkyl, optionally substituted amino, optionally substituted alkyloxy, optionally substituted cycloalkyl, optionally substituted heterocycloalkyl, optionally substituted aryl and optionally substituted heteroaryl. R¹ and R² may be independently a bond, halogen, optionally substituted amino, optionally substituted alkylamino, optionally substituted cycloamino, optionally substituted heterocycloamino, optionally substituted alkyl, optionally substituted cycloalkyl, optionally substituted aryl or optionally substituted heteroaryl. R¹ and R² may independently a bond, halogen, optionally substituted amino, optionally substituted alkylamino, optionally substituted cycloamino, optionally substituted heterocycloamino, optionally substituted arylamino, optionally substituted heteroarylamino, optionally substituted alkyl, optionally substituted cycloalkyl, optionally substituted aryl or optionally substituted heteroaryl. R¹ may be an optionally substituted heterocycloamino, optionally substituted heteroaryl or optionally substituted aryl.

R¹ may be an optionally substituted phenyl, optionally substituted pyrimidinyl, optionally substituted pyridinyl, optionally substituted pyrazinyl, optionally substituted thiomorpholino or optionally substituted morpholino.

R² may be a halogen, optionally substituted amino, optionally substituted alkylamino, optionally substituted cycloamino, optionally substituted heterocycloamino, optionally substituted aryl or optionally substituted heteroaryl. R² may be a Cl, Br, F, NH₂, dimethylamino, diethylamino, optionally substituted pyrrolidinyl, optionally substituted piperidinyl, optionally substituted morpholino, optionally substituted phenyl, optionally substituted pyridinyl, optionally substituted pyrimidinyl, optionally substituted pyrazinyl, or optionally substituted benzimidazolyl.

R³ and R⁴ may be independently selected from the group consisting of a bond, hydrogen, halogen, optionally substituted alkyl, optionally substituted amino, optionally substituted alkyloxy, optionally substituted cycloalkyl, optionally substituted heterocycloalkyl, optionally substituted aryl and optionally substituted heteroaryl. R³ and R⁴ may be independently a bond, hydrogen, optionally substituted alkyl, optionally substituted amino, optionally substituted alkylamino, optionally substituted cycloamino, optionally substituted heterocycloamino, optionally substituted arylamino, optionally substituted heteroarylamino, optionally substituted alkyloxy, optionally substituted aryloxy, optionally substituted heteroaryloxyl or optionally substituted cycloalkyl. $R^3$ and $R^4$ may be independently a bond, hydrogen, optionally substituted alkyl, optionally substituted amino, optionally substituted alkylamino, optionally substituted cycloamino, arylamino, optionally substituted heteroarylamino, optionally substituted alkyloxy, optionally substituted aryloxy, optionally substituted heteroaryloxyl or optionally substituted cycloalkyl.

$R^3$ may be a bond, hydrogen, optionally substituted alkyl, optionally substituted amino, optionally substituted alkylamino or optionally substituted cycloamino $R^3$ may be a bond, hydrogen, $NH_2$, diethylamino, optionally substituted pyrrolidinyl or optionally substituted piperidinyl.

$R^4$ may be a bond or optionally substituted alkyl. $R^4$ may be a bond, ethyl, 1-propyl, 2-propyl, 2-butyl, 3-pentyl or cyclopentyl.

At least one of $R^1$, $R^2$, $R^3$ or $R^4$ may be further independently substituted by an hydroxamate group $-L^1-R^5-L^2-R^6-L^3-CON(R^a)OR^b$.

$R^a$ and $R^b$ may be independently selected from the group consisting of a bond, hydrogen, optionally substituted alkyl, optionally substituted acyl and optionally substituted amino acid residue. $R^a$ and $R^b$ may be hydrogen. The amino acid residue may improve the solubility and bioavailability of the prodrug.

$L^1$, $L^2$ and $L^3$ may be independently selected from the group consisting of a bond, optionally substituted alkyl, optionally substituted alkenyl and optionally substituted alkynyl. $L^1$, $L^2$ and $L^3$ independently may have a carbon chain length of $C_1$ to $C_{10}$.

$R^5$ and $R^6$ may be independently selected from the group consisting of a bond, O, S, $NR^c$, $S(O)_n$, optionally substituted amide, optionally substituted urea, optionally substituted carbonylurea, optionally substituted thiourea, optionally substituted sulfonamide, optionally substituted aminosulfonamide, optionally substituted sulfonylurea, optionally substituted oxime, optionally substituted cycloalkyl, optionally substituted heterocycloalkyl, optionally substituted aryl and optionally substituted heteroaryl. $R^5$ and $R^6$ may be independently a bond, —O—, —S—, —NH—, —N(Me)-, —N(Ac)—, —S(O)—, —S(O)$_2$—, —CONH—, —NHCO—, —NHCONH—, —S(O)$_2$NH—, NHS(O)$_2$—, —NHS(O)$_2$NH—, optionally substituted heterocycloalkyl or optionally substituted aryl. $R^5$ and $R^6$ may be independently a bond, —O—, —NH—, —N(Me)-, —NHCO—, 1,3-piperidinylene, 1,4-piperidinylene, 2,4-pyrimidinylene, 2,5-pyrimidinylene, 1,2-phenylene, 1,3-phenylene or 1,4-phenylene.

$R^c$ may be independently selected from the group consisting of a bond, hydrogen, optionally substituted alkyl, optionally substituted alkenyl, optionally substituted alkynyl and optionally substituted acyl.

n may be an integer from 0 to 2.

The optionally substituted alkyl may be an optionally substituted $C_1$-$C_{12}$ alkyl, optionally substituted $C_1$-$C_2$ alkyl, optionally substituted $C_1$-$C_4$ alkyl, optionally substituted $C_2$-$C_5$ alkyl, optionally substituted $C_1$-$C_6$ alkyl, optionally substituted $C_1$-$C_8$ alkyl, optionally substituted $C_1$-$C_{10}$ alkyl, optionally substituted $C_2$-$C_4$ alkyl, optionally substituted $C_2$-$C_6$ alkyl, optionally substituted $C_2$-$C_8$ alkyl, optionally substituted $C_2$-$C_{10}$ alkyl, optionally substituted $C_1$-$C_{12}$ alkyl, substituted $C_4$-$C_6$ alkyl, optionally substituted $C_4$-$C_8$ alkyl, optionally substituted $C_4$-$C_{10}$ alkyl, optionally substituted $C_4$-$C_{12}$ alkyl, optionally substituted $C_6$-$C_8$ alkyl, optionally substituted $C_6$-$C_{10}$ alkyl, optionally substituted $C_6$-$C_{12}$ alkyl, optionally substituted $C_8$-$C_{10}$ alkyl, optionally substituted $C_8$-$C_{12}$ alkyl, or optionally substituted $C_{10}$-$C_{12}$ alkyl. The optionally substituted alkyl may be an optionally substituted $C_1$, $C_2$, $C_3$, $C_4$, $C_5$, $C_6$, $C_7$, $C_8$, $C_9$, $C_{10}$, $C_{11}$ or $C_{12}$ alkyl.

The optionally substituted alkyloxy may be an optionally substituted $C_1$-$C_{16}$ alkyloxy, optionally substituted $C_1$-$C_2$ alkoxy, optionally substituted $C_1$-$C_4$ alkoxy, optionally substituted $C_1$-$C_6$ alkoxy, optionally substituted $C_1$-$C_8$ alkoxy, optionally substituted $C_1$-$C_{10}$ alkoxy, optionally substituted $C_1$-$C_{12}$ alkoxy, optionally substituted $C_1$-$C_{14}$ alkoxy, optionally substituted $C_2$-$C_4$ alkoxy, optionally substituted $C_2$-$C_6$ alkoxy, optionally substituted $C_2$-$C_8$ alkoxy, optionally substituted $C_2$-$C_{10}$ alkoxy, optionally substituted $C_2$-$C_{12}$ alkoxy, optionally substituted $C_2$-$C_{14}$ alkoxy, optionally substituted $C_2$-$C_{16}$ alkoxy, optionally substituted $C_4$-$C_6$ alkoxy, optionally substituted $C_4$-$C_8$ alkoxy, optionally substituted $C_4$-$C_{10}$ alkoxy, optionally substituted $C_4$-$C_{12}$ alkoxy, optionally substituted $C_4$-$C_{14}$ alkoxy, optionally substituted $C_4$-$C_{16}$ alkoxy, optionally substituted $C_6$-$C_8$ alkoxy, optionally substituted $C_6$-$C_{10}$ alkoxy, optionally substituted $C_6$-$C_{12}$ alkoxy, optionally substituted $C_6$-$C_{14}$ alkoxy, optionally substituted $C_6$-$C_{16}$ alkoxy, optionally substituted $C_8$-$C_{10}$ alkoxy, optionally substituted $C_8$-$C_{12}$ alkoxy, optionally substituted $C_8$-$C_{14}$ alkoxy, optionally substituted $C_8$-$C_{16}$ alkoxy, optionally substituted $C_{10}$-$C_{12}$ alkoxy, optionally substituted $C_{10}$-$C_{14}$ alkoxy, optionally substituted $C_{10}$-$C_{16}$ alkoxy, optionally substituted $C_{12}$-$C_{14}$ alkoxy, optionally substituted $C_{12}$-$C_{16}$ alkoxy or optionally substituted $C_{14}$-$C_{16}$ alkoxy. The optionally substituted alkoxy may be an optionally substituted $C_1$, $C_2$, $C_3$, $C_4$, $C_5$, $C_6$, $C_7$, $C_8$, $C_9$, $C_{10}$, $C_{11}$, $C_{12}$, $C_H$, $C_{14}$, $C_{15}$ or $C_{16}$ alkoxy.

The optionally substituted cycloalkyl may be an optionally substituted $C_3$-$C_9$ cycloalkyl, optionally substituted $C_3$-$C_6$ cycloalkyl or optionally substituted $C_3$-$C_9$ cycloalkyl. The optionally substituted cycloalkyl may be an optionally substituted $C_3$, $C_4$, $C_5$, $C_6$, $C_7$, $C_8$ or $C_9$ cycloalkyl.

The optionally substituted heterocycloalkyl may be an optionally substituted heterocycloalkyl having a ring atom number of 3 to 8, optionally substituted heterocycloalkyl having a ring atom number of 3 to 4, an optionally substituted heterocycloalkyl having a ring atom number of 3 to 5, an optionally substituted heterocycloalkyl having a ring atom number of 3 to 6, an optionally substituted heterocycloalkyl having a ring atom number of 3 to 7, an optionally substituted heterocycloalkyl having a ring atom number of 4 to 5, an optionally substituted heterocycloalkyl having a ring atom number of 4 to 6, an optionally substituted heterocycloalkyl having a ring atom number of 4 to 7, an optionally substituted heterocycloalkyl having a ring atom number of 4 to 8, an optionally substituted heterocycloalkyl having a ring atom number of 5 to 6, an optionally substituted heterocycloalkyl having a ring atom number of 5 to 7, an optionally substituted heterocycloalkyl having a ring atom number of 5 to 8, an optionally substituted heterocycloalkyl having a ring atom number of 6 to 7, an optionally substituted heterocycloalkyl having a ring atom number of 6 to 8 or an optionally substituted heterocycloalkyl having a ring atom number of 7 to 8. The optionally substituted heterocycloalkyl may be an optionally substituted have a ring atom number of 3, 4, 5, 6, 7 or 8. The optionally substituted heterocycloalkyl may have 1 to 3 heteroatoms independently selected from the group consisting of N, O and S. The optionally substituted heterocycloalkyl may have 1 to 2 heteroatoms independently selected from the group consisting of N, O and S. The optionally substituted heterocycloalkyl may have 2 to 3 heteroatoms independently selected from the group consisting of N, O and S.

The optionally substituted aryl may be an optionally substituted $C_6$-$C_{18}$ aryl, optionally substituted $C_6$-$C_{10}$ aryl, optionally substituted $C_6$-$C_{12}$ aryl, optionally substituted $C_6$-$C_{14}$ aryl, optionally substituted $C_6$-$C_{16}$ aryl, substituted $C_8$-$C_{10}$ aryl, optionally substituted $C_8$-$C_{12}$ aryl, optionally substituted $C_8$-$C_{14}$ aryl, optionally substituted $C_8$-$C_{16}$ aryl, optionally substituted $C_8$-$C_{18}$ aryl, optionally substituted $C_{10}$-$C_{12}$ aryl, optionally substituted $C_{10}$-$C_{14}$ aryl, optionally substituted $C_{10}$-$C_{16}$ aryl, optionally substituted $C_{10}$-$C_{18}$ aryl, optionally substituted $C_{12}$-$C_{14}$ aryl, optionally substituted $C_{12}$-$C_{16}$ aryl, optionally substituted $C_{12}$-$C_{18}$ aryl, optionally substituted $C_{14}$-$C_{16}$ aryl, optionally substituted $C_{14}$-$C_{18}$ aryl or optionally substituted $C_{14}$-$C_{18}$ aryl. The optionally substituted aryl may be an optionally substituted $C_6$, $C_7$, $C_8$, $C_9$, $C_{10}$, $C_{11}$, $C_{12}$, $C_{13}$, $C_{14}$, $C_{15}$, $C_{16}$, $C_{17}$ or $C_{18}$ aryl.

The optionally substituted heteroaryl may be heteroaryl having a ring atom number of 3 to 8, optionally substituted heteroaryl having a ring atom number of 3 to 4, an optionally substituted heteroaryl having a ring atom number of 3 to 5, an optionally substituted heteroaryl having a ring atom number of 3 to 6, an optionally substituted heteroaryl having a ring atom number of 3 to 7, an optionally substituted heteroaryl having a ring atom number of 4 to 5, an optionally substituted heteroaryl having a ring atom number of 4 to 6, an optionally substituted heteroaryl having a ring atom number of 4 to 7, an optionally substituted heteroaryl having a ring atom number of 4 to 8, an optionally substituted heteroaryl having a ring atom number of 5 to 6, an optionally substituted heteroaryl having a ring atom number of 5 to 7, an optionally substituted heteroaryl having a ring atom number of 5 to 8, an optionally substituted heteroaryl having a ring atom number of 6 to 7, an optionally substituted heteroaryl having a ring atom number of 6 to 8 or an optionally substituted heteroaryl having a ring atom number of 7 to 8. The optionally substituted heteroaryl may be an optionally substituted have a ring atom number of 3, 4, 5, 6, 7 or 8. The optionally substituted heteroaryl may have 1 to 3 heteroatoms independently selected from the group consisting of N, O and S. The optionally substituted heteroaryl may have 1 to 2 heteroatoms independently selected from the group consisting of N, O and S. The optionally substituted heteroaryl may have 2 to 3 heteroatoms independently selected from the group of consisting of N, O and S.

The optionally substituted alkenyl may be an optionally substituted $C_2$-$C_{12}$ alkenyl, optionally substituted $C_2$-$C_4$ alkenyl, optionally substituted $C_2$-$C_6$ alkenyl, optionally substituted $C_2$-$C_8$ alkenyl, optionally substituted $C_2$-$C_{10}$ alkenyl, optionally substituted $C_1$-$C_{12}$ alkenyl, substituted $C_4$-$C_6$ alkenyl, optionally substituted $C_4$-$C_8$ alkenyl, optionally substituted $C_4$-$C_{10}$ alkenyl, optionally substituted $C_4$-$C_{12}$ alkenyl, optionally substituted $C_6$-$C_8$ alkenyl, optionally substituted $C_6$-$C_{10}$ alkenyl, optionally substituted $C_6$-$C_{12}$ alkenyl, optionally substituted $C_8$-$C_{10}$ alkenyl, optionally substituted $C_8$-$C_{12}$ alkenyl, or optionally substituted $C_{10}$-$C_{12}$ alkenyl. The optionally substituted alkenyl may be an optionally substituted $C_2$, $C_3$, $C_4$, $C_5$, $C_6$, $C_7$, $C_8$, $C_9$, $C_{10}$, $C_{11}$ or $C_{12}$ alkenyl.

The optionally substituted alkynyl is an optionally substituted $C_2$-$C_{12}$ alkynyl, optionally substituted $C_2$-$C_4$ alkynyl, optionally substituted $C_2$-$C_6$ alkynyl, optionally substituted $C_2$-$C_8$ alkynyl, optionally substituted $C_2$-$C_{10}$ alkynyl, optionally substituted $C_1$-$C_{12}$ alkynyl, substituted $C_4$-$C_6$ alkynyl, optionally substituted $C_4$-$C_8$ alkynyl, optionally substituted $C_4$-$C_{10}$ alkynyl, optionally substituted $C_4$-$C_{12}$ alkynyl, optionally substituted $C_6$-$C_8$ alkynyl, optionally substituted $C_6$-$C_{10}$ alkynyl, optionally substituted $C_6$-$C_{12}$ alkynyl, optionally substituted $C_8$-$C_{10}$ alkynyl, optionally substituted $C_8$-$C_{12}$ alkynyl, or optionally substituted $C_{10}$-$C_{12}$ alkynyl. The optionally substituted alkynyl may be an optionally substituted $C_2$, $C_3$, $C_4$, $C_5$, $C_6$, $C_7$, $C_8$, $C_9$, $C_{10}$, $C_{11}$ or $C_{12}$ alkynyl.

The hydroxamate group -$L^1$-$R^5$-$L^2$-$R^6$-$L^3$-CON($R^a$)O$R^b$ may be selected from any one of the following structures;

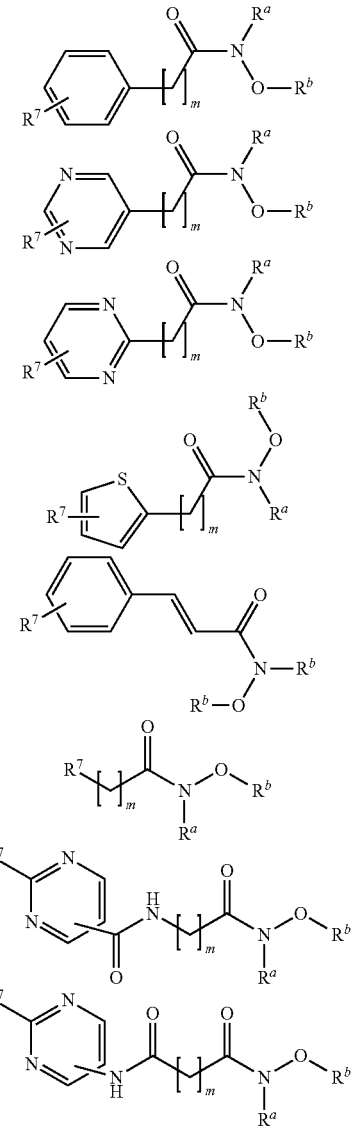

$R^7$ may be selected from the group consisting of a bond, optionally substituted alkyl, optionally substituted aryl, optionally substituted heteroaryl, O, S, optionally substituted amino, —$CH_2$O—, —O$CH_2$—, —$CH_2$S(O)$_n$—, —S(O)$_n$$CH_2$—, —S(O)$_n$—, —$CH_2$N($R^c$)—, —N($R^c$)$CH_2$—, —N($R^c$)—, —CO—, —C(=NO$R^a$)—, —CON($R^a$)—, —N($R^c$)CO—, —N($R^c$)CON($R^c$)CO—, —CON($R^c$)CONH—, —N($R^c$)CON($R^b$)—, —S(O)$_2$N($R^c$)—, —S(O)$_2$N($R^a$)CON($R^c$)—, —N($R^c$)CON($R^a$)S(O)$_2$—, —N($R^c$)S(O)$_2$N($R^a$)— and —N($R^c$)S(O)$_2$—; and m may be an integer from 0 to 10.

$R^2$ or $R^4$ may contain the hydroxamate group -$L^1$-$R^5$-$L^2$-$R^6$-$L^3$-CON($R^a$)O$R^b$.

$R^1$ may not be a morpholine when $R^2$ or $R^3$ contains the hydroxamate group.

$R^1$ may be a substituted amino when $R^2$ or $R^3$ contains the hydroxamate group. The substituted amino may be morpholine.

The compound may have the following Formula (Ib):

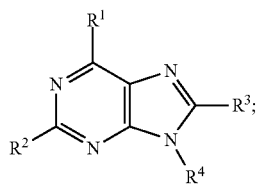

wherein $R^1$ may be an optionally substituted phenyl, optionally substituted pyrimidinyl, optionally substituted pyridinyl, optionally substituted pyrazinyl, optionally substituted thiomorpholino or optionally substituted morpholino;

$R^2$ may be a Cl, Br, F, $NH_2$, dimethylamino, diethylamino, optionally substituted pyrrolidinyl, optionally substituted piperidinyl, optionally substituted morpholino, optionally substituted phenyl, optionally substituted pyridinyl, optionally substituted pyrimidinyl, optionally substituted pyrazinyl, or optionally substituted benzimidazolyl;

$R^3$ may be a bond, hydrogen, $NH_2$, diethylamino, optionally substituted pyrrolidinyl or optionally substituted piperidinyl; and $R^4$ may be a bond, ethyl, 1-propyl, 2-propyl, 2-butyl, 3-pentyl or cyclopentyl.

Specific compounds of the disclosure include the following:

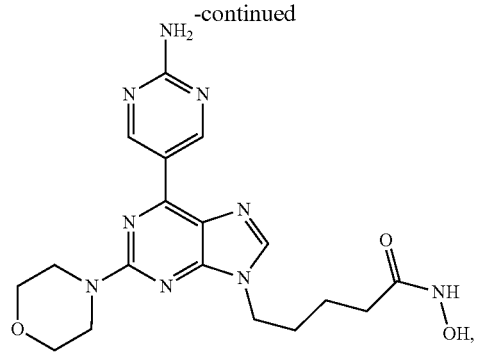

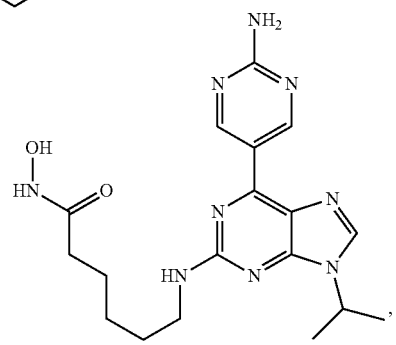

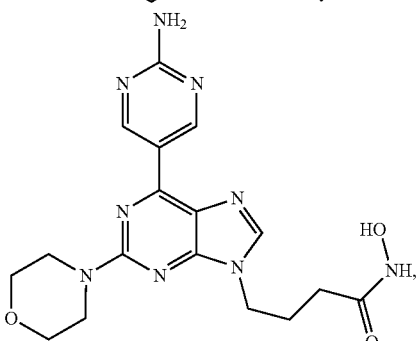

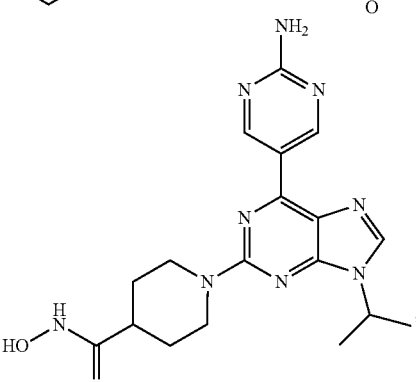

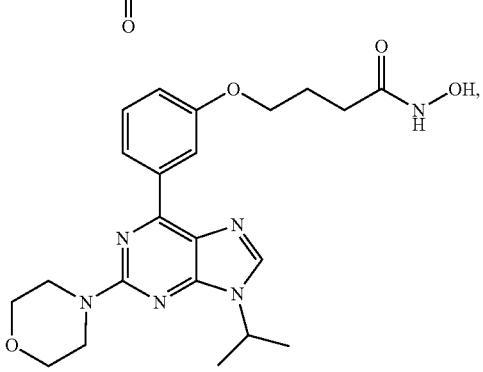

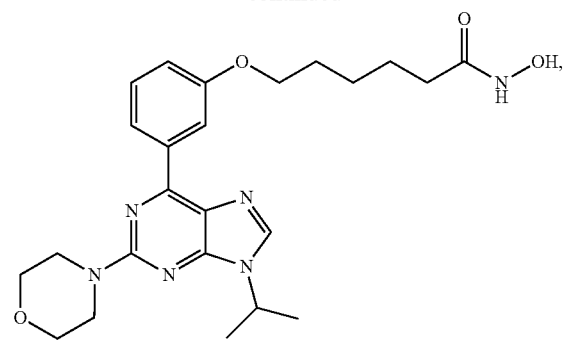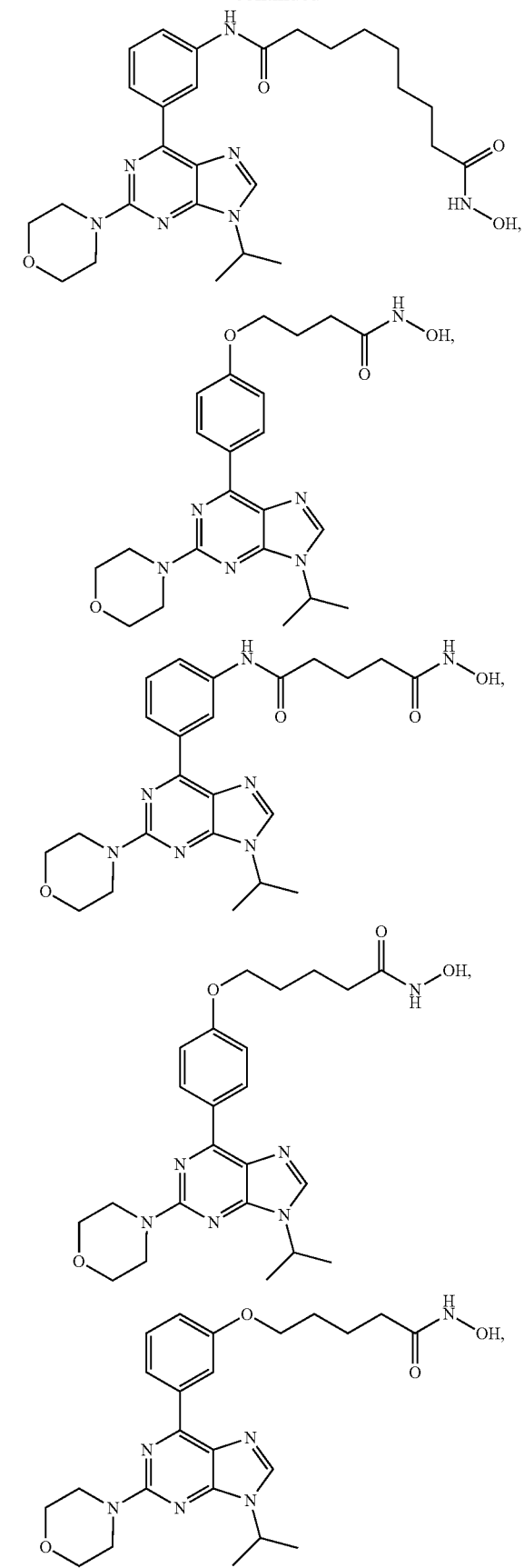

US 9,957,270 B2
33
-continued
34
-continued
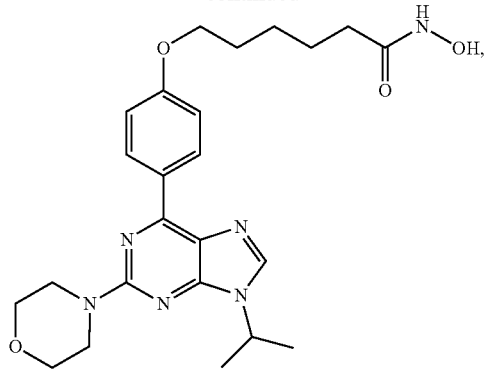

35
-continued
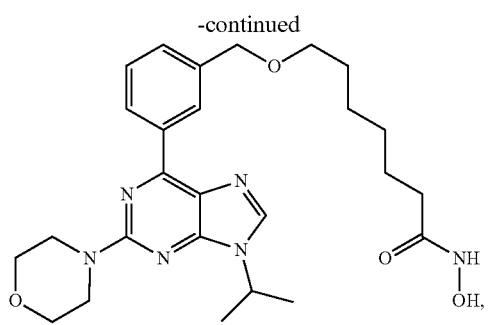
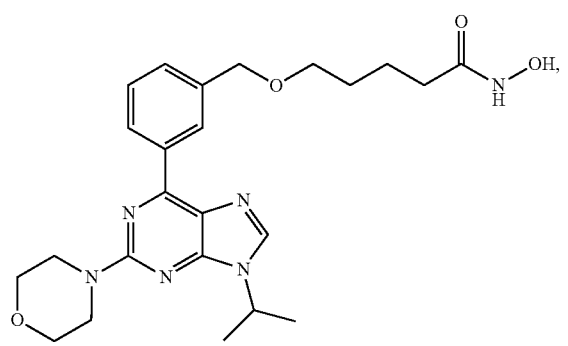
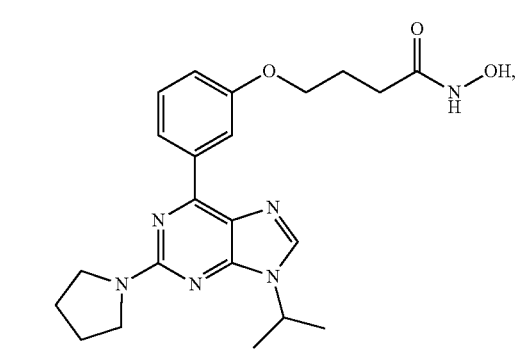
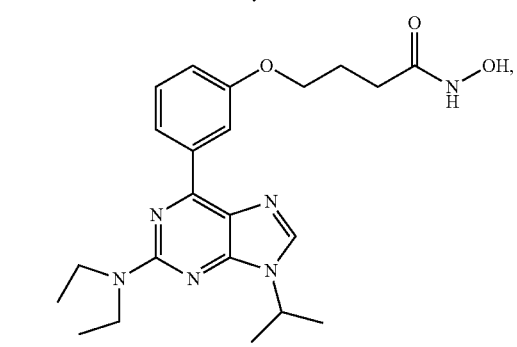
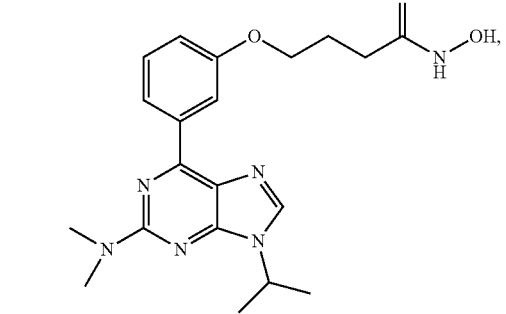
36
-continued
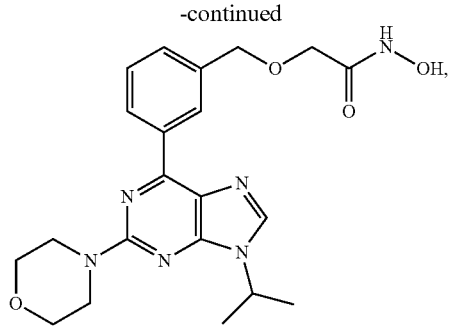
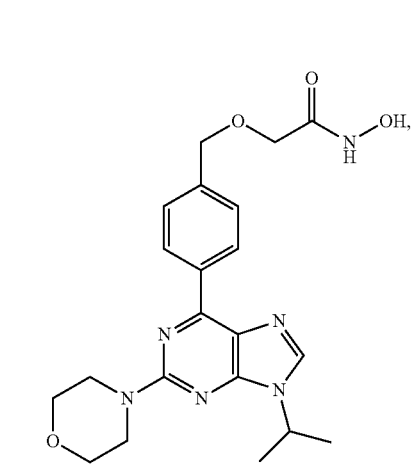
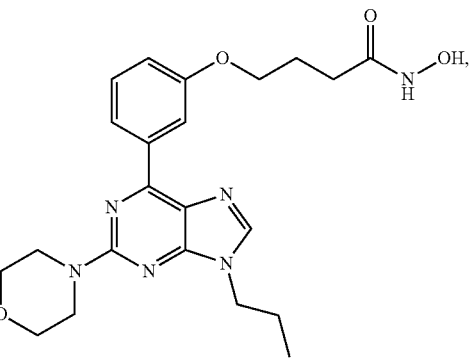
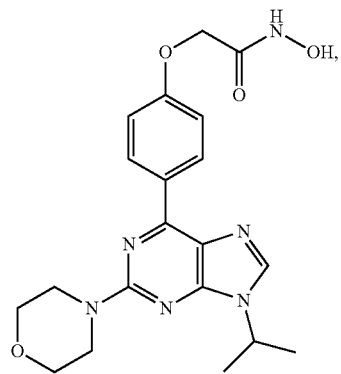

37
-continued
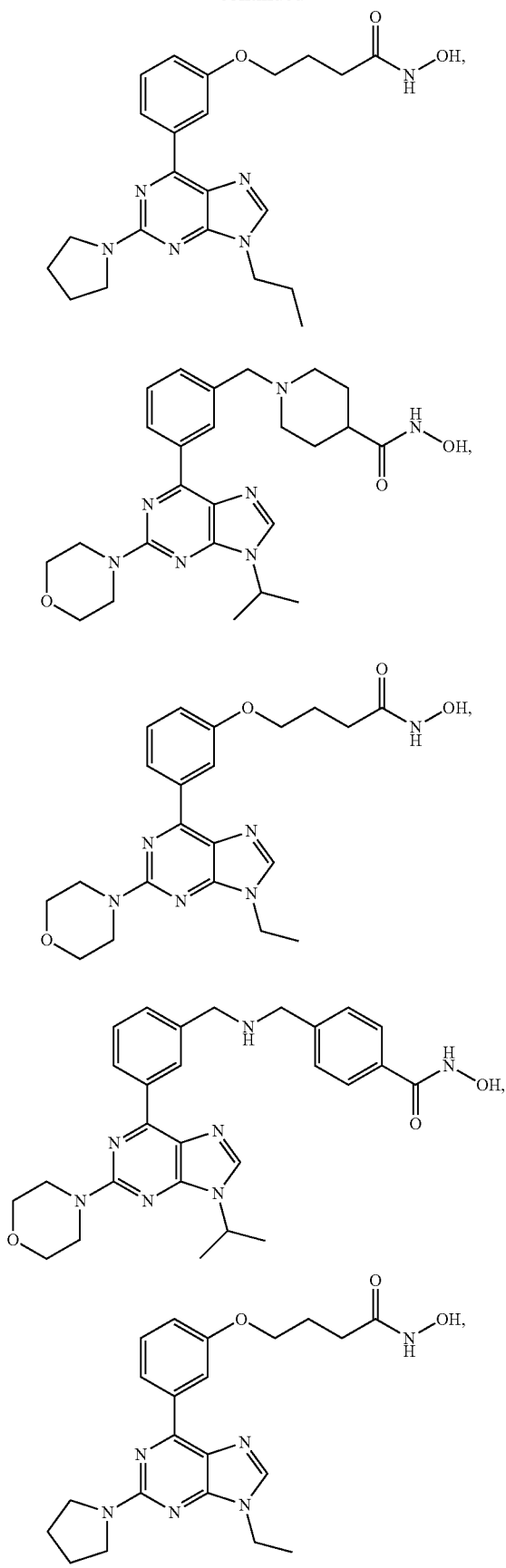
38
-continued
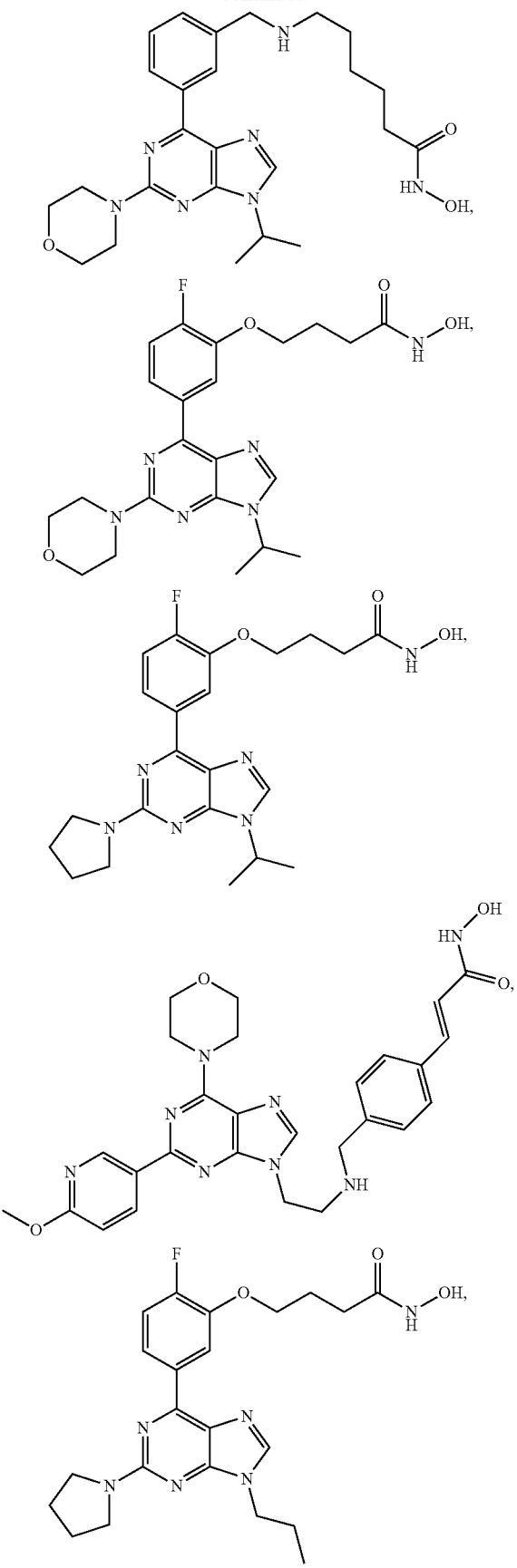

39
-continued
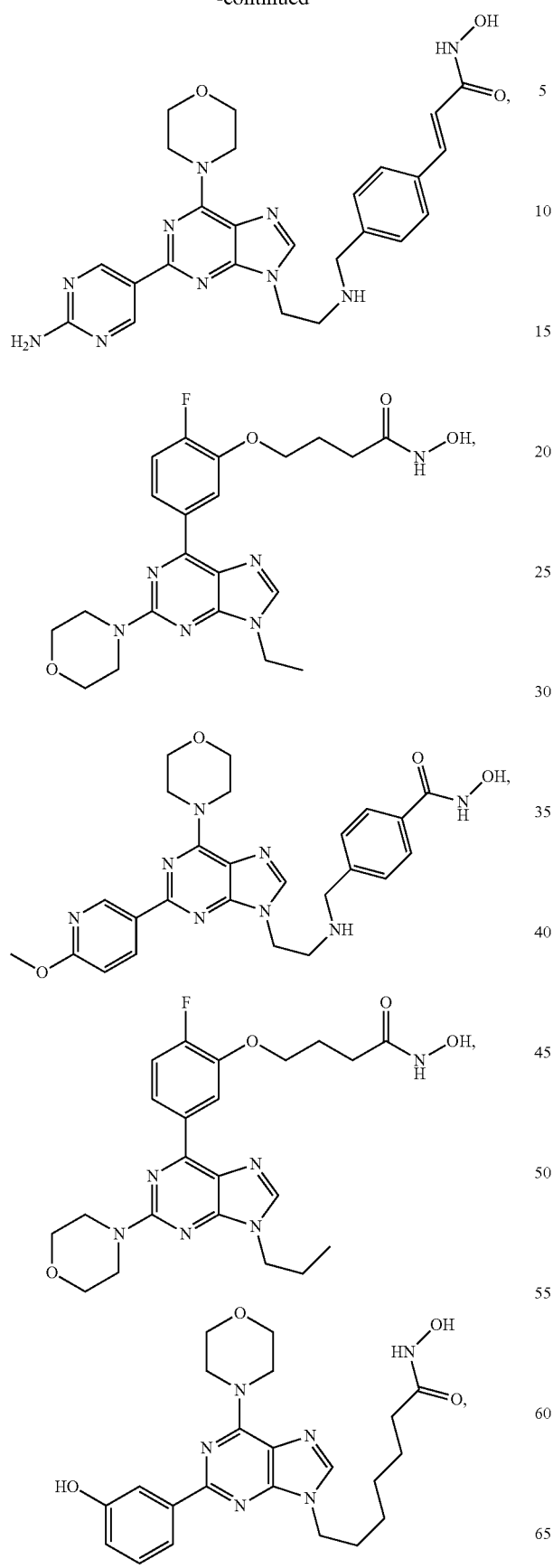
40
-continued
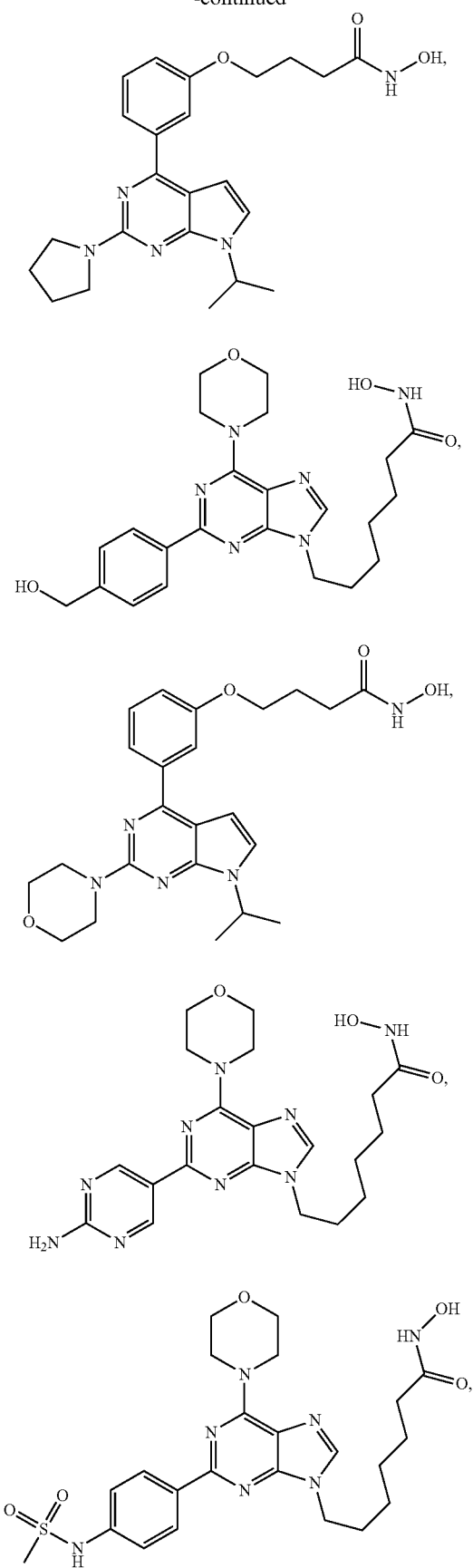

-continued
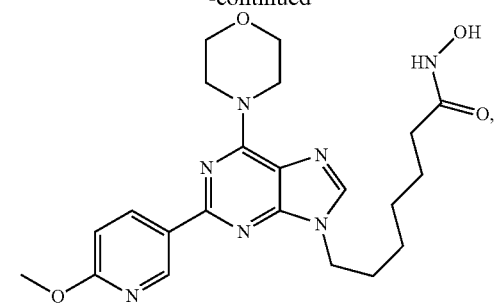
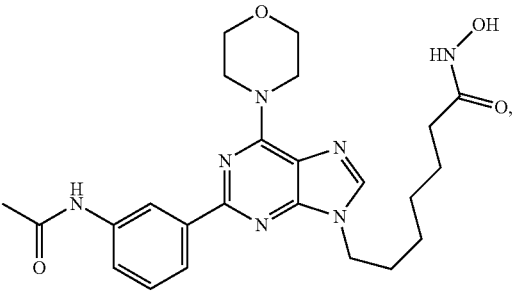
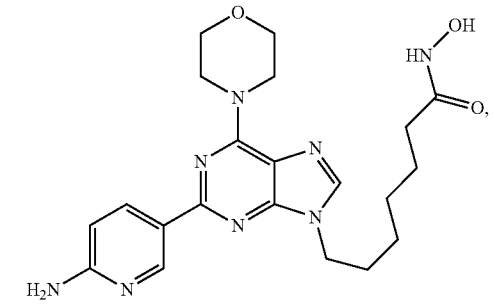
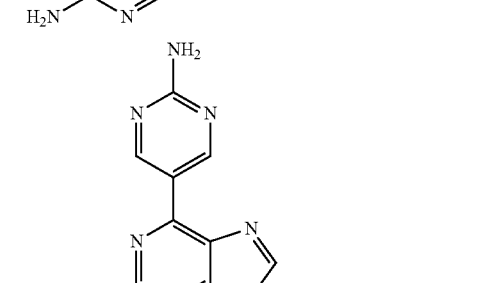
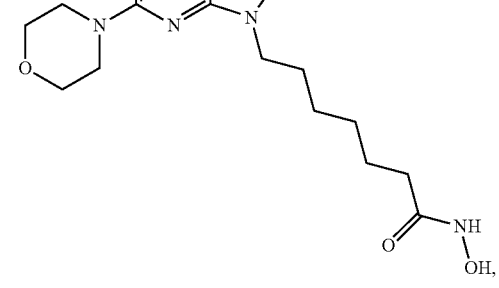
-continued
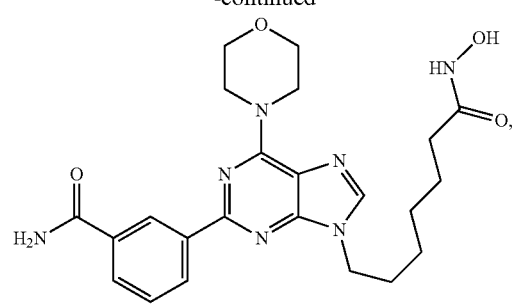
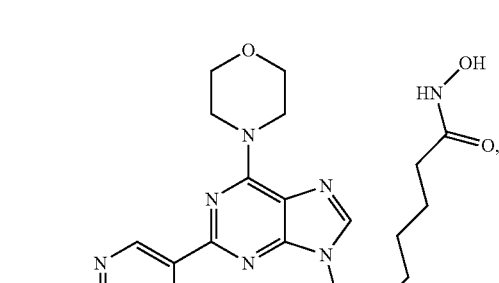
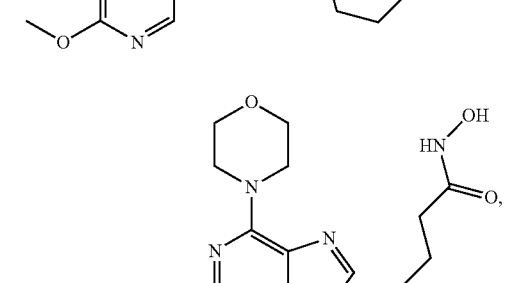
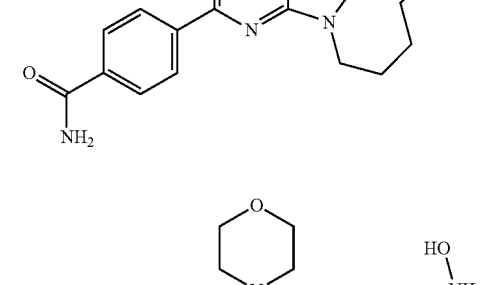
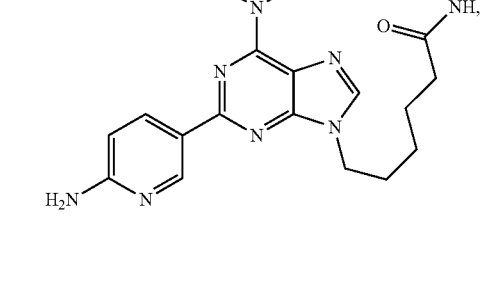

43
-continued
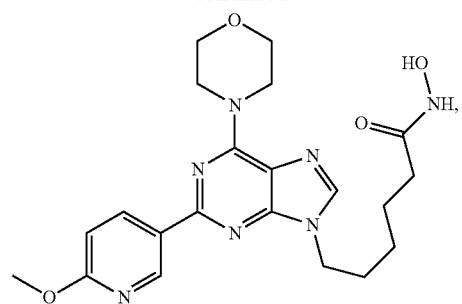
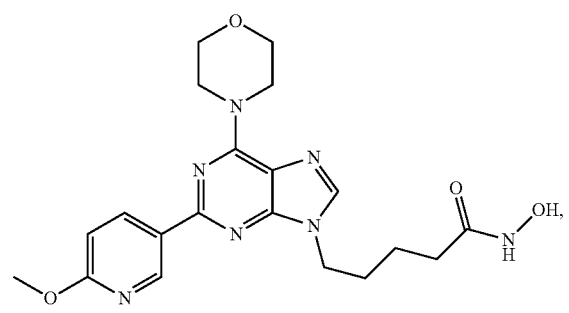
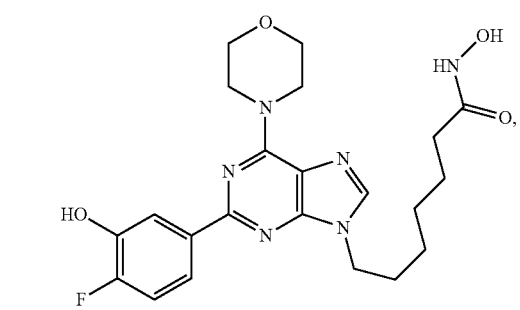
44
-continued
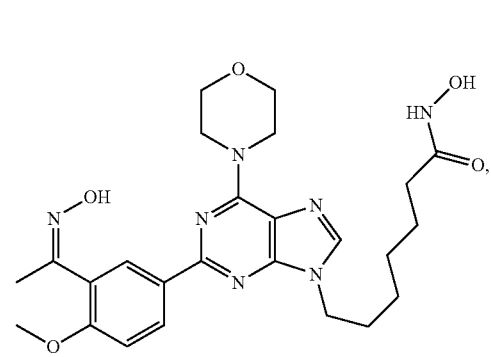
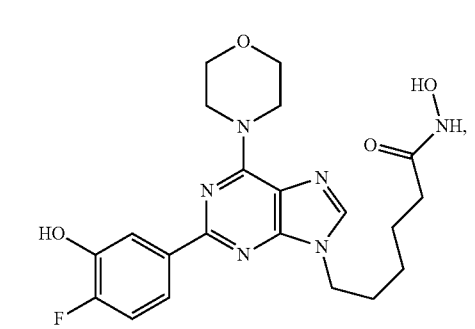
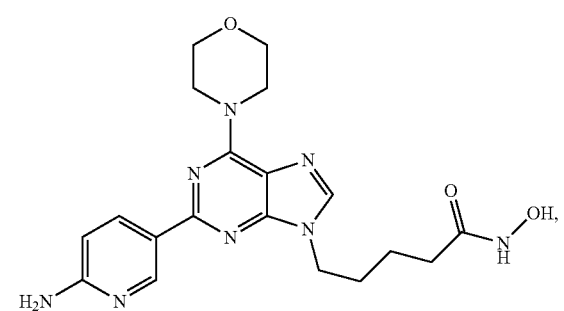
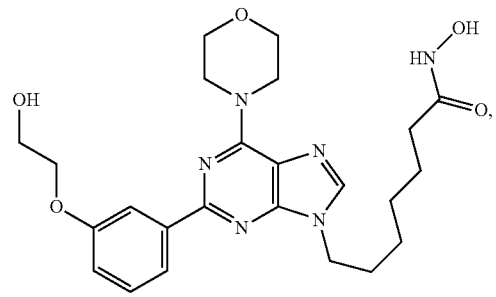
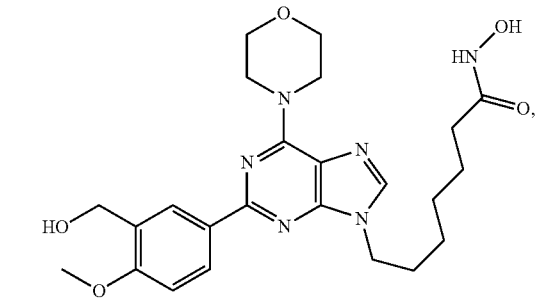
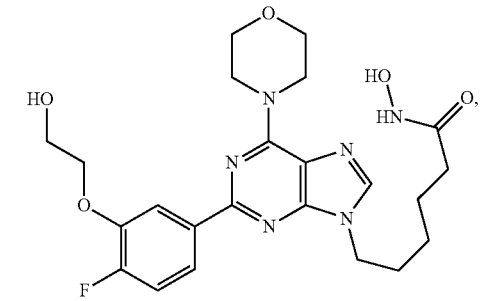

45
-continued
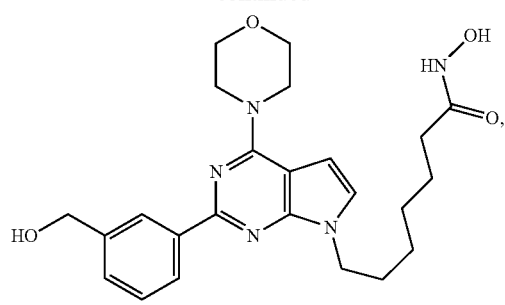
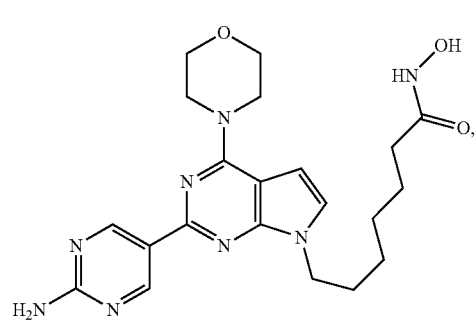
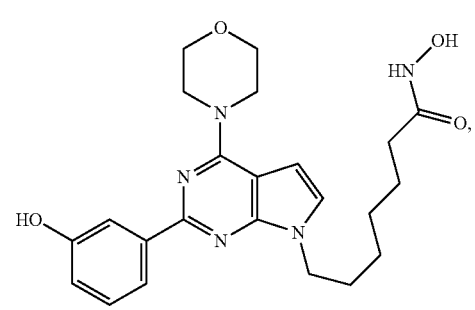
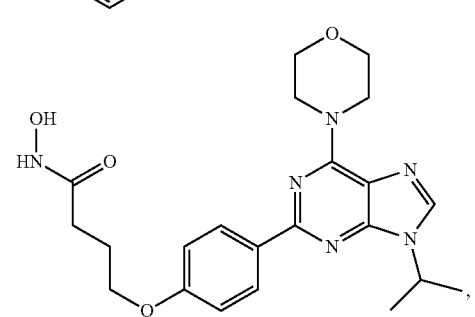
46
-continued
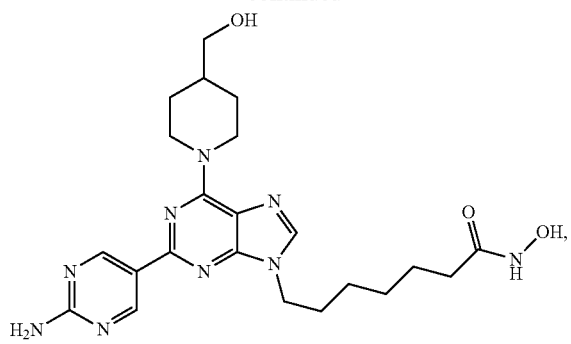
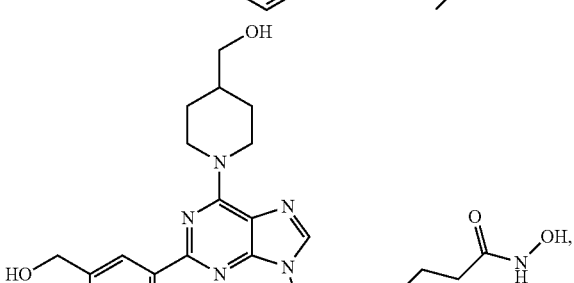
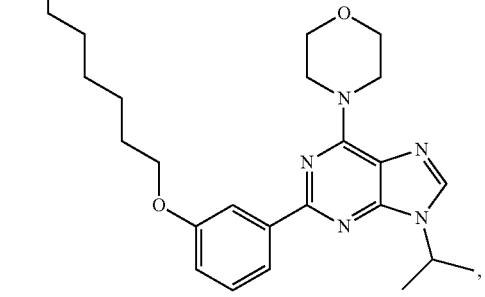
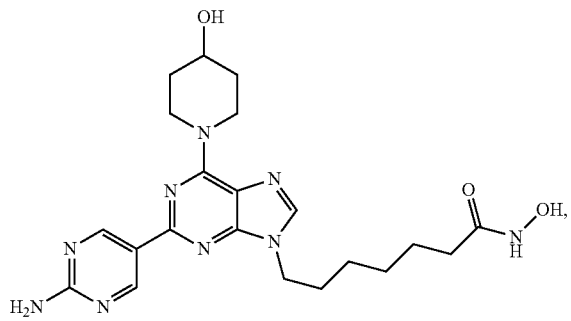

47
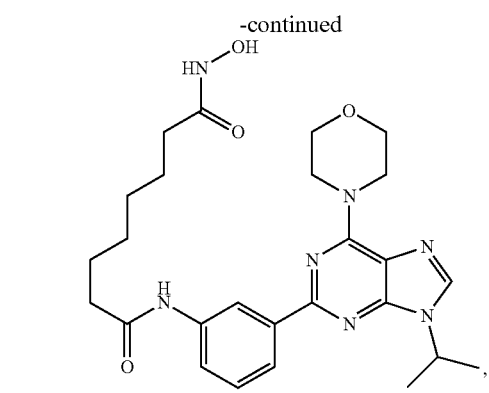
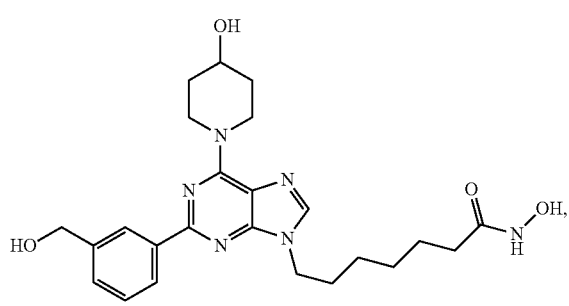 [SMILES: O=C(CCCCCCn1cnc2c(N3CCC(O)CC3)nc(-c3cccc(CO)c3)nc21)NO]
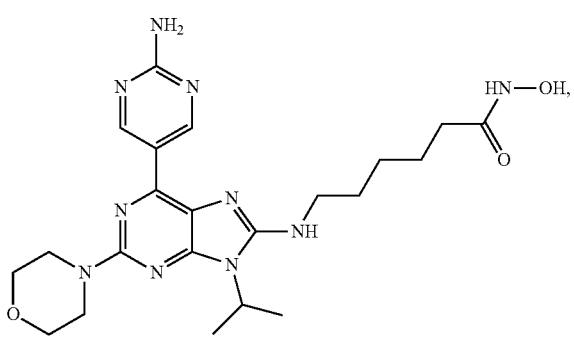
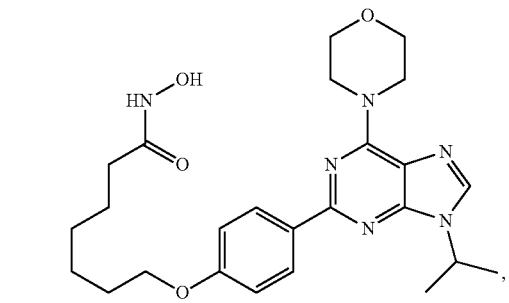
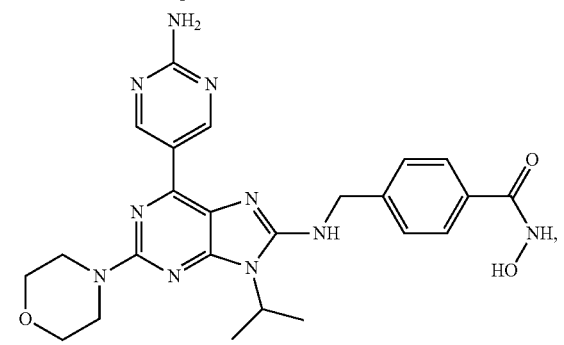
48
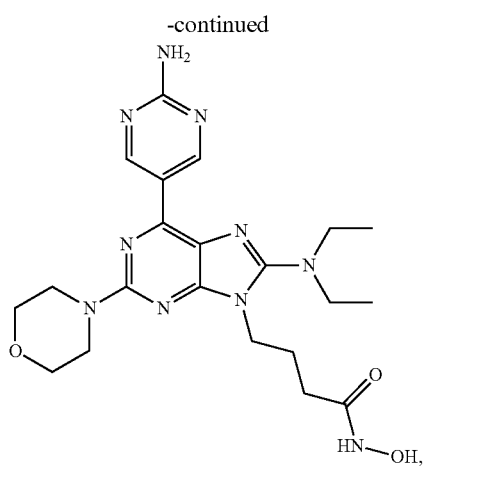
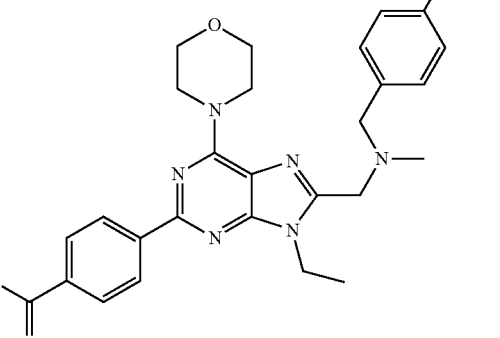
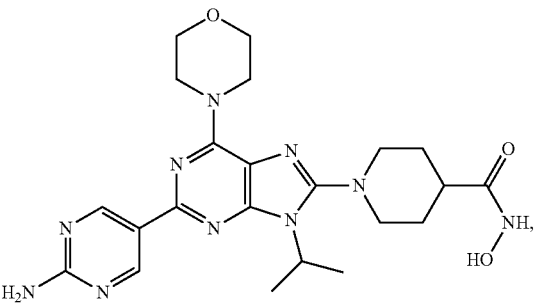
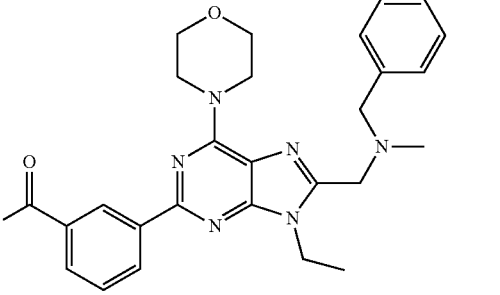

49
-continued
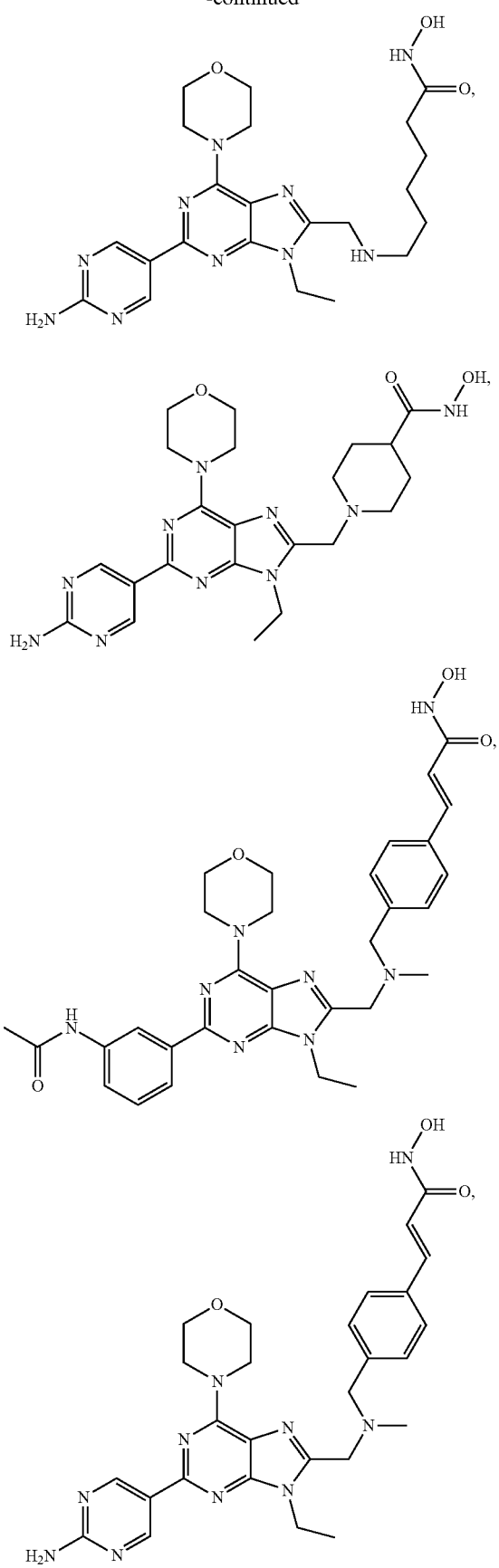
50
-continued
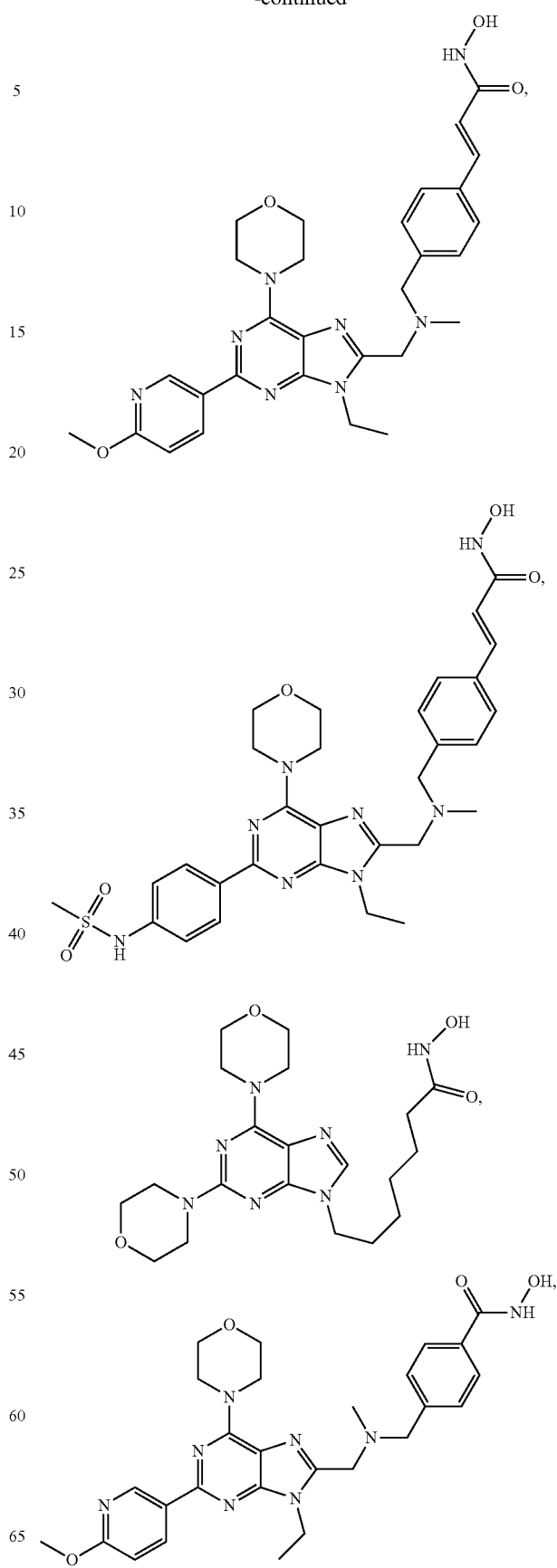

51
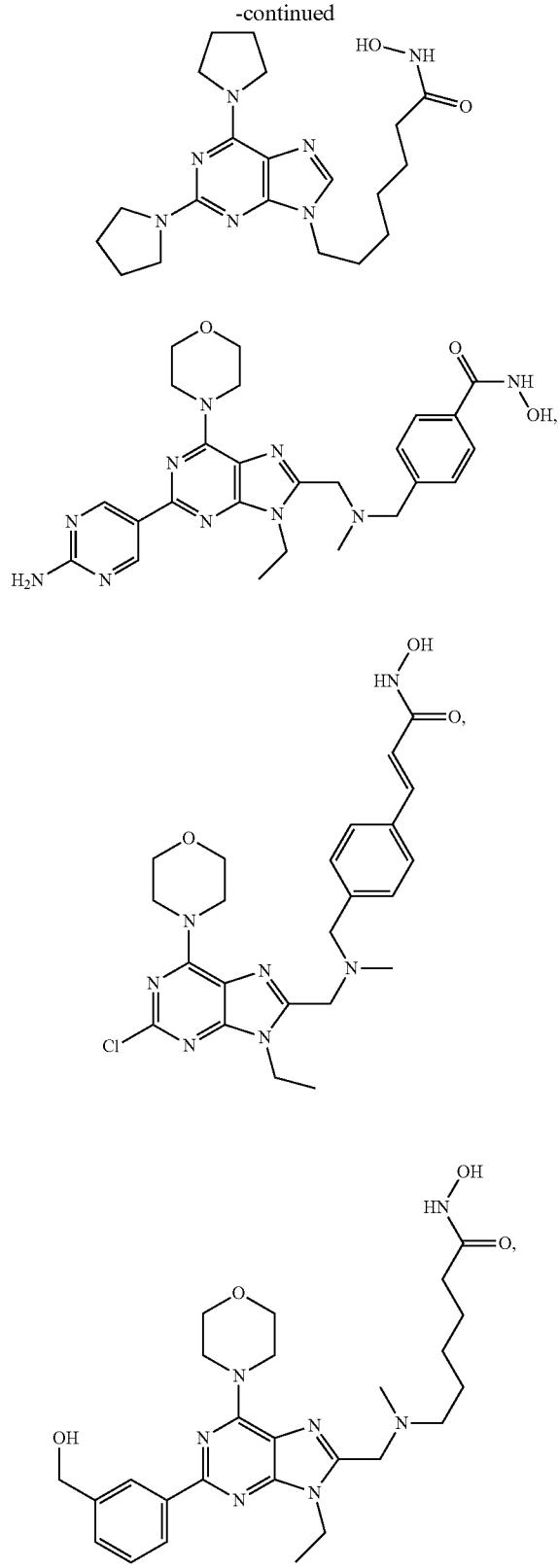
or a pharmaceutically acceptable salt or prodrug thereof.
Specific compounds when R¹ is not a morpholine when R² or R³ contains the hydroxamate group may include the following:
52
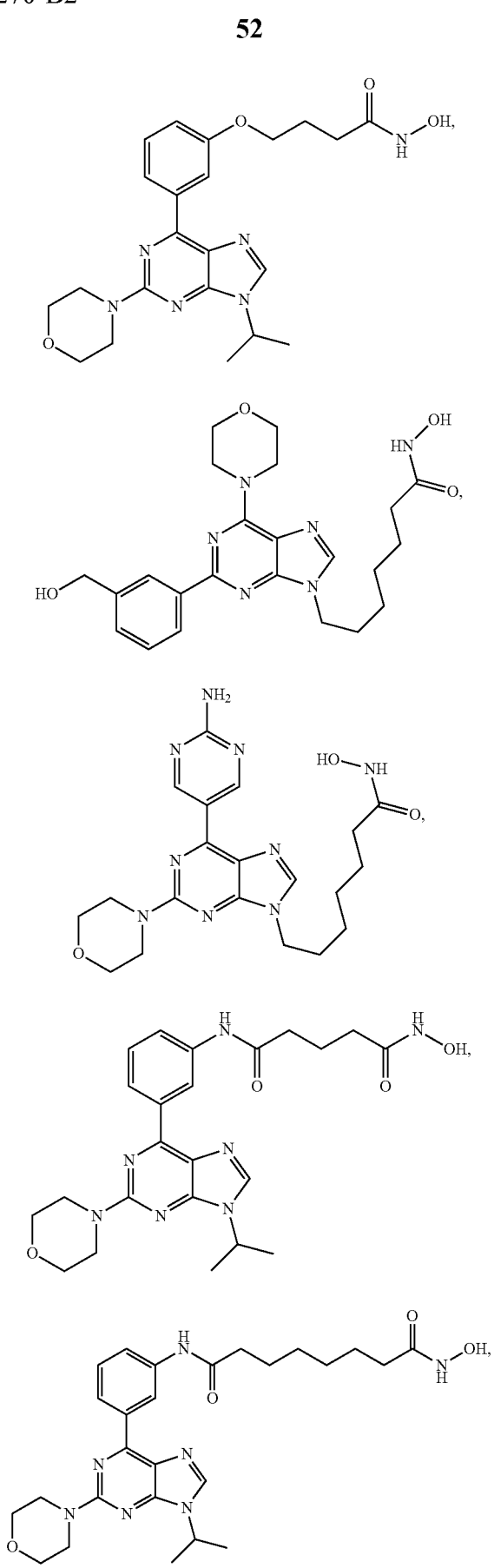

53
-continued
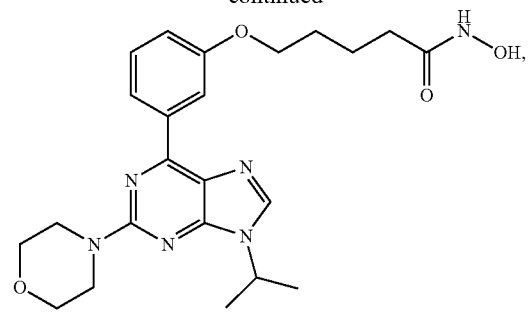
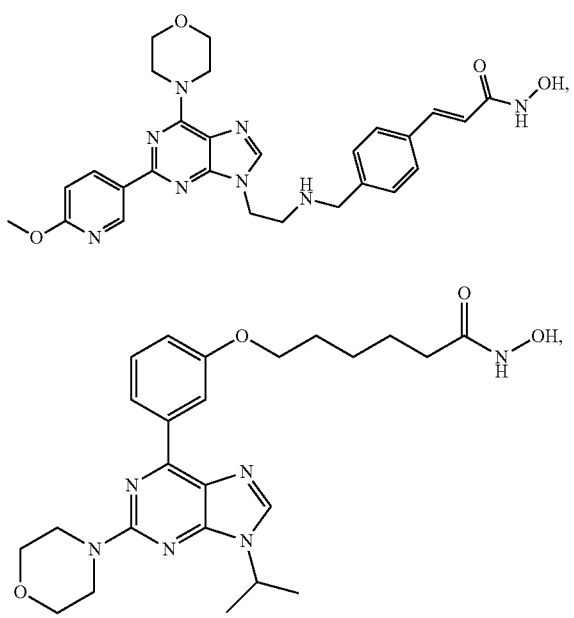
54
-continued
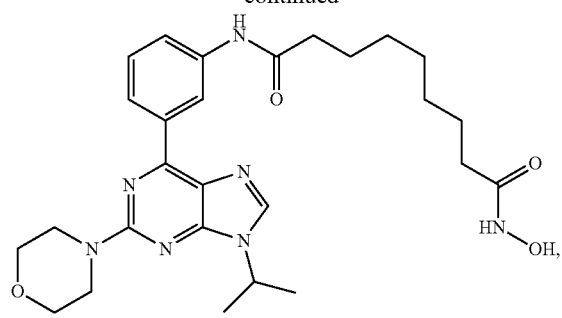
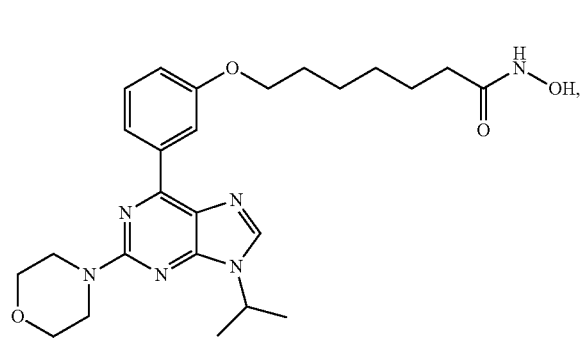
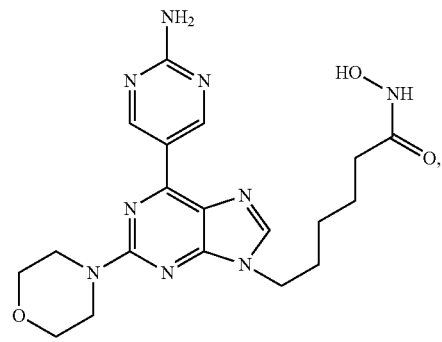

55
-continued
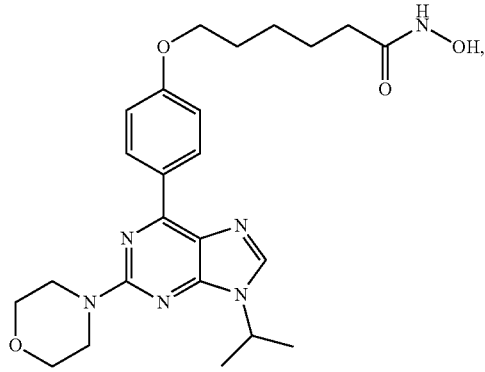
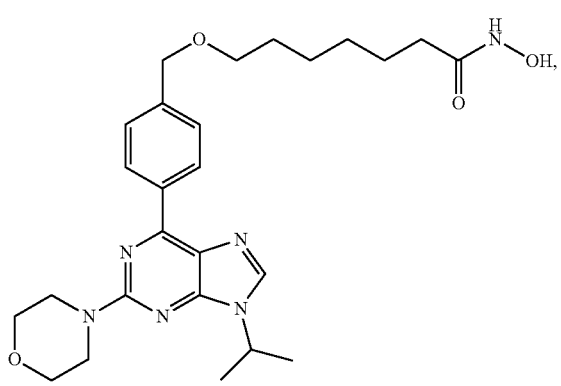
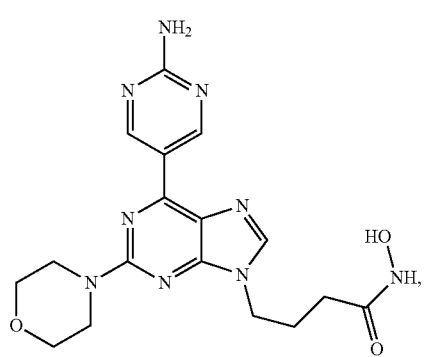
56
-continued
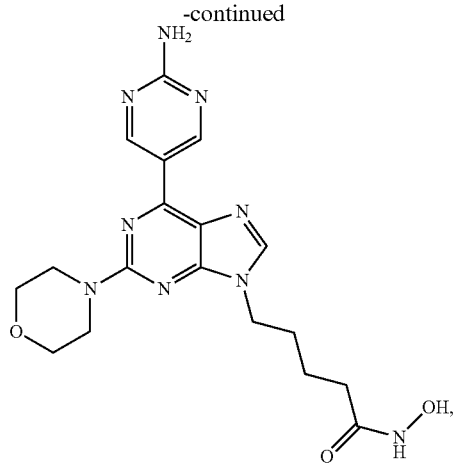
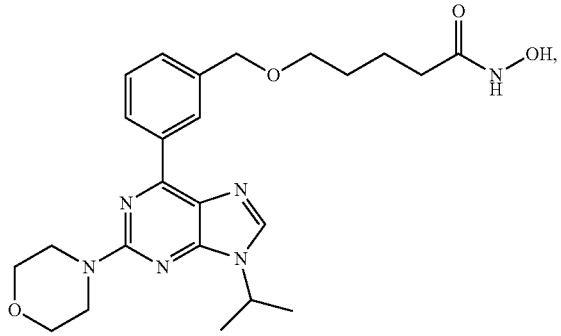

57
-continued
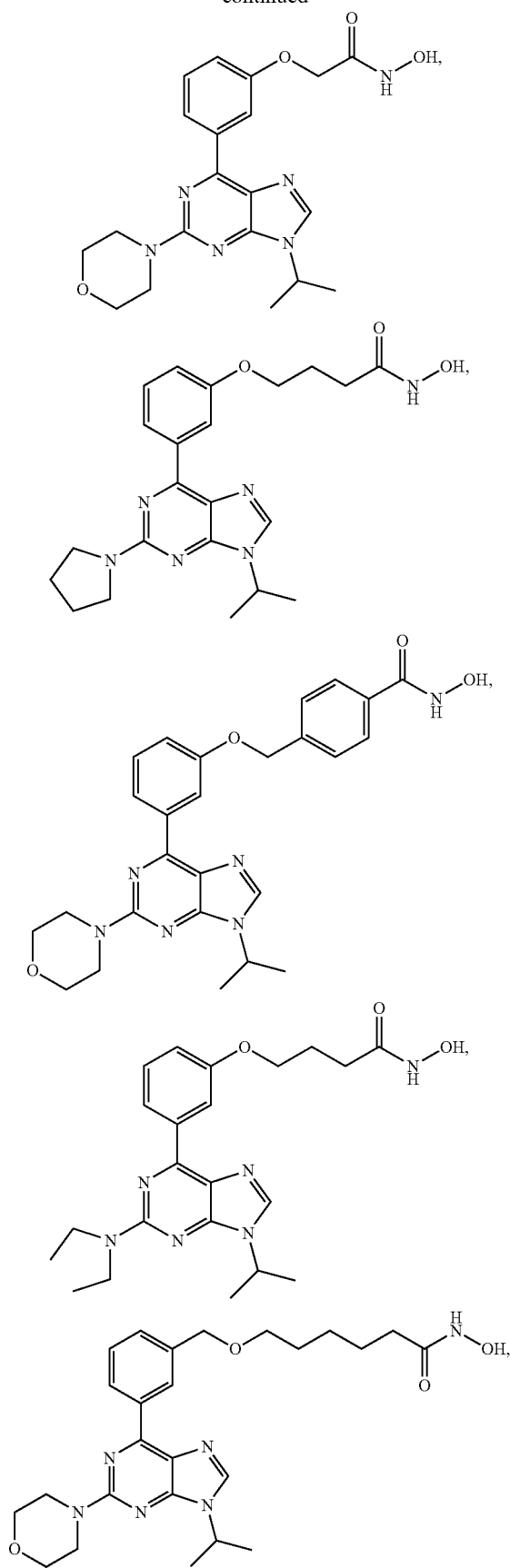
58
-continued
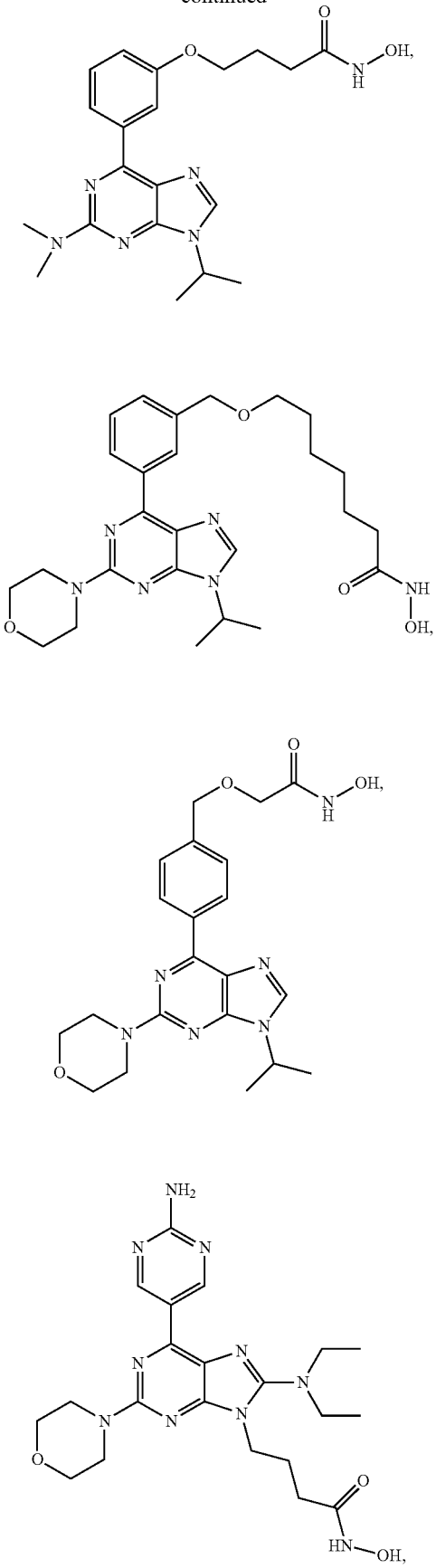

59
-continued
60
-continued
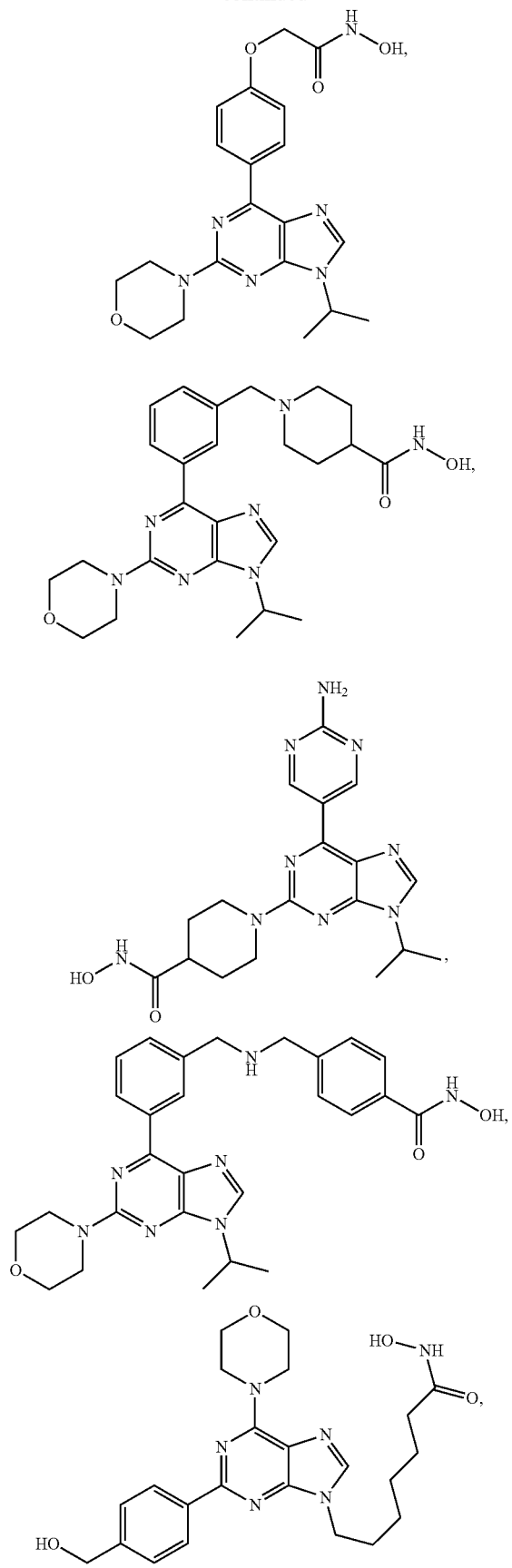
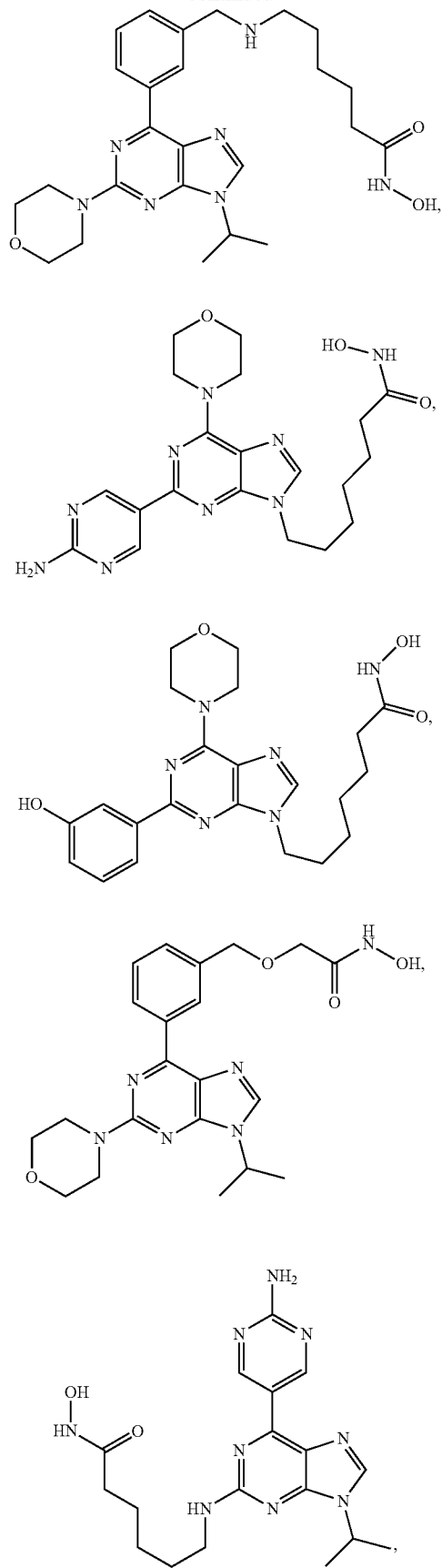

61
-continued
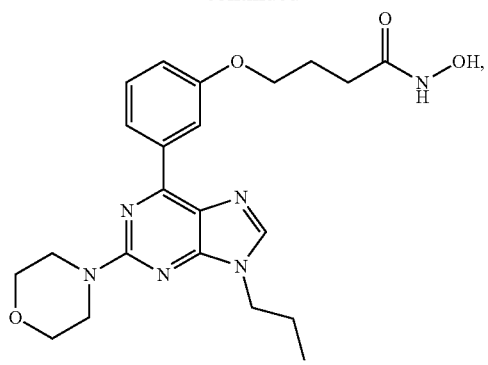
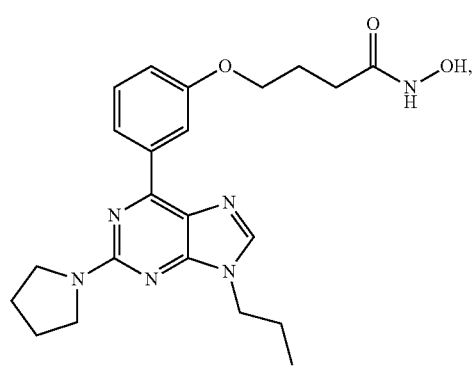
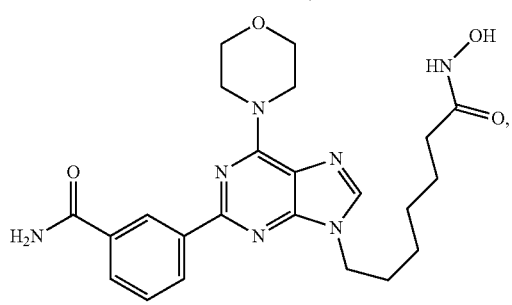
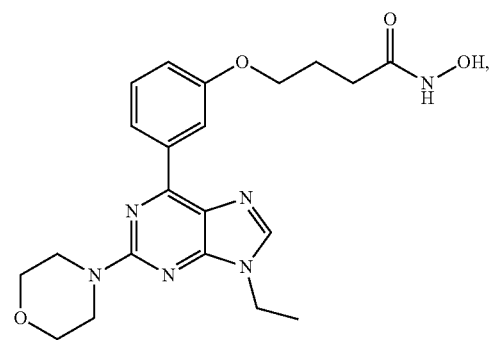
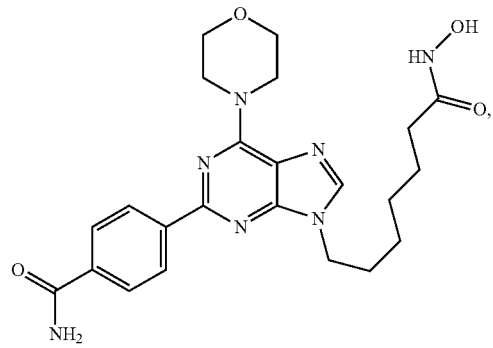
62
-continued
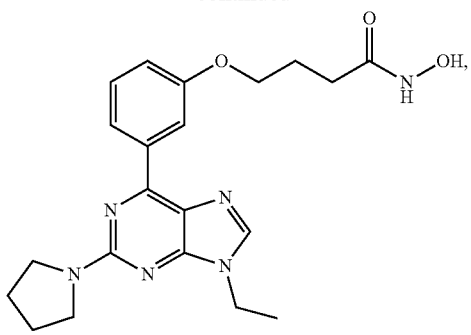
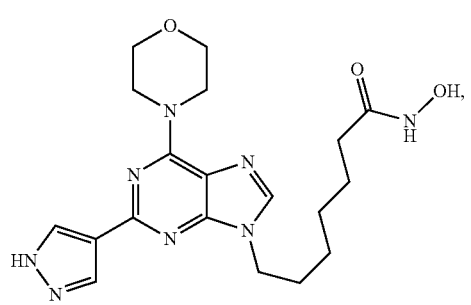
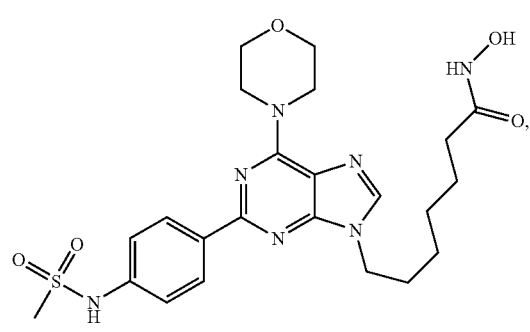
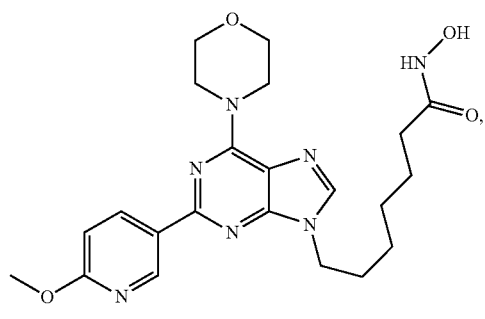
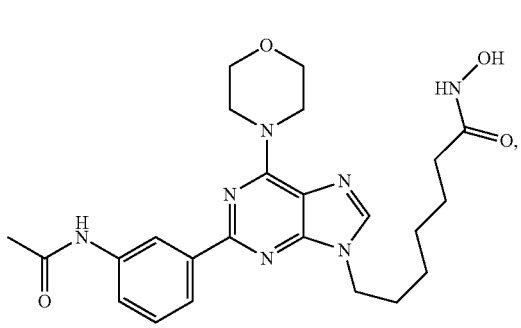

63
-continued
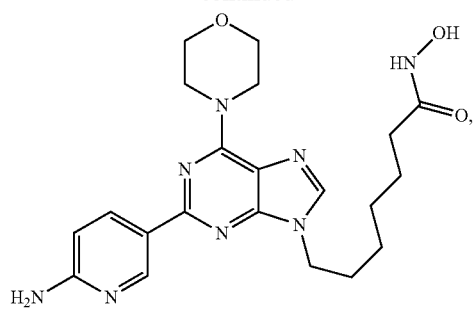
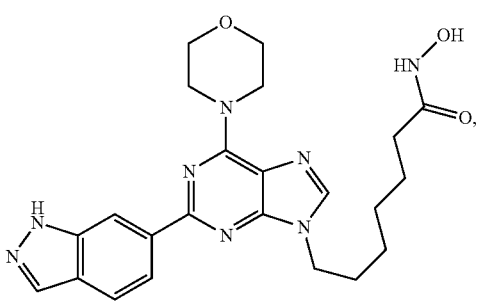
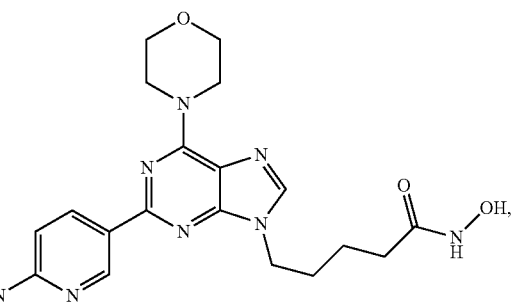
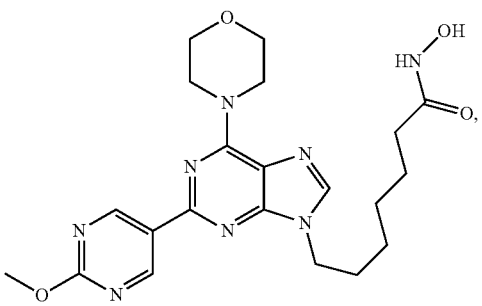
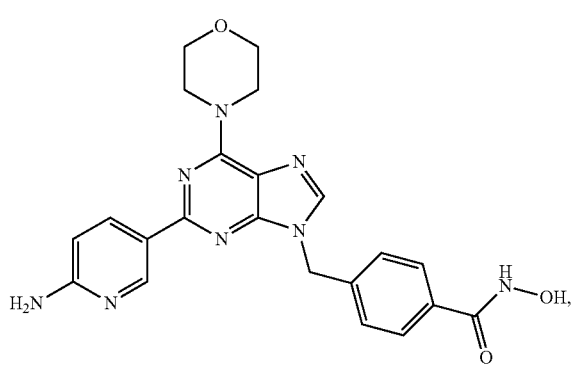
64
-continued
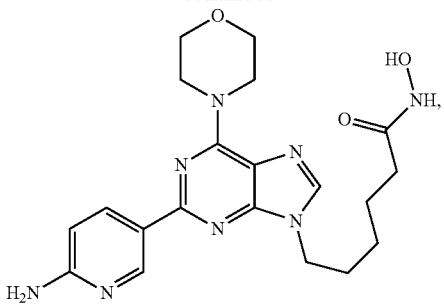
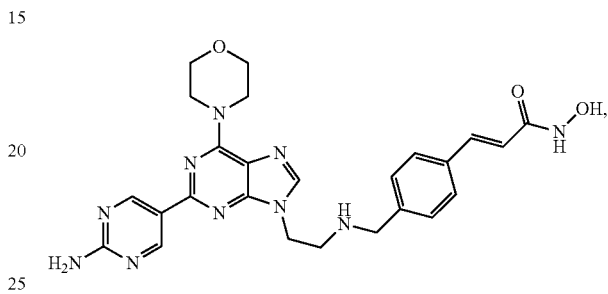
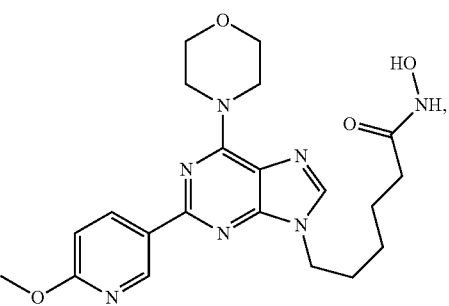
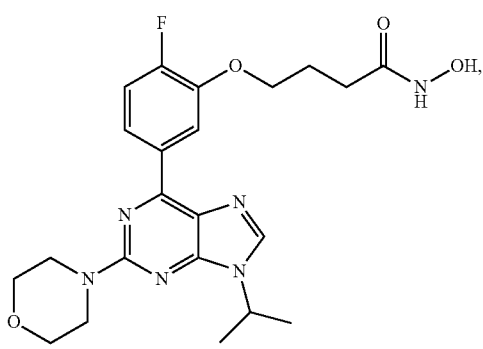
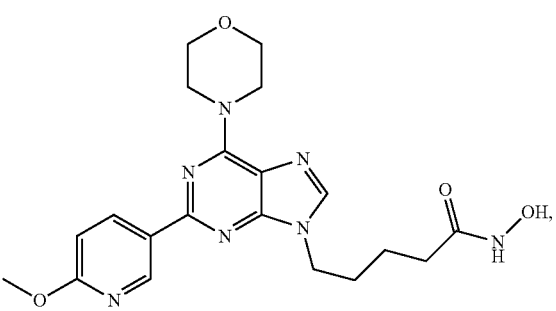

65
-continued
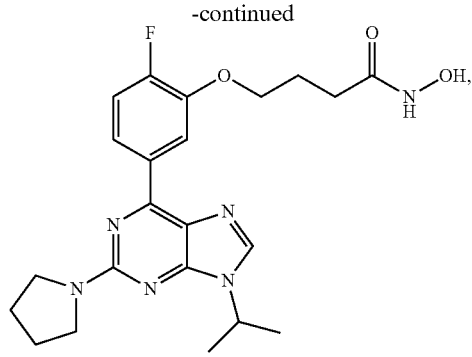
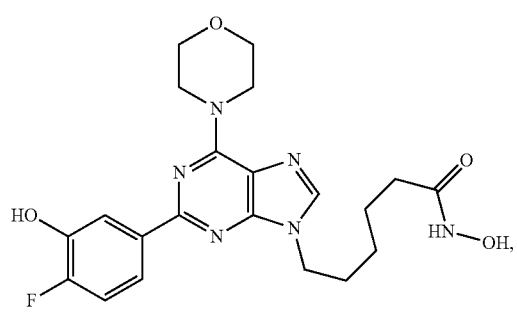
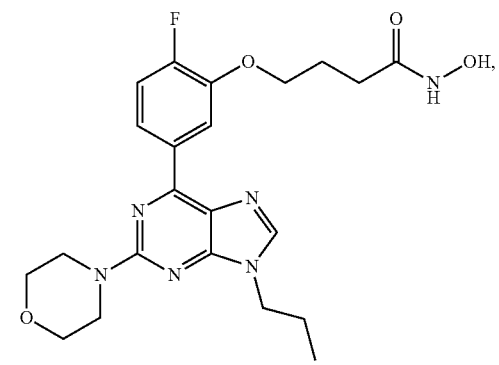
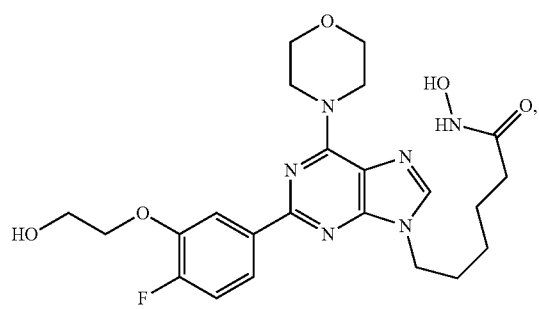
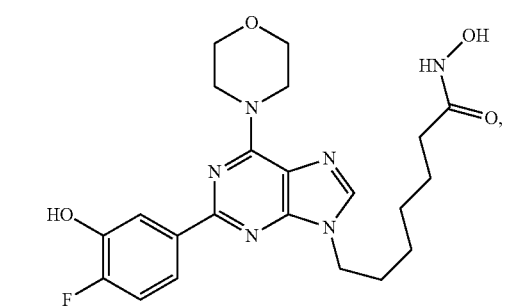
66
-continued
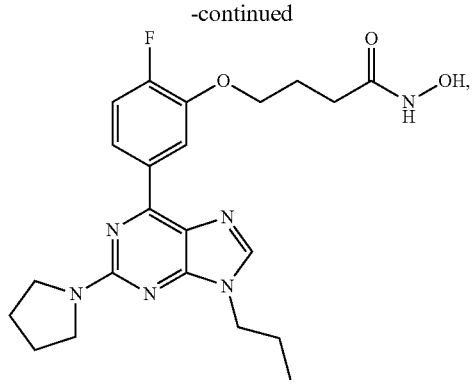
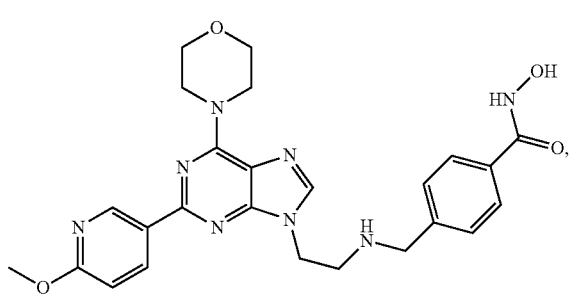
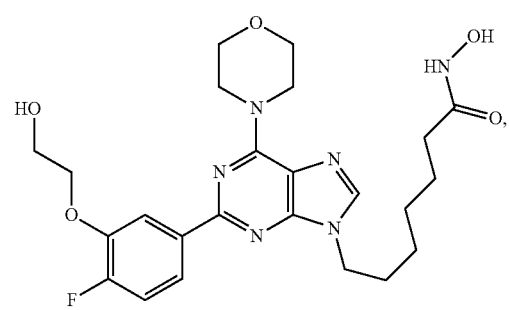
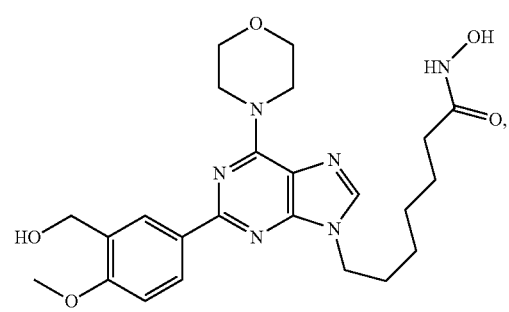
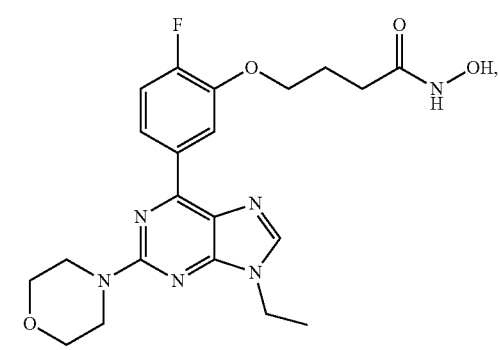

67
-continued
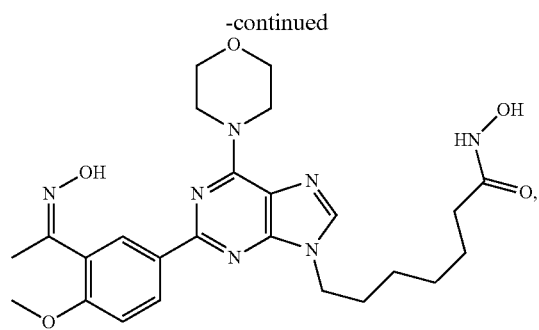
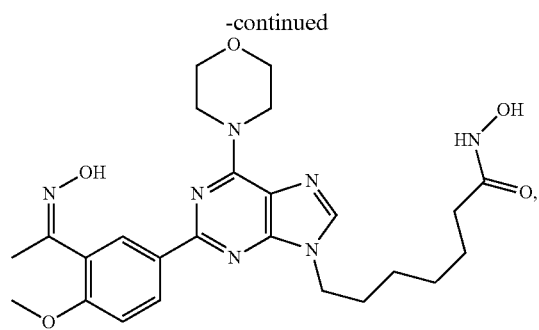
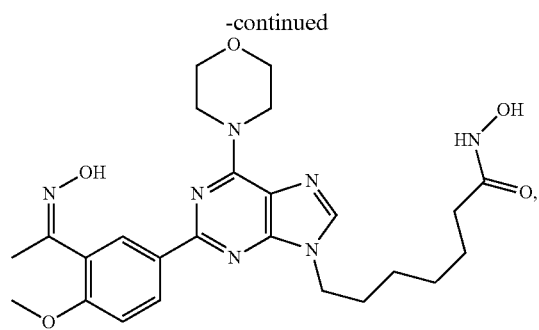
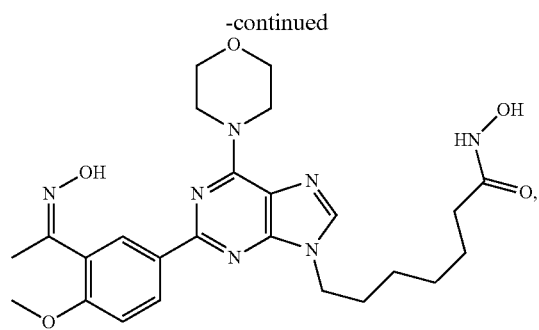
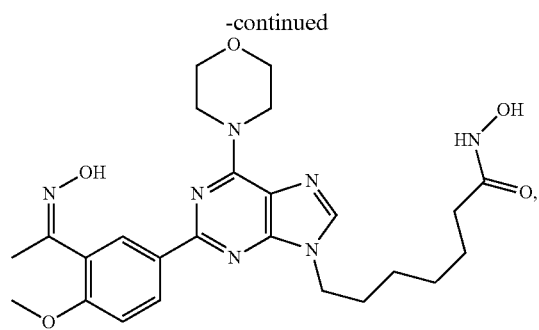
68
-continued
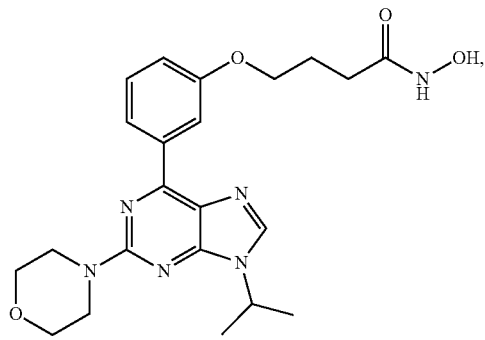
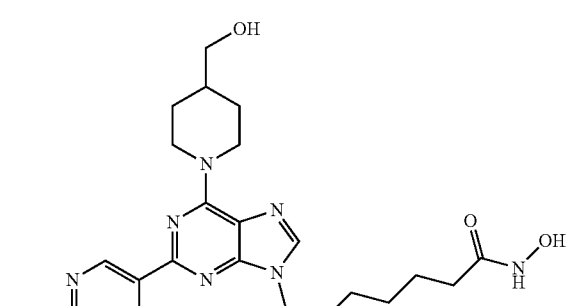
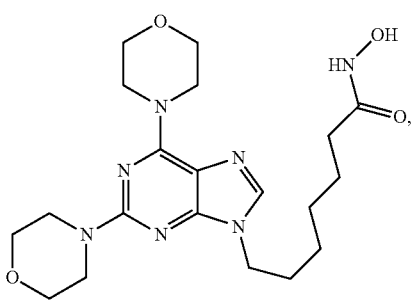
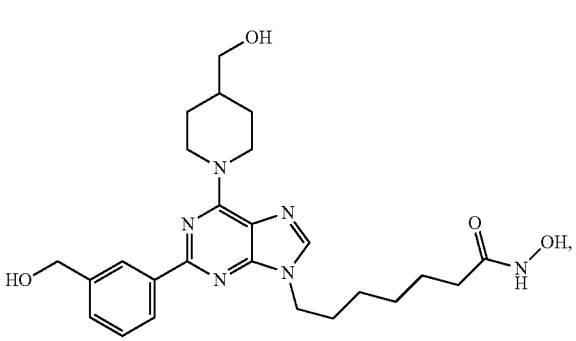
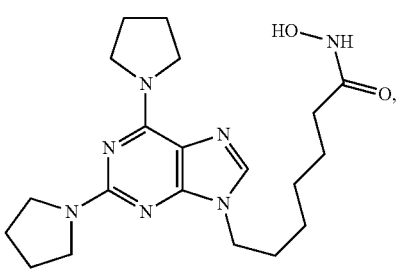

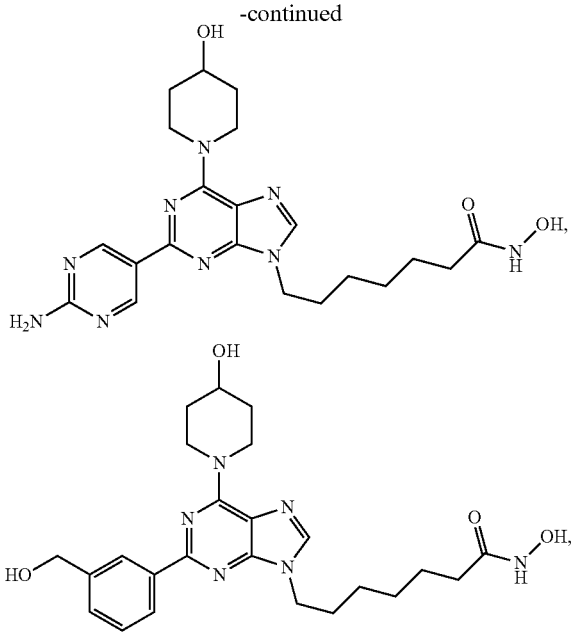
or a pharmaceutically acceptable salt or prodrug thereof.
Specific compounds wherein $R^1$ is a substituted amino when $R^2$ or $R^3$ contains the hydroxamate group and the substituted amino is morpholine may include the following:
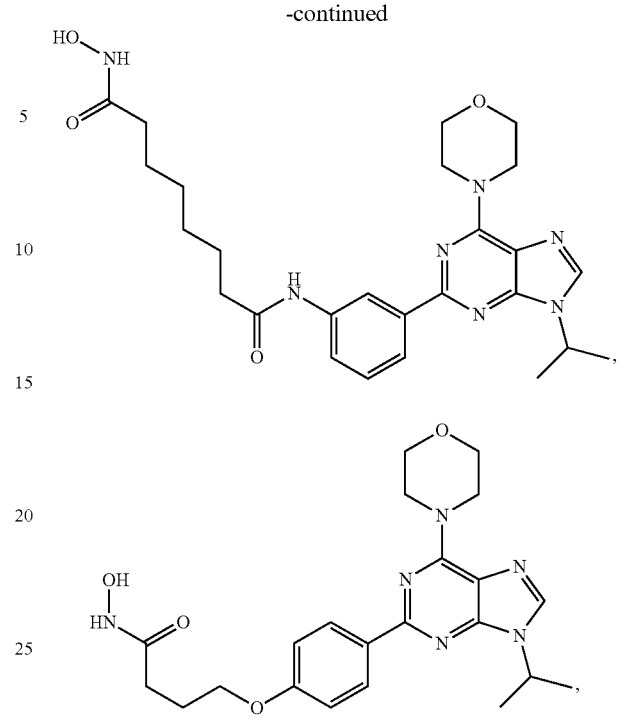
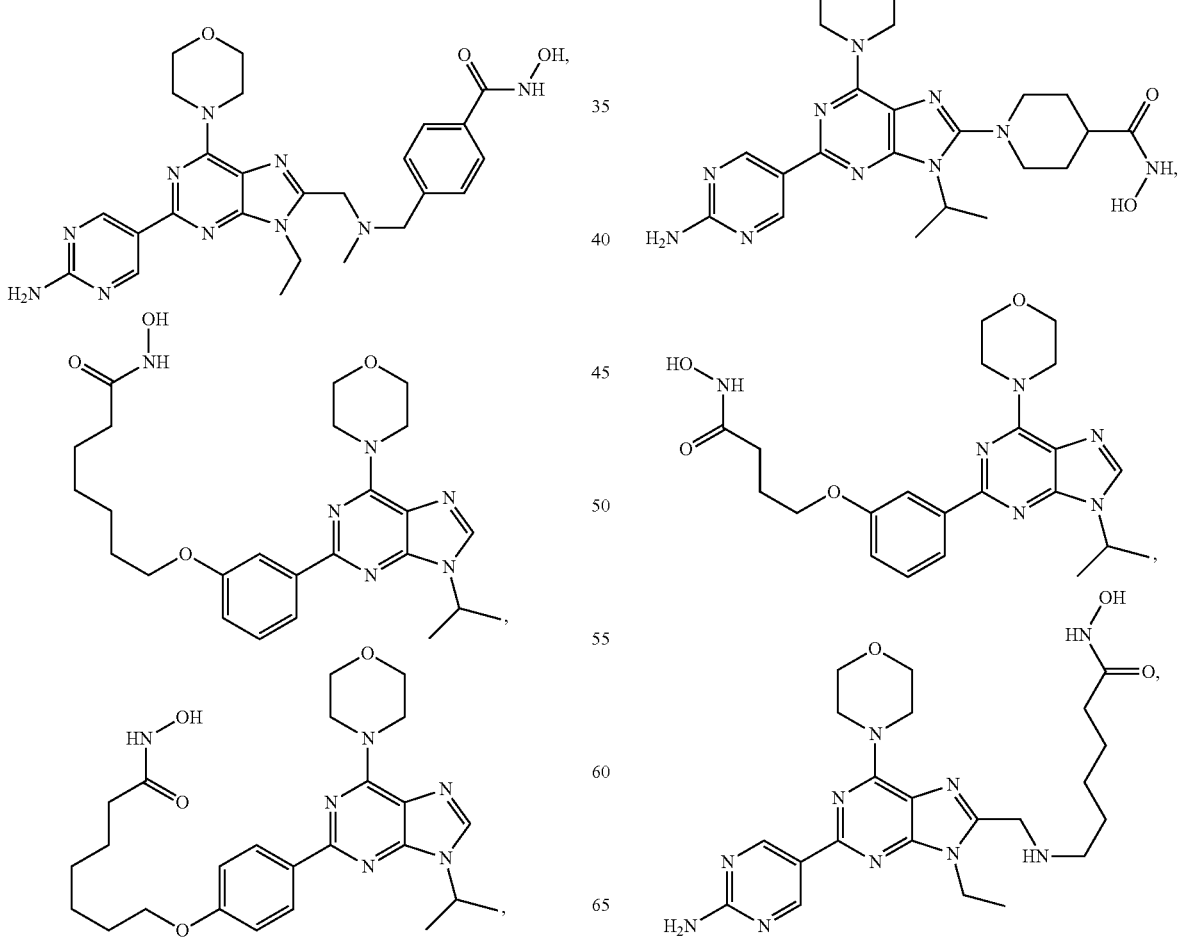

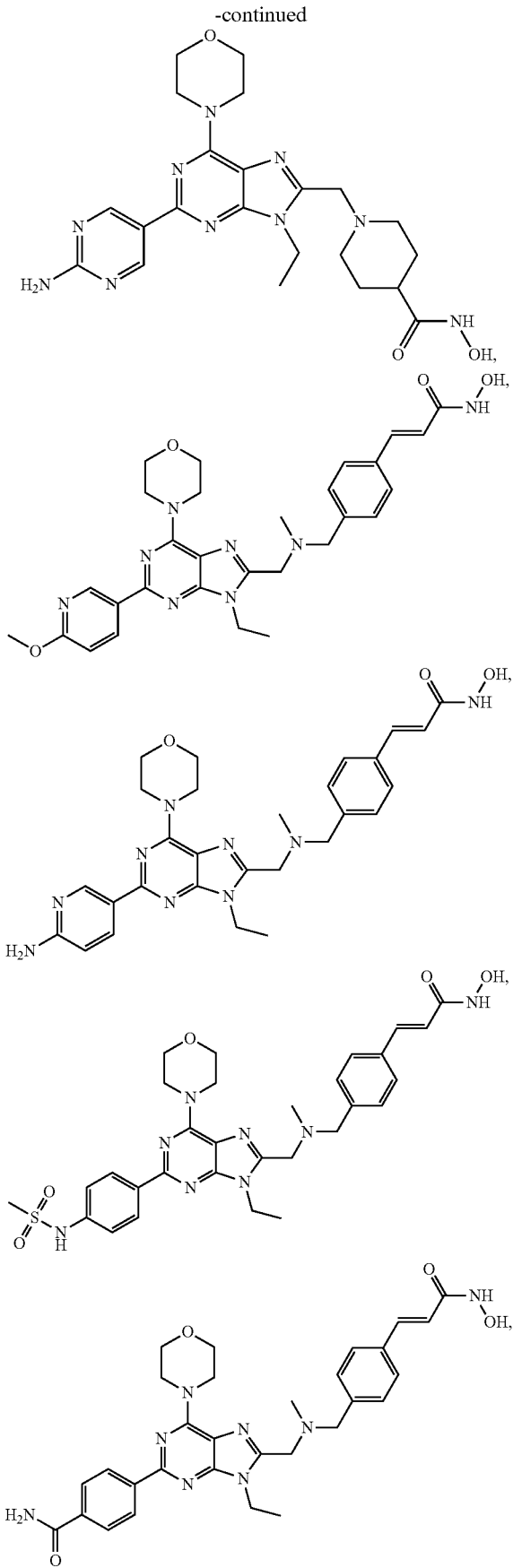
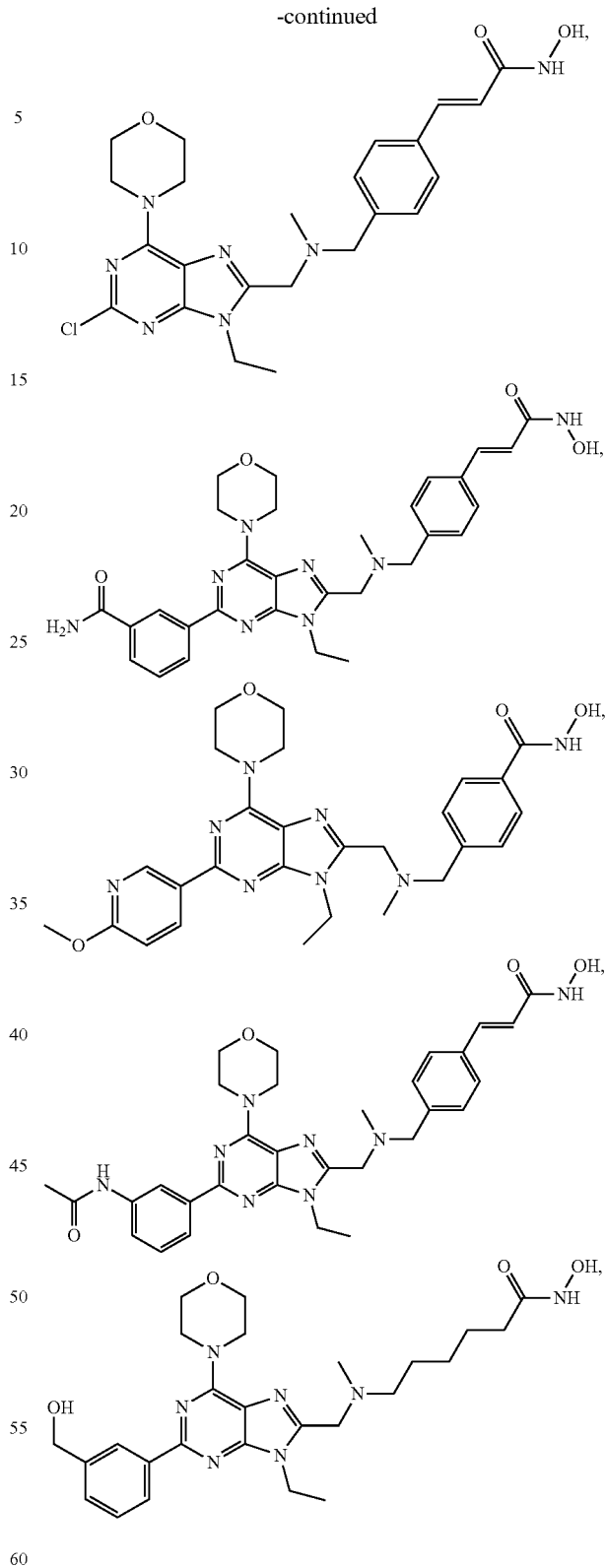

or a pharmaceutically acceptable salt or prodrug thereof.

The compounds as defined above may be an enzyme inhibitor. The compounds as defined above may have the ability to inhibit the activity of certain deacetylases and protein kinases. The deacetylase may be histone deacetylase. The ability to inhibit deacetylase activity may be a result of the compounds acting directly and solely on the histone deacetylase and/or non-histone deacetylase molecule to inhibit biological activity. The kinase may be a lipid kinase or a protein kinase. The kinase may be a lipid kinase and a protein kinase. The kinase may be phosphatidylinositate-3-kinase (PI3K). The ability to inhibit kinase activity may be a result of the compounds acting directly and solely on the kinase molecule to inhibit biological activity. However, it is understood that the compounds may also act at least partially on co-factors of the kinase in question that are involved in the phosphorylation process.

The compounds disclosed herein may act directly and solely on the deacetylase molecule or a complex or fragment thereof to inhibit biological activity. However, it is understood that the compounds may also act at least partially on co-factors that are involved in the deacetylation process. Known kinase co-factors include ionic species (such as zinc).

The compounds disclosed herein may act directly and solely on the kinase molecule or a complex or fragment thereof to inhibit biological activity. However, it is understood that the compounds may also act at least partially on co-factors that are involved in the phosphorylation process. Known kinase co-factors include ionic species (such as zinc and calcium), lipids (such as phosphatidylserine), and diacylglycerols.

The compounds as defined above may have activity against HDACs and/or PI3K kinases or a fragment or a complex or a functional equivalent thereof. The compounds as defined above may be a histone deacetylase inhibitor (HDAC) or a phosphatidylinositate-3-kinase (PI3K) inhibitor. The compounds as defined above may be a histone deacetylase (HDAC) inhibitor and a phosphatidylinositate-3-kinase (PI3K) inhibitor. The compounds as defined above may be an inhibitor of the PI3K-AKT-mTOR pathway. The compounds as defined above may be a multi-target inhibitor. The compounds as defined above may inhibit histone deacetylase (HDAC) and phosphatidylinositate-3-kinase (PI3K) simultaneously.

The compounds as defined above may have activity against certain serine/threonine kinases such as mTOR or Akt or a fragment or complex or functional equivalent thereof.

The inhibition of the lipid kinase and protein kinase may be carried out in any of a number of well-known ways in the art. For example if inhibition of the protein kinase in vitro is desired, an appropriate amount of the compound may be added to a solution containing the kinase. In circumstances where it is desired to inhibit the activity of the kinase in a mammal, the inhibition of the kinase may typically involve administering the compound to a mammal containing the kinase.

A method of inhibiting HDAC and/or PI3K in a cell may comprise administering to a cell a compound as defined above, or a pharmaceutically acceptable form or prodrug thereof. The inhibition of HDAC and/or PI3K may further comprise the inhibition of cell proliferation. The inhibition of HDAC and/or PI3K may further comprise reprogramming cells to induce pluripotent stem cells (iPS cells).

The cell may be in vitro. The cell may be from a cell line. The cell line may be an immortalized cell line, a genetically modified cell line or a primary cell line. The cell line may be selected from the group consisting of MV4-11, MOLT-4, PC-3, MCF7, SUP-B15, HL-60, K-562, RPMI-8226, Daudi, Raji, Ramos, Pfeiffer, A431, ACHN, A549, COLO 205, HCT116, HEL92.1.7, NCI-H522, A375, NCI-H460, BxPC-3, PANC-1, SK-OV-3, U87MG, U138MG, HpeG2, SK-HEP1, HuH-7, HCCLM3, PLC/PRF/5, HeLa, BT 474, MDA-MB-231, MDA-MB-436 and MDA-MB-468.

The cell may be from tissue of a subject. The cell may be in a subject.

These compounds as defined above may be used as modulators or inhibitors for oncology indications as well as non-oncology indications and applications such as autoimmune and inflammatory disorders, self-renewal and differentiation of stem cells.

Accordingly the compounds as defined above may find a multiple number of applications in which their ability to inhibit lipid and protein kinases of the type mentioned above can be utilised. For example the compounds as defined above may be used to inhibit serine/threonine protein kinases. The compounds may also be used in treating or preventing a condition in a mammal in which inhibition of a protein kinase and/or co-factor thereof prevents, inhibits or ameliorates a pathology or a symptomology of the condition.

The compound as defined above, or a pharmaceutically form or prodrug thereof, or a composition as defined above, may be for use in therapy.

A method of treating a HDAC- or PI3K-related disorder may comprise administering to a subject in need of treatment a compound as defined above, or a pharmaceutically acceptable form or prodrug thereof, or a composition as defined above. A method of treating a HDAC- and PI3K-related disorder may comprise administering to a subject in need of treatment a compound as defined above, or a pharmaceutically acceptable form or prodrug thereof, or a composition as defined above.

The method may further comprise the step of administering an additional therapeutic agent in the subject. A method of modulating the self-renewal or differentiation of stem-cells may comprise administering to a subject in need of treatment a compound as defined above, or a pharmaceutically acceptable form or prodrug thereof, or a composition as defined above.

The compounds as defined above may also be used in the preparation of a medicament for treating a condition in an animal in which inhibition of a protein kinase can prevent, inhibit or ameliorate the pathology or symptomology of the condition. The compounds as defined above may also be used in the preparation of a medicament for the treatment or prevention of a kinase-related disorder.

A use of a compound as defined above, or a pharmaceutically acceptable form or prodrug thereof, or a composition according as defined above, may be in the manufacture of a medicament for treatment of a HDAC- or PI3K-related disorder. A use of a compound as defined above, or a pharmaceutically acceptable form or prodrug thereof, or a composition as defined above, may be in the manufacture of a medicament for treatment of a HDAC- and PI3K-related disorder.

A use of the compound as defined above, or a pharmaceutically acceptable form or prodrug thereof, or a composition as defined above, may be in the manufacture of a medicament for modulating the self-renewal or differentiation of stem-cells.

The use may further comprise the medicament to be administered with an additional therapeutic agent, wherein said medicament may be administered in combination or alteration with the additional therapeutic agent.

The conditions or disorders may be selected from the group consisting of cancer, angiogenic disorder or pathological angiogenesis, fibrosis, inflammatory conditions, asthma, neurological disorders, neurodegenerative disorders, muscle degenerative disorders, autoimmune disorders, disorders of the blood or disorders of the bone marrow. The condition or disorder may be lymphoma, cutaneous T-cell lymphoma, follicular lymphoma, or Hodgkin lymphoma, cervical cancer, ovarian cancer, breast cancer, lung cancer, prostate cancer, colorectal cancer, sarcoma, hepatocellular carcinoma, leukemia or myeloma, retinal angiogenic disease, liver fibrosis, kidney fibrosis, Alzheimer's disease or Huntington's disease, spinal muscular atrophy, HIV/AIDS, polycythemia vera or essential thrombocythemia or myelofibrosis.

It is anticipated that the compounds as defined above will be useful in treating various cancers including but not limited to bone cancers, brain and CNS tumours, breast cancers, colorectal cancers, endocrine cancers including adrenocortical carcinoma, pancreatic cancer, pituitary cancer, thyroid cancer, parathyroid cancer, thymus cancer, gastrointestinal cancers, liver cancer, extra hepatic bile duct cancer, gastrointestinal carcinoid tumour, gall bladder cancer, genitourinary cancers, gynaecological cancers, head and neck cancers, leukemias, myelomas, hematological disorders, lung cancers, lymphomas, eye cancers, skin cancers, soft tissue sarcomas, adult soft tissue sarcoma, Kaposi's sarcoma, urinary system cancers.

Exemplary cancers that may be treated by the compounds as defined above include hematologic cancer and solid tumor such as myeloproliferative disorders (idiopathic myelofibrosis, polycythemia vera, essential thrombocythemia, chronic myeloid leukemia), myeloid metaplasia, chronic myelomonocytic leukemia, acute lymphocytic leukemia, acute erythroblastic leukemia, Hodgkin's and Non Hodgkin's disease, B-cell lymphoma, diffuse large B cell lymphoma, acute T-cell leukemia, myelodysplastic syndromes, plasma cell disorder, hairy cell leukemia, kaposi's sarcoma, lymphoma; gynaecologic cancer such as breast carcinoma, ovarian cancer, cervical cancer, vaginal and vulva cancer, endometrial hyperplasia; gastrointestinal tract cancer such as colorectal carcinoma, polyps, liver cancer, gastric cancer, pancreatic cancer, gall bladder cancer; urinary tract cancer such as prostate cancer, kidney and renal cancer; urinary bladder cancer, urethral cancer, penile cancer; skin cancer such as melanoma; brain tumour such as glioblastoma, neuroblastoma, astrocytoma, ependynoma, brain-stem gliomas, medulloblastoma, menigiomas, astrocytoma, oligodendroglioma; head and neck cancer such as nasopharyngeal carcinoma, laryngeal carcinoma; respiratory tract cancer such as lung carcinoma (NSCLC and SCLC), mesothelioma; eye disease such as retinoblastoma; musculoskeleton diseases such as osteosarcoma, musculoskeleletal neoplasm; Squamous cell carcinoma and fibroid tumour.

Administration of compounds as defined above to humans may be done by any of the accepted modes for enteral administration such as oral or rectal, or by parenteral administration such as subcutaneous, intramuscular, intravenous and intradermal routes. Injection may be bolus or via constant or intermittent infusion. The active compound as defined above may typically be included in a pharmaceutically acceptable carrier or diluent and in an amount sufficient to deliver to the patient at a therapeutically effective dose. In various embodiments, the inhibitor compound may be selectively toxic or more toxic to rapidly proliferating cells, e.g. cancerous tumours, than to normal cells.

In using the compounds as defined above, they may be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances.

The compounds as defined above may be administered alone or in the form of a pharmaceutical composition in combination with a pharmaceutically acceptable carrier, diluent or excipient. The compounds, while effective themselves, are typically formulated and administered in the form of their pharmaceutically acceptable salts as these forms are typically more stable, more easily crystallised and have increased solubility.

The compounds as defined above are, however, typically used in the form of pharmaceutical compositions which are formulated depending on the desired mode of administration. A pharmaceutical composition may comprise a compound as defined above, or a pharmaceutically acceptable form or prodrug thereof, and a pharmaceutically acceptable excipient. As such in some embodiments the present disclosure provides a pharmaceutical composition including a compound of Formula (I) and a pharmaceutically acceptable carrier, diluent or excipient. The compositions may be prepared in manners well known in the art.

In other embodiments there is provided a pharmaceutical pack or kit comprising one or more containers filled with one or more of the ingredients of the pharmaceutical compositions. In such a pack or kit, a container having a unit dosage of the agent (s) may be found. The kits may include a composition comprising an effective agent either as concentrates (including lyophilized compositions), which may be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) may be various written materials such as instructions for use, or a notice in the form prescribed by a governmental agency regulating the manufacture, use or sale of pharmaceuticals or biological products, which notice reflects approval by the agency of manufacture, use or sale for human administration.

The compounds may be used or administered in combination with one or more additional drug(s) for the treatment of the disorder/diseases mentioned. The components may be administered in the same formulation or in separate formulations. If administered in separate formulations the compounds may be administered sequentially or simultaneously with the other drug(s).

In addition to being able to be administered in combination with one or more additional drugs, the compounds may be used in a combination therapy. When this is done the compounds are typically administered in combination with each other. Thus one or more of the compounds may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions for parenteral injection may comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds may be incorporated into slow release or targeted delivery systems such as polymer matrices, liposomes, and microspheres.

The injectable formulations may be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration may include capsules, tablets, pills, powders, and granules. In such solid dosage forms, the active compound may be mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules may be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions which may be used include polymeric substances and waxes.

The active compounds may also be in microencapsulated form, if appropriate, with one or more of the above-mentioned excipients.

Liquid dosage forms for oral administration may include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide, oils (in particular, cottonseed, groundnut, corn, germ, olive, castor, and sesame oils), glycerol, tetrahydrofurfuryl alcohol, Solutol® HS 15, Cremophor EL, polyethylene glycols and fatty acid esters of sorbitan, and mixtures thereof.

Besides inert diluents, the oral compositions may also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which may be prepared by mixing the compounds with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound include powders, patches, sprays, ointments and inhalants. The active compound may be mixed under sterile conditions with a pharmaceutically acceptable carrier and any needed preservatives, buffers, or propellants which may be required.

The amount of compound administered will preferably treat and reduce or alleviate the condition. A therapeutically effective amount may be readily determined by an attending diagnostician by the use of conventional techniques and by observing results obtained under analogous circumstances. In determining the therapeutically effective amount, a number of factors are to be considered including but not limited to, the species of animal, its size, age and general health, the specific condition involved, the severity of the condition, the response of the patient to treatment, the particular compound administered, the mode of administration, the bioavailability of the preparation administered, the dose regime selected, the use of other medications and other relevant circumstances.

A preferred dosage may be a range from about 0.01 to 400 mg per kilogram of body weight per day. A more preferred dosage may be in the range from 0.1 to 200 mg per kilogram of body weight per day, more preferably from 0.2 to 100 mg per kilogram of body weight per day, even more preferably 0.2 to 50 mg per kilogram of body weight per day. A suitable dose may be administered in multiple sub-doses per day.

The process for synthesizing the compound of formula (I) may comprise the steps of; (a) providing a halogen-disubstituted purine-based or halogen di-substituted fused pyrimidine-based compound; (b) alkylating the amine (—NH— group) in the compound of step (a); (c) selectively or sequentially displacing the halide atoms of the intermediary compound of step (b) with an optionally substituted boronic ester or an optionally substituted amine to form a substituted aromatic or a substituted amine, respectively; (d) selectively coupling the intermediary compound of step (c) with a protected hydroxamic acid group having the structure -$L^1$-$R^5$-$L^2$-$R^6$-$L^3$-CON($R^a$)O$R^b$ or an ester (hydroxamic acid precursor); and (e) converting the protected hydroxamate or the ester of the intermediary compound of step (d) to a hydroxamic acid under reaction conditions to form the compound of formula (I).

A process for synthesizing the compound of formula (I) may comprise the steps of; (a) providing a halogen-disubstituted purine-based or halogen di-substituted fused pyrimidine-based compound; (b) selectively displacing one of the halide atoms of said compound with an optionally substituted boronic ester or an optionally substituted amine to form a substituted aromatic or a substituted amine, respectively; (c) alkylating the amine (—NH— group) in the intermediary compound of step (b); (d) selectively displacing the remaining halide atom of the intermediary compound of step (c) with an optionally substituted boronic ester or an optionally substituted amine to form a substituted aromatic or a substituted amine, respectively; (e) selectively coupling the intermediary compound of step (d) with a protected hydroxamic acid group having the structure -$L^1$-$R^5$-$L^2$-$R^6$-$L^3$-CON($R^a$)O$R^b$ or an ester (hydroxamic acid precursor); and (f) converting the protected hydroxamate or the ester of the intermediary compound of step (e) to a hydroxamic acid under reaction conditions to form the compound of formula (I).

A process for synthesizing the compound of formula (I);

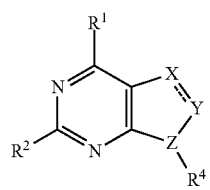

(I)

may comprise the steps of; (a) providing a halogen-disubstituted purine-based or halogen di-substituted fused pyrimidine-based compound; (b) alkylating the amine in the compound of step (a); (c) selectively or sequentially displacing the halide atoms of the intermediary compound of step (b) with an optionally substituted boronic ester or an optionally substituted amine to form a substituted aromatic or a substituted amine, respectively; (d) alkylating, in the intermediary compound of step (c), the carbon atom that corresponds to the Y-position of formula (I); (e) selectively coupling the intermediary compound of step (d) with a protected hydroxamic acid group having the structure -$L^1$-$R^5$-$L^2$-$R^6$-$L^3$-CON($R^a$)O$R^b$ or an ester (hydroxamic ester precursor); and (f) converting the protected hydroxamate or the ester of the intermediary compound of step (e) to a hydroxamic acid under reaction conditions to form the compound of formula (I).

A process for synthesizing the compound of formula (I) may comprise the steps of; (a) providing a halogen-disubstituted purine-based or halogen di-substituted fused pyrimidine-based compound; (b) selectively displacing one of the halide atoms of said compound with an optionally substituted boronic ester or an optionally substituted amine to form a substituted aromatic or a substituted amine, respectively; (c) alkylating the amine (—NH— group) in the intermediary compound of step (b); (d) alkylating, in the intermediary compound of step (c), the carbon atom that corresponds to the Y-position of formula (I); (e) selectively displacing the remaining halide atom of the intermediary compound of step (d) with an optionally substituted boronic ester or an optionally substituted amine to form a substituted aromatic or a substituted amine, respectively; (f) selectively coupling the compound of step (e) with a protected hydroxamic acid group having the structure -$L^1$-$R^5$-$L^2$-$R^6$-$L^3$-CON($R^a$)O$R^b$ or an ester (hydroxamic acid precursor); and (g) converting the protected hydroxamate or the ester of the intermediary compound of step (f) to a hydroxamic acid under reaction conditions to form the compound of formula (I).

EXAMPLES

Non-limiting examples of the disclosure and a comparative example will be further described in greater detail by reference to specific Examples, which should not be construed as in any way limiting the scope of the invention.

List of Abbreviations Used

| Names/terms | Abbreviations |
|---|---|
| Dichloroethane (1,2-) | DCE |
| Dichloromethane | DCM |
| Dimethylformamide (N,N-) | DMF |
| Dimethyl sulfoxide | DMSO |
| equivalent | equiv |
| High-performance liquid chromatography or high-pressure liquid chromatography | HPLC |
| high-resolution mass spectrometry | HRMS |
| N-Bromosuccinimide | NBS |
| N-Methyl-2-pyrrolidone | NMP |
| Nuclear Magnetic Resonance | NMR |
| Trifluoroacetic acid | TFA |
| Tetrahydrofuran | THF |

Example 1: Materials and Methods

In the examples described below, unless otherwise indicated, all temperatures in the following description are in degrees Celsius and all parts and percentages are by weight, unless indicated otherwise. Reagents useful for synthesizing compounds may be purchased from commercial suppliers, such as Sigma-Aldrich Pte Ltd (Singapore 117528, Singapore), Boron Molecular Inc. (Raleigh, N.C. 27616, USA), or Combi-Blocks, Inc. (San Diego, Ca. 92126, USA), and used without further purification, unless otherwise indicated, or obtained or prepared according to techniques known in the art.

The reactions set forth below were performed under a positive pressure of nitrogen, argon or with a drying tube, at ambient temperature (unless otherwise stated), in anhydrous solvents, and the reaction flasks are fitted with rubber septa for the introduction of substrates and reagents via syringe. Glassware was oven-dried and/or heat-dried. Analytical thin-layer chromatography (TLC) was performed on glass-backed silica gel 60 F 254 plates (E Merck (0.25 mm)) and eluted with the appropriate solvent ratios (v/v) and visualized by UV absorption. The reactions were assayed by TLC and/or LC-MS and terminated as judged by the consumption of starting material or the formation of desire product.

Work-ups were typically done by doubling the reaction volume with the reaction solvent or extraction solvent and then washing with the indicated aqueous solutions using 25% by volume of the extraction volume (unless otherwise indicated). Product solutions were dried over anhydrous sodium sulphate ($Na_2SO_4$) or magnesium sulphate ($MgSO_4$) prior to filtration, and evaporation of the solvents was under reduced pressure on a rotary evaporator and noted as solvents removed in vacuo. Flash column chromatography was conducted using silica gel 60 (Merck KGaA, 0.040-0.063 mm, 230-400 mesh ASTM).

Reverse-phase preparative high performance liquid chromatography (RPHPLC) was conducted on a Gilson HPLC system (331/332 pumps, GX-271 liquid handler, 172 diode array doctor (DAD), Trilution LC software) using a Phenomenex column (Luna, 5 µm, C18 100A, 150 mm×21.2 mm) with adjustable solvent gradients, usually 5-95% of acetonitrile in water+0.05% TFA in 15 or 20 min of gradient at flow rate of 20 mL/min, and was used for routine purification. The preliminary purity and identity of all compounds were assessed after purification by LCMS analyses on a Waters Micromass ZQ mass spectrometer in electrospray ionization (ESI) positive mode after separation on a Waters 2795 separations module. The HPLC separations were performed on a Phenomenex column (Luna, 5 µm, C18 100A, 50 mm×2.00 mm) with a flow rate of 0.8 mL/min and a 4 min gradient of X-95% (X=5, 30 or 50) of acetonitrile in water+0.05% TFA, using a Waters 2996 photodiode array detector. Purity and identity were assessed on the integrated UV chromatograms (220-400 nm) and the mass spectra. The final purity was determined using a Shimadzu LC-20AD UFLC system on a Phenomenex column (Luna, 5 µm, C18 100A, 50 mm×2.00 mm) with a flow rate of 0.8 mL/min and a gradient of 5-95% of acetonitrile in water+0.05% TFA over 6 min. All final products had greater than 90% purity (by HPLC at wavelengths of 220 nm and 254 nm).

All the 1D and 2D NMR experiments for $^1$H (400.13 MHz), $^{13}$C (100.61 MHz), $^{15}$N (40.55 MHz), and $^{19}$F (376.47 MHz) nuclei were performed on a Bruker AVANCE-400 digital NMR spectrometer. NMR spectra are reported in ppm with reference to an internal tetramethylsilane standard (0.00 ppm for $^1$H and $^{13}$C) or solvent peak(s) of CDCl$_3$ (7.26 and 77.1 ppm) or CD$_3$OD (3.31 and 49.0 ppm), or DMSO-d$_6$ (2.50 and 39.5 ppm). Other NMR solvents were used as needed. When peak multiplicities are reported, the following abbreviations are used: s=singlet, d=doublet, t=triplet, q=quartet, m=multiplet, br=broadened, dd=doublet of doublets, dt=doublet of triplets, bs=broadened singlet. Coupling constants, when given, are reported in hertz.

Elemental analyses of CHN were performed on a Perkin-Elmer 2400 CHN/CHNS Elemental Analyzers. HRMS results were obtained from a Bruker micrOTOF-Q II (ESI, positive mode) with direct injection of purified compounds.

The agents of the various embodiments may be prepared using the reaction routes and synthesis schemes as described below, employing the techniques available in the art using starting materials that are readily available. The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in both T. W. Greene and P. G. Wuts' Protective Groups in Organic Synthesis, 3$^{rd}$ Edition, John Wiley & Sons, New York, 1991 and P. J. Kocienski's Protecting Groups, 3rd ed., Georg Thieme Verlag, New York, 2005. Alternatively, other reactions disclosed herein or known in the art will be recognized as having applicability for preparing other compounds of the various embodiments.

Example 2: General Reaction Schemes

In practice, design and synthesis of a working multi-target molecule by hybridising, merging or by de novo design is not a simple task to achieve. The first step was to achieve dual inhibition of both HDAC and kinases. HDAC inhibitor moieties were introduced to a variety of positions to explore Structure Activity Relationship (SAR) and the same was done for PI3K inhibition by exploring a variety combination of groups for potency and isoform selectivity. Substituent groups with a variety of properties, including aromatic and non-aromatic, cyclic and acyclic, polar and lipophilic, acidic, basic and neutral groups were used to cover the SAR. As there is no known best HDAC/PI3K combination profile available, the molecules were designed to have a broad range of potency to achieve the best outcomes in the in vitro and in vivo evaluations.

Scheme 1

Figure 3:
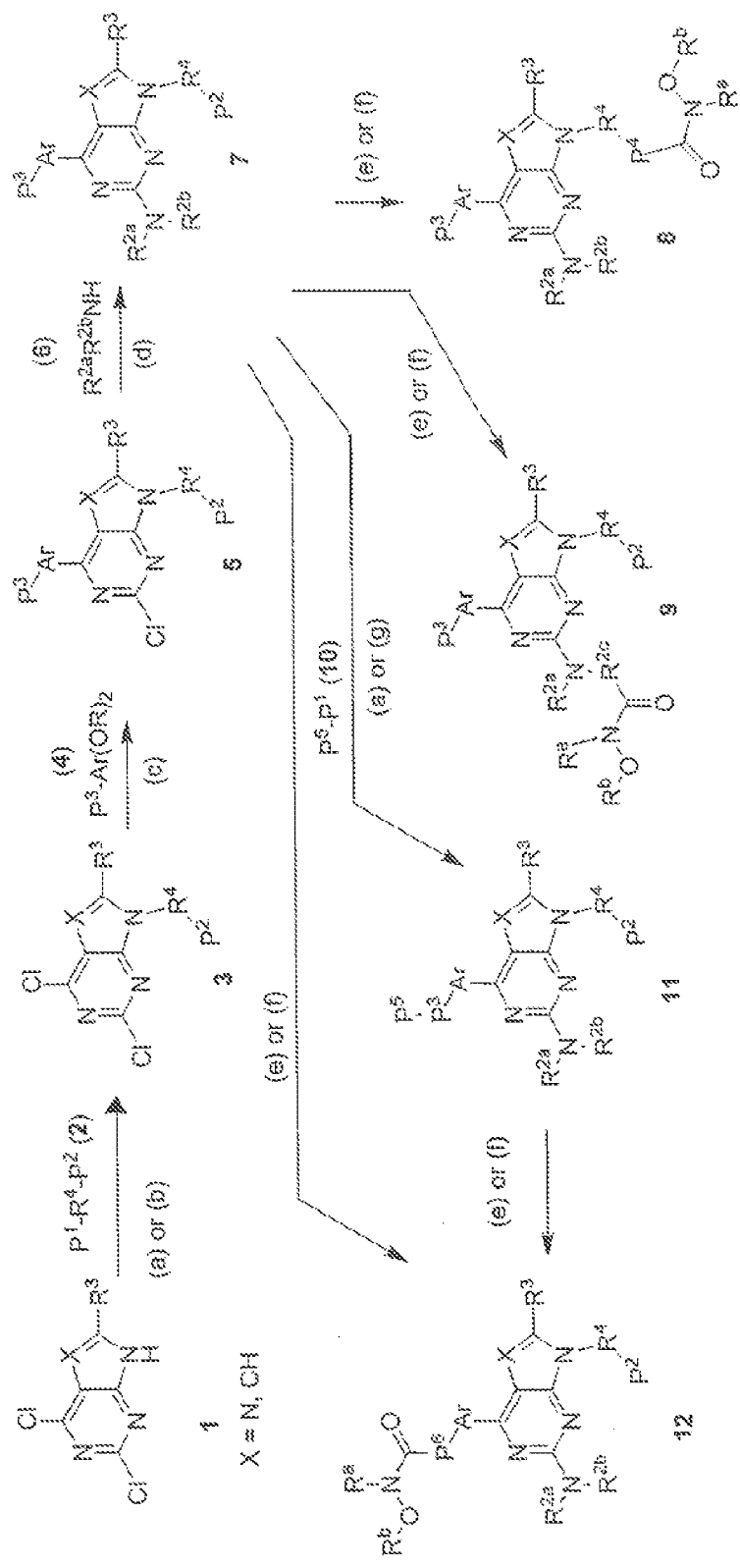
FIG. 3 shows a scheme for a typical procedure to prepare key intermediate 7 which can be further derivatized to compounds 8, 9, 11 and 12.

A wide range of substituted purines and pyrrolo[2,3-d] pyrimidines can be prepared in a straightforward four- or five-step procedure starting from 2,6-dichloropurine or 2,4-dichloro-7H-pyrrolo[2,3-d]pyrimidine which are commercially available from a number of sources. As depicted in FIG. 3, a typical procedure uses an alkyl halide in the presence of a suitable base such as potassium carbonate to alkylate the NH group of compound 1. Alternatively, under Mitsunobu reaction conditions, an alcohol may be reacted with 1 in the presence of a phosphine and an activating agent, such as diethylazodicarboxylate, to afford a similar alkylation product 2. The two chlorine atoms can be displaced selectively or sequentially under optimal reaction conditions. Under Suzuki reaction conditions, a boronic ester (4) is used to replace the more active chlorine atom and form mono-chloro compound 5. The 2$^{nd}$ chlorine atom can be displaced by an amine (6), e.g., morpholine, at elevated temperature, in a suitable solvent such as 1,4-dioxane, DMF, NMP, or THF, to give the desired compound 7. Functional group P$^2$ or R$^{2b}$ or P$^3$ of 7 may contain an ester, a precursor of hydroxamic acid, or protected hydroxamate, which can be easily converted to a hydroxamic acid 8 or 9 or 12. If P$^3$ group of 7 contains a hydroxyl group (phenol or alcohol) or aldehyde, compound 7 can be further varied by either alkylation of the hydroxyl group by a halide (e.g., P$^5$-P$^1$, P$^1$=Br) or reductive amination of the aldehyde with an amine (e.g., P$^5$-P$^1$, P$^1$=—NH$_2$ or NH—) to afford 11 which is then converted to hydroxamic acid 12 subsequently.

In FIG. 3 the reagents and conditions used are as follows: (a) NaI/K$_2$CO$_3$ for P$^1$=Br; (b) Mitsunobu reaction for P$^1$=OH, Ph$_3$P/DEAD; (c) Suzuki coupling, Pd(dppf) Cl$_2$·CH$_2$Cl$_2$, K$_2$CO$_3$/dioxane, microwave irradiation or heat; (d) displacement; (e) NH$_2$OH.HCl (10 equiv)/NaOMe (20 equiv)/MeOH, 0° C. to room temp; (f) 5-50% TFA/dichloromethane; (g) reductive amination, P$^5$-P$^1$(10), P$^1$=—NH— or —NH$_2$ and P$^3$ containing —CHO, NaBH(OAc)$_3$, DCE, room temp.

Scheme 2

Figure 4:
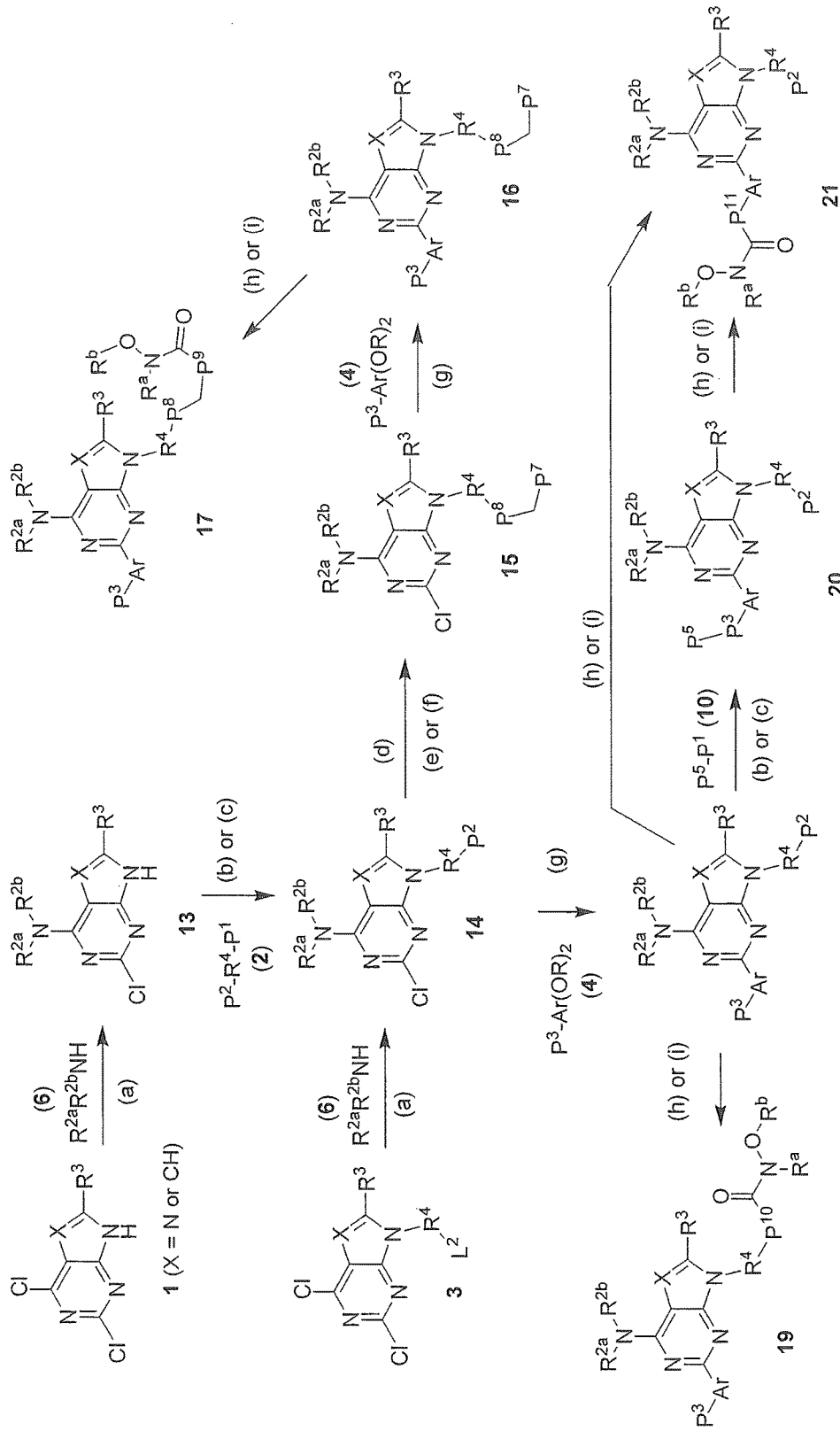
FIG. 4 shows a scheme depicting an alternative displacement sequence of the two chlorine atoms in compound 1 or 3 and preparation of compounds 17, 19 and 21.

FIG. 4 depicts an alternative displacement sequence of the two chlorine atoms in compound 1 or 3. The more active chlorine atom is displaced first by an amine 6 to give 13 via 1 or 14 via 3. The NH group of 13 is alkylated later to form 14. In case of P$^2$ group of 14 is a nitrile, the nitrile group is reduced to an amine, the latter then converted to a further substituted amine 15 either by alkylation with a halide or reductive amination with an aldehyde. Amine 15 is further varied by Suzuki coupling reaction to afford 16 which is subsequently converted to hydroxamic acid 17. There are two options for compound 18 which is also derived from mono-chloro compound 14: if the P$^2$ or P$^3$ group contains an ester or protected hydroxamate, then it will be converted to hydroxamic acid 19 or 21; if the P$^3$ group contains either a hydroxyl group (phenol or alcohol) or aldehyde, it will be processed similar to compound 7 in Scheme 1, i.e., either alkylation of the hydroxyl or reductive amination of the aldehyde to form 20 which is subsequently converted to hydroxamic acid 21.

The reagents and conditions used in FIG. 4 are as follows: (a) displacement, amine (6) neat or in dioxane, heat; (b) $K_2CO_3$/DMF for $P^1$=halide; c) Mitsunobu reaction for $P^1$=OH, $Ph_3P$/DEAD; (d) $P^2$ contains a terminal nitrile group: reduction, $NaBH_4$/$NiCl_2$, THF-MeOH (1:2), room temp.; (e) alkylation with $P^2CH_2P^1$, $P^1$ is halide or leaving group; (f) reductive amination with $P^7CHO$, $NaBH(OAc)_3$, DCE, room temp.; (g) Suzuki coupling, Pd(dppf)$Cl_2 \cdot CH_2Cl_2$, $K_2CO_3$/dioxane, microwave or heat; (h) $NH_2OH \cdot HCl$ (10 equiv)/NaOMe (20 equiv)/MeOH, —20° C. to room temp; (i) 5-50% TFA/dichloromethane Scheme 3

Figure 5:
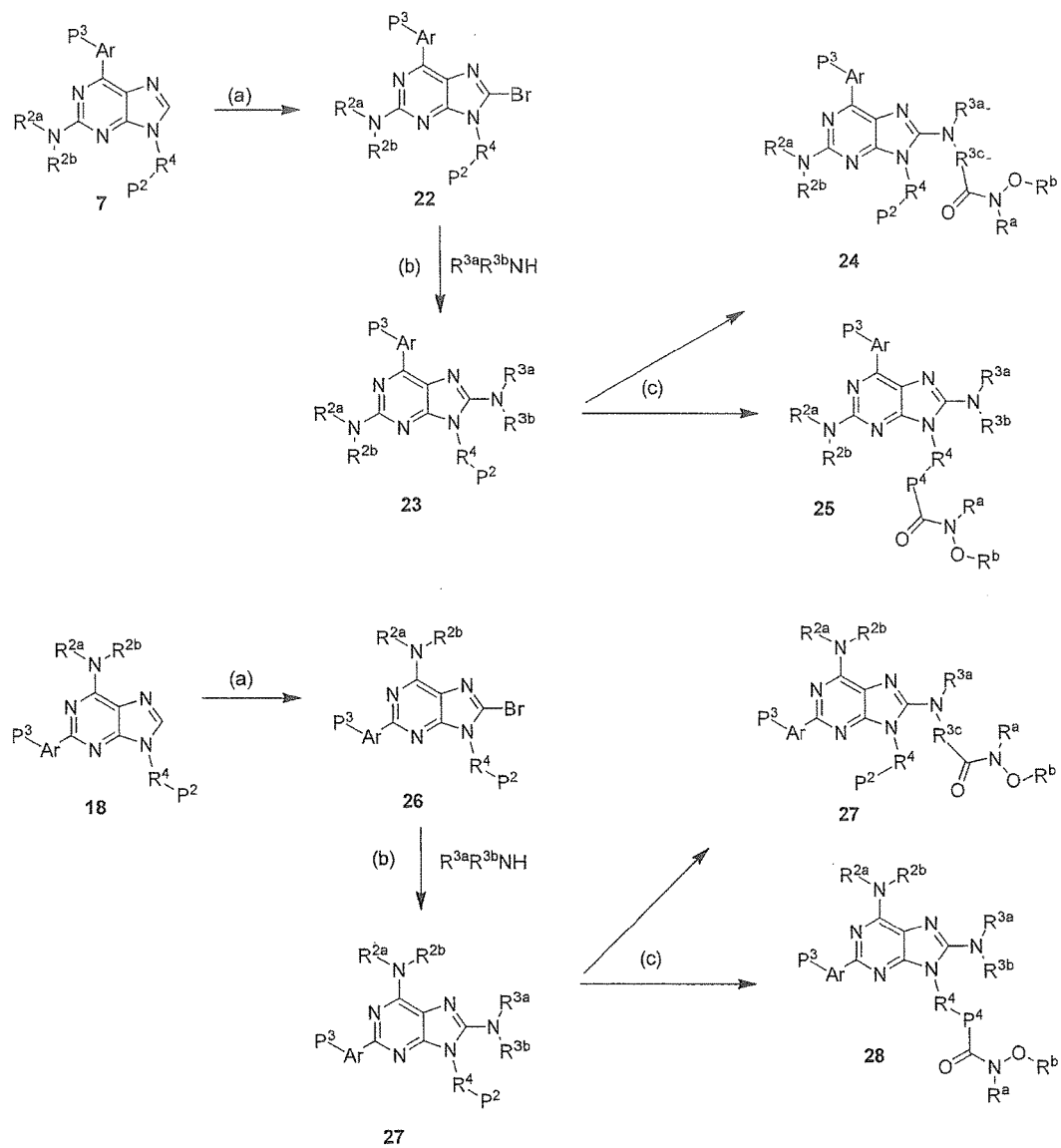
FIG. 5 shows a scheme depicting how to further vary $R^1$ group of compound 7 (scheme 1, FIG. 3) and 18 (scheme 2, FIG. 4) when $R^3$ is a hydrogen and X is a nitrogen.

FIG. 5 depicts how to further vary $R^3$ group of compound 7 (scheme 1) and 18 (scheme 2) when $R^3$ is a hydrogen and X is a nitrogen. Both purines 7 and 18 are brominated with NBS to afford bromides 22 and 26 respectively. The bromine atom at position 8 is then displaced by an amine. An ester or protected hydroxamic acid may exist either in $P^2$ or $R^{3b}$ group of 23 and 27, thus four types of hydroxamic acids 24, 25, 27 and 28 may form after subsequent transformation.

In FIG. 5, the reagents and conditions used are as follows: (a) NBS, $CHCl_3$; (b) NMP or DMSO, 130° C., 12 h; (c) $NH_2OH \cdot HCl$ (10 equiv)/NaOMe (20 equiv)/MeOH, -20° C. to room temp.

Scheme 4

Figure 6:
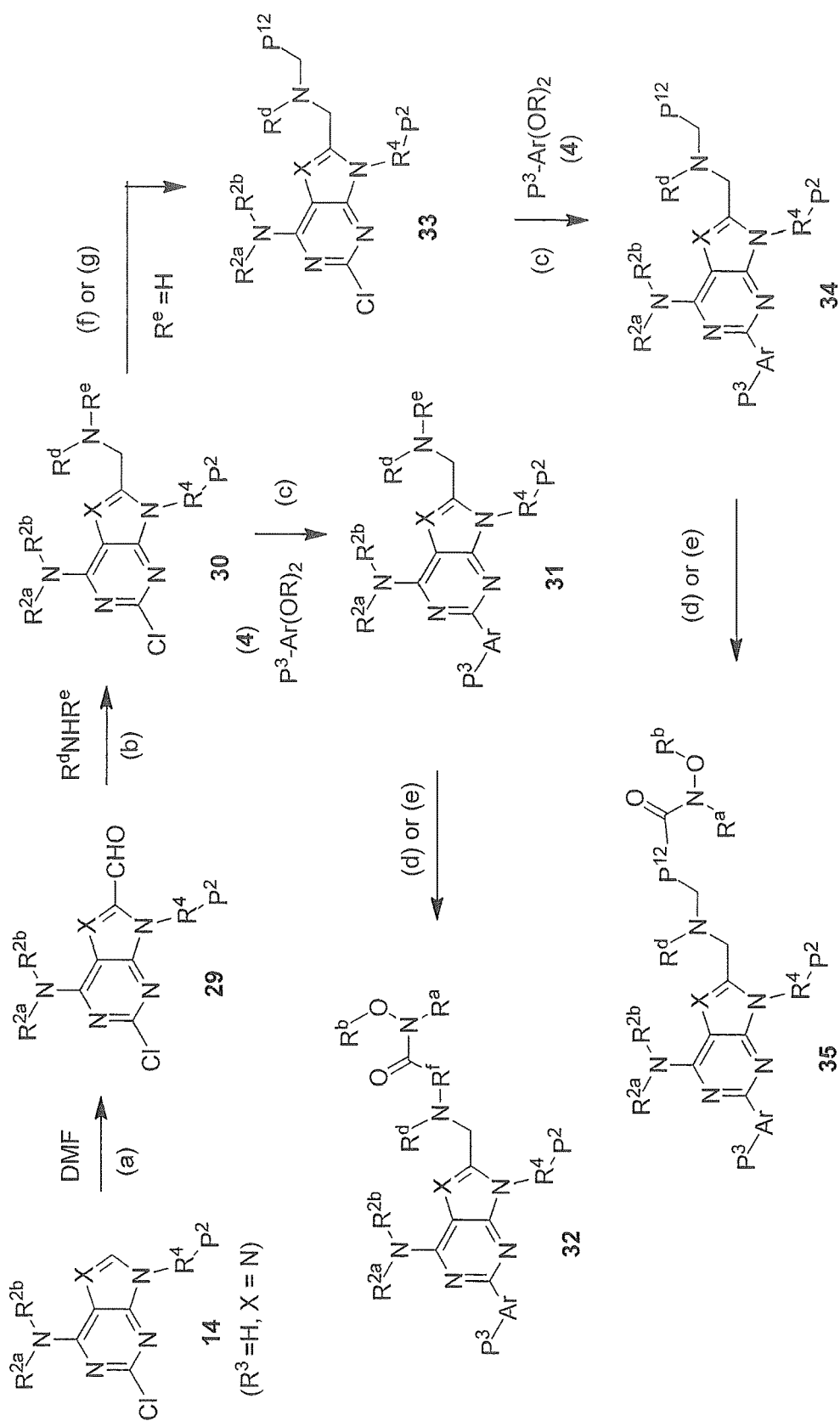
FIG. 6 shows a scheme depicting an alternative method to vary $R^3$ group of compound 14 (scheme 2, FIG. 4) when $R^3$ is a hydrogen and X is a nitrogen.

FIG. 6 depicts an alternative method to vary $R^3$ group of compound 14 (scheme 2) when $R^3$ is a hydrogen and X is a nitrogen. Firstly, the position 8 of purine 14 is introduced an aldehyde 29, then the latter is transformed to an amine 30. If the $R^f$ group of 30 contains an ester or protected hydroxamate, it will be converted to hydroxamic acid 32 via Suzuki product 31. When 30 is a secondary amine ($R^f$=H), it can be further varied by either alkylation with a halide or reductive amination with an aldehyde to afford amine 33. Monochloroamine 33 is finally converted to hydroxamic acid 35 via Suzuki reaction product 34.

In FIG. 6, the reagents and conditions used are as follows: (a) DMF, n-BuLi; b) reductive amination with amine $R^dNH_2$, $NaBH_4$, DCE-MeOH; (c) Suzuki coupling, Pd(dppf)$Cl_2 \cdot CH_2Cl_2$, $K_2CO_3$/dioxane, microwave or heat; (d) $NH_2OH \cdot HCl$ (10 equiv)/NaOMe (20 equiv)/MeOH, 0° C. to room temp; (e) 5-50% TFA/DCM; (f) alkylation with $P^{12}CH_2P^1$, $P^1$ is halide or leaving group, $Et_3N$; (g) reductive amination with $P^{12}CHO$, $NaBH(OAc)_3$, DCE, room temp.;

Scheme 5

Figure 7:
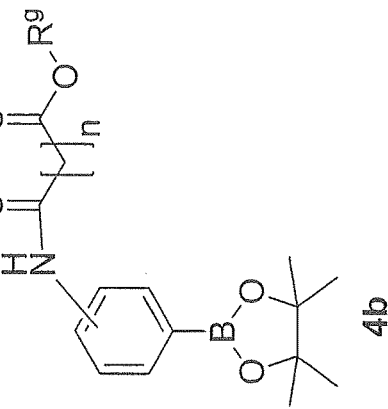
FIG. 7 shows a scheme depicting the general synthetic routes for further derivatization of readily or commercially available starting materials (e.g., 4) and procedures for preparation of protected or substituted hydroxamic acid (38).
Figure 7:
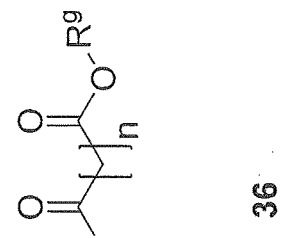
Figure 7:
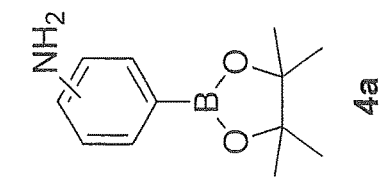
Figure 7:
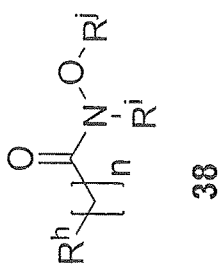
Figure 7:
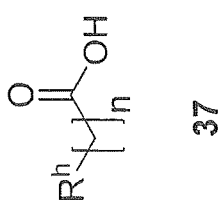
Figure 7:
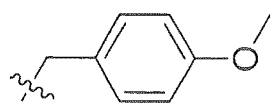
Figure 7:
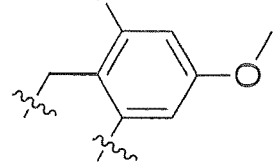
Figure 7:
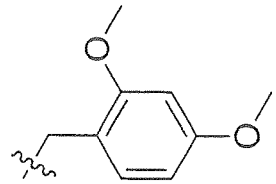
Figure 7:
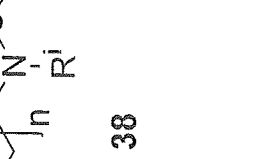

FIG. 7 depicts the general synthetic routes for further derivatization of readily or commercially available starting materials (e.g., 4) and procedures for preparation of protected or substituted hydroxamic acid (38). Boronic ester (4) is the key material for Suzuki coupling reactions used by both Schemes 1 and 2, it can be modified prior to subjecting to Suzuki reaction. For example, the amino group of boronic ester (4a) is coupled with an acid to form an amide (4b) which has an ester group and is a precursor for hydroxamic acid. Hydroxamic acid can be easily generated from corresponding methyl or ethyl ester by treating it with excessive hydroxylamine [i.e., $NH_2OH \cdot HCl$ (10 equiv), NaOMe (20 equiv) in MeOH]. Other methods of preparation of protected or substituted hydroxylamine are described in Scheme 5. An acid (37) can be converted to a hydroxamic acid (36) by following methods. (i) the acid is converted to acid chloride under milder conditions by treating it with ClCOCOCl, or $SOCl_2$, or other reagents under neutral conditions (such as $Ph_3P$ with $CBr_4$, or 2,4,6-Trichloro-[1,3,5]triazine); or (ii) the acid is converted to an active ester by reacting it with isobutyl chloroformate; (iii) the acid chloride or active ester is reacted with hydroxylamine or the protected hydroxylamine $R^gNHOR^h$ [e.g., O-benzylhydroxylamine, O-(2,4-dimethoxy-benzyl)-hydroxylamine, O,N-bis-(2,4-dimethoxybenzyl)-hydroxylamine, O-(tetrahydro-pyran-2-yl)-hydroxylamine, O-(tert-butyl-dimethyl-silyl)-hydroxylamine] to give the hydroxamic acid or the protected hydroxamic acid; iv) coupling the acid with hydroxylamine or protected hydroxylamine $RgNHOR^h$ with a coupling reagent. The protecting group can be removed by methods known in the literature such as hydrogenolysis to remove the (substituted) benzyl group or acidic cleavage (e.g., TFA in DCM with or without cation scavenger) to cleave the acid labile protecting groups.

In FIG. 7, the reagents and conditions used are as follows: (a) EDCI-HOBT/DCM; b) i) acid chloride formation ii) hydroxylamine $R^iNHOR^j$; c) EDCI-HOBt, $R^iNHOR^j$.

Example 3: Synthesis of N-hydroxy-4-(3-(9-isopropyl-2-morpholino-9H-purin-6-yl)phenoxy)butanamide (FIG. 3, Compound 12a)

Figure 8:
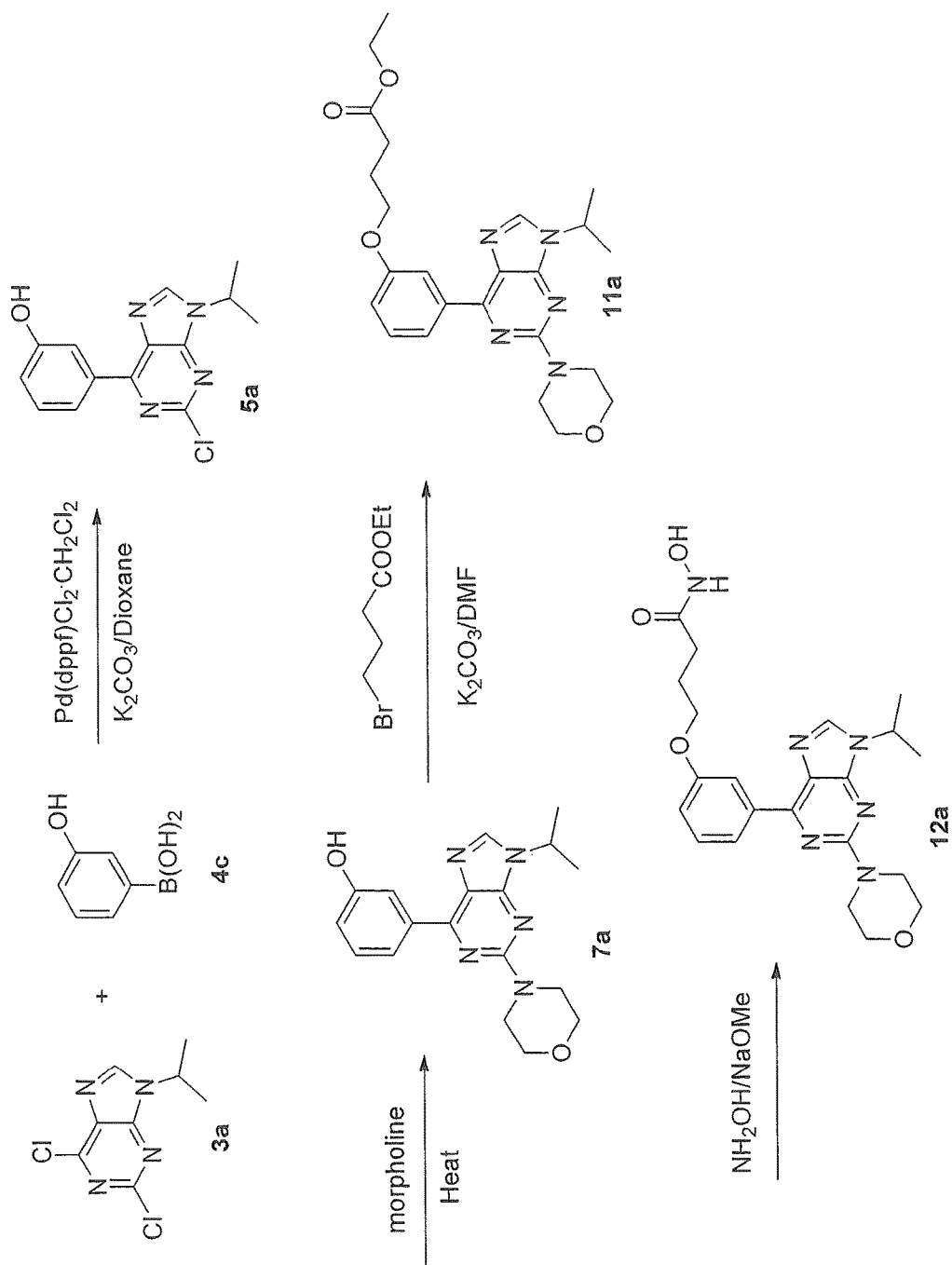
FIG. 8 shows the reaction scheme for the synthesis of N-hydroxy-4-(3-(9-isopropyl-2-morpholino-9H-purin-6-yl)phenoxy)butanamide.

The reaction scheme for the synthesis of N-hydroxy-4-(3-(9-isopropyl-2-morpholino-9H-purin-6-yl)phenoxy)butanamide is shown in FIG. 8.

Step 1: Synthesis of 3-(2-chloro-9-isopropyl-9H-purin-6-yl)phenol (5a)

To a pre-stirred of solution of 2,6-dichloro-9-isopropyl-9H-purine 3a (230 mg, 1.0 mmol), (3-hydroxyphenyl)boronic acid 4c (152 mg, 1.1 mmol) in dioxane (10 mL), were added a solution of $K_2CO_3$ (345 mg, 2.5 mmol) in deionized water (1.0 mL). The mixture was degassed for 30 min then added Pd(dppf)$Cl_2 \cdot CH_2Cl_2$ (41 mg), and the resulting mixture was heated at 70° C. for 5 hours. LC-MS showed the reaction completed. After a simple workup, the product 5a (215 mg, 75%) was obtained by flash chromatography (silica, 20% to 50% ethyl acetate in hexanes).

Step 2: Synthesis of 3-(9-isopropyl-2-morpholino-9H-purin-6-yl)phenol (7a)

3-(2-chloro-9-isopropyl-9H-purin-6-yl)phenol 5a (300 mg, 1.04 mmol) was dissolved in morpholine (5 mL). The resulting mixture was heated at 80° C. for 10 hours. LC-MS showed the reaction completed. After a simple workup, the crude was purified by flash chromatography (silica, ethyl acetate/hexanes=1:2) to afford 7a (290 mg, 82%).

Step 3: Synthesis of ethyl 4-(3-(9-isopropyl-2-morpholino-9H-purin-6 yl)phenoxy)butanoate (11a)

To a pre-stirred of solution of 7a (80 mg, 0.24 mmol), ethyl 6-bromobutyrate (69 mg, 0.35 mmol) in DMF (2 mL), was added anhydrous potassium carbonate (98 mg, 0.79 mmol). The resulting mixture was heated at 100° C. overnight (16 h). After workup, the crude was purified by flash chromatography (silica, 17% to 25% of ethyl acetate in hexanes) to afford 11a (86 mg, 80%). LC-MS m/z 454.2 ([M+H]$^+$). $^1$HNMR (CDCl$_3$) δ 8.32 (d, J=7.6 Hz, 1H), 8.20 (s, 1H), 7.96 (s, 1H), 7.43 (t, J=8.0 Hz, 1H), 7.02 (dd, J=8.0, 2.4 Hz, 1H), 4.80 (septet, J=6.8 Hz, 1H), 4.14 (m, 4H), 3.93 (t, J=4.8 Hz, 4H), 3.84 (t, J=4.8 Hz, 4H), 2.56 (t, J=7.4 Hz, 2H), 2.15 (quintet, J=6.8 Hz, 2H), 1.61 (d, J=6.8 Hz, 6H), 1.25 (t, J=7.2 Hz, 3H). $^{13}$C NMR (CDCl$_3$) δ 173.3, 159.0, 158.7, 154.4, 153.9, 139.2, 137.6, 129.5, 124.3, 122.3, 117.0, 115.0, 67.0, 66.7, 60.4, 46.8, 45.1, 30.8, 24.6, 23.4, 14.3.

Step 4: Synthesis of N-hydroxy-4-(3-(9-isopropyl-2-morpholino-9H-purin-6-yl)phenoxy)butanamide (12a)

To a pre-stirred of solution of 11a (55 mg, 0.12 mmol), hydroxylamine hydrochloride (85 mg, 1.2 mmol) in dry MeOH (1.5 mL), pre-cooled down over dry ice, was added slowly with sodium methoxide (0.7 mL, 3.0 mmol). The resulting mixture was stirred at −20° C. for 1 hour before it was warmed up to the room temp. LC-MS showed the reaction completed after 2 hours. After workup, the mixture was purified by RPHPLC to afford 12a as white solid (25 mg, 49% calcd as TFA salt) after lyophilisation of the HPLC fractions. LC-MS m/z 441.1 ([M+H]$^+$). HPLC purity (254 nm): 94.7%.

Preparation of freebase of 12a. The TFA salt was dissolved in acetonitrile and water, and then basified using saturated aqueous NaHCO$_3$ to pH around 8. After removal of acetonitrile under reduced pressure, the aqueous solution was extracted with ethyl acetate (×3). The combined organic layers was dried and evaporated to afford crude freebase which was further purified by recrystallization in MeOH. LC-MS m/z 441.2 ([M+H]$^+$). HPLC purity (254 nm): 99.8%. $^1$H NMR (DMSO-d$_6$) δ 10.44 (s, 1H), 8.72 (s, 1H), 8.38 (d, J=2.4 Hz, 1H), 8.36 (d, J=8.0 Hz, 1H), 8.36 (s, 1H), 7.46 (t, J=8.0 Hz, 1H), 7.10 (dd, J=7.8, 2.2 Hz, 1H), 4.75 (septet, J=6.6 Hz, 1H), 4.05 (t, J=6.2 Hz, 2H), 3.81 (t, J=4.8 Hz, 4H), 3.74 (t, J=4.8 Hz, 4H), 2.18 (t, J=7.0 Hz, 2H), 1.99 (quintet, J=7.0 Hz, 2H), 1.55 (d, J=6.8 Hz, 6H). $^{13}$C NMR (DMSO-d$_6$) δ 169.1, 159.0, 158.4, 154.3, 152.9, 142.1, 137.9, 130.0, 125.2, 121.9, 116.9, 115.8, 67.8, 66.5, 45.7, 45.2, 29.3, 25.3, 22.3. HRMS (ESI) m/z [M+H]$^+$ calcd for C$_{22}$H$_{28}$N$_6$O$_4$, 441.2245; found, 441.2256.

Example 4: Synthesis of N-hydroxy-7-(2-(3-(hydroxymethyl)phenyl)-6-morpholino-9H-purin-9-yl)heptanamide (FIG. 4, Compound 19f)

Figure 9:
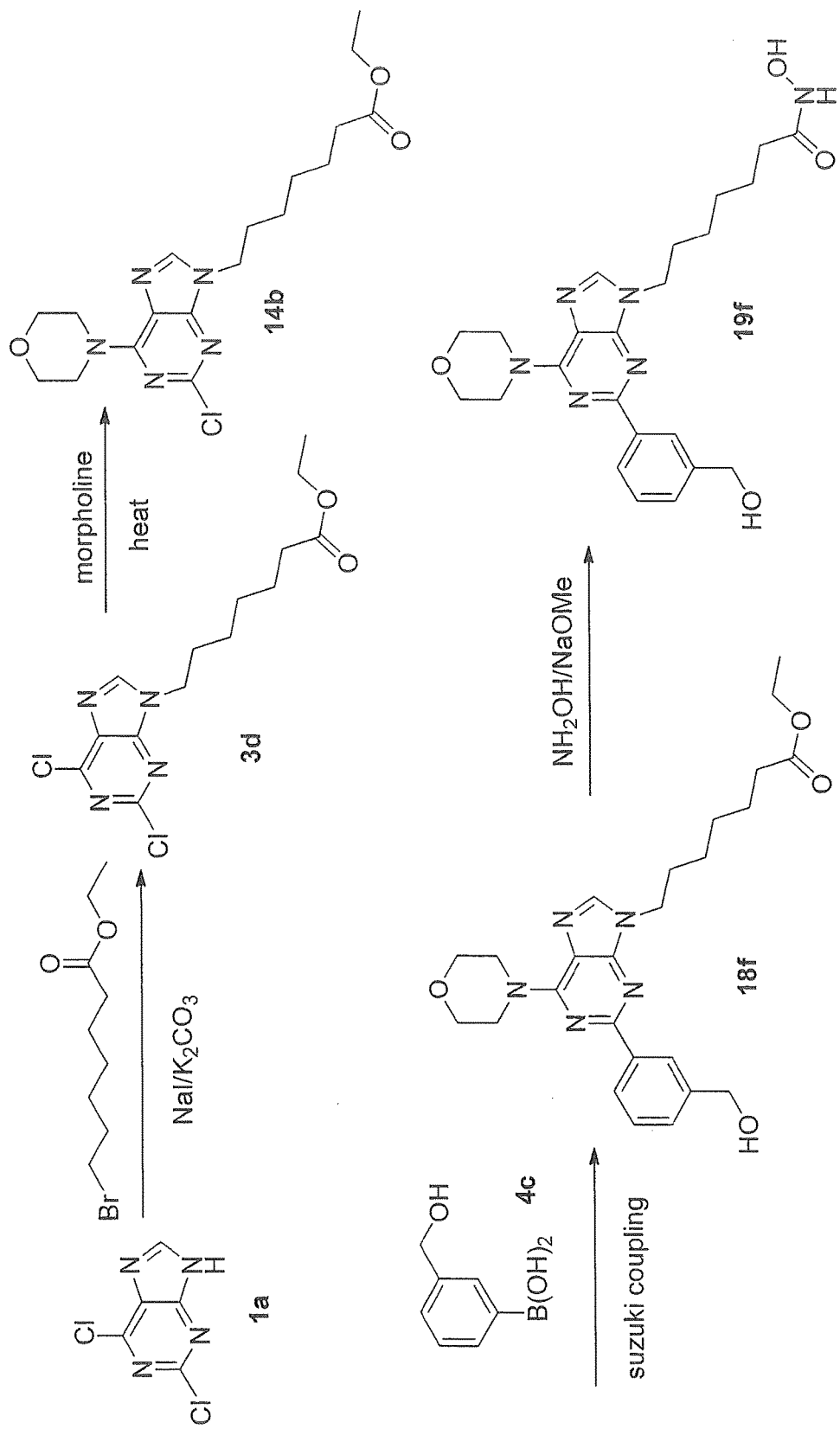
FIG. 9 shows the reaction scheme for the synthesis of N-hydroxy-7-(2-(3-(hydroxymethyl)phenyl)-6-morpholino-9H-purin-9-yl)heptanamide.

The reaction scheme for the synthesis of N-hydroxy-7-(2-(3-(hydroxymethyl)phenyl)-6-morpholino-9H-purin-9-yl)heptanamide is shown in FIG. 9.

Step 1: Synthesis of ethyl 7-(2,6-dichloro-9H-purin-9-yl)heptanoate (3d)

To a pre-stirred of solution of 2,6-dichloro-9H-purine 1a (376 mg, 2.0 mmol), ethyl 7-bromoheptanoate (521 mg, 2.2 mmol) in DMF (15 mL), was added anhydrous potassium carbonate (552 mg, 4.0 mmol) and NaI (64 mg, 0.4 mmol). The resulting mixture was stirred at 40° C. for 12 hours. LC-MS showed the reaction completed. After workup, the crude was purified by flash chromatography (silica, ethyl acetate/hexanes from 1:3 to 1:2) to afford 3d (480 mg, 69%).

Step 2: Synthesis of ethyl 7-(2-chloro-6-morpholino-9H-purin-9-yl)heptanoate (14b)

To a pre-stirred of solution of 3d (344 mg, 1.0 mmol) in dioxane (10 mL), were added with morpholine (435 mg, 5.0 mmol). The resulting mixture was stirred at 60° C. for 3 hour. LC-MS showed the reaction completed. After simple workup, crude product of 14b (404 mg, 100%) was obtained and used for the next step of reaction without further purification. LC-MS m/z 397.2 ([M+H]$^+$). $^1$HNMR (CDCl$_3$) δ 7.70 (s, 1H), 4.00-5.60 (m, 8H), 3.82 (t, J=4.6 Hz, 4H), 2.27 (t, J=7.2 Hz, 2H), 1.85 (m, 2H), 1.60 (quintet, J=7.0 Hz, 2H), 1.34 (m, 4H), 1.24 (t, J=7.0 Hz, 3H). $^{13}$C NMR (CDCl$_3$) δ 173.6, 153.94, 153.93, 152.2, 118.6, 66.9, 60.3, 45.7 (br), 43.8, 34.1, 29.8, 28.5, 26.3, 24.7, 14.3.

Step 3: Synthesis of ethyl 7-(2-(3-(hydroxymethyl)phenyl)-6-morpholino-9H-purin-9-yl)heptanoate (18f)

To a pre-stirred of solution of crude 14b (100 mg, 0.254 mmol), boronic acid 4c (76 mg, 0.5 mmol) in dioxane (5.0 mL), was added with potassium carbonate (86 mg, 0.62 mmol) and Pd(dppf)Cl$_2$.CH$_2$Cl$_2$ (10 mg). The resulting mixture was stirred at 150° C. for 1 hour under the microwave irradiation. LC-MS showed the reaction completed after 1 hour. After removing the solvent, the crude was suspended in DCM and purified by flash chromatography (silica, 1% to 2% MeOH in DCM) to afford 18f (30 mg, 52.6%). LC-MS m/z 468.3 ([M+H]$^+$). $^1$HNMR (DMSO-d$_6$) δ 8.34 (s, 1H), 8.27 (dt-like, J=7.2 Hz, 1H), 8.22 (s, 1H), 7.44-7.37 (m, 2H), 5.28 (t, J=5.0 Hz, 1H), 4.58 (d, J=4.4 Hz, 2H), 4.30 (br s, 4H), 4.23 (t, J=6.8 Hz, 2H), 4.01 (q, J=7.2 Hz, 2H), 3.77 (t, J=4.8 Hz, 4H), 2.24 (t, J=7.2 Hz, 2H), 1.86 (quintet, J=7.2 Hz, 2H), 1.49 (quintet, J=7.4 Hz, 2H), 1.22-1.38 (m, 4H), 1.14 (t, J=7.0 Hz, 3H). $^{13}$C NMR (DMSO-d$_6$) δ 173.3, 157.3, 153.5, 152.3, 142.9, 141.1, 138.6, 128.4, 128.3, 126.7, 126.2, 118.7, 66.7, 63.5, 60.1, 45.6, 43.2, 33.8, 29.5, 28.2, 26.1, 24.7, 14.5.

Step 4: Synthesis of N-hydroxy-7-(2-(3-(hydroxymethyl)phenyl)-6-morpholino-9H-purin-9-yl)heptanamide (19f)

To a pre-stirred of solution of 18f (30 mg, 0.064 mmol), hydroxylamine hydrochloride (67 mg, 0.96 mmol) in dry MeOH (1.0 mL), pre-cooled down over dry ice, was added slowly with sodium methoxide (0.37 mL, 1.6 mmol). The resulting mixture was stirred at −20° C. for 1 hour before it was warmed up to the room temperature. LC-MS showed the reaction completed after 2 hours. After simple workup, the mixture was purified by RPHPLC to afford N-hydroxy-7-(2-(3-(hydroxymethyl)phenyl)-6-morpholino-9H-purin-9-yl)heptanamide 19f as white solid (8 mg, 22% as calcd as TFA salt). The TFA salt was dissolved in acetonitrile and water, and then basified using saturated aqueous NaHCO3 to pH around 8. After removal of acetonitrile under reduced pressure, the aqueous solution was extracted with ethyl acetate (×3). The combined organic layers was dried and evaporated to afford crude freebase which was further purified by recrystallization in MeOH. Freebase of 19f: LC-MS m/z 455.1 ([M+H]$^+$). HPLC purity (254 nm): 97.4%. $^1$H NMR (DMSO-d$_6$) δ 10.33 (s, 1H), 8.66 (s, 1H), 8.35 (s, 1H), 8.27 (dt-like, J=7.6 Hz, 1H), 8.23 (s, 1H), 7.44 (t, J=7.6 Hz, 1H), 7.40 (dt-like, J=7.6 Hz, 1H), 5.29 (t, J=7.6 Hz, 1H), 4.59 (d, J=5.6 Hz, 2H), 4.31 (m, 4H), 4.23 (t, J=7.0 Hz, 2H), 3.78 (t, 4H), 1.93 (t, J=7.4 Hz, 2H), 1.87 (quintet, 2H), 1.48 (quintet, 2H), 1.29 (m, 4H); $^{13}$C NMR (DMSO-d$_6$) δ 169.0, 156.9, 153.0, 151.8, 142.5, 140.6, 138.2, 128.0, 127.9, 126.2, 125.8, 118.2, 66.3, 63.0, 45.1, 42.8, 32.2, 29.1, 28.0, 25.7, 25.0. HRMS (ESI) m/z [M+H]$^+$ calcd for C$_{23}$H$_{30}$N$_6$O$_4$, 455.2402; found, 455.2405.

Example 5: Synthesis of 7-(6-(2-aminopyrimidin-5-yl)-2-morpholino-9H-purin-9-yl)-N-hydroxyheptanamide (FIG. 3, Compound 8a)

Figure 10:
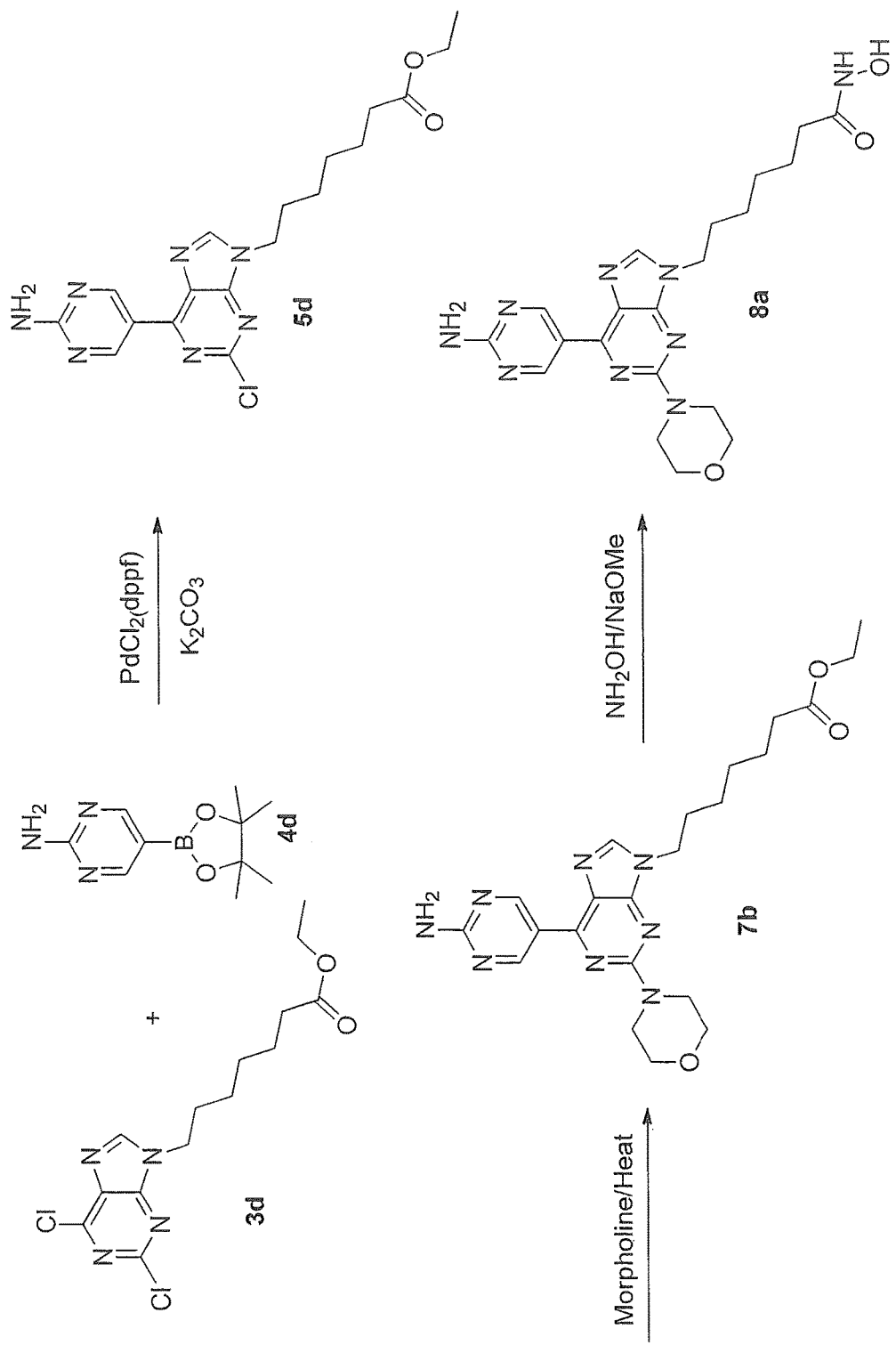
FIG. 10 shows the reaction scheme for the synthesis of 7-(6-(2-aminopyrimidin-5-yl)-2-morpholino-9H-purin-9-yl)-N-hydroxyheptanamide.

The reaction scheme for the synthesis of 7-(6-(2-aminopyrimidin-5-yl)-2-morpholino-9H-purin-9-yl)-N-hydroxyheptanamide is shown in FIG. 10.

Step 1: Synthesis of ethyl 7-(6-(2-aminopyrimidin-5-yl)-2-chloro-9H-purin-9-yl)heptanoate (5d)

To a pre-stirred of solution of 3d (from Example 2, step 1) (344 mg, 1.0 mmol), 544,4,5,5-tetramethyl-1,3,2-dioxaborolan-2-yl)pyrimidin-2-amine 4d (240 mg, 1.1 mmol) in dioxane (15 mL), were added a solution of $K_2CO_3$ (345 mg, 2.5 mmol) in DI water (2.0 mL). The mixture was degassed for 30 min before it were added Pd(dppf)Cl$_2$·CH$_2$Cl$_2$ (41 mg, 0.05 equiv). The resulting mixture was heated at 82° C. for 6 hours. LC-MS showed the reaction completed. After workup, the crude was purified by flash chromatography (silica, 33% to 50% to 100% of ethyl acetate in hexanes) to afford 5d (150 mg, 37%).

Step 2. Synthesis of ethyl 7-(6-(2-aminopyrimidin-5-yl)-2-morpholino-9H-purin-9-yl)heptanoate (7b)

To a pre-stirred of solution of 5d (150 mg, 0.37 mmol) in DMF (5 mL), was added with morpholine (0.70 mL, 3.0 mmol). The resulting mixture was heated at 80° C. for 12 hours. LC-MS showed the reaction completed. After workup, 7b (120 mg, 72%) was obtained by recrystallization of the crude in 10% MeOH in DCM.

Step 3: Synthesis of 7-(6-(2-aminopyrimidin-5-yl)-2-morpholino-9H-purin-9-yl)-N-hydroxyheptanamide (8a)

To a pre-stirred of solution of 7b (70 mg, 0.155 mmol), hydroxylamine hydrochloride (108 mg, 15.5 mmol) in dry MeOH (1.5 mL), pre-cooled down over dry ice, was added slowly with sodium methoxide (901 uL, 3.9 mmol). The resulting mixture was stirred at −20° C. for 1 hour before it was warmed up to the room temp. LC-MS showed the reaction completed after 3 hours. After workup, the crude was purified by RPHPLC to afford 7-(6-(2-aminopyrimidin-5-yl)-2-morpholino-9H-purin-9-yl)-N-hydroxyheptanamide 8a (15 mg, 21% calcd as TFA salt). LC-MS m/z 442.1 ([M+H]$^+$). HPLC purity (254 nm): 96.6%. $^1$H NMR (DMSO-d$_6$) δ 10.34 (s, 1H), 9.54 (s, 2H), 8.25 (s, 1H), 7.45 (s, 2H), 4.12 (t, J=6.8 Hz, 2H), 3.78 (m, 4H), 3.72 (m, 4H), 1.93 (t, J=7.2 Hz, 2H), 1.85 (m, 2H), 1.48 (m, 2H), 1.26 (m, 4H). HRMS (ESI) m/z [M+H]$^+$ calcd for $C_{20}H_{27}N_9O_3$, 442.2310; found, 442.2308.

Example 6: Synthesis of N$^1$-hydroxy-N$^8$-(3-(9-isopropyl-2-morpholino-9H-purin-6-yl)phenyl)octanediamide (FIG. 3, Compound 12f)

Figure 11:
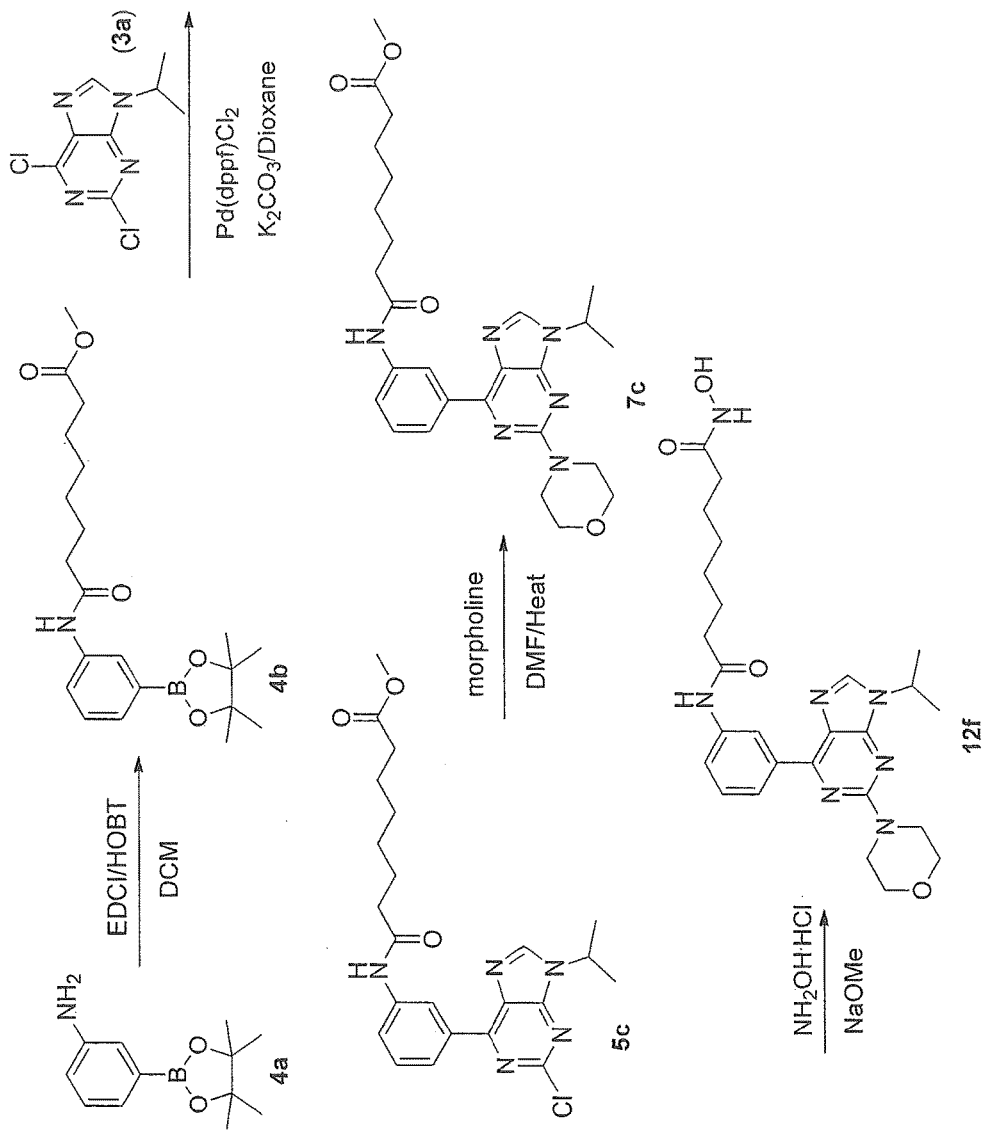
FIG. 11 shows the reaction scheme for the synthesis of $N^1$-hydroxy-$N^8$-(3-(9-isopropyl-2-morpholino-9H-purin-6-yl)phenyl)octanediamide.

The reaction scheme for the synthesis of N$^1$-hydroxy-N$^8$-(3-(9-isopropyl-2-morpholino-9H-purin-6-yl)phenyl)octanediamide is shown in FIG. 11.

Step 1: Synthesis of methyl 8-oxo-8-((3-(4,4,5,5-tetramethyl-1,3,2-dioxaborolan-2-yl)phenyl)amino)octanoate (Scheme 5, 4b)

To a pre-stirred of solution of (3-aminophenyl)boronic ester (164 mg, 0.75 mmol), monomethyl suberate (155 mg, 0.83 mmol), 1-ethyl-3-(3-dimethylaminopropyl) carbodiimide hydrochloride (EDCI) (159 mg, 0.83 mmol) in dry DCM (15 mL), were added hydroxybenzotriazole (HOBT, 112 mg). The mixture was stirred at room temp for 4 hours. LC-MS showed the reaction completed. After workup, the crude was purified by flash chromatography (silica, 20% to 25% ethyl acetate in hexanes) to afford the product 4b (149 mg, 46%).

Step 2: Synthesis of methyl 8-((3-(2-chloro-9-isopropyl-9H-purin-6-yl)phenyl)amino)-8-oxooctanoate (5c)

To a pre-stirred of solution of 2,6-dichloro-9-isopropyl-9H-purine 3a (59 mg, 0.26 mmol), 4b (100 mg, 0.26 mmol) in dioxane (10 mL), were added a solution of $K_2CO_3$ (88 mg, 0.64 mmol) in DI water (1.0 mL). The mixture was degassed for 30 min before it were added Pd(dppf)Cl$_2$CH$_2$Cl$_2$ (10 mg, 0.05 equiv). The resulting mixture was heated at 82° C. for 6 hours. LC-MS showed the reaction completed. After workup, the crude was purified by flash chromatography (silica, 25% to 33% of ethyl acetate in hexanes) to afford 5c (100 mg, 85%).

Step 3: Synthesis of methyl 8-((3-(9-isopropyl-2-morpholino-9H-purin-6-yl)phenyl)amino)-8-oxooctanoate (7c)

To a pre-stirred of solution of 5c (75 mg, 0.16 mmol) in DMF (2 mL), was added morpholine (140 mg, 1.6 mmol). The resulting mixture was heated at 80° C. for 16 hours. After workup, the crude was purified by flash chromatography (silica, 33% to 50% ethyl acetate in hexanes) to afford 7c (46 mg, 55%).

Step 4: Synthesis of N$^1$-hydroxy-N$^8$-(3-(9-isopropyl-2-morpholino-9H-purin-6-yl)phenyl)octanediamide (12f)

To a pre-stirred of solution of 7c (46 mg, 0.09 mmol), hydroxylamine hydrochloride (70 mg, 0.9 mmol) in dry MeOH (1 mL), pre-cooled down over dry ice, was added slowly with sodium methoxide (520 μL, 2.2 mmol). The resulting mixture was stirred at −20° C. for 1 hour before it was warmed up to the room temperature. LC-MS showed the reaction completed after 2 hours. After workup, the crude was purified by RPHPLC to afford 12f (20 mg, 35% calcd as TFA salt). LC-MS m/z 510.2 ([M+H]$^+$). $^1$H NMR (DMSO-d$_6$) δ 10.34 (s, 1H), 10.07 (s, 1H), 8.75 (s, 1H), 8.51 (d, J=8.0 Hz, 1H), 8.37 (s, 1H), 7.92 (d, J=8.8 Hz, 1H), 7.45 (t, J=8.0 Hz, 1H), 4.75 (m, J=6.4 Hz, 1H), 3.81 (m, 4H), 3.74 (m, 4H), 2.34 (t, J=7.2 Hz, 2H), 1.94 (t, J=7.2 Hz, 2H), 1.61 (m, 2H), 1.54 (d, J=6.8 Hz, 6H), 1.50 (m, 2H), 1.29 (m, 4H). HPLC purity (254 nm): 98.4%; HRMS (ESI) m/z [M+H]$^+$ calcd for $C_{26}H_{35}N_7O_4$, 510.2824; found, 510.2835.

Example 7: Synthesis of (E)-N-hydroxy-3-(4-(((2-(2-(6-methoxypyridin-3-yl)-6-morpholino-9H-purin-9-yl)ethyl)amino)methyl)phenyl)acrylamide (FIG. 4, Compound 17a)

Figure 12:
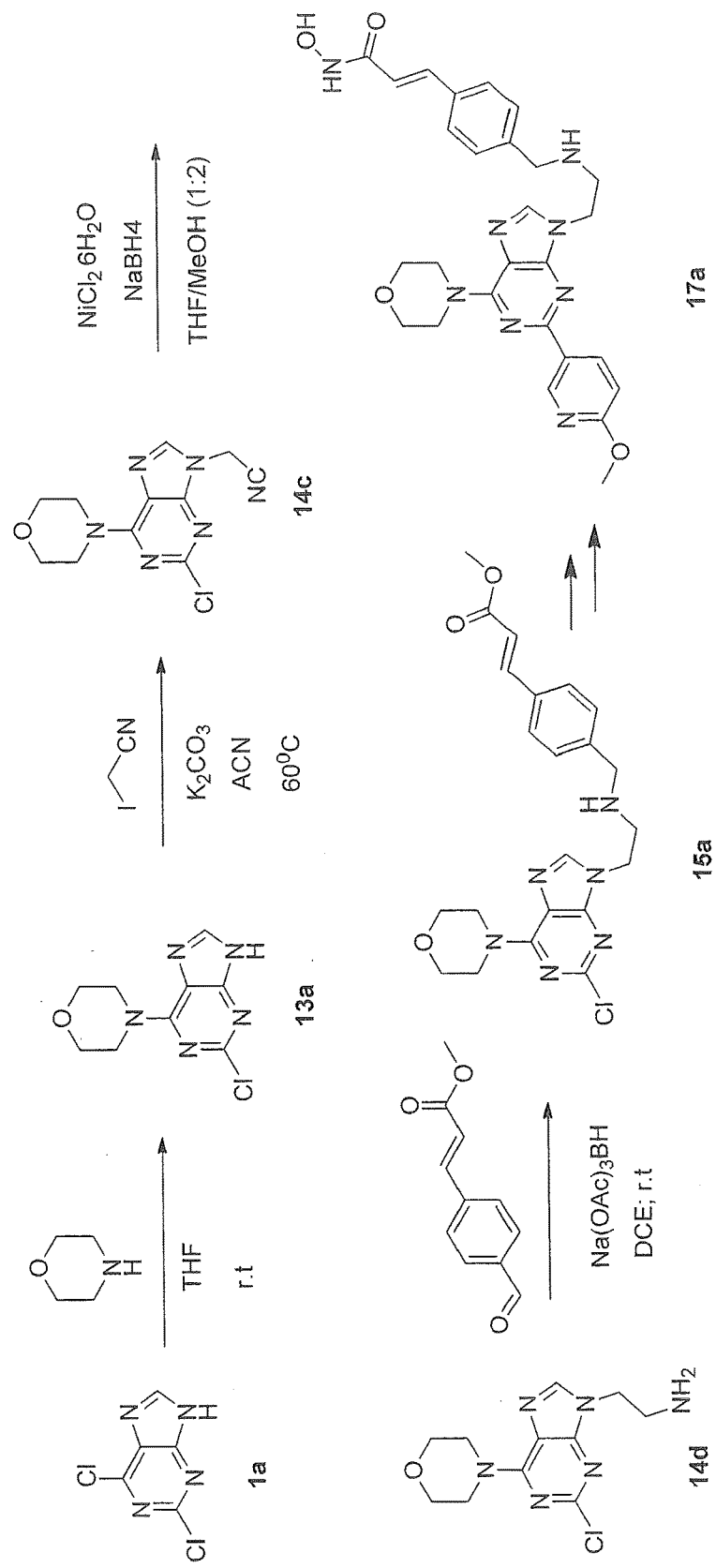
FIG. 12 shows the reaction scheme for the synthesis of (E)-N-hydroxy-3-(4-(((2-(2-(6-methoxypyridin-3-yl)-6-morpholino-9H-purin-9-yl)ethyl)amino)methyl)phenyl)acrylamide.

The reaction scheme for the synthesis of (E)-N-hydroxy-3-(4-(((2-(2-(6-methoxypyridin-3-yl)-6-morpholino-9H-purin-9-yl)ethyl)amino)methyl)phenyl)acrylamide is shown in FIG. 12.

Step 1: Synthesis of 4-(2-chloro-9H-purin-6-yl)morpholine (13a)

Morpholine (1.39 mL, 15.87 mmol) was added to a solution of 1a (1.0 g, 5.29 mmol) in THF (26 mL). The resulting mixture was stirred at room temperature for 16 h. White precipitate was observed immediately upon addition of morpholine. The white precipitate was filtered off and washed with water (×2) and methanol (×2) to afford 13a (1.13 g, 90%).

Step 2: Synthesis of 2-(2-chloro-6-morpholino-9H-purin-9-yl)acetonitrile (14c)

To a solution of 13a (1.18 g, 4.94 mmol) in acetonitrile/DMSO (19:1) was added 2-iodoacetonitrile (0.71 mL, 9.87 mmol) and $K_2CO_3$ (1.36 g, 9.87 mmol). The resulting mixture was heated at 60° C. for 3 h. Then the solvents were removed in vacuo and water was added. The aqueous layer was extracted with DCM (×2) and the combined organic layers was washed with brine (×1), dried over $MgSO_4$ and evaporated in vacuo. The crude oil was purified by flash chromatography (silica, 50% ethyl acetate in hexanes) to afford 14c (1.31 g, 95%) as pale brown solid.

Step 3: Synthesis of 2-(2-chloro-6-morpholino-9H-purin-9-yl)ethanamine (14d)

To a stirred solution of 14c (1.23 g, 4.42 mmol) and $NiCl_2.6H_2O$ (105 mg, 0.44 mmol) in MeOH/THF (2:1) was added sodium borohydride (1.17 g, 30.97 mmol) in portions. The resulting mixture was allowed to stir at room temperature for 1 h. Then the solvents were removed in vacuo and a saturated solution of sodium bicarbonate was added. The aqueous layer was extracted with DCM (×2) and the combined organic layers was washed with brine (×1), dried over $MgSO_4$ and evaporated in vacuo. The crude was purified by flash chromatography (silica, 10% methanol in DCM) to afford 14d (577 mg, 46%) as colourless oil.

Step 4: Synthesis of (E)-methyl 3-(4-(((2-(2-chloro-6-morpholino-9H-purin-9-yl)ethyl)amino)methyl)phenyl)acrylate (15a)

To a stirred solution of 14d (576 mg, 2.04 mmol) in DCE (10 mL) was added (E)-methyl 3-(4-formylphenyl)acrylate (466 mg, 2.45 mmol), acetic acid (0.12 mL, 2.04 mmol) and sodium triacetoxyborohydride (649 mg, 3.06 mmol) sequentially. The resulting mixture was stirred at room temp. for 5 h. A saturated solution of sodium bicarbonate was added to quench the reaction and the aqueous layer was extracted with methylene chloride (×2). The combined organic layers was washed with brine (×1), dried over $MgSO_4$ and evaporated in vacuo. The crude was purified by flash chromatography (silica, 4% methanol in DCM) to 15a (414 mg, 44%) as off-white solid.

Steps 5 and 6: by following analogous procedures of Example 4, steps 3 and 4, the title compound (E)-N-hydroxy-3-(4-(((2-(2-(6-methoxypyridin-3-yl)-6-morpholino-9H-purin-9-yl)ethyl)amino)methyl)phenyl)acrylamide (17a) was obtained as TFA salt. LC-MS m/z 531 ([M+H]$^+$). $^1$HNMR (DMSO-$d_6$) δ 10.82 (br s, 1H), 9.16 (d, J=2.4 Hz, 1H), 9.07 (br s, 2H), 8.54 (dd, J=2.4 Hz, 8.8 Hz, 1H), 8.20 (s, 1H), 7.56 (d, J=8.0 Hz, 2H), 7.46 (d, J=8.0 Hz, 2H), 7.42 (overlapping, 1H), 6.88 (d, J=8.8 Hz, 1H), 6.50 (d, J=16 Hz, 1H), 4.60 (t, J=5.2 Hz, 2H), 4.34-4.28 (m, 6H), 3.92 (s, 3H), 3.77 (t, J=4.8 Hz, 4H), 3.60 (t-like, 2H). HRMS (ESI) m/z [M+H]$^+$ calcd for $C_{27}H_{31}N_8O_4$, 531.2463; found, 531.2473.

Example 8: Synthesis of 6-((6-(2-aminopyrimidin-5-yl)-9-isopropyl-2-morpholino-9H-purin-8-yl)amino)-N-hydroxyhexanamide (FIG. 5, Compound 24a)

Figure 13:
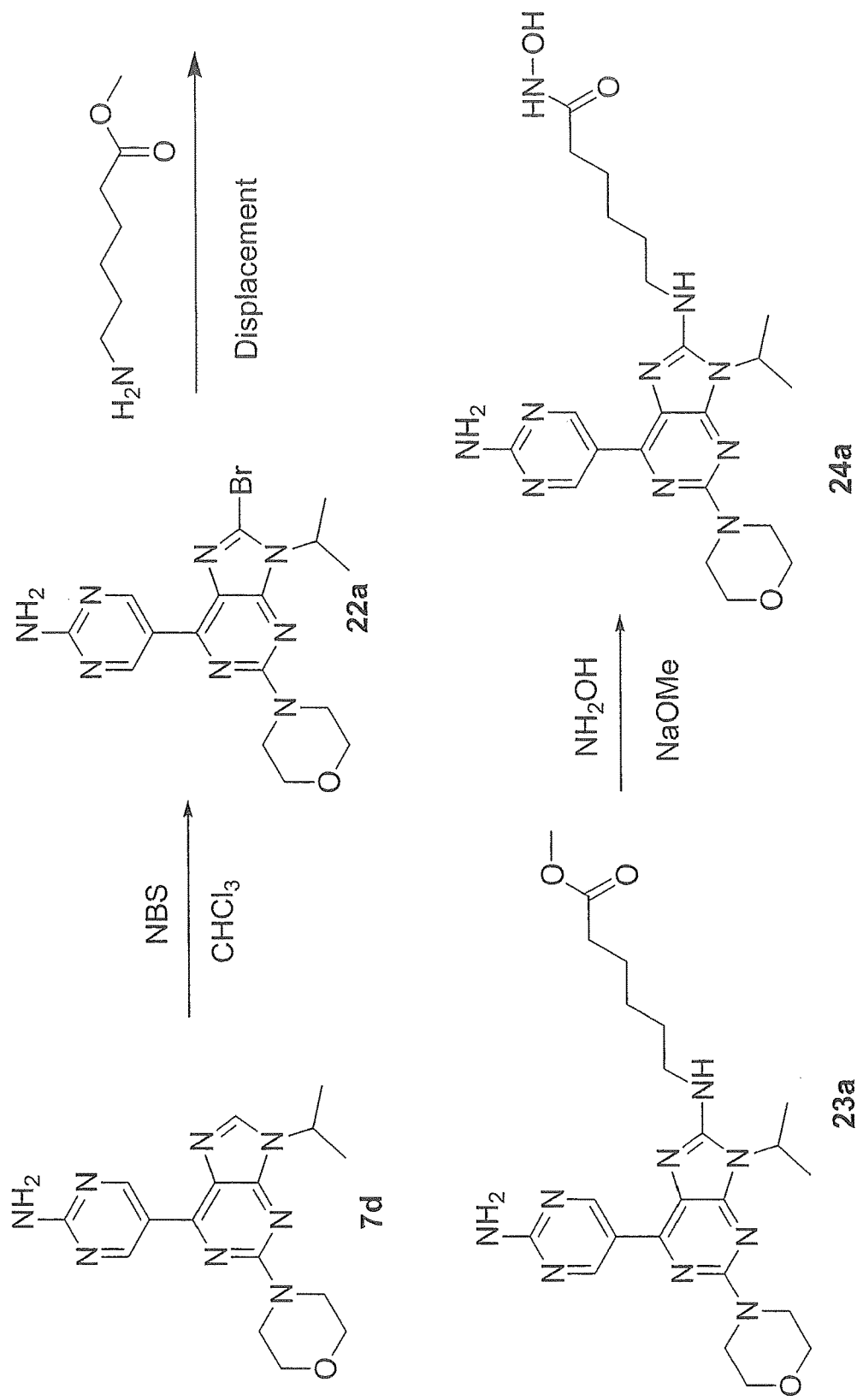
FIG. 13 shows the reaction scheme for the synthesis of 6-((6-(2-aminopyrimidin-5-yl)-9-isopropyl-2-morpholino-9H-purin-8-yl)amino)-N-hydroxyhexanamide.

The reaction scheme for the synthesis of 6-((6-(2-aminopyrimidin-5-yl)-9-isopropyl-2-morpholino-9H-purin-8-yl)amino)-N-hydroxyhexanamide is shown in FIG. 13.

Step 1: Synthesis of 5-(8-bromo-9-isopropyl-2-morpholino-9H-purin-6-yl)pyrimidin-2-amine (22a)

To a pre-stirred of solution of 5-(9-isopropyl-2-morpholino-9H-purin-6-yl)pyrimidin-2-amine 7d (400 mg, 1.13 mmol) in $CHCl_3$ (15 mL) was added slowly with NBS (362 mg, 2.03 mmol) in ice-water bath. The resulting mixture was warmed up to room temperature for 2 hours. After workup, the crude was purified by flash chromatography (silica, 25% to 33% of ethyl acetate in DCM) to afford 22a (225 mg, 44%).

Step 2: Synthesis of methyl 6-((6-(2-aminopyrimidin-5-yl)-9-isopropyl-2-morpholino-9H-purin-8-yl)amino)hexanoate (23a)

To a pre-stirred solution of 22a (52 mg, 0.12 mmol) in NMP (1 mL), was added with methyl 6-amino hexanoate hydrochloride (380 mg, 1.88 mmol). The resulting mixture was heated at 130° C. for 12 hours. After workup, the crude was purified by flash chromatography (silica, 20% to 80% ethyl acetate in hexanes) to afford 23a (44 mg, 73%).

Step 3: Synthesis of 6-((6-(2-aminopyrimidin-5-yl)-9-isopropyl-2-morpholino-9H-purin-8-yl)amino)-N-hydroxyhexanamide (24a)

To a pre-stirred solution of 23a (35 mg, 0.072 mmol), hydroxylamine hydrochloride (51 mg, 0.72 mmol) in dry MeOH (1.0 mL), pre-cooled down over dry ice, was added slowly with sodium methoxide (334 μL, 1.44 mmol). The resulting mixture was stirred at −20° C. for 1 hour before it was warmed up to the room temperature. LC-MS showed the reaction completed after 2 hours. After workup, the crude was purified by RPHPLC to afford 24a (30 mg, 69% calcd with TFA salt). LCMS m/z 485.3 ([M+H]$^+$). $^1$H NMR (DMSO-$d_6$) δ 10.40 (s, 1H), 9.21 (s, 2H), 7.78 (s, 1H), 7.41 (s, 2H), 4.65 (m, J=6.8 Hz, 1H), 3.43 (m, 4H), 1.98 (m, 2H), 1.65 (m, 2H), 1.58 (d, J=6.8 Hz, 6H), 1.33 (m, 2H). HPLC purity (254 nm): 99.2%. HRMS (ESI) m/z [M+H]$^+$ calcd for $C_{22}H_{32}N_{10}O_3$, 485.2732; found, 485.2749.

Example 9: Synthesis of 4-((((2-(2-aminopyrimidin-5-yl)-9-ethyl-6-morpholino-9H-purin-8-yl)methyl)(methyl)amino)methyl)-N-hydroxybenzamide (FIG. 6, Compound 35h)

Figure 14:
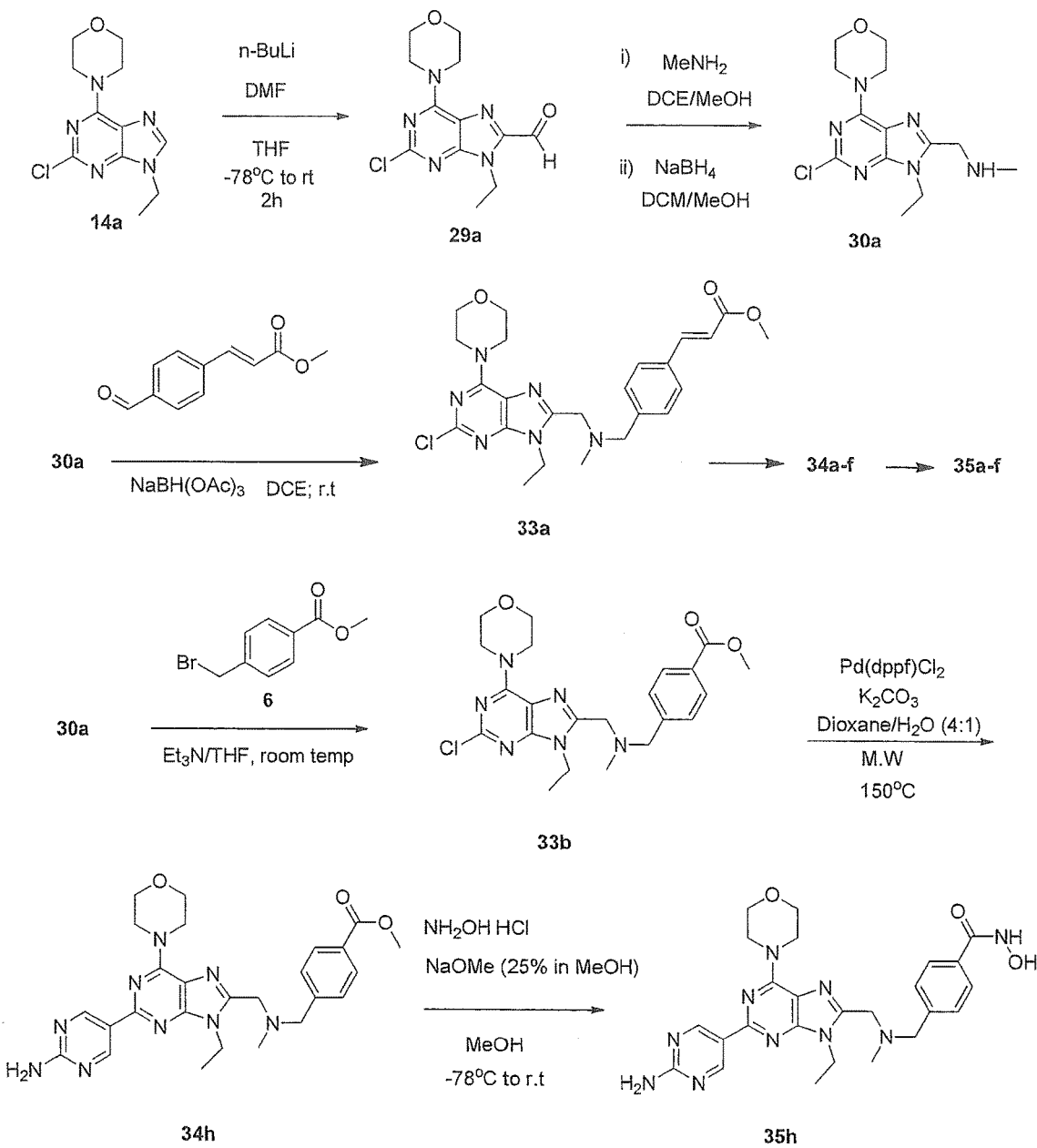
FIG. 14 shows the reaction scheme for the synthesis of 4-((((2-(2-aminopyrimidin-5-yl)-9-ethyl-6-morpholino-9H-purin-8-yl)methyl)(methyl)amino)methyl)-N-hydroxybenzamide (35h) and compounds 35a-f.

The reaction scheme for the synthesis of 4-((((2-(2-aminopyrimidin-5-yl)-9-ethyl-6-morpholino-9H-purin-8-yl)methyl)(methyl)amino)methyl)-N-hydroxybenzamide is shown in FIG. 14.

Step 1: Synthesis of 2-chloro-9-ethyl-6-morpholino-9H-purine-8-carbaldehyde (29a)

To a solution of 4-(2-chloro-9-ethyl-9H-purin-6-yl)morpholine 14a (600 mg, 2.25 mmol) in THF (11 mL) was added a solution of n-BuLi in hexanes (2.5 M, 1.08 ml, 2.7 mmol) at −78° C. The resulting mixture was stirred at −78° C. for 1 h and then DMF (0.26 mL, 3.37 mmol) was added dropwise over a period of 10 min. Then the reaction mixture was allowed to stir at room temperature for additional 2 h before quenching the reaction mixture with ice. The aqueous layer was extracted with ethyl acetate (×2) and washed with brine (×1), dried over MgSO$_4$, filtered and concentrated in vacuo to yield crude yellow oil. The crude was purified by flash chromatography eluting with hexanes/ethyl acetate (7:3) to afford 29a (398 mg, 60%) as off-white solid. LC-MS m/z 296 ([M+H]$^+$). $^1$HNMR (CDCl$_3$) δ 9.88 (s, 1H), 4.70 (br s, 2H), 4.59 (q, J=7.1 Hz, 2H), 4.06 (br s, 2H), 3.86 (s, 4H), 1.41 (t, J=7.1 Hz, 3H).

Step 2: Synthesis of 1-(2-chloro-9-ethyl-6-morpholino-9H-purin-8-yl)-N-methylmethanamine (30a)

To a solution of 2-chloro-9-ethyl-6-morpholino-9H-purine-8-carbaldehyde 29a (300 mg, 1.02 mmol) in DCE/MeOH (2:1) was added a solution of methylamine in methanol (9.8 M, 0.83 mL, 8.14 mmol). White precipitate was observed after 30 min of stirring at room temperature. The resulting mixture was then stirred for additional 5 h and the solvent was removed in vacuo to afford off-white solid. Then the crude solid was dissolved in a solution of DCM/MeOH (4:1) and sodium borohydride (115 mg, 3.05 mmol) was added in portions. The resulting mixture was stirred at room temperature for 15 h. The reaction mixture was evaporated in vacuo and water was added. The aqueous layer was extracted with methylene chloride (×2), washed with brine (×1), dried over MgSO$_4$, filtered and concentrated in vacuo to yield crude off-white solid. The crude was purified by flash chromatography eluting with methylene chloride/methanol (24:1) to afford 30a (256 mg, 82%) as white solid.

Step 3A: synthesis of (E)-methyl 3-(4-((((2-chloro-9-ethyl-6-morpholino-9H-purin-8-yl)methyl)(methyl)amino)methyl)phenyl)acrylate (33a)

To a stirred solution of 30a (242 mg, 0.78 mmol) in DCE (4.0 mL) was added (E)-methyl 3-(4-formylphenyl)acrylate (163 mg, 0.86 mmol), acetic acid (47 μL, 0.78 mmol) and sodium triacetoxyborohydride (248 mg, 1.17 mmol) sequentially. The resulting mixture was stirred at room temperature for 5 h. A saturated solution of sodium bicarbonate was added to quench the reaction and the aqueous layer was extracted with methylene chloride (×2). The combined organic layers was washed with brine (×1), dried with MgSO$_4$ and evaporated in vacuo. The crude was purified by flash chromatography eluting with hexanes/ethyl acetate (3:2) to afford 33a (328 mg, 87%) as white solid. LC-MS m/z 485 ([M+H]$^+$). $^1$HNMR (CDCl$_3$) δ 7.68 (d, J=16 Hz, 1H), 7.49 (d, J=8.0 Hz, 2H), 7.33 (d, J=8.0 Hz, 2H), 6.43 (d, J=16 Hz, 1H), 4.27 (q, J=7.2 Hz, 2H), 4.27 (masked peak, 4H), 3.81 (s, 3H), 3.83-3.80 (masked peak, 4H), 3.70 (s, 2H), 3.59 (s, 2H), 2.23 (s, 3H), 1.34 (t, J=7.2 Hz, 3H).

Step 3B: synthesis of methyl 4-((((2-chloro-9-ethyl-6-morpholino-9H-purin-8-yl)methyl)(methyl)amino)methyl)benzoate (33b)

To a solution of 1-(2-chloro-9-ethyl-6-morpholino-9H-purin-8-yl)-N-methylmethanamine 30a (485 mg, 1.57 mmol) in THF (7.8 mL) was added methyl 4-(bromomethyl)benzoate (466 mg, 2.03 mmol) and triethylamine (0.28 mL, 2.03 mmol). The resulting mixture was stirred at room temperature for 16 h and the solvent was removed in vacuo. Then saturated sodium bicarbonate was added and the aqueous layer was extracted with ethyl acetate (×2) and washed with brine (×1), dried over MgSO$_4$, filtered and concentrated in vacuo to yield crude yellow oil. The crude was purified by flash chromatography eluting with hexanes/ethyl acetate (3:2) to afford 33b (703 mg, 98%) as colourless oil.

Step 4: Synthesis of methyl 4-((((2-(2-aminopyrimidin-5-yl)-9-ethyl-6-morpholino-9H-purin-8-yl)methyl)(methyl)amino)methyl)benzoate (34h)

To a solution of 33b (203 mg, 0.44 mmol) in dioxane (0.9 mL) was added an aqueous solution of K$_2$CO$_3$ (122 mg, 0.89 mmol) followed by 5-(4,4,5,5-tetramethyl-1,3,2-dioxaborolan-2-yl)pyrimidin-2-amine 4a (147 mg, 0.66 mmol) and Pd(dppf)Cl$_2$.CH$_2$Cl$_2$ (18 mg, 0.02 mmol). The reaction mixture was then heated up in a microwave reactor at 150° C. for a period of 20 min. Dioxane was removed and the aqueous layer was extracted with ethyl acetate (×3). The combined organic extracts were dried with MgSO$_4$ and evaporated in vacuo. The brown residue was purified by flash chromatography eluting with hexanes/ethyl acetate (2:3) to DCM/MeOH (24:1) to afford 34h (168 mg, 70%) as a pale brown solid. LC-MS m/z 518 ([M+H]$^+$). $^1$HNMR (CDCl$_3$) δ 9.26 (s, 2H), 7.99 (d, J=8.0 Hz, 2H), 7.40 (d, J=8.0 Hz, 2H), 5.25 (s, 2H), 4.37-4.32 (m, 6H), 3.91 (s, 3H), 3.86 (t, J=4.8 Hz, 4H), 3.75 (s, 2H), 3.65 (s, 2H), 2.25 (s, 3H), 1.41 (t, J=7.2 Hz, 3H).

Step 5: Synthesis of 4-((((2-(2-aminopyrimidin-5-yl)-9-ethyl-6-morpholino-9H-purin-8-yl)methyl)(methyl)amino)methyl)-N-hydroxybenzamide (35h)

NaOMe (1.23 mL, 5.36 mmol) was added dropwise to a solution of 34h (79 mg, 0.15 mmol) and hydroxylamine hydrochloride (106 mg, 1.53 mmol) in DCM/MeOH (4.2 mL, 2:3 v/v) at −78° C. The reaction mixture was then warmed to room temp and stirred for 30 min. Then the reaction mixture was diluted with water to obtain a clear solution and neutralised with 6N HCl. The crude mixture was purified by RPHPLC to provide the title compound 35h (60 mg, 53% as bis-TFA salt). Alternatively, the solvent of the RPHPLC fractions was removed in vacuo and saturated solution of sodium bicarbonate was added into purified compound and extracted with ethyl acetate (×3). The combined organic layer was washed with brine (×1), dried over MgSO$_4$, and concentrated in vacuo to deliver 35h (17 mg, 22% as freebase) as white solid. TFA salt of 35h: LC-MS m/z 519 ([M+H]$^+$). $^1$HNMR (DMSO-d$_6$) δ 11.32 (br s, 1H), 9.14 (s, 2H), 7.84 (d, J=8.0 Hz, 2H), 7.58 (d, J=7.6 Hz, 2H), 7.20 (br s, 2H), 4.63 (br s, 2H), 4.30-4.27 (m, 8H), 3.79 (t, J=4.4 Hz, 4H), 2.78 (br s, 3H), 1.35 (t, J=7.2 Hz, 3H). Freebase of 35h: LC-MS m/z 519 ([M+H]$^+$). $^1$HNMR (DMSO-d$_6$) δ 11.20 (s, 1H), 9.10 (s, 2H), 9.03 (s, 1H), 7.73 (d, J=8.4 Hz, 2H), 7.41 (d, J=8.0 Hz, 2H), 7.07 (s, 2H), 4.34-4.25 (m, 6H), 3.79 (s, 2H), 3.76-3.74 (m, 4H), 3.64 (s, 2H), 2.11 (s, 3H), 1.36 (t, J=6.8 Hz, 3H). HRMS (ESI) m/z [M+H]$^+$ calcd for C$_{25}$H$_{31}$N$_{10}$O$_3$, 519.2575; found, 519.2593.

The following compounds in Table 1 were made by using synthetic routes described in Schemes 1-5 and procedures analogous to those in Examples 3-9.

TABLE 1

| | Table showing selected compounds | |
|---|---|---|
| Compound | Chemical Structure | Chemical Name and Analytical Data |
| 5b | | 4-(9-isopropyl-2-morpholino-9H-purin-6-yl)phenol. LC-MS m/z 340 ([M + H]⁺). ¹HNMR (CDCl₃) δ 8.56 (d, J = 8.8 Hz, 1H), 7.88 (s, 1H), 6.92 (d, J = 8.4 Hz, 1H), 4.80 (septet, J = 6.8 Hz, 1H), 3.95-3.85 (m, 8H), 1.61 (d, J = 6.8 Hz, 6H). |
| 5c | | (4-(9-isopropyl-2-morpholino-9H-purin-6-yl)phenyl)methanol. LC-MS m/z 354 ([M + H]⁺). ¹HNMR (CDCl₃) δ 8.72 (d, J = 8.4 Hz, 2H), 7.86 (s, 1H), 7.50 (d, J = 8.0 Hz, 2H), 4.82-4.76 (m, 3H), 3.95-3.84 (m, 8H), 1.89 (t, J = 6.0 Hz, 1H), 1.61 (d, J = 6.8 Hz, 6H). |
| 5d | | [4-(2-Chloro-9-isopropyl-9H-purin-6-yl)-phenyl]-methanol. LC-MS m/z 303; 305 ([M + H]⁺). ¹HNMR (CDCl₃) δ 8.79 (d, J = 8.4 Hz, 2H), 8.17 (s, 1H), 7.55 (d, J = 8.6 Hz, 2H), 5.02-4.93 (m, 1H), 4.80 (d, J = 5.9 Hz, 2H), 1.89 (t, J = 6.0 Hz, 1H), 1.64 (d, J = 6.8 Hz, 6H). |
| 5e | | (3-(2-chloro-9-isopropyl-9H-purin-6-yl)phenyl)methanol. LC-MS m/z 303; 305 ([M + H]⁺). ¹HNMR (CDCl₃) δ 8.73-8.70 (masked peak, 2H), 8.16 (s, 1H), 7.57-7.55 (masked peak, 2H), 5.00-4.94 (m, 1H), 4.83 (s, 2H), 1.66 (d, J = 6.8 Hz, 6H). |

TABLE 1-continued

| Compound | Chemical Structure | Chemical Name and Analytical Data |
|---|---|---|
| 5f | 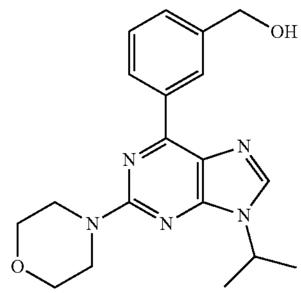 [SMILES: CC(C)n1cnc2c(-c3cccc(CO)c3)nc(N3CCOCC3)nc21] | [3-(9-Isopropyl-2-morpholin-4-yl-9H-purin-6-yl)-phenyl]-methanol. LC-MS m/z 354 ([M + H]+). 1HNMR (CDCl3) δ 8.68 (s, 1H), 8.61 (dt, J = 6.8, 2.0 Hz, 1H), 7.82 (s, 1H), 7.54-7.50 (m, 2H), 4.81 (s, 2H), 4.78 (masked peak, 1H), 3.94-3.83 (m, 8H), 1.59 (d, J = 6.8 Hz, 6H). |
| 11i | 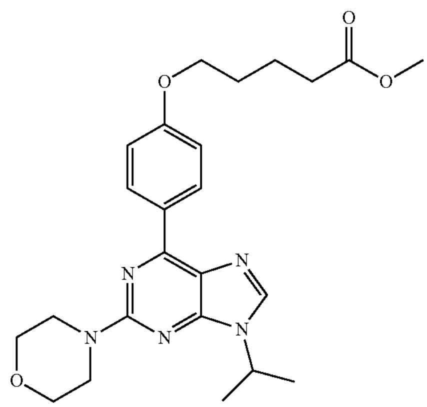 [SMILES: COC(=O)CCCCOc1ccc(-c2nc(N3CCOCC3)nc3c2ncn3C(C)C)cc1] | Methyl 5-(4-(9-isopropyl-2-morpholino-9H-purin-6-yl)phenoxy)pentanoate. LC-MS m/z 454 ([M + H]+). 1HNMR (CDCl3) δ 8.72 (dd, J = 9.2, 2.0 Hz, 2H), 7.84 (s, 1H), 7.01 (dd, J = 9.2, 2.0 Hz, 2H), 4.81-4.73 (m, 1H), 4.06 (t, J = 5.6 Hz, 2H), 3.94-3.83 (m, 8H), 3.68 (s, 3H), 2.42 (t, J = 7.0 Hz, 2H), 1.88-1.85 (m, 4H), 1.60 (d, J = 6.4 Hz, 6H). |
| 11h | 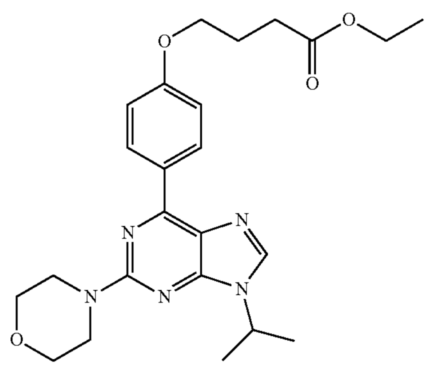 [SMILES: CCOC(=O)CCCOc1ccc(-c2nc(N3CCOCC3)nc3c2ncn3C(C)C)cc1] | Ethyl 4-(4-(9-isopropyl-2-morpholino-9H-purin-6-yl)phenoxy)butanoate. LC-MS m/z 454 ([M + H]+). 1HNMR (CDCl3) δ 8.72 (dd, J = 9.2, 2.0 Hz, 2H), 7.84 (s, 1H), 7.01 (dd, J = 8.8, 2.0 Hz, 2H), 4.81-4.75 (m, 1H), 4.15 (q, J = 7.2 Hz, 2H), 4.09 (t, J = 6.0 Hz, 2H), 3.94-3.83 (m, 8H), 2.54 (t, J = 7.2 Hz, 2H), 2.18-2.12 (m, 2H), 1.60 (d, J = 6.8 Hz, 6H), 1.27 (t, J = 7.2 Hz, 3H). |
| 11j | 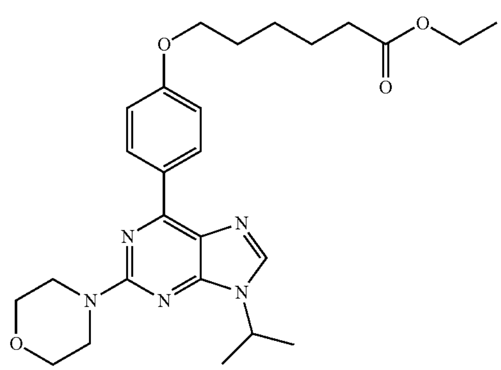 [SMILES: CCOC(=O)CCCCCOc1ccc(-c2nc(N3CCOCC3)nc3c2ncn3C(C)C)cc1] | Ethyl 6-(4-(9-isopropyl-2-morpholino-9H-purin-6-yl)phenoxy)hexanoate. LC-MS m/z 482 ([M + H]+). 1HNMR (CDCl3) δ 8.72 (dd, J = 9.2, 2.0 Hz, 2H), 7.84 (s, 1H), 7.01 (dd, J = 8.8, 2.0 Hz, 2H), 4.81-4.75 (m, 1H), 4.13 (q, J = 7.2 Hz, 2H), 4.04 (t, J = 6.4 Hz, 2H), 3.94-3.83 (m, 8H), 2.35 (t, J = 7.2 Hz, 2H), 1.88-1.81 (m, 2H), 1.76-1.68 (m, 2H), 1.60 (d, J = Hz, 6 H) 1.57-1.53 (m, 2H), 1.26 (t, J = 7.2 Hz, 3H). |

TABLE 1-continued

Table showing selected compounds

| Compound | Chemical Structure | Chemical Name and Analytical Data |
|---|---|---|
| 11k | 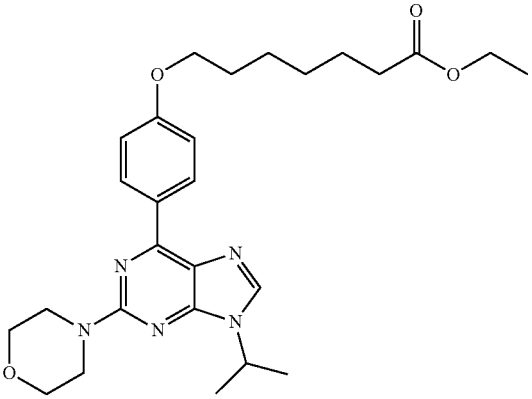 [SMILES: CCOC(=O)CCCCCCOc1ccc(-c2nc(N3CCOCC3)nc3c2ncn3C(C)C)cc1] | Ethyl 7-(4-(9-isopropyl-2-morpholino-9H-purin-6-yl)phenoxy)heptanoate. LC-MS m/z 496 ([M + H]$^+$). $^1$HNMR (CDCl3) δ 8.72 (dd, J = 8.8, 2.0 Hz, 2H), 7.84 (s, 1H), 7.01 (dd, J = 8.8, 2.0 Hz, 2H), 4.81-4.75 (m, 1H), 4.13 (q, J = 7.2 Hz, 2H), 4.04 (t, J = 6.4 Hz, 2H), 3.94-3.83 (m, 8H), 2.32 (t, J = 7.4 Hz, 2H), 1.86-1.79 (m, 2H), 1.71-1.64 (m, 2H), 1.60 (d, J = 6.8 Hz, 6H), 1.55-1.45 (m, 4H), 1.26 (t, J = 7.2 Hz, 3H). |
| 11l | 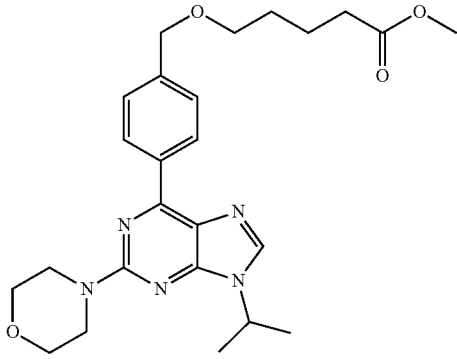 [SMILES: COC(=O)CCCCOCc1ccc(-c2nc(N3CCOCC3)nc3c2ncn3C(C)C)cc1] | Methyl 5-((4-(9-isopropyl-2-morpholino-9H-purin-6-yl)benzyl)oxy)pentanoate. LC-MS m/z 468 ([M + H]$^+$). $^1$HNMR (CDCl3) δ 8.70 (d, J = 8.4 Hz, 2H), 7.86 (s, 1H), 7.48 (d, J = 8.0 Hz, 2H), 4.82-4.76 (m, 1H), 4.58 (s, 2H), 3.95-3.84 (m, 8H), 3.68 (s, 3H), 3.50 (t, J = 6.0 Hz, 2H), 2.35 (t, J = 7.2 Hz, 2H), 1.77-1.60 (m, 10H). |
| 11m | 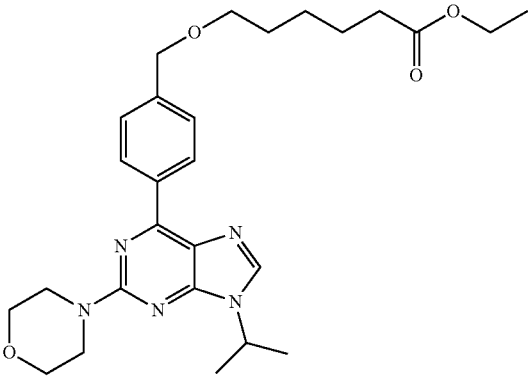 [SMILES: CCOC(=O)CCCCCOCc1ccc(-c2nc(N3CCOCC3)nc3c2ncn3C(C)C)cc1] | 6-[4-(9-Isopropyl-2-morpholin-4-yl-9H-purin-6-yl)-benzyloxy]-hexanoic acid ethyl ester. LC-MS m/z 496 ([M + H]$^+$). $^1$HNMR (CDCl3) δ 8.74 (d, J = 8.4 Hz, 2 H), 7.90 (s, 1H), 7.51 (d, J = 8.4 Hz, 2 H), 4.85-4.79 (m, 1H), 4.62 (s, 2 H), 4.16 (q, J = 7.1 Hz, 2H), 3.99-3.88 (m, 8H), 3.52 (t, J = 6.6 Hz, 2H), 2.35 (t, J = 7.5 Hz, 2H), 1.71-1.65 (masked peak, 4H), 1.65 (d, J = 6.8 Hz, 6H), 1.48-1.44 (m, 2H), 1.29 (t, J = 7.1 Hz, 3H). |
| 11n | 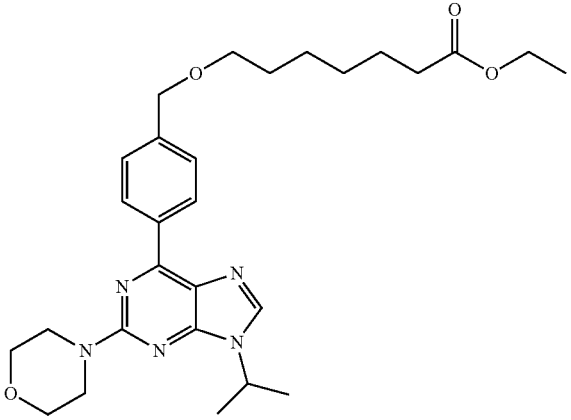 [SMILES: CCOC(=O)CCCCCCOCc1ccc(-c2nc(N3CCOCC3)nc3c2ncn3C(C)C)cc1] | 7-[4-(9-Isopropyl-2-morpholin-4-yl-9H-purin-6-yl)-benzyloxy]-heptanoic acid ethyl ester. LC-MS m/z 510 ([M + H]$^+$). $^1$HNMR (CDCl3) δ 8.70 (d, J = 8.3 Hz, 2H), 7.86 (s, 1H), 7.48 (d, J = 8.4 Hz, 2H), 4.82-4.78 (m, 1H), 4.59 (s, 2H), 4.12 (q, J = 7.1 Hz, 2H), 3.95-3.84 (m, 8H), 3.47 (t, J = 6.6 Hz, 2H), 2.29 (t, J = 7.5 Hz, 2H), 1.65-1.60 (masked peak, 8H), 1.40-1.34 (m, 6H), 1.25 (t, J = 7.2 Hz, 3H). |

TABLE 1-continued

Table showing selected compounds

| Compound | Chemical Structure | Chemical Name and Analytical Data |
|---|---|---|
| 11s | 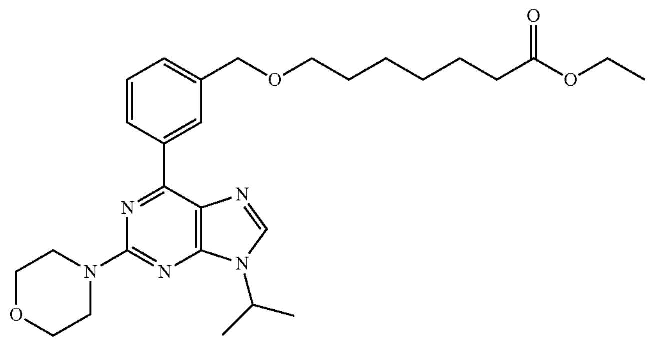 [SMILES: CCOC(=O)CCCCCCOCc1cccc(-c2nc(N3CCOCC3)nc3c2ncn3C(C)C)c1] | 7-[3-(9-Isopropyl-2-morpholin-4-yl-9H-purin-6-yl)-benzyloxy]-heptanoic acid ethyl ester. LC-MS m/z 510 ([M + H]+). ¹HNMR (CDCl₃) δ 8.71 (dt, J = 6.8, 2.0 Hz, 1H), 8.67 (s, 1H), 7.91 (s, 1H), 7.55-7.53 (m, 2H), 4.85-4.81 (m, 1H), 4.67 (s, 2H), 4.15 (q, J = 7.1 Hz, 2H), 3.99-3.88 (m, 8H), 3.54 (t, J = 6.6 Hz, 2H), 2.32 (t, J = 7.6 Hz, 2H), 1.66 (masked peak, 10H), 1.46-1.35 (m, 4H), 1.28 (t, J = 7.1 Hz, 3H). |
| 11w | 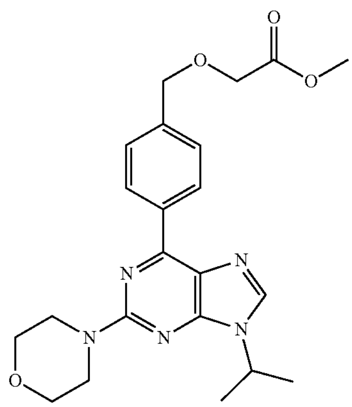 [SMILES: COC(=O)COCc1ccc(-c2nc(N3CCOCC3)nc3c2ncn3C(C)C)cc1] | Methyl 2-((4-(9-isopropyl-2-morpholino-9H-purin-6-yl)benzyl)oxy)acetate. LC-MS m/z 426 ([M + H]+). ¹HNMR (CDCl₃) δ 8.72 (d, J = 8.3 Hz, 2H), 7.87 (s, 1H), 7.51 (d, J = 8.4 Hz, 2H), 4.82-4.76 (m, 1H), 4.73 (s, 2H), 4.13 (s, 2H), 3.95-3.83 (m, 8H), 3.78 (s, 3H), 1.61 (d, J = 6.8 Hz, 6H). |
| 11p | 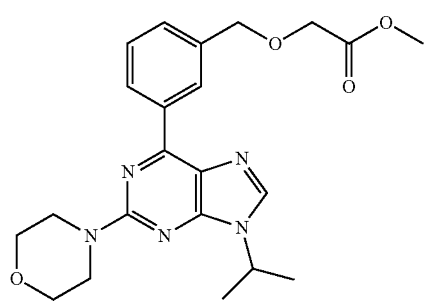 [SMILES: COC(=O)COCc1cccc(-c2nc(N3CCOCC3)nc3c2ncn3C(C)C)c1] | Methyl 2-((3-(9-isopropyl-2-morpholino-9H-purin-6-yl)benzyl)oxy)acetate. LC-MS m/z 426 ([M + H]+). ¹HNMR (CDCl₃) δ 8.73-8.70 (m, 1H), 8.65 (s, 1H), 7.87 (s, 1H), 7.53 (d, J = 5.2 Hz, 2H), 4.83-4.76 (masked peak, 3H), 4.15 (s, 2H), 3.95-3.84 (m, 8H), 3.77 (s, 3H), 1.61 (d, 6H). |
| 11x | 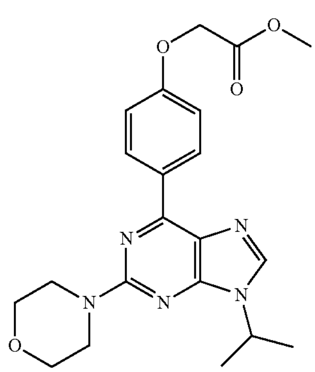 [SMILES: COC(=O)COc1ccc(-c2nc(N3CCOCC3)nc3c2ncn3C(C)C)cc1] | Methyl 2-(4-(9-isopropyl-2-morpholino-9H-purin-6-yl)phenoxy)acetate. LC-MS m/z 412 ([M + H]+). ¹HNMR (CDCl₃) δ 8.74 (dd, J = 6.9, 2.1 Hz, 2H), 7.84 (s, 1H), 7.04 (dd, J = 6.9, 2.1 Hz, 2H), 4.80-4.76 (m, 1H), 4.72 (s, 2H), 3.94-3.83 (m, 11H), 1.60 (d, J = 6.8 Hz, 6H). |

TABLE 1-continued

Table showing selected compounds

| Compound | Chemical Structure | Chemical Name and Analytical Data |
|---|---|---|
|  |  | Methyl 4-((4-(9-isopropyl-2-morpholino-9H-purin-6-yl)phenoxy)methyl)benzoate. LC-MS m/z 488 ([M + H]+). ¹HNMR (CDCl₃) δ 8.74 (d, J = 9.0 Hz, 2H), 8.06 (d, J = 8.4 Hz, 2H), 7.84 (s, 1H), 7.53 (d, J = 8.4 Hz, 2H), 7.09 (d, J = 9.0 Hz, 2H), 5.21 (s, 1H), 4.62-4.58 (m, 1H), 3.93-3.83 (m, 11H), 1.60 (d, J = 6.8 Hz, 6H). |
| 30b | 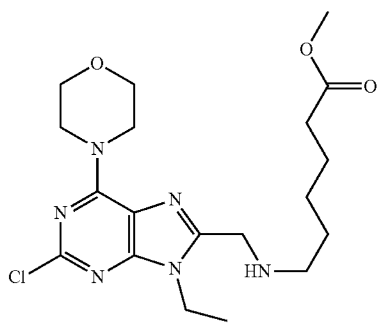 [SMILES: CCn1c(CNCCCCCC(=O)OC)nc2c(N3CCOCC3)nc(Cl)nc21] | Methyl 6-(((2-chloro-9-ethyl-6-morpholino-9H-purin-8-yl)methyl)amino)hexanoate. LC-MS m/z 425 ([M + H]+). ¹HNMR (CDCl₃) δ 4.34-4.18 (m, 6H), 3.95 (s, 2H), 3.83-3.80 (m, 4H), 3.67 (s, 3H), 2.70 (t, J = 7.1 Hz, 2H), 2.32 (t, J = 7.5 Hz, 2H), 1.69-1.63 (m, 2H), 1.59-1.51 (m, 2H), 1.44-1.34 (m, 5H). |
| 31a | 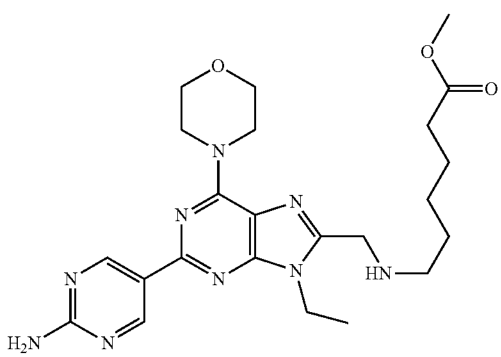 [SMILES: CCn1c(CNCCCCCC(=O)OC)nc2c(N3CCOCC3)nc(-c3cnc(N)nc3)nc21] | Methyl 6-(((2-(2-aminopyrimidin-5-yl)-9-ethyl-6-morpholino-9H-purin-8-yl)methyl)amino)hexanoate. LC-MS m/z 484 ([M + H]+). ¹HNMR (CDCl₃) δ 9.27 (s, 2H), 4.34-4.27 (m, 6H), 3.98 (s, 2H), 3.87-3.85 (m, 4H), 3.67 (s, 3H), 2.72 (t, J = 7.0 Hz, 2H), 2.32 (t, J = 7.4 Hz, 2H), 1.69-1.62 (m, 2H), 1.58-1.53 (m, 2H), 1.47-1.37 (m, 5H). |
| 33a | 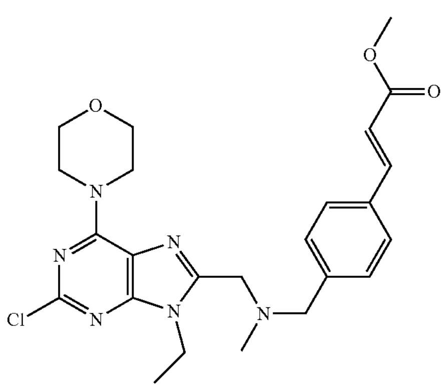 [SMILES: CCn1c(CN(C)Cc2ccc(/C=C/C(=O)OC)cc2)nc2c(N3CCOCC3)nc(Cl)nc21] | (E)-methyl 3-(4-((((2-chloro-9-ethyl-6-morpholino-9H-purin-8 yl)methyl)(methyl)amino)methyl)phenyl) acrylate. LC-MS m/z 485 ([M + H]+). ¹HNMR (CDCl₃) δ 7.68 (d, J = 16 Hz, 1H), 7.49 (d, J = 8.0 Hz, 2H), 7.33 (d, J = 8.0 Hz, 2H), 6.43 (d, J = 16 Hz, 1H), 4.27 (q, J = 7.2 Hz, 2H), 4.27 (masked peak, 4H), 3.81 (s, 3H), 3.83-3.80 (masked peak, 4H), 3.70 (s, 2H), 3.59 (s, 2H), 2.23 (s, 3H), 1.34 (t, J = 7.2 Hz, 3H). |

TABLE 1-continued

Table showing selected compounds

| Compound | Chemical Structure | Chemical Name and Analytical Data |
|---|---|---|
| 34a | 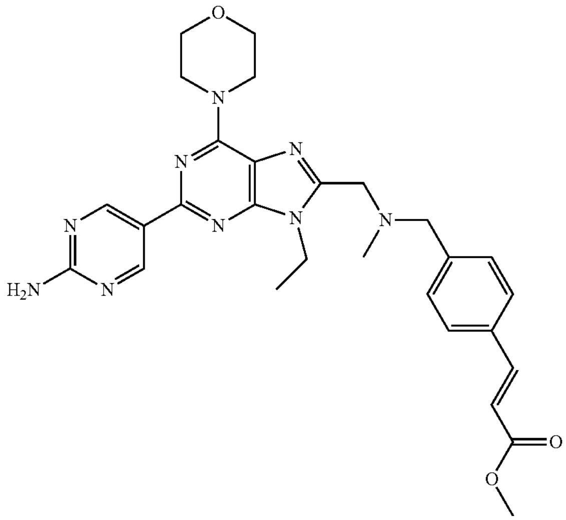 [SMILES: CCn1c(CN(C)Cc2ccc(/C=C/C(=O)OC)cc2)nc2c(N3CCOCC3)nc(-c3cnc(N)nc3)nc21] | (E)-methyl 3-(4-((((2-(2-aminopyrimidin-5-yl)-9-ethyl-6-morpholino-9H-purin-8-yl)methyl)(methyl)amino)methyl)phenyl)acrylate. LC-MS m/z 544 ([M + H]$^+$). $^1$HNMR (CDCl$_3$) δ 9.26 (s, 2H), 7.67 (d, J = 16 Hz, 1H), 7.48 (d, J = 8.0 Hz, 2H), 7.35 (d, J = 8.0 Hz, 2H), 6.42 (d, J = 16 Hz, 1H), 5.28 (s, 2H), 4.38-4.32 (m, 6H), 3.86 (t, J = 4.8 Hz, 4H), 3.81 (s, 3H), 3.74 (s, 2H), 3.61 (s, 2H), 2.25 (s, 3H), 1.40 (t, J = 7.2 Hz, 3H). |
| 34b | 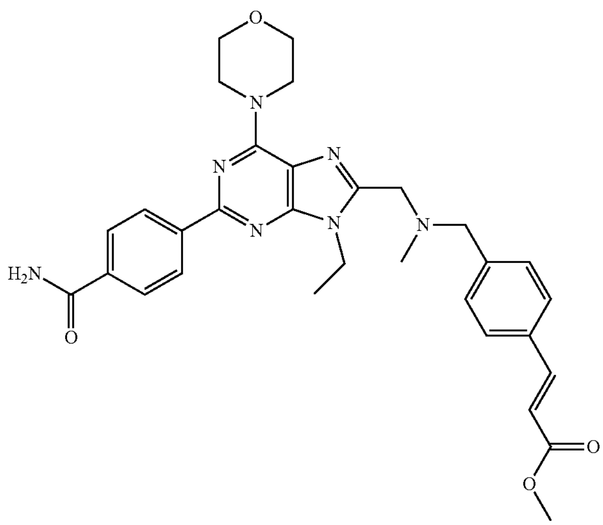 [SMILES: CCn1c(CN(C)Cc2ccc(/C=C/C(=O)OC)cc2)nc2c(N3CCOCC3)nc(-c3ccc(C(N)=O)cc3)nc21] | (E)-methyl 3-(4-((((2-(4-carbamoylphenyl)-9-ethyl-6-morpholino-9H-purin-8-yl)methyl)(methyl)amino)methyl)phenyl)acrylate. LC-MS m/z 570 ([M + H]$^+$). $^1$HNMR (CDCl$_3$) δ 8.56 (d, J = 8.4 Hz, 2H), 7.92 (d, J = 8.4 Hz, 2H), 7.72 (d, J = 16.0 Hz, 1H), 7.52 (d, J = 8.0 Hz, 2H), 7.39 (d, J = 8.0 Hz, 2H), 6.46 (d, J = 16.0 Hz, H), 4.46-4.40 (m, 6H), 3.92 (t, J = 4.8 Hz, 4H), 3.84 (s, 3H), 3.80 (s, 2H), 3.66 (s, 2H), 2.30 (s, 3H), 1.47 (t, J = 7.2 Hz, 3H). |
| 34c | 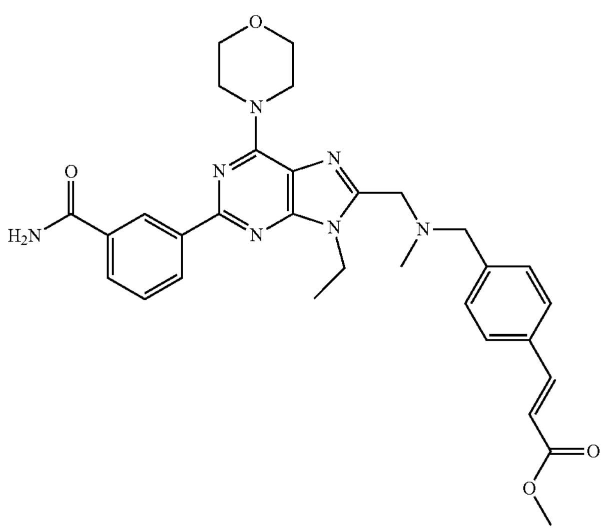 [SMILES: CCn1c(CN(C)Cc2ccc(/C=C/C(=O)OC)cc2)nc2c(N3CCOCC3)nc(-c3cccc(C(N)=O)c3)nc21] | (E)-methyl 3-(4-((((2-(3-carbamoylphenyl)-9-ethyl-6-morpholino-9H-purin-8-yl)methyl)(methyl)amino)methyl)phenyl)acrylate. LC-MS m/z 570 ([M + H]$^+$). $^1$HNMR (CDCl$_3$) δ 8.84 (t, J = 1.6 Hz, 1H), 8.62 (dt, J = 8.0, 1.2 Hz, 1H), 7.89 (dt, J = 7.6, 1.2 Hz, 1H), 7.67 (d, J = 16.0 Hz, 1H), 7.54 (t, J = 7.6 Hz, 1H), 7.47 (d, J = 8.0 Hz, 2H), 7.34 (d, J = 8.0 Hz, 2H), 6.42 (d, J = 16.0 Hz, 1H), 4.42-4.37 (m, 6H), 3.88 (t, J = 4.8 Hz, 4H), 3.80 (s, 3H), 3.76 (s, 2H), 3.62 (s, 2H), 2.27 (s, 3H), 1.43 (t, J = 7.2 Hz, 3H). |

TABLE 1-continued

Table showing selected compounds

| Compound | Chemical Structure | Chemical Name and Analytical Data |
|---|---|---|
| 34d | 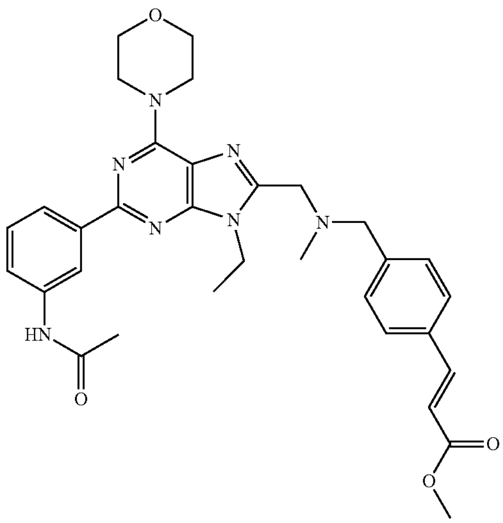 [SMILES: CCn1c(CN(C)Cc2ccc(/C=C/C(=O)OC)cc2)nc2c(N3CCOCC3)nc(-c3cccc(NC(C)=O)c3)nc21] | (E)-methyl 3-(4-((((2-(3-acetamidophenyl)-9-ethyl-6-morpholino-9H-purin-8-yl)methyl)(methyl)amino)methyl)phenyl)acrylate. LC-MS m/z 584 ([M + H]$^+$). $^1$HNMR (CDCl$_3$) δ 8.35 (t-like, 1H), 8.24 (d, J = 8.0 Hz, 1H), 7.87 (dd, J = 8.0, 1.6 Hz, 1H), 7.71 (d, J = 16.0 Hz, 1H), 7.51 (d, J = 8.4 Hz, 2H), 7.45 (t, J = 8.0 Hz, 1H), 7.38 (d, J = 8.4 Hz, 2H), 7.36 (overlapped peak, 1H), 6.46 (d, J = 16.0 Hz, 1H), 4.45-4.41 (m, 6H), 3.91 (t, J = 4.8 Hz, 4H), 3.85 (s, 3H), 3.79 (s, 2H), 3.65 (s, 2H), 2.30 (s, 3H), 2.26 (s, 3H), 1.46 (t, J = 7.2 Hz, 3H). |

The following hydroxamates were made by using synthetic routes described in Schemes 1-5 and procedures analogous to those in Examples 3-9. The compounds have been assigned an arbitrary identification number (denoted by EX) and the corresponding compounds found in the schemes in Example 2 as well as their structures and analytical data are shown below in Table 2.

TABLE 2

Table showing selected hydroxamate compounds

| EX | Compound | Chemical Structure | Chemical Name and Data |
|---|---|---|---|
| 1 | 12a | See FIG. 8, compound 12a | See Example 3, Step 4, compound 12a |
| 2 | 19f | See FIG. 9, compound 19f | See Example 4, Step 4, compound 19f |
| 3 | 8a | See FIG. 10, compound 8a | See Example 5, Step 3, compound 8a |
| 4 | 12f | See FIG. 11, compound 12f | See Example 6, Step 4, compound 12f |
| 5 | 17a | See FIG. 12, compound 17a | See Example 7, steps 5 and 6, compound 17a |
| 6 | 24a | See FIG. 13, compound 24a | See Example 8, Step 3, compound 24a |
| 7 | 35h | See FIG. 14, compound 35h | See Example 9, Step 5, compound 35h |
| 8 | 12b | 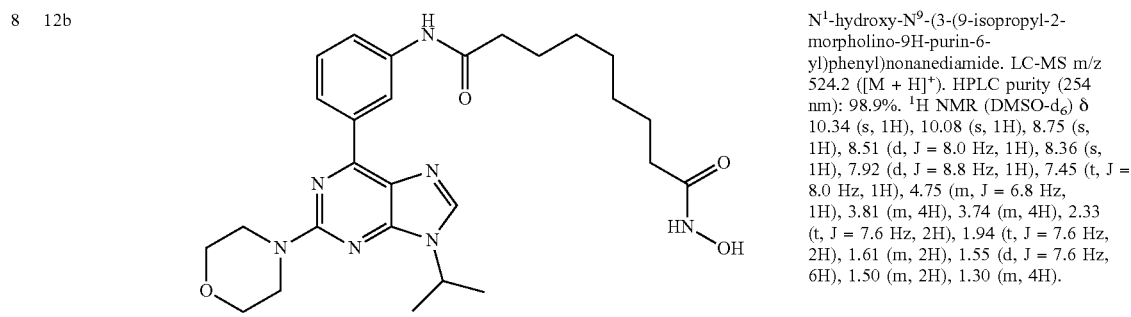 | N$^1$-hydroxy-N$^9$-(3-(9-isopropyl-2-morpholino-9H-purin-6-yl)phenyl)nonanediamide. LC-MS m/z 524.2 ([M + H]$^+$). HPLC purity (254 nm): 98.9%. $^1$H NMR (DMSO-d$_6$) δ 10.34 (s, 1H), 10.08 (s, 1H), 8.75 (s, 1H), 8.51 (d, J = 8.0 Hz, 1H), 8.36 (s, 1H), 7.92 (d, J = 8.8 Hz, 1H), 7.45 (t, J = 8.0 Hz, 1H), 4.75 (m, J = 6.8 Hz, 1H), 3.81 (m, 4H), 3.74 (m, 4H), 2.33 (t, J = 7.6 Hz, 2H), 1.94 (t, J = 7.6 Hz, 2H), 1.61 (m, 2H), 1.55 (d, J = 7.6 Hz, 6H), 1.50 (m, 2H), 1.30 (m, 4H). |

TABLE 2-continued

Table showing selected hydroxamate compounds

| EX | Compound | Chemical Structure | Chemical Name and Data |
|---|---|---|---|
| 9 | 12c | 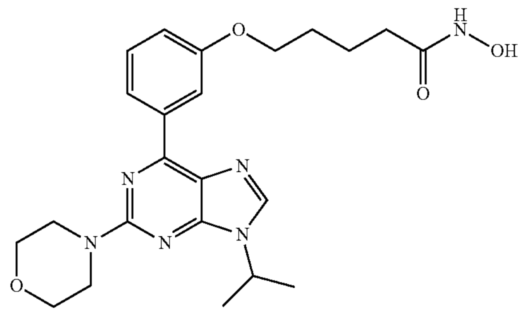 | $N^1$-hydroxy-$N^5$-(3-(9-isopropyl-2-morpholino-9H-purin-6-yl)phenyl)glutaramide. LC-MS m/z 468.1 ([M + H]$^+$). HPLC purity (254 nm): 94.0%. $^1$H NMR (DMSO-d$_6$) δ 10.41 (s, 1H), 10.11 (s, 1H), 8.75 (s, 1H), 8.51 (d, J = 8.0 Hz, 1H), 8.36 (s, 1H), 7.92 (d, J = 8.0 Hz, 1H), 7.45 (t, J = 8.0 Hz, 1H), 4.75 (m, J = 6.8 Hz, 1H), 3.81 (m, 4H), 3.74 (m, 4H), 2.36 (t, J = 7.6 Hz, 2H), 2.03 (t, J = 7.6 Hz, 2H), 1.83 (m, 2H), 1.54 (d, J = 6.8 Hz, 6H). |
| 10 | 12d | 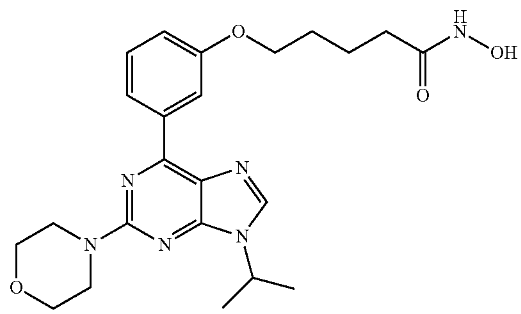 [SMILES: CC(C)n1cnc2c(-c3cccc(OCCCCC(=O)NO)c3)nc(N3CCOCC3)nc21] | N-hydroxy-5-(3-(9-isopropyl-2-morpholino-9H-purin-6-yl)phenoxy)pentanamide. LC-MS m/z 455.1 ([M + H]$^+$). HPLC purity (254 nm): 95.1%. $^1$H NMR (DMSO-d$_6$) δ 10.42 (s, 1H), 10.13 (s, 1H), 8.39 (s, 1H), 8.34 (s, 1H), 8.31 (d, J = 7.6 Hz, 1H), 7.45 (t, J = 8.0 Hz, 1H), 7.11 (dd, J = 8.4, 2.4 Hz, 1H), 4.75 (m, J = 6.8 Hz, 1H), 4.05 (m, 4H), 3.74 (m, 4H), 2.04 (t, J = 7.2 Hz, 2H), 1.72 (m, 4H), 1.54 (d, J = 6.8 Hz, 6H). |
| 11 | 12e | 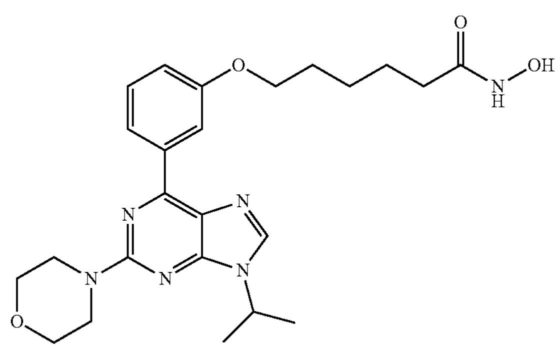 [SMILES: CC(C)n1cnc2c(-c3cccc(OCCCCCC(=O)NO)c3)nc(N3CCOCC3)nc21] | N-hydroxy-6-(3-(9-isopropyl-2-morpholino-9H-purin-6-yl)phenoxy)hexanamide. LC-MS m/z 469.1 ([M + H]$^+$). HPLC purity (254 nm): 97.0%. $^1$H NMR (DMSO-d$_6$) δ 10.40 (s, 1H), 10.16 (s, 1H), 8.41 (s, 1H), 8.35 (s, 1H), 8.31 (d, J = 7.6 Hz, 1H), 7.45 (t, J = 8.0 Hz, 1H), 7.10 (dd, J = 8.0, 2.4 Hz, 1H), 4.75 (m, J = 6.8 Hz, 1H), 4.03 (m, 4H), 3.79 (m, 4H), 1.99 (t, J = 7.2 Hz, 2H), 1.76 (m, 4H), 1.59 (m, 2H), 1.54 (d, J = 6.8 Hz, 6H), 1.43 (m, 2H). |
| 12 | 12g | 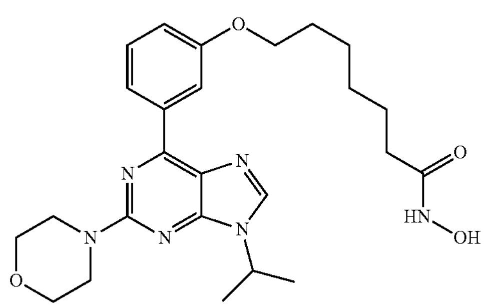 [SMILES: CC(C)n1cnc2c(-c3cccc(OCCCCCCC(=O)NO)c3)nc(N3CCOCC3)nc21] | N-hydroxy-7-(3-(9-isopropyl-2-morpholino-9H-purin-6-yl)phenoxy)heptanamide. LC-MS m/z 483.2 ([M + H]$^+$). HPLC purity (254 nm): 98.8%. $^1$H NMR (DMSO-d$_6$) δ 10.37 (s, 1H), 9.75 (s, 1H), 8.39 (s, 1H), 8.35 (s, 1H), 8.31 (d, J = 7.2 Hz, 1H), 7.45 (t, J = 8.0 Hz, 1H), 7.10 (dd, J = 8.4, 2.4 Hz, 1H), 4.75 (m, J = 6.8 Hz, 1H), 4.03 (t, J = 6.4 Hz, 2H), 3.80 (m, 4H), 3.74 (m, 4H), 1.96 (t, J = 7.2 Hz, 2H), 1.75 (m, 2H), 1.55 (d, J = 6.8 Hz, 6H), 1.52 (m, 2H), 1.43 (m, 2H), 1.32 (m, 2H). |

TABLE 2-continued

Table showing selected hydroxamate compounds

| EX | Compound | Chemical Structure | Chemical Name and Data |
|---|---|---|---|
| 13 | 12h | 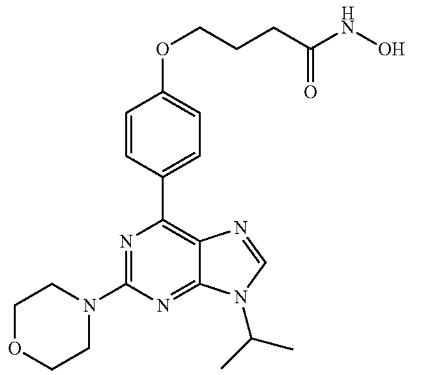 [SMILES: CC(C)n1cnc2c(-c3ccc(OCCCC(=O)NO)cc3)nc(N3CCOCC3)nc21] | N-hydroxy-4-(4-(9-isopropyl-2-morpholino-9H-purin-6-yl)phenoxy)butanamide. LC-MS m/z 441 ([M + H]$^+$). $^1$HNMR (CD$_3$OD) δ 8.72 (s, 1H), 8.39 (d, J = 8.4 Hz, 2H), 7.12 (d, J = 8.4 Hz, 2H), 4.96-4.85 (masked peak, 1H), 4.14 (t, J = 6.0 Hz, 2H), 3.96-3.82 (m, 8H), 2.36 (br s, 2H), 2.18-2.11 (m, 2H), 1.67 (d, J = 6.8 Hz, 6H). HRMS (ESI) m/z [M + H]$^+$ calcd for C$_{22}$H$_{29}$N$_6$O$_4$, 441.2245; found, 441.2260. |
| 14 | 12i | 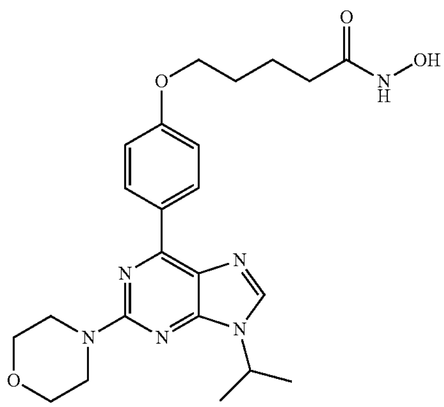 [SMILES: CC(C)n1cnc2c(-c3ccc(OCCCCC(=O)NO)cc3)nc(N3CCOCC3)nc21] | N-hydroxy-5-(4-(9-isopropyl-2-morpholino-9H-purin-6-yl)phenoxy)pentanamide. LC-MS m/z 455 ([M + H]$^+$). $^1$HNMR (CD$_3$OD) δ 8.50 (d, J = 8.4 Hz, 2H), 8.41 (s, 1H), 7.08 (d, J = 8.4 Hz, 2H), 4.94-4.84 (masked peak, 1H), 4.11 (t, J = 5.2 Hz, 2H), 3.94-3.81 (m, 8H), 2.21 (br s, 2H), 1.86 (br s, 4H), 1.65 (d, J = 6.8 Hz, 6H). |
| 15 | 12j | 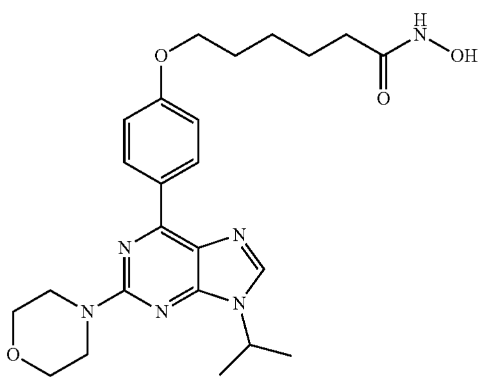 [SMILES: CC(C)n1cnc2c(-c3ccc(OCCCCCC(=O)NO)cc3)nc(N3CCOCC3)nc21] | N-hydroxy-6-(4-(9-isopropyl-2-morpholino-9H-purin-6-yl)phenoxy)hexanamide. LC-MS m/z 469 ([M + H]$^+$). $^1$HNMR (CD$_3$OD) δ 8.65 (br s, 1H), 8.24 (d, J = 6.0 Hz, 2H), 6.98 (d, J = 7.2 Hz, 2H), 4.87 (masked peak, 1H), 3.98 (t, J = 6.2 Hz, 2H), 3.84-3.69 (m, 8H), 2.06 (br s, 2H), 1.78-1.73 (m, 2H), 1.63-1.59 (m, 2H), 1.55 (d, J = 6.8 Hz, 6H) 1.48-1.44 (m, 2H). |
| 16 | 12k | 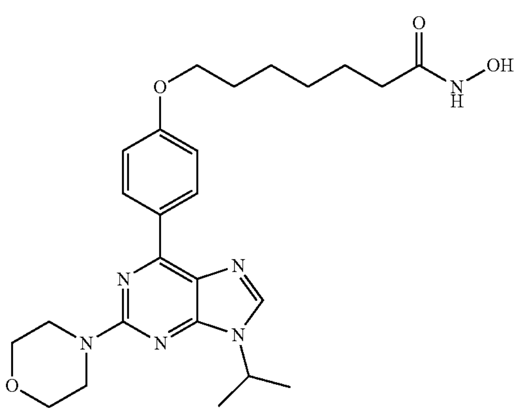 [SMILES: CC(C)n1cnc2c(-c3ccc(OCCCCCCC(=O)NO)cc3)nc(N3CCOCC3)nc21] | N-hydroxy-7-(4-(9-isopropyl-2-morpholino-9H-purin-6-yl)phenoxy)heptanamide. LC-MS m/z 483 ([M + H]$^+$). $^1$HNMR (CD$_3$OD) δ 8.62 (br s, 1H), 8.25 (d, J = 6.4 Hz, 2H), 6.98 (d, J = 7.2 Hz, 2H), 4.78 (masked peak, 1H), 3.98 (t, J = 6.4 Hz, 2H), 3.84-3.70 (m, 8H), 2.02 (br s, 2H), 1.76-1.70 (m, 2H), 1.55 (d, J = 6.8 Hz, 8H), 1.47-1.42 (m, 2H), 1.40-1.34 (m, 2H). |

TABLE 2-continued

Table showing selected hydroxamate compounds

| EX | Compound | Chemical Structure | Chemical Name and Data |
|----|----------|--------------------|-----------------------|
| 17 | 8b | 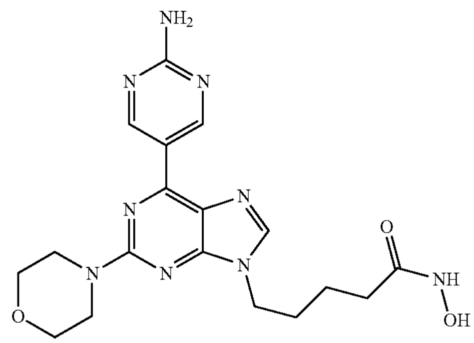 [SMILES: Nc1ncc(-c2nc(N3CCOCC3)nc3c2ncn3CCCCC(=O)NO)cn1] | 5-(6-(2-aminopyrimidin-5-yl)-2-morpholino-9H-purin-9-yl)-N-hydroxypentanamide. LC-MS m/z 414.1 ([M + H]$^+$). HPLC purity (254 nm): 98.6%. $^1$H NMR (DMSO-d$_6$) δ 10.34 (s, 1H), 9.54 (s, 2H), 8.25 (s, 1H), 7.45 (s, 2H), 4.14 (t, J = 6.4 Hz, 2H), 3.79 (m, 4H), 3.72 (m, 4H), 1.99 (t, J = 7.2 Hz, 2H), 1.82 (m, 2H), 1.47 (m, 2H). |
| 18 | 8c | 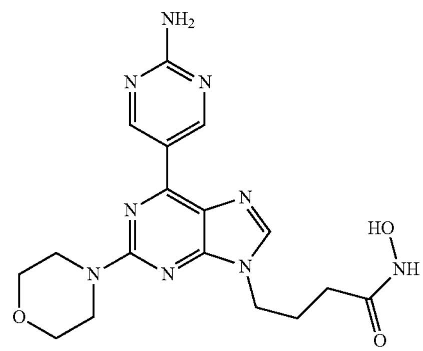 [SMILES: Nc1ncc(-c2nc(N3CCOCC3)nc3c2ncn3CCCC(=O)NO)cn1] | 4-(6-(2-aminopyrimidin-5-yl)-2-morpholino-9H-purin-9-yl)-N-hydroxybutanamide. LC-MS m/z 400.1 ([M + H]$^+$). HPLC purity (254 nm): 99.9%. $^1$H NMR (DMSO-d$_6$) δ 10.34 (s, 1H), 9.55 (s, 2H), 8.25 (s, 1H), 7.50 (s, 2H), 4.14 (t, J = 6.4 Hz, 2H), 3.79 (m, 4H), 3.72 (m, 4H), 2.10 (m, 2H), 1.95 (m, 2H). |
| 19 | 8d | 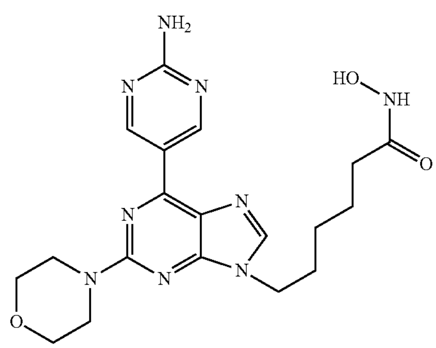 [SMILES: Nc1ncc(-c2nc(N3CCOCC3)nc3c2ncn3CCCCCC(=O)NO)cn1] | 6-(6-(2-aminopyrimidin-5-yl)-2-morpholino-9H-purin-9-yl)-N-hydroxyhexanamide. LC-MS m/z 428.1 ([M + H]$^+$). HPLC purity (254 nm): 95.8%. $^1$H NMR (DMSO-d$_6$) δ 10.32 (s, 1H), 9.54 (s, 2H), 8.24 (s, 1H), 7.42 (s, 2H), 4.12 (t, J = 6.8 Hz, 2H), 3.79 (m, 4H), 3.72 (m, 4H), 1.95 (t, J = 7.6 Hz, 2H), 1.82 (m, 2H), 1.54 (m, 2H), 1.23 (m, 2H). |
| 20 | 12l | 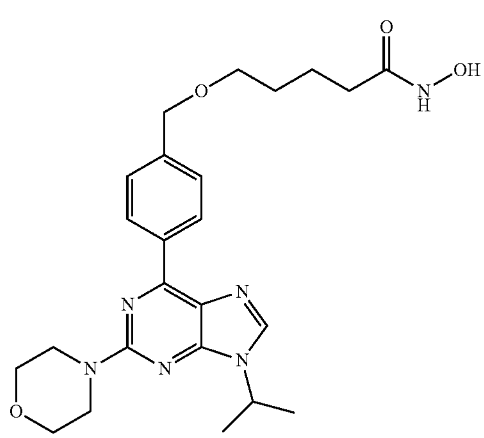 [SMILES: CC(C)n1cnc2c(-c3ccc(COCCCCC(=O)NO)cc3)nc(N3CCOCC3)nc21] | N-hydroxy-5-((4-(9-isopropyl-2-morpholino-9H-purin-6-yl)benzyl)oxy)pentanamide. LC-MS m/z 469 ([M + H]$^+$). $^1$HNMR (DMSO-d$_6$) δ 10.37 (s, 1H), 8.77 (d, J = 8.0 Hz, 2H), 8.38 (s, 1H), 7.50 (d, J = 8.0 Hz, 2H), 4.80-4.73 (m, 1H), 4.55 (s, 2H), 3.84-3.74 (m, 8H), 3.47 (t, J = 6.0 Hz, 2H), 1.99 (t, J = 6.0 Hz, 2H), 1.62 (masked peak, 10H). |

TABLE 2-continued

Table showing selected hydroxamate compounds

| EX | Compound | Chemical Structure | Chemical Name and Data |
|---|---|---|---|
| 21 | 12m | 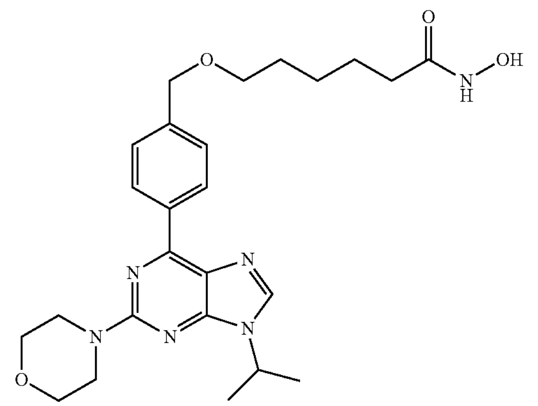 [SMILES: CC(C)n1cnc2c(-c3ccc(COCCCCCC(=O)NO)cc3)nc(N3CCOCC3)nc21] | N-hydroxy-6-((4-(9-isopropyl-2-morpholino-9H-purin-6-yl)benzyl)oxy)hexanamide. LC-MS m/z 483 ([M + H]$^+$). $^1$HNMR (DMSO-d$_6$) δ 10.37 (s, 1H), 8.76 (d, J = 8.0 Hz, 2H), 8.40 (s, 1H), 7.50 (d, J = 8.0 Hz, 2H), 4.78-4.73 (m, 1H), 4.55 (s, 2H), 3.84-3.74 (m, 8H), 3.47 (t, J = 6.0 Hz, 2H), 1.96 (t, J = 8.0 Hz, 2H), 1.57 (masked peak, 10H), 1.34-1.30 (m, 2H). HRMS (ESI) m/z [M + H]$^+$ calcd for C$_{25}$H$_{35}$N$_6$O$_4$, 483.2714; found, 483.2738. |
| 22 | 12n | 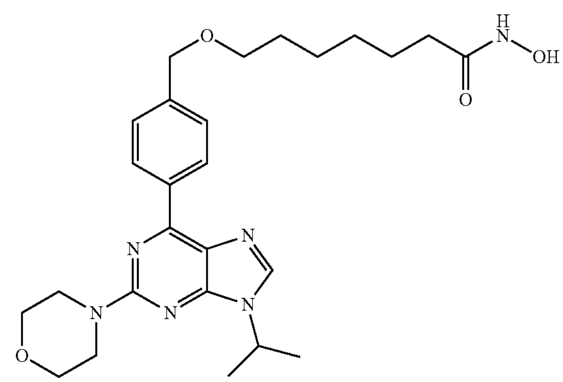 [SMILES: CC(C)n1cnc2c(-c3ccc(COCCCCCCC(=O)NO)cc3)nc(N3CCOCC3)nc21] | N-hydroxy-7-((4-(9-isopropyl-2-morpholino-9H-purin-6-yl)benzyl)oxy)heptanamide. LC-MS m/z 497 ([M + H]$^+$). $^1$HNMR (DMSO-d$_6$) δ 10.37 (s, 1H), 8.76 (d, J = 8.0 Hz, 2H), 8.40 (s, 1H), 7.50 (d, J = 8.0 Hz, 2H), 4.80-4.73 (m, 1H), 4.55 (s, 2H), 3.84-3.74 (m, 8H), 3.47 (t, J = 6.0 Hz, 2H), 1.95 (t, J = 6.0 Hz, 2H), 1.55 (masked peak,10 H), 1.46-1.28 (m, 4H). |
| 23 | 12o | 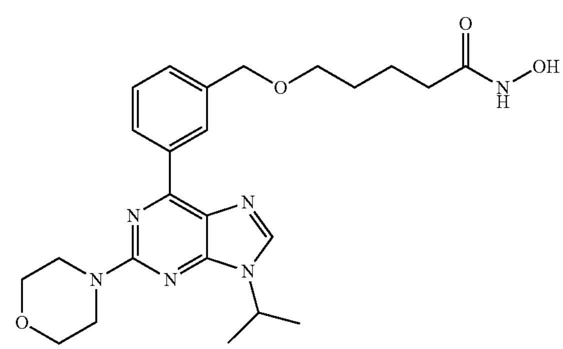 [SMILES: CC(C)n1cnc2c(-c3cccc(COCCCCC(=O)NO)c3)nc(N3CCOCC3)nc21] | N-hydroxy-5-((3-(9-isopropyl-2-morpholino-9H-purin-6-yl)benzyl)oxy)pentanamide. LC-MS m/z 469 ([M + H]$^+$). $^1$HNMR (DMSO-d$_6$) δ 10.29 (s, 1H), 8.65-8.62 (masked peak, 2H), 8.31 (s, 1H), 7.49-7.40 (m, 2H), 4.72-4.66 (m, 1H), 4.50 (s, 2H), 3.77-3.66 (m, 8H), 3.41 (t, J = 6.0 Hz, 2H), 1.90 (t, J = 7.0 Hz, 2H), 1.50 (masked peak, 10 H). HRMS (ESI) m/z [M + H]$^+$ calcd for C$_{24}$H$_{33}$N$_6$O$_4$, 469.2558; found, 469.2570. |
| 24 | 12p | 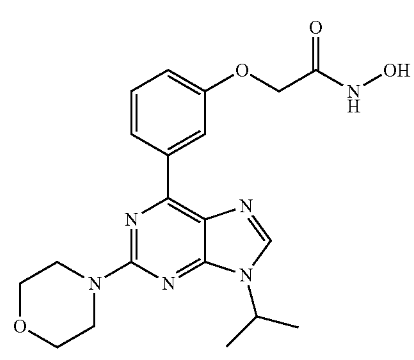 [SMILES: CC(C)n1cnc2c(-c3cccc(OCC(=O)NO)c3)nc(N3CCOCC3)nc21] | N-hydroxy-2-(3-(9-isopropyl-2-morpholino-9H-purin-6-yl)phenoxy)acetamide. LC-MS m/z 413.1 ([M + H]$^+$). HPLC purity (254 nm): 97.9%. $^1$H NMR (DMSO-d$_6$) δ 10.95 (s, 1H), 8.45 (d, J = 8.0Hz, 1H), 8.42 (s, 1H), 8.32 (s, 1H), 7.49 (t, J = 8.0 Hz, 1H), 7.14 (dd, J = 8.4, 2.4 Hz, 1H), 4.76 (m, J = 6.8 Hz, 1H), 4.56 (s, 2H), 3.82 (m, 4H), 3.75 (m, 4H), 1.55 (d, J = 6.8 Hz, 6H). |

TABLE 2-continued

Table showing selected hydroxamate compounds

| EX | Compound | Chemical Structure | Chemical Name and Data |
|----|----------|--------------------|-----------------------|
| 25 | 12q | 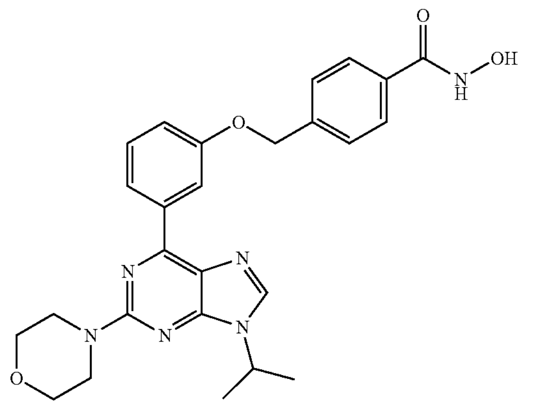 [SMILES: CC(C)n1cnc2c(-c3cccc(OCc4ccc(C(=O)NO)cc4)c3)nc(N3CCOCC3)nc21] | N-hydroxy-4-((3-(9-isopropyl-2-morpholino-9H-purin-6-yl)phenoxy)methyl)benzamide. LC-MS m/z 489.2 ([M + H]$^+$). HPLC purity (254 nm): 91.2%. $^1$H NMR (DMSO-d$_6$) δ 11.25 (s, 1H), 8.43 (d, J = 7.6 Hz, 1H), 8.39 (s, 1H), 8.35 (m, 1H), 7.80 (d, J = 8.0 Hz, 1H), 7.58 (d, J = 8.0 Hz, 1H), 7.49 (t, J = 8.0 Hz, 1H), 7.21 (dd, J = 7.8, 2.2 Hz, 1H), 5.28 (s, 2H), 4.76 (m, J = 6.8 Hz, 1H), 3.77 (m, 4H), 3.74 (m, 4H), 1.55 (d, J = 6.8 Hz, 6H). HRMS (ESI) m/z [M + H]$^+$ calcd for C$_{26}$H$_{28}$N$_6$O$_4^+$, 489.2245; found, 489.2250. |
| 26 | 12r | 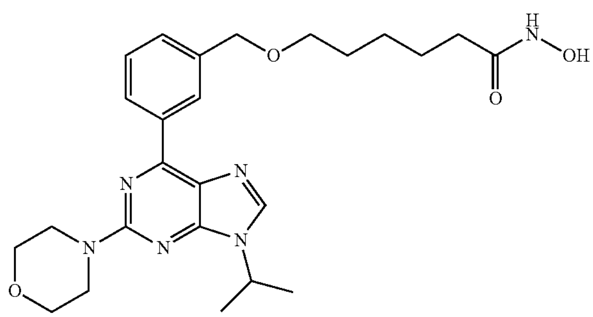 [SMILES: CC(C)n1cnc2c(-c3cccc(COCCCCCC(=O)NO)c3)nc(N3CCOCC3)nc21] | N-hydroxy-6-((3-(9-isopropyl-2-morpholino-9H-purin-6-yl)benzyl)oxy)hexanamide. LC-MS m/z 483 ([M + H]$^+$). $^1$HNMR (DMSO-d$_6$) δ 10.34 (s, 1H), 8.72-8.70 (masked peak, 2H), 8.39 (s, 1H), 7.56-7.48 (m, 2H), 4.82-4.76 (m, 1H), 4.58 (s, 2H), 3.84-3.74 (m, 8H), 3.48 (t, J = 6.4 Hz, 2H), 1.95 (t, J = 7.2 Hz, 2H), 1.60-1.48 (masked peak, 10 H), 1.37-1.33 (m, 2H). |
| 27 | 12s | 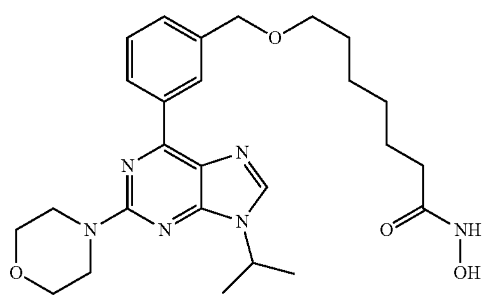 [SMILES: CC(C)n1cnc2c(-c3cccc(COCCCCCCC(=O)NO)c3)nc(N3CCOCC3)nc21] | N-hydroxy-7-((3-(9-isopropyl-2-morpholino-9H-purin-6-yl)benzyl)oxy)heptanamide. LC-MS m/z 497 ([M + H]$^+$). $^1$HNMR (DMSO-d$_6$) δ 10.34 (br s, 1H), 8.73-8.69 (masked peak, 2H), 8.40 (s, 1H), 7.56-7.48 (m, 2H), 4.80-4.74 (m, 1H), 4.57 (s, 2H), 3.84-3.74 (m, 8H), 3.48 (t, J = 6.8 Hz, 2H), 1.94 (t, J = 7.2 Hz, 2H), 1.56 (d, J = 6.8 Hz, 6H), 1.57-1.45 (masked peak, 4 H), 1.37-1.31 (m, 4H). |
| 28 | 25a | 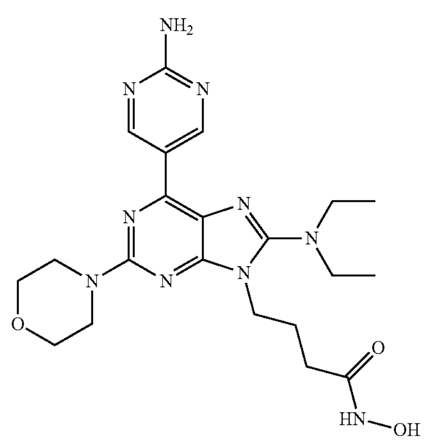 [SMILES: CCN(CC)c1nc2c(-c3cnc(N)nc3)nc(N3CCOCC3)nc2n1CCCC(=O)NO] | 4-(6-(2-aminopyrimidin-5-yl)-8-(diethylamino)-2-morpholino-9H-purin-9-yl)-N-hydroxybutanamide. LC-MS m/z 471.1 ([M + H]$^+$). HPLC purity (254 nm): 95.5%. $^1$H NMR DMSO-d$_6$) δ 10.40 (s, 1H), 9.47 (s, 2H), 7.56 (s, 2H), 4.01 (m, 1H), 3.72 (m, 8H), 3.38 (m, 4H), 1.99 (m, 4H), 1.17 (m, 6H). |

TABLE 2-continued

Table showing selected hydroxamate compounds

| EX | Compound | Chemical Structure | Chemical Name and Data |
|---|---|---|---|
| 29 | 12t | 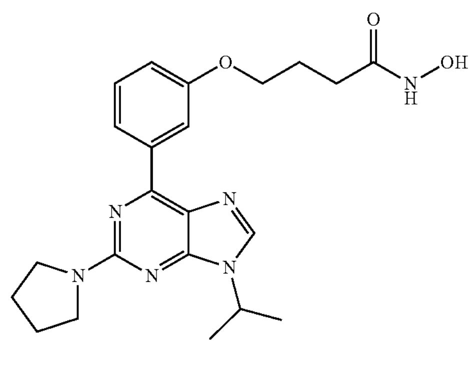 [SMILES: CC(C)n1cnc2c(-c3cccc(OCCCC(=O)NO)c3)nc(N3CCCC3)nc21] | N-hydroxy-4-(3-(9-isopropyl-2-(pyrrolidin-1-yl)-9H-purin-6-yl)phenoxy)butanamide. LC-MS m/z 425.2 ([M + H]$^+$). HPLC purity (254 nm): 98.8%. $^1$H NMR (DMSO-d$_6$) δ 10.45 (s, 1H), 8.33-8.36 (m, 3H), 7.46 (t, J = 8.0 Hz, 1H), 7.11 (m, 1H), 4.73 (m, J = 6.8 Hz, 1H), 4.06 (t, J = 6.4 Hz, 2H), 2.19 (t, J = 6.8 Hz, 2H), 1.98 (m, 6H), 1.56 (d, J = 6.8 Hz, 6H). HRMS (ESI) m/z [M + H]$^+$ calcd for C$_{22}$H$_{28}$N$_6$O$_3$, 425.2296; found, 425.2305. |
| 30 | 12u | 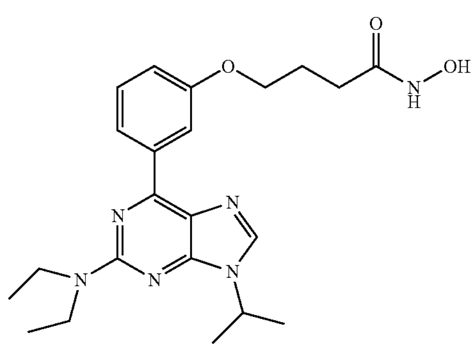 [SMILES: CCN(CC)c1nc(-c2cccc(OCCCC(=O)NO)c2)c2ncn(C(C)C)c2n1] | 4-(3-(2-(diethylamino)-9-isopropyl-9H-purin-6-yl)phenoxy)-N-hydroxybutanamide. LC-MS m/z 427.1 ([M + H]$^+$). HPLC purity (254 nm): 98.2%. $^1$H NMR (DMSO-d$_6$) δ 10.19 (s, 1H), 8.32 (s, 1H), 8.23-8.25 (m, 2H), 7.46 (t, J = 8.0 Hz, 1H), 7.11 (dd-like, J = 8.0 Hz, 1H), 4.71 (m, J = 6.8 Hz, 1H), 4.04 (m, 2H), 3.89 (m, 4H), 2.17 (t, J = 6.8 Hz, 2H), 1.98 (m, 2H), 1.56 (d, J = 6.8 Hz, 6H), 1.20 (t, J = 8.0, 6H). |
| 31 | 12v | 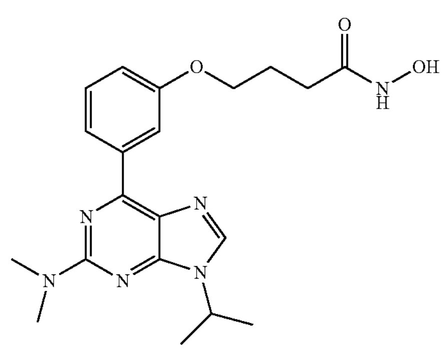 [SMILES: CC(C)n1cnc2c(-c3cccc(OCCCC(=O)NO)c3)nc(N(C)C)nc21] | 4-(3-(2-(dimethylamino)-9-isopropyl-9H-purin-6-yl)phenoxy)-N-hydroxybutanamide. LC-MS m/z 399.1 ([M + H]$^+$). HPLC purity (254 nm): 97.8%. $^1$H NMR (DMSO-d$_6$) δ 8.37-8.40 (m, 3H), 7.52 (t, J = 8.0 Hz, 1H), 7.16 (dt-like, J = 8.8 Hz, 1H), 4.79 (m, J = 6.8 Hz, 1H), 4.10 (m, 2H), 3.30 (s, 6H), 2.24 (m, 2H), 2.05 (m, 2H), 1.60 (d, J = 6.8 Hz, 6H). HRMS (ESI) m/z [M + H]$^+$ calcd for C$_{20}$H$_{26}$N$_6$O$_3$, 399.2140; found, 399.2137. |
| 32 | 12w | 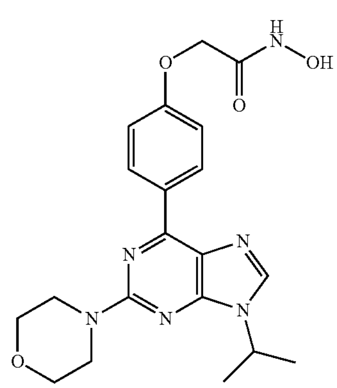 | N-hydroxy-2-((4-(9-isopropyl-2-morpholino-9H-purin-6-yl)benzyl)oxy)acetamide. LC-MS m/z 427 ([M + H]$^+$). $^1$HNMR (DMSO-d$_6$) δ 10.72 (br s, 1H), 8.77 (d, J = 8.4 Hz, 2H), 8.40 (s, 1H), 7.55 (d, J = 8.4 Hz, 2H), 4.80-4.73 (m, 1H), 4.63 (s, 2H), 3.94 (s, 2H), 3.84-3.74 (m, 8H), 1.55 (d, J = 6.8 Hz, 6H). |

TABLE 2-continued

Table showing selected hydroxamate compounds

| EX | Compound | Chemical Structure | Chemical Name and Data |
|---|---|---|---|
| 33 | 12x | 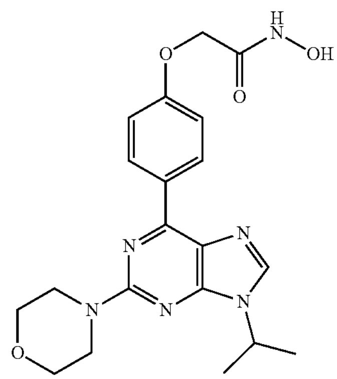 [SMILES: CC(C)n1cnc2c(-c3ccc(OCC(=O)NO)cc3)nc(N3CCOCC3)nc21] | N-hydroxy-2-(4-(9-isopropyl-2-morpholino-9H-purin-6-yl)phenoxy)acetamide. LC-MS m/z 413 ([M + H]$^+$). $^1$HNMR (DMSO-d$_6$) δ 10.92 (br s, 1H), 8.78 (d, J = 8.8 Hz, 2H), 8.35 (s, 1H), 7.13 (d, J = 8.8 Hz, 2H), 4.80-4.72 (m, 1H), 4.58 (s, 2H), 3.83- 3.73 (m, 8H), 1.55 (d, J = 6.8 Hz, 6H). |
| 34 | 12y | 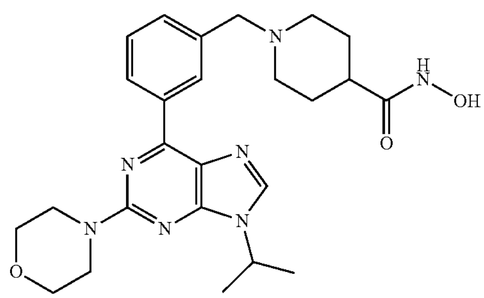 [SMILES: CC(C)n1cnc2c(-c3cccc(CN4CCC(C(=O)NO)CC4)c3)nc(N3CCOCC3)nc21] | N-hydroxy-1-(3-(9-isopropyl-2-morpholino-9H-purin-6-yl)benzyl)piperidine-4-carboxamide. LC-MS m/z 480 ([M + H]$^+$). $^1$HNMR (DMSO-d$_6$) δ 10.63 (br s, 1H), 9.79 (br s, 1H), 8.91-8.88 (m, 1H), 8.80 (s, 1H), 8.41 (s, 1H), 7.68 (d, J = 4.8 Hz, 2H), 4.82-4.75 (m, 1H), 4.45 (br s, 2H), 3.85-3.76 (m, 8H), 3.46-3.43 (m, 2H), 3.04 (br s, 2H), 2.29-2.26 (m, 1H), 1.92-1.85 (m, 4H), 1.56 (d, J = 6.4 Hz, 6H). HRMS (ESI) m/z [M + H]$^+$ calcd for C$_{25}$H$_{34}$N$_7$O$_3$, 480.2718; found, 480.2716 |
| 35 | 12z | 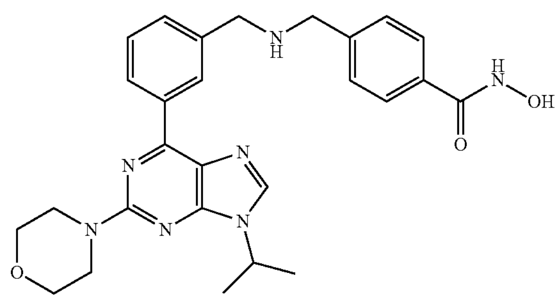 [SMILES: CC(C)n1cnc2c(-c3cccc(CNCc4ccc(C(=O)NO)cc4)c3)nc(N3CCOCC3)nc21] | N-hydroxy-4-(((3-(9-isopropyl-2-morpholino-9H-purin-6-yl)benzyl)amino)methyl)benzamide. LC-MS m/z 502 ([M + H]$^+$). $^1$HNMR (DMSO-d$_6$) δ 11.32 (br s, 1H), 8.91 (d, J = 8.8 Hz, 1H), 8.81 (s, 1H), 8.41 (s, 1H), 7.84 (d, J = 8.4 Hz, 2H), 7.68-7.60 (m, 4H), 4.81-4.74 (m, 1H), 4.35-4.31 (m, 4H), 3.85-3.76 (m, 8H), 1.56 (d, J = 6.4 Hz, 6H). HRMS (ESI) m/z [M + H]$^+$ calcd for C$_{27}$H$_{32}$N$_7$O$_3$, 502.2561; found, 502.2570. |
| 36 | 12aa | 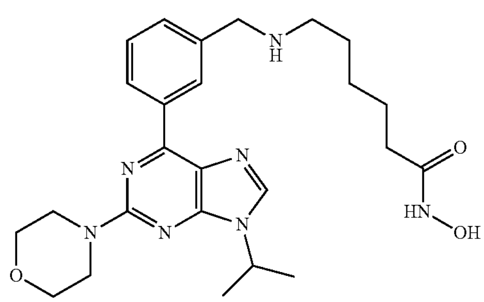 [SMILES: CC(C)n1cnc2c(-c3cccc(CNCCCCCC(=O)NO)c3)nc(N3CCOCC3)nc21] | N-hydroxy-6-((3-(9-isopropyl-2-morpholino-9H-purin-6-yl)benzyl)amino)hexanamide. LC-MS m/z 482 ([M + H]$^+$). $^1$HNMR (DMSO-d$_6$) δ 10.42 (br s, 1H), 9.02 (br s, 2H), 8.90 (dt, J = 7.2, 1.6 Hz, 1H), 8.79 (s, 1H), 8.42 (s, 1H), 7.70-7.63 (m, 2H), 4.82-4.75 (m, 1H), 4.30 (t, J = 5.2 Hz, 2H), 3.87-3.75 (m, 8H), 3.00 (m, 2H), 1.98 (t, J = 7.2 Hz, 2H), 1.67-1.61 (m, 2H), 1.57 (d, J = 6.4 Hz, 6H), 1.56-1.50 (overlapping, 2H), 1.34-1.30 (m, 2H). HRMS (ESI) m/z [M + H]$^+$ calcd for C$_{25}$H$_{36}$N$_7$O$_3$, 482.2874; found, 482.2891. |

TABLE 2-continued

Table showing selected hydroxamate compounds

| EX | Compound | Chemical Structure | Chemical Name and Data |
|---|---|---|---|
| 37 | 19a | 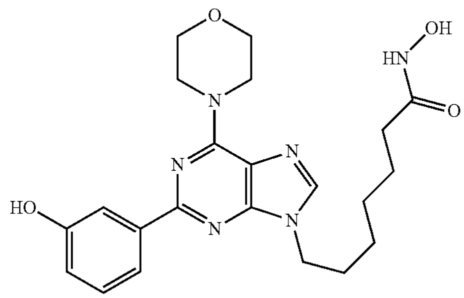 [SMILES: O=C(CCCCCCn1cnc2c(N3CCOCC3)nc(-c3cccc(O)c3)nc21)NO] | N-hydroxy-7-(2-(3-hydroxyphenyl)-6-morpholino-9H-purin-9-yl)heptanamide. LC-MS m/z 441.1 (FM ([M + H]$^+$). HPLC purity (254 nm): 87.0%. $^1$H NMR (DMSO-d$_6$) δ 10.34 (s, 1H), 8.20 (s, 2H), 7.80-7.82 (m, 2H), 7.23 (t, J = 8.0 Hz, 1H), 6.81 (dm, J = 8.0 Hz, 1H), 4.26 (m, 4H), 4.19 (m, 2H), 3.75 (m, 4H), 1.90 (t, J = 7.6 Hz, 2H), 1.83 (m, 2H), 1.45 (m, 2H), 1.25 (m, 4H). |
| 38 | 9a | 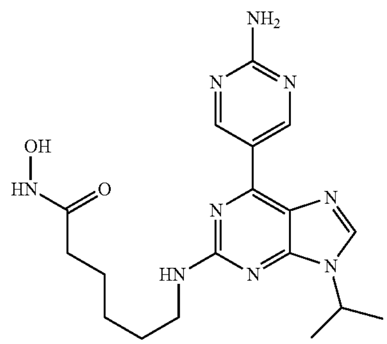 [SMILES: CC(C)n1cnc2c(-c3cnc(N)nc3)nc(NCCCCCC(=O)NO)nc21] | 6-((6-(2-aminopyrimidin-5-yl)-9-isopropyl-9H-purin-2-yl)amino)-N-hydroxyhexanamide. LC-MS m/z 400.1 ([M + H]$^+$). HPLC purity (254 nm): 91.6%. $^1$H NMR (DMSO-d$_6$) δ 10.35 (s, 1H), 9.47 (s, 2H), 8.24 (s, 1H), 7.33 (s, 2H), 4.69 (m, J = 8.0 Hz, 1H), 3.35 (m, 2H), 2.52 (m, 2H), 1.96 (m, 2H), 1.59 (m, 2H), 1.53 (d, J = 6.8 Hz, 6H), 1.34 (m, 2H). |
| 39 | 9b | 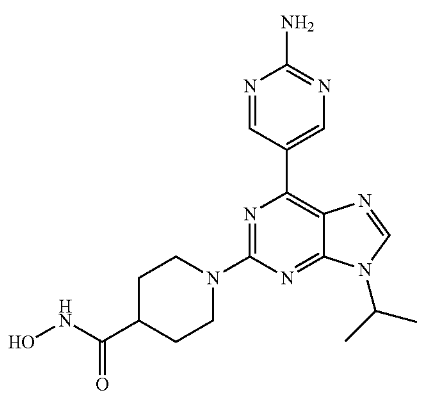 | 1-(6-(2-aminopyrimidin-5-yl)-9-isopropyl-9H-purin-2-yl)-N hydroxypiperidine-4-carboxamide. LC-MS m/z 442.1 ([M + H]$^+$). HPLC purity (254 nm): 93.1 %. $^1$H NMR (DMSO-d$_6$) δ 10.52 (s, 1H), 9.52 (s, 2H), 8.32 (s, 1H), 7.43 (s, 2H), 4.73 (m, J = 6.8 Hz, 1H), 2.93 (m, 2H), 2.32 (m, 1H), 1.71 (m, 2H), 1. 60 (m, 2H), 1.54 (d, J = 6.8 Hz, 6H). |
| 40 | 19b | 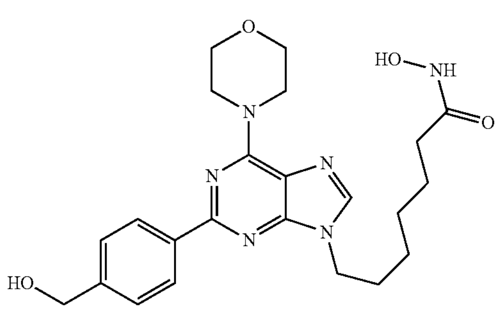 [SMILES: O=C(CCCCCCn1cnc2c(N3CCOCC3)nc(-c3ccc(CO)cc3)nc21)NO] | N-hydroxy-7-(2-(4-hydroxymethyl)phenyl)-6-morpholino-9H-purin-9-yl)heptanamide. LC-MS m/z 455.2 ([M + H]$^+$). HPLC purity (254 nm): 97.0%. $^1$H NMR (DMSO-d$_6$) δ 10.34 (s, 1H), 8.36 (d, J = 8.4 Hz, 2H), 8.23 (s, 1H), 7.42 (d, J = 8.4 Hz, 2H), 4.57 (s, 2H), 4.30 (m, 2H), 4.23 (m, 4H), 3.78 (m, 4H), 1.94 (m, 2H), 1.86 (m, 2H), 1.48 (m, 2H), 1.29 (m, 4H). |

TABLE 2-continued

Table showing selected hydroxamate compounds

| EX | Compound | Chemical Structure | Chemical Name and Data |
|---|---|---|---|
| 41 | 19c | 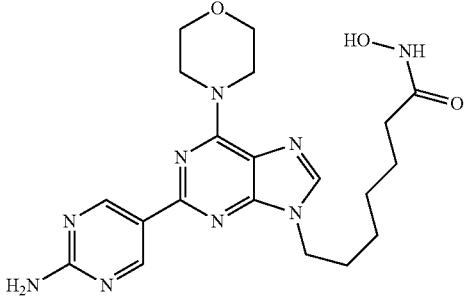 | 7-(2-(2-aminopyrimidin-5-yl)-6-morpholino-9H-purin-9-yl)-N-hydroxyheptanamide. LC-MS m/z 442.1 ([M + H]$^+$). HPLC purity (254 nm): 97.8%. $^1$H NMR (DMSO-d$_6$) δ 10.25 (s, 1H), 9.07 (s, 2H), 8.12 (s, 1H), 7.16 (bs, 2H), 4.25 (m, 4H), 4.13 (m, 2H), 3.68 (m, 4H), 1.85 (m, 2H), 1.77 (m, 2H), 1.40 (m, 2H), 1.20 (m, 4H). HRMS (ESI) m/z [M + H]$^+$ calcd for C$_{20}$H$_{27}$N$_9$O$_3$, 442.2310; found, 442.2326. |
| 42 | 12ab | 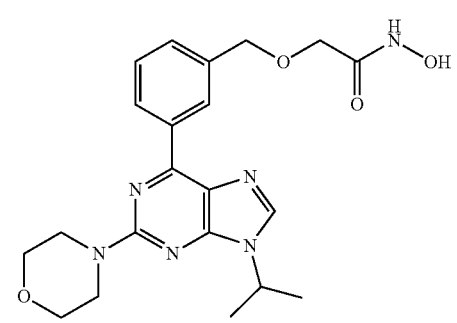 [SMILES: CC(C)n1cnc2c(-c3cccc(COCC(=O)NO)c3)nc(N3CCOCC3)nc21] | N-hydroxy-2-((3-(9-isopropyl-2-morpholino-9H-purin-6-yl)benzyl)oxy)acetamide. LC-MS m/z 427 ([M + H]$^+$). $^1$HNMR (CD$_3$OD) δ 8.72-8.70 (m, 2H), 8.41 (s, 1H), 7.57-7.54 (m, 2H), 4.80-4.73 (m, 1H), 4.65 (s, 2H), 3.95 (s, 2H), 3.83-3.74 (m, 8H), 1.56 (d, J = 6.8 Hz, 6H). HRMS (ESI) m/z [M + H]$^+$ calcd for C$_{21}$H$_{27}$N$_6$O$_4$, 427.2088; found, 427.2101. |
| 43 | 12ac | 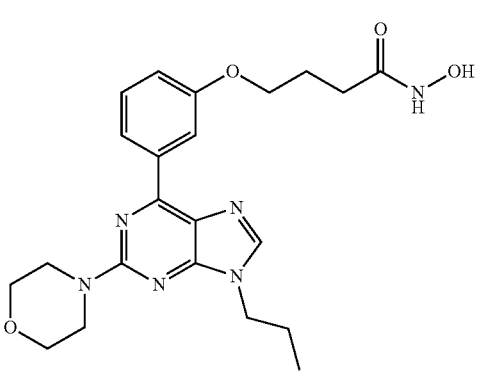 [SMILES: CCCn1cnc2c(-c3cccc(OCCCC(=O)NO)c3)nc(N3CCOCC3)nc21] | N-hydroxy-4-(3-(2-morpholino-9-propyl-9H-purin-6-yl)phenoxy)butanamide. LC-MS m/z 441.1 ([M + H]$^+$). HPLC purity (254 nm): 99.6%. $^1$H NMR (DMSO-d$_6$) δ 10.46 (s, 1H), 8.39 (s, 1H), 8.36 (d, J = 7.6 Hz, 1H), 8.30 (s, 1H), 7.46 (t, J = 8.0 Hz, 1H), ), 7.11 (d, J = 8.0 Hz, 1H), 4.11 (t, J = 7.2 Hz, 2H), 4.05 (t, J = 7.2 Hz, 2H), 3.82 (m, 4H), 3.75 (m, 4H), 2.19 (m, 2H), 2.00 (m, 2H), 1.87 (m, 2H), 0.88 (t, J = 7.2 Hz, 3H). |
| 44 | 12ad | 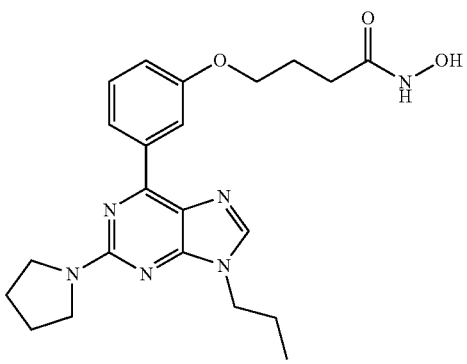 [SMILES: CCCn1cnc2c(-c3cccc(OCCCC(=O)NO)c3)nc(N3CCCC3)nc21] | N-hydroxy-4-(3-(9-propyl-2-(pyrrolidin-1-yl)-9H-purin-6-yl)phenoxy)butanamide. LC-MS m/z 425.2 ([M + H]$^+$). HPLC purity (254 nm): 94.3% $^1$H NMR (DMSO-d$_6$) δ 10.47 (s, 1H), 8.37 (s, 1H), 8.34 (d, J = 7.6 Hz, 1H), 8.26 (s, 1H), 7.46 (t, J = 8.0 Hz, 1H), ), 7.11 (d, J = 8.0 Hz, 1H), 4.11 (m, 2H), 4.06 (m, 2H), 3.62 (m, 4H), 2.19 (m, 2H), 1.98 (m, 6H), 1.88 (m, 2H), 0.88 (t, J = 7.2 Hz, 3H). HRMS (ESI) m/z calcd for C$_{22}$H$_{28}$N$_6$O$_3$, 425.2296; found, 425.2304. |

TABLE 2-continued

Table showing selected hydroxamate compounds

| EX | Compound | Chemical Structure | Chemical Name and Data |
|---|---|---|---|
| 45 | 12ae | 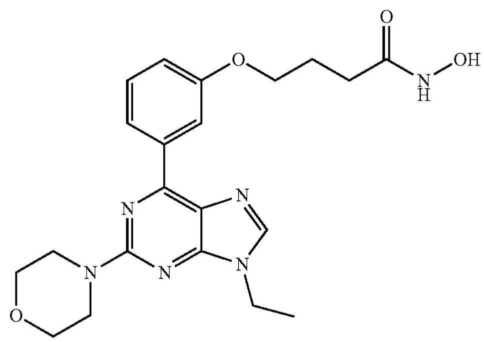 | 4-(3-(9-ethyl-2-morpholino-9H-purin-6-yl)phenoxy)-N-hydroxybutanamide. LC-MS m/z 427.1 ([M + H]$^+$). LC purity (254 nm): 90.3%. $^1$H NMR (DMSO-d$_6$) δ 10.52 (s, 1H), 8.40 (s, 1H), 8.37-8.39 (m, 2H), 7.51 (t, J = 8.0 Hz, 1H), ), 7.16 (d, J = 8.0 Hz, 1H), 4.22 (t, J = 7.2 Hz, 2H), 4.10 (t, J = 7.2 Hz, 2H), 3.86 (m, 4H), 3.79 (m, 4H), 2.24 (m, 2H), 2.06 (m, 2H), 1.48 (t, J = 7.2 Hz, 3H). HP |
| 46 | 12af | 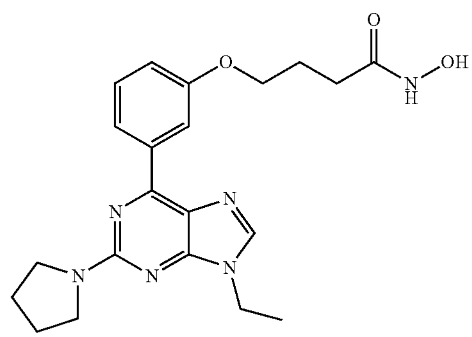 [SMILES: CCn1cnc2c(-c3cccc(OCCCC(=O)NO)c3)nc(N3CCCC3)nc21] | 4-(3-(9-ethyl-2-(pyrrolidin-1-yl)-9H-purin-6-yl)phenoxy)-N-hydroxybutanamide. LC-MS m/z 411.2 ([M + H]$^+$). HPLC purity (254 nm): 97.7%. $^1$H NMR (DMSO-d$_6$) δ 10.46 (s, 1H), 8.36 (s, 1H), 8.35 (d, J = 7.6 Hz, 1H), 8.28 (s, 1H), 7.46 (t, J = 8.0 Hz, 1H), ), 7.11 (d, J = 8.0 Hz, 1H), 4.17 (m, 2H), 4.06 (m, 2H), 3.64 (m, 4H), 2.19 (m, 2H), 1.99 (m, 6H), 1.44 (t, J = 7.2 Hz, 3H). HRMS (ESI) m/z [M + H]$^+$ calcd for C$_{21}$H$_{26}$N$_6$O$_3$, 411.2140; found, 411.2149. |
| 47 | 19d | 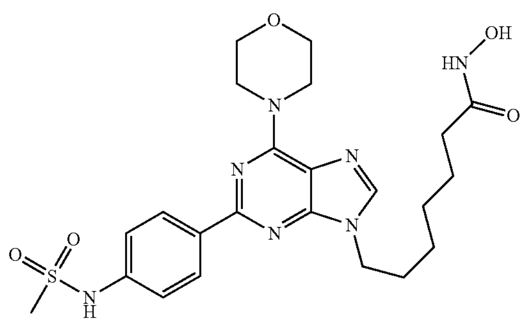 [SMILES: CS(=O)(=O)Nc1ccc(-c2nc(N3CCOCC3)c3ncn(CCCCCCC(=O)NO)c3n2)cc1] | N-hydroxy-7-(2-(4-(methylsulfonamido)phenyl)-6-morpholino-9H-purin-9-yl)heptanamide. LC-MS m/z 518.1 ([M + H]$^+$). HPLC purity (254 nm): 96.7 %. $^1$H NMR (DMSO-d$_6$) δ 10.33 (s, 1H), 9.96 (s, 1H), 8.33 (d, J = 8.8 Hz, 2H), 8.21 (s, 1H), 7.29 (d, J = 8.8 Hz, 2H), 4.29 (m, 4H), 4.21 (m, 2H), 3.76 (m, 4H), 3.05 (s, 3H), 1.92 (m, 2H), 1.85 (m, 2H), 1.47 (m, 2H), 1.27 (m, 4H). |
| 48 | 19e | 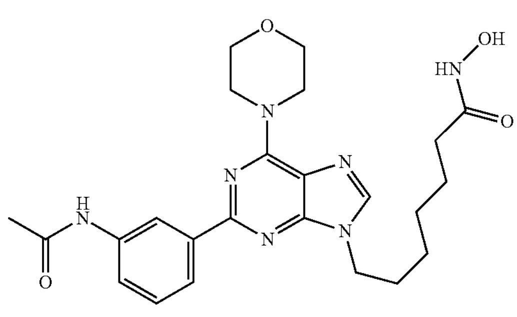 [SMILES: CC(=O)Nc1cccc(-c2nc(N3CCOCC3)c3ncn(CCCCCCC(=O)NO)c3n2)c1] | 7-(2-(3-acetamidophenyl)-6-morpholino-9H-purin-9-yl)-N-hydroxyheptanamide. LC-MS m/z 482.2 ([M + H]$^+$). HPLC purity (254 nm): 98.8%. $^1$H NMR (DMSO-d$_6$) δ 10.35 (s, 1H), 10.09 (s, 1H), 8.48 (s, 1H), 8.25 (s, 1H), 8.07 (d, J = 8.0 Hz, 1H), 7.84 (d, J = 8.0 Hz, 1H), 7.39 (t, J = 8.0 Hz, 1H), 4.32 (m, 4H), 4.23 (m, 2H), 3.79 (m, 4H), 2.09 (s, 3H), 1.94 (m, 2H), 1.87 (m, 2H), 1.48 (m, 2H), 1.29 (m, 4H). |

TABLE 2-continued

Table showing selected hydroxamate compounds

| EX | Compound | Chemical Structure | Chemical Name and Data |
|---|---|---|---|
| 49 | 19g | 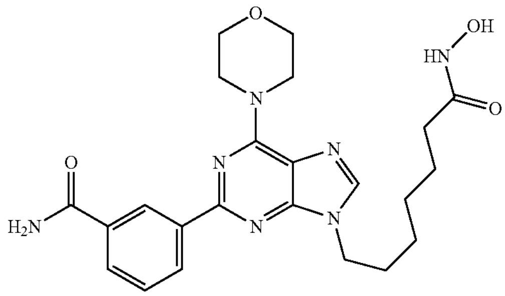 [SMILES: NC(=O)c1cccc(-c2nc(N3CCOCC3)c3ncn(CCCCCCC(=O)NO)c3n2)c1] | 3-(9-(7-(hydroxyamino)-7-oxoheptyl)-6-morpholino-9H-purin-2-yl)benzamide. LC-MS m/z 468.2 ([M + H]$^+$). HPLC purity (254 nm): 99.2%. $^1$H NMR (DMSO-d$_6$) δ 10.33 (s, 1H), 8.84 (s, 1H), 8.53 (d, J = 8.0 Hz, 1H), 8.26 (s, 1H), 8.13 (s, 1H), 7.93 (d, J = 8.0 Hz, 1H), 7.56 (t, J = 8.0 Hz, 1H), 7.47 (s, 1H), 4.33 (m, 4H), 4.26 (m, 2H), 3.79 (m, 4H), 1.94 (m, 2H), 1.88 (m, 2H), 1.48 (m, 2H), 1.29 (m, 4H). |
| 50 | 19h | 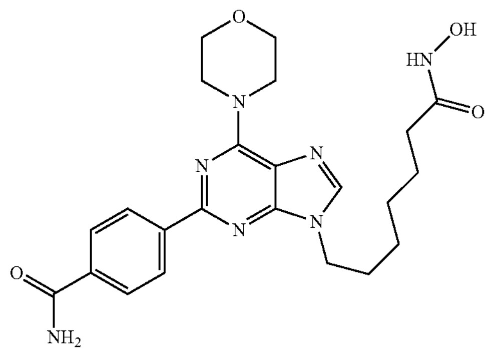 [SMILES: NC(=O)c1ccc(-c2nc(N3CCOCC3)c3ncn(CCCCCCC(=O)NO)c3n2)cc1] | 4-(9-(7-(hydroxyamino)-7-oxoheptyl)-6-morpholino-9H-purin-2-yl)benzamide. LC-MS m/z 468.2 ([M + H]$^+$). HPLC purity (254 nm): 99.3%. $^1$H NMR (DMSO-d$_6$) δ 10.34 (s, 1H), 8.45 (d, J = 8.4 Hz, 2H), 8.27 (s, 1H), 8.05 (s, 1H), 7.97 (d, J = 8.4 Hz, 2H), 7.46 (s, 1H), 4.32 (m, 4H), 4.26 (m, 2H), 3.79 (m, 4H), 1.94 (m, 2H), 1.88 (m, 2H), 1.48 (m, 2H), 1.29 (m, 4H). |
| 51 | 19i | 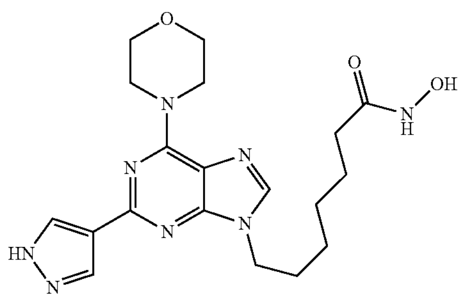 [SMILES: O=C(CCCCCCn1cnc2c(N3CCOCC3)nc(-c3cn[nH]c3)nc21)NO] | N-hydroxy-7-(6-morpholino-2-(1H-pyrazol-4-yl)-9H-purin-9-yl)heptanamide. LC-MS m/z 415.2 ([M + H]$^+$). HPLC purity (254 nm): 97.3%. $^1$H NMR (DMSO-d$_6$) δ 10.33 (s, 1H), 8.18 (s, 2H), 8.14 (s, 1H), 4.26 (m, 4H), 4.18 (m, 2H), 3.75 (m, 4H), 1.93 (m, 2H), 1.83 (m, 2H), 1.48 (m, 2H), 1.27 (m, 4H). HRMS (ESI) m/z [M + H]$^+$ calcd for C$_{19}$H$_{26}$N$_8$O$_3$, 415.2201; found, 415.2214. |
| 52 | 19j | 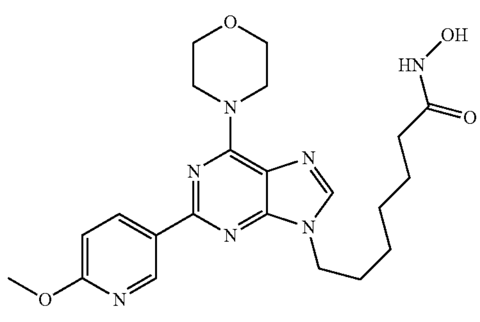 [SMILES: COc1ccc(-c2nc(N3CCOCC3)c3ncn(CCCCCCC(=O)NO)c3n2)cn1] | N-hydroxy-7-(2-(6-methoxypyridin-3-yl)-6-morpholino-9H-purin-9-yl)heptanamide. LC-MS m/z 456.1 ([M + H]$^+$). HPLC purity (254 nm): 98.8%. $^1$H NMR (DMSO-d$_6$) δ 10.34 (s, 1H), 9.15 (s, 1H), 8.57 (d, J = 8.0 Hz, 1H), 8.22 (s, 1H), 6.92 (d, J = 8.4 Hz, 1H), 4.30 (m, 4H), 4.22 (m, 2H), 3.93 (s, 3H), 3.77 (m, 4H), 1.93 (m, 2H), 1.86 (m, 2H), 1.48 (m, 2H), 1.28 (m, 4H). HRMS (ESI) m/z [M + H]$^+$, calcd for C$_{22}$H$_{29}$N$_7$O$_4$, 456.2354; found, 456.2369. |
| 53 | 19k | 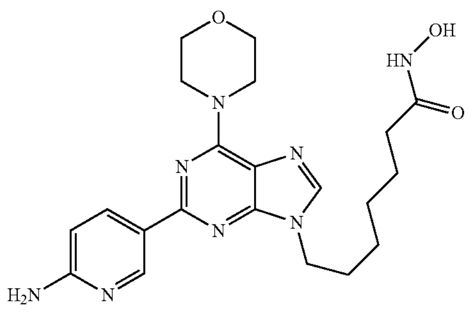 [SMILES: Nc1ccc(-c2nc(N3CCOCC3)c3ncn(CCCCCCC(=O)NO)c3n2)cn1] | 7-(2-(6-aminopyridin-3-yl)-6-morpholino-9H-purin-9-yl)-N-hydroxyheptanamide. LC-MS m/z 441.2 ([M + H]$^+$). HPLC purity (254 nm): 97.3%. $^1$H NMR (DMSO-d$_6$) δ 10.36 (s, 1H), 8.76 (m, 2H), 8.42 (s, 2H), 8.26 (s, 1H), 7.11 (d, J = 9.6 Hz, 1H), 4.30 (m, 4H), 4.22 (m, 2H), 3.77 (m, 4H), 1.93 (m, 2H), 1.85 (m, 2H), 1.47 (m, 2H), 1.28 (m, 4H). HRMS (ESI) m/z [M + H]$^+$ calcd for C$_{21}$H$_{29}$N$_8$O$_3$, 441.2357; found, 441.2374. |

TABLE 2-continued

Table showing selected hydroxamate compounds

| EX | Compound | Chemical Structure | Chemical Name and Data |
|---|---|---|---|
| 54 | 19l | 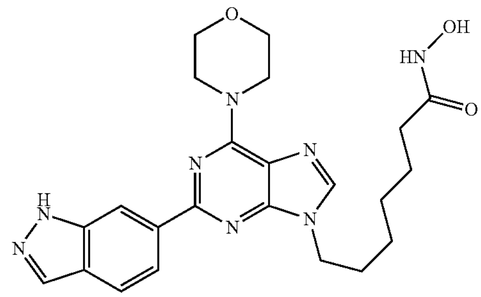 [SMILES: O=C(CCCCCCn1cnc2c(N3CCOCC3)nc(-c3ccc4cn[nH]c4c3)nc21)NO] | 7-(2-(1H-indazol-6-yl)-6-morpholino-9H-purin-9-yl)-N-hydroxyheptanamide. LC-MS m/z 465.2 ([M + H]$^+$). HPLC purity (254 nm): 98.0%. $^1$H NMR (DMSO-d$_6$) δ 10.38 (s, 1H), 8.60 (s, 1H), 8.25 (s, 1H), 8.22 (d, J = 8.8 Hz, 1H), 8.12 (s, 1H), 7.83 (d, J = 8.8 Hz, 1H), 4.34 (m, 4H), 4.27 (m, 2H), 3.80 (m, 4H), 1.95 (m, 2H), 1.90 (m, 2H), 1.51 (m, 2H), 1.32 (m, 4H). |
| 55 | 19m | 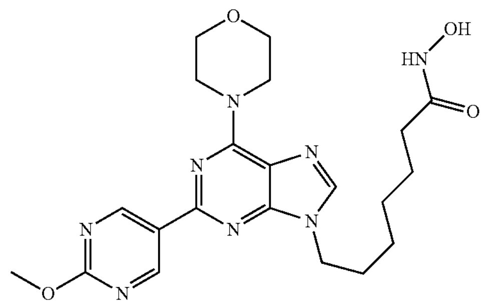 | N-hydroxy-7-(2-(2-methoxypyrimidin-5-yl)-6-morpholino-9H-purin-9-yl)heptanamide. LC-MS m/z 457.2 ([M + H]$^+$). HPLC purity (254 nm): 97.5%. $^1$H NMR (DMSO-d$_6$) δ 10.35 (s, 1H), 9.39 (s, 2H), 8.25 (s, 1H), 4.28 (m, 4H), 4.22 (m, 2H), 3.99 (s, 3H), 3.76 (m, 4H), 1.93 (m, 2H), 1.85 (m, 2H), 1.47 (m, 2H), 1.28 (m, 4H). HRMS (ESI) m/z [M + H]$^+$ calcd for C$_{21}$H$_{29}$N$_8$O$_4$, 457.2306; found, 457.2327. |
| 56 | 19n | 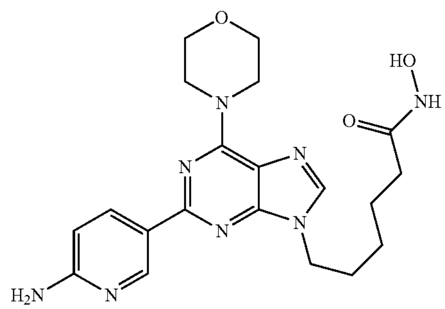 [SMILES: Nc1ccc(-c2nc(N3CCOCC3)c3ncn(CCCCCC(=O)NO)c3n2)cn1] | 6-(2-(6-aminopyridin-3-yl)-6-morpholino-9H-purin-9-yl)-N-hydroxyhexanamide. LC-MS m/z 427.2 ([M + H]$^+$). HPLC purity (254 nm): 93.3%. $^1$H NMR (DMSO-d$_6$) δ 10.27 (s, 1H), 8.68-8.71 (m, 2H), 8.37 (bs, 2H), 8.18 (s, 1H), 7.02 (d, J = 8.8 Hz, 1H), 4.22 (m, 4H), 4.14 (t, J = 6.8 Hz, 2H), 3.69 (m, 4H), 1.87 (m, 2H), 1.78 (m, 2H), 1.49 (m, 2H), 1.16 (m, 2H). |
| 57 | 19o | 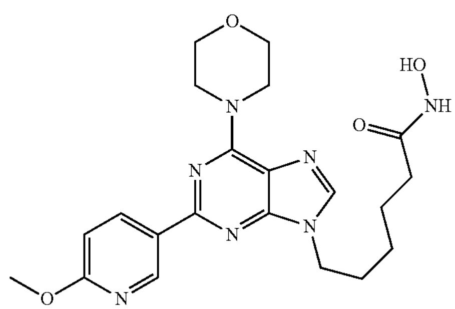 [SMILES: COc1ccc(-c2nc(N3CCOCC3)c3ncn(CCCCCC(=O)NO)c3n2)cn1] | N-hydroxy-6-(2-(6-methoxypyridin-3-yl)-6-morpholino-9H-purin-9-yl)hexanamide. LC-MS m/z 442.2 ([M + H]$^+$). HPLC purity (254 nm): 95.7%. $^1$H NMR (DMSO-d$_6$) δ 10.33 (s, 1H), 9.15 (s, 1H), 8.60 (d, J = 8.4 Hz, 1H), 8.22 (s, 1H), 6.92 (d, J = 8.4 Hz, 1H), 4.25 (m, 4H), 4.22 (t, J = 6.8 Hz, 2H), 3.93 (s, 3H), 3.77 (m, 4H), 1.94 (t, J = 6.8 Hz, 2H), 1.87 (m, 2H), 1.57 (m, 2H), 1.25 (m, 2H). HRMS (ESI) m/z [M + H]$^+$ calcd for C$_{21}$H$_{28}$N$_7$O$_4$, 442.2197; found, 442.2204. |
| 58 | 19p | 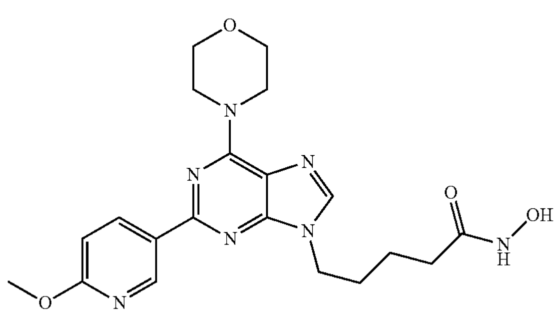 [SMILES: COc1ccc(-c2nc(N3CCOCC3)c3ncn(CCCCC(=O)NO)c3n2)cn1] | N-hydroxy-5-(2-(6-methoxypyridin-3-yl)-6-morpholino-9H-purin-9-yl)pentanamide. LC-MS m/z 428.1 ([M + H]$^+$). HPLC purity (254 nm): 92.3%. $^1$H NMR (DMSO-d$_6$) δ 10.38 (s, 1H), 9.16 (s, 1H), 8.58 (d, J = 8.8 Hz, 1H), 8.22 (s, 1H), 6.92 (d, J = 8.8 Hz, 1H), 4.30 (m, 4H), 4.22 (t, J = 6.8 Hz, 2H), 3.93 (s, 3H), 3.77 (m, 4H), 2.01 (t, J = 7.2 Hz, 2H), 1.84 (m, 2H), 1.49 (m, 2H). HRMS (ESI) m/z [M + H]$^+$, calcd for C$_{20}$H$_{26}$N$_7$O$_4$, 428.2041; found, 428.2042. |

TABLE 2-continued

Table showing selected hydroxamate compounds

| EX | Compound | Chemical Structure | Chemical Name and Data |
|---|---|---|---|
| 59 | 19q | 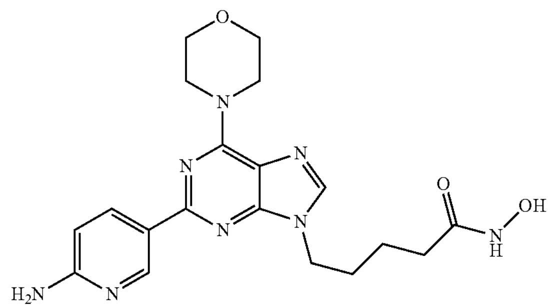 [SMILES: Nc1ccc(-c2nc(N3CCOCC3)c3ncn(CCCCC(=O)NO)c3n2)cn1] | 5-(2-(6-aminopyridin-3-yl)-6-morpholino-9H-purin-9-yl)-N-hydroxypentanamide. LC-MS m/z 413.2 ([M + H]$^+$). HPLC (254 nm): 80.5%. |
| 60 | 19r | 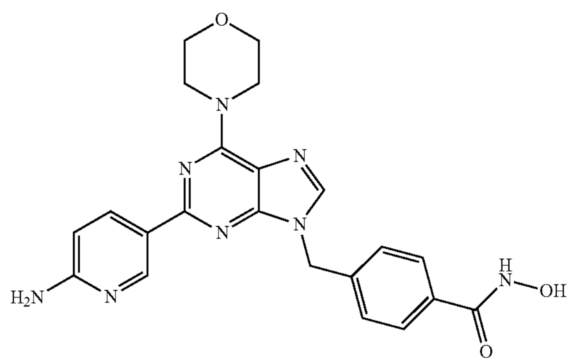 [SMILES: Nc1ccc(-c2nc(N3CCOCC3)c3ncn(Cc4ccc(C(=O)NO)cc4)c3n2)cn1] | 4-((2-(6-aminopyridin-3-yl)-6-morpholino-9H-purin-9-yl)methyl)-N-hydroxybenzamide. LC-MS m/z 447.1 ([M + H]$^+$). HPLC purity (254 nm): 92.1%. $^1$H NMR (DMSO-d$_6$) δ 11.17 (s, 1H), 9.01 (s, 1H), 8.77 (s, 1H), 8.67 (d, J = 8.4 Hz, 1H), 8.35 (s, 1H), 7.98 (bs, 1H), 7.69 (d, J = 8.4 Hz, 2H), 7.42 (d, J = 8.4 Hz, 2H), 6.97 (d, J = 8.4 Hz, 1H), 5.49 (s, 2H), 4.28 (m, 4H), 3.74 (m, 4H). |
| 61 | 17b | 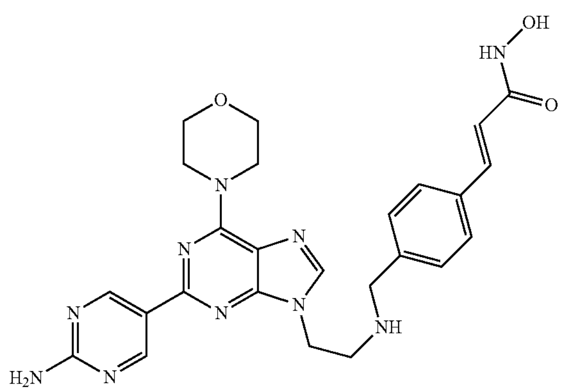 [SMILES: Nc1ncc(-c2nc(N3CCOCC3)c3ncn(CCNCc4ccc(/C=C/C(=O)NO)cc4)c3n2)cn1] | (E)-3-(4-(((2-(2-(2-aminopyrimidin-5-yl)-6-morpholino-9H-purin-9-yl)ethyl)amino)methyl)phenyl)-N-hydroxyacrylamide. LC-MS m/z 531 ([M + H]$^+$). $^1$HNMR (DMSO-d$_6$) δ 10.81 (br s, 1H), 9.16 (s, 2H), 9.02 (br s, 2H), 8.17 (s, 1H), 7.58 (d, J = 8.0 Hz, 2H), 7.48-7.43 (m, 3H), 7.16 (br s, 2H), 6.49 (d, J = 16.0 Hz, 1H), 4.58 (t, J = 5.2 Hz, 2H), 4.28 (t-like, 4H), 3.77-3.58 (m, 8H). HRMS (ESI) m/z [M + H]$^+$, calcd for C$_{29}$H$_{29}$N$_{10}$O$_3$, 517.2419; found, 517.2421. |
| 62 | 12ag | 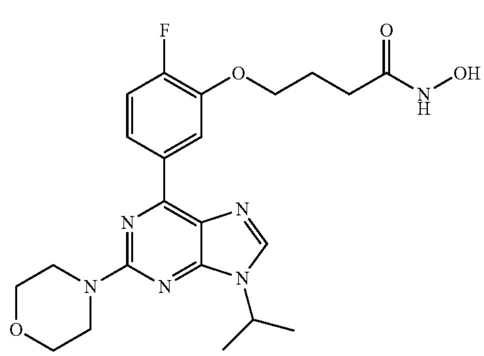 [SMILES: CC(C)n1cnc2c(-c3ccc(F)c(OCCCC(=O)NO)c3)nc(N3CCOCC3)nc21] | 4-(2-fluoro-5-(9-isopropyl-2-morpholino-9H-purin-6-yl)phenoxy)-N-hydroxybutanamide. LC-MS m/z 459.2 ([M + H]$^+$). HPLC purity (254 nm): 94.7%. $^1$H NMR (DMSO-d$_6$) δ 10.48 (s, 1H), 8.62 (d, J = 7.2 Hz, 1H), 8.41 (m, 2H), 7.40 (t, J = 8.4 Hz, 1H), 4.76 (m, J = 6.8 Hz, 1H), 4.16 (m, 2H), 3.81 (m, 4H), 3.75 (m, 4H), 2.20 (m, 2H), 2.04 (m, 2H), 1.55 (d, J = 6.8 Hz, 6H). HRMS (ESI) m/z [M + H]$^+$, calcd for C$_{22}$H$_{28}$FN$_6$O$_4$, 459.2151; found, 459.2154. |

TABLE 2-continued

Table showing selected hydroxamate compounds

| EX | Compound | Chemical Structure | Chemical Name and Data |
|---|---|---|---|
| 63 | 12ah | 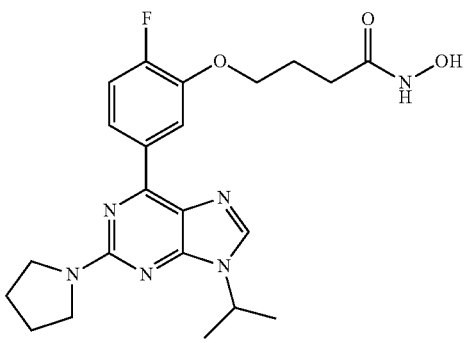 [SMILES: CC(C)n1cnc2c(-c3ccc(F)c(OCCCC(=O)NO)c3)nc(N3CCCC3)nc21] | 4-(2-fluoro-5-(9-isopropyl-2-(pyrrolidin-1-yl)-9H-purin-6-yl)phenoxy)-N-hydroxybutanamide. LC-MS m/z 443.1 ([M + H]$^+$). HPLC purity (254 nm): 98.6%. $^1$H NMR (DMSO-d$_6$) δ 10.48 (s, 1H), 8.61 (d, J = 8.4 Hz, 1H), 8.42 (m, 1H), 8.34 (s, 1H), 7.41 (t, J = 8.4 Hz, 1H), 4.74 (m, J = 6.8 Hz, 1H), 4.16 (m, 2H), 3.63 (m, 4H), 2.21 (m, 2H), 2.01 (m, 2H), 1.98 (m, 4H), 1.56 (d, J = 6.8 Hz, 6H). HRMS (ESI) m/z [M + H]$^+$, calcd for C$_{22}$H$_{28}$FN$_6$O$_3$, 443.2201; found, 443.2216. |
| 64 | 19s | 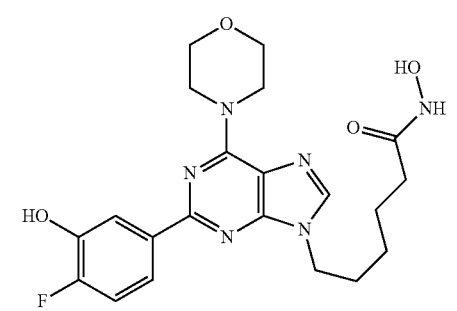 [SMILES: O=C(CCCCCn1cnc2c(N3CCOCC3)nc(-c3ccc(F)c(O)c3)nc21)NO] | 6-(2-(4-fluoro-3-hydroxyphenyl)-6-morpholino-9H-purin-9-yl)-N-hydroxyhexanamide. LC-MS m/z 445.2 ([M + H]$^+$). HPLC purity (254 nm): 98.0%. $^1$H NMR (DMSO-d$_6$) δ 10.36 (s, 1H), 8.22 (s, 1H), 8.04 (d, J = 7.2 Hz, 1H), 7.85 (m, 1H), 7.21 (t, J = 8.4 Hz, 2H), 4.25 (m, 4H), 4.22 (m, 2H), 3.78 (m, 4H), 1.95 (m, 2H), 1.87 (m, 2H), 1.57 (m, 2H), 1.24 (m, 2H). |
| 65 | 19t | 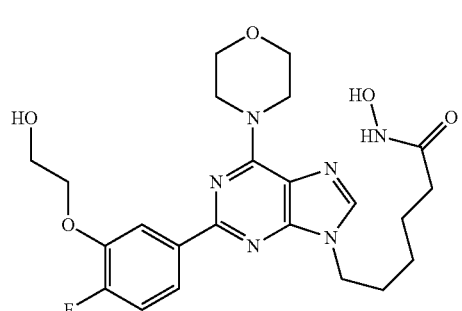 | 6-(2-(4-fluoro-3-(2-hydroxyethoxy)phenyl)-6-morpholino-9H-purin-9-yl)-N-hydroxyhexanamide. LC-MS m/z 489.2 ([M + H]$^+$). HPLC (254 nm): 90.3%. |
| 66 | 12ai | 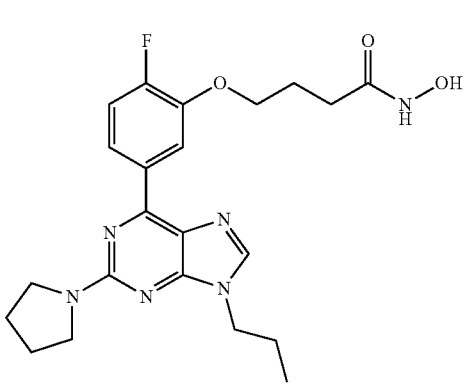 [SMILES: CCCn1cnc2c(-c3ccc(F)c(OCCCC(=O)NO)c3)nc(N3CCCC3)nc21] | 4-(2-fluoro-5-(9-propyl-2-(pyrrolidin-1-yl)-9H-purin-6-yl)phenoxy)-N-hydroxybutanamide. LC-MS m/z 443.2 ([M + H]$^+$). HPLC purity (254 nm): 99.3 %. $^1$H NMR (DMSO-d$_6$) δ 10.46 (s, 1H), 8.65 (d, J = 8.4 Hz, 1H), 8.45 (m, 1H), 8.22 (s, 1H), 7.40 (t, J = 8.8 Hz, 1H), 4.16 (m, 2H), 4.10 (m, 2H), 2.20 (m, 2H), 2.03 (m, 2H), 1.98 (m, 4H), 1.87 (m, 2H), 0.87 (t, J = 7.6 Hz, 3H). |

TABLE 2-continued

Table showing selected hydroxamate compounds

| EX | Compound | Chemical Structure | Chemical Name and Data |
|----|----------|-------------------|------------------------|
| 67 | 19u | 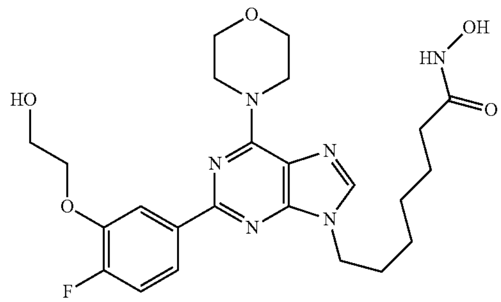 [SMILES: O=C(CCCCCCn1cnc2c(N3CCOCC3)nc(-c3ccc(F)c(OCCO)c3)nc21)NO] | 7-(2-(4-fluoro-3-(2-hydroxyethoxy)phenyl)-6-morpholino-9H-purin-9-yl)-N-hydroxyheptanamide. LC-MS m/z 503.1 ([M + H]$^+$). HPLC purity (254 nm): 97.3%. $^1$H NMR (DMSO-d$_6$) δ 10.26 (s, 1H), 8.16 (s, 1H), 8.04 (d, J = 8.8 Hz, 1H), 7.92 (m, 1H), 7.23 (t, J = 8.8 Hz, 1H), 4.22 (m, 4H), 4.16 (m, 2H), 4.10 (m, 2H), 3.73 (m, 2H), 3.70 (m, 4H), 1.85 (m, 2H), 1.79 (m, 2H), 1.40 (m, 2H), 1.21 (m, 4H). HRMS (ESI) m/z [M + H]$^+$ calcd for C$_{24}$H$_{32}$FN$_6$O$_5$, 503.2413; found, 503.2432. |
| 68 | 12aj | 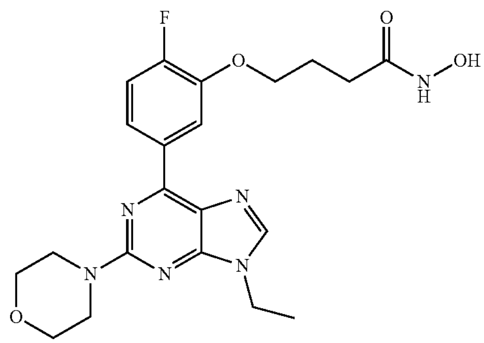 [SMILES: CCn1cnc2c(-c3ccc(F)c(OCCCC(=O)NO)c3)nc(N3CCOCC3)nc21] | 4-(5-(9-ethyl-2-morpholino-9H-purin-6-yl)-2-fluorophenoxy)-N-hydroxybutanamide. LC-MS m/z 445.1 ([M + H]$^+$). HPLC purity (254 nm): 98.8%. $^1$H NMR (DMSO-d$_6$) δ 10.46 (s, 1H), 8.59 (d, J = 8.4 Hz, 1H), 8.40 (m, 1H), 8.30 (s, 1H), 7.37 (t, J = 8.4 Hz, 1H), 4.15 (m, 4H), 3.79 (m, 4H), 3.72 (m, 4H), 2.17 (m, 2H), 2.01 (m, 2H), 1.41 (t, J = 7.6 Hz, 3H). |
| 69 | 12ak | 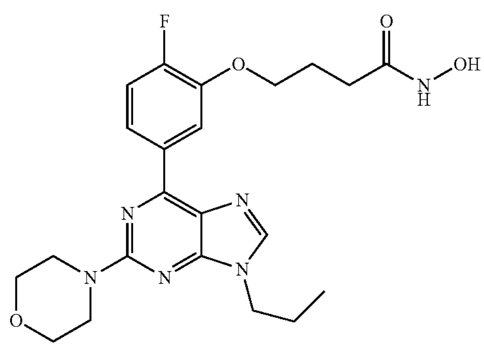 [SMILES: CCCn1cnc2c(-c3ccc(F)c(OCCCC(=O)NO)c3)nc(N3CCOCC3)nc21] | 4-(2-fluoro-5-(2-morpholino-9-propyl-9H-purin-6-yl)phenoxy)-N-hydroxybutanamide. LC-MS m/z 459.1 ([M + H]$^+$). HPLC purity (254 nm): 99.0%. $^1$H NMR (DMSO-d$_6$) δ 10.47 (s, 1H), 8.62 (d, J = 8.4 Hz, 1H), 8.42 (m, 1H), 8.31 (s, 1H), 7.39 (t, J = 8.4 Hz, 1H), 4.16 (m, 4H), 4.11 (m, 2H), 3.81 (m, 4H), 3.74 (m, 4H), 2.18 (m, 2H), 2.03 (m, 2H), 1.85 (m, 2H), 0.87 (t, J = 7.6 Hz, 3H). |
| 70 | 19v | 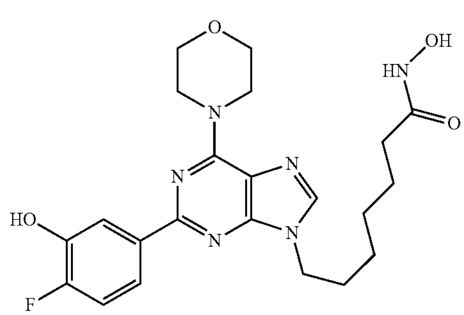 [SMILES: O=C(CCCCCCn1cnc2c(N3CCOCC3)nc(-c3ccc(F)c(O)c3)nc21)NO] | 7-(2-(4-fluoro-3-hydroxyphenyl)-6-morpholino-9H-purin-9-yl)-N-hydroxyheptanamide. LC-MS m/z 459.1 ([M + H]$^+$). HPLC purity (254 nm): 99.5%. $^1$H NMR (DMSO-d$_6$) δ 10.35 (s, 1H), 9.97 (s, 1H), 8.19 (s, 1H), 8.02 (d, J = 8.8 Hz, 1H), 7.82 (m, 1H), 7.18 (t, J = 8.8 Hz, 1H), 4.23 (m, 4H), 4.19 (m, 2H), 3.75 (m, 4H), 1.92 (m, 2H), 1.84 (m, 2H), 1.46 (m, 2H), 1.26 (m, 4H). |

TABLE 2-continued

Table showing selected hydroxamate compounds

| EX | Compound | Chemical Structure | Chemical Name and Data |
|----|----------|-------------------|------------------------|
| 71 | 17c | 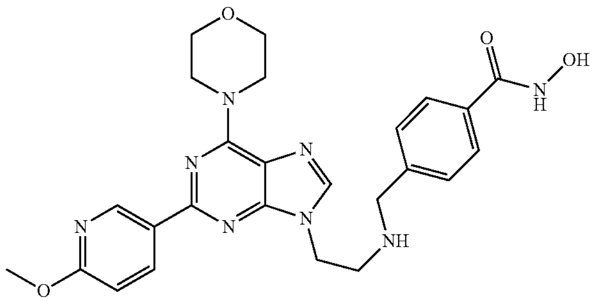 [SMILES: COc1ccc(-c2nc(N3CCOCC3)c3ncn(CCNCc4ccc(C(=O)NO)cc4)c3n2)cn1] | N-hydroxy-4-(((2-(2-(6-methoxypyridin-3-yl)-6-morpholino-9H-purin-9-yl)ethyl)amino)methyl)benzamide. LC-MS m/z 505 ([M + H]$^+$). $^1$HNMR (DMSO-d$_6$) δ 11.27 (br s, 1H), 9.16 (d, J = 2.0 Hz, 1H), 8.54 (dd, J = 2.4 Hz, 8.8 Hz, 1H), 8.18 (s, 1H), 7.73 (d, J = 8.0 Hz, 2H), 7.59 (d, J = 8.4 Hz, 2H), 6.88 (d, J = 8.4 Hz, 1H), 4.59 (t, J = 5.6 Hz, 2H), 4.33-4.28 (m, 6H), 3.91 (s, 3H), 3.74 (t, J = 4.8 Hz, 4H), 3.58 (t-like, 2H). |
| 72 | 19w | 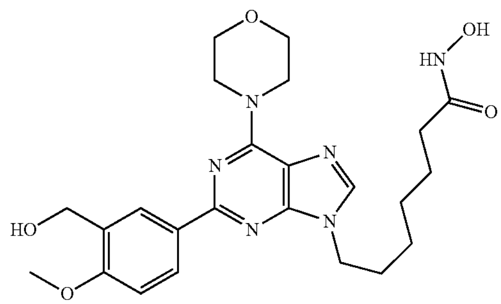 [SMILES: COc1ccc(-c2nc(N3CCOCC3)c3ncn(CCCCCCC(=O)NO)c3n2)cc1CO] | N-hydroxy-7-(2-(3-(hydroxymethyl)-4-methoxyphenyl)-6-morpholino-9H-purin-9-yl)heptanamide. LC-MS m/z 485.2 ([M + H]$^+$). HPLC purity (254 nm): 97.9%. $^1$H NMR (DMSO-d$_6$) δ 10.32 (s, 1H), 8.44 (s, 1H), 8.28 (d, J = 8.4 Hz, 1H), 8.19 (s, 1H), 7.03 (d, J = 8.8 Hz, 1H), 4.55 (m, 2H), 4.30 (m, 4H), 4.22 (m, 2H), 3.85 (s, 3H), 3.77 (m, 4H), 1.93 (m, 2H), 1.86 (m, 2H), 1.48 (m, 2H), 1.28 (m, 4H). HRMS (ESI) m/z [M + H]$^+$ calcd for C$_{24}$H$_{33}$N$_6$O$_5$, 485.2507; found, 485.2506 |
| 73 | 19x | 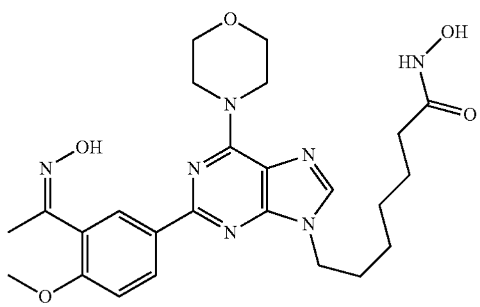 | (N-hydroxy-7-(2-(3-(1-(hydroxyimino)ethyl)-4-methoxyphenyl)-6-morpholino-9H-purin-9-yl)heptanamide. LC-MS m/z 498.2 ([M + H]$^+$). HPLC purity (254 nm): 99.1%. $^1$H NMR (DMSO-d$_6$) δ 11.35 (s, 1H), 10.33 (s, 1H), 8.70 (s, 1H), 8.40 (d, J = 8.8 Hz, 1H), 8.35 (s, 1H), 8.20 (s, 1H), 7.17 (d, J = 8.8 Hz, 1H), 4.29 (m, 4H), 4.22 (m, 2H), 3.90 (s, 3H), 3.77 (m, 4H), 1.93 (m, 2H), 1.86 (m, 2H), 1.47 (m, 2H), 1.28 (m, 4H). |
| 74 | 19y | 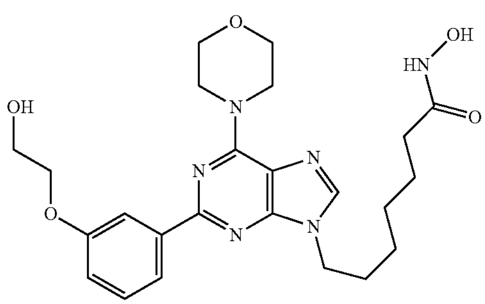 [SMILES: O=C(CCCCCCn1cnc2c(N3CCOCC3)nc(-c3cccc(OCCO)c3)nc21)NO] | N-hydroxy-7-(2-(3-(2-hydroxyethoxy)phenyl)-6-morpholino-9H-purin-9-yl)heptanamide. LC-MS m/z 485.2 ([M + H]$^+$). HPLC purity (254 nm): 99.1%. $^1$H NMR (DMSO-d$_6$) δ 10.31 (s, 1H), 8.22 (s, 1H), 7.95 (m, 1H), 7.90 (m, 1H), 7.35 (t, J = 8.0 Hz, 1H), 7.01 (m, 1H), 4.27 (m, 4H), 4.22 (m, 2H), 4.04 (m, 2H), 3.75 (m, 6H), 1.91 (m, 2H), 1.85 (m, 2H), 1.45 (m, 2H), 1.26 (m, 4H). |
| 75 | 12al | 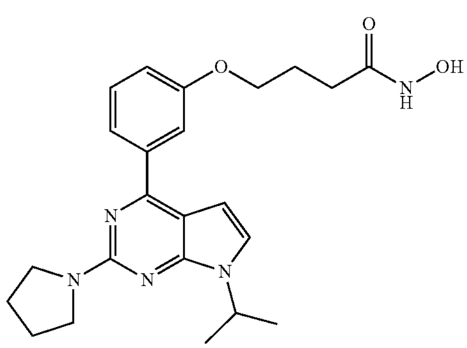 [SMILES: CC(C)n1ccc2c(-c3cccc(OCCCC(=O)NO)c3)nc(N3CCCC3)nc21] | N-hydroxy-4-(3-(7-isopropyl-2-(pyrrolidin-1-yl)-7H-pyrrolo[2,3-d]pyrimidin-4-yl)phenoxy)butanamide. LC-MS m/z 424.2 ([M + H]$^+$). HPLC purity (254 nm): 97.9%. $^1$H NMR (DMSO-d$_6$) δ 10.46 (s, 1H), 7.62 (m, 1H), 7.57 (s, 1H), 7.46 (t, J = 8.0 Hz, 1H), 7.39 (m, 1H), 7.12 (dd, J = 8.0, 2.0 Hz, 1H), 6.61 (d, J = 3.6 Hz, 1H), 4.89 (m, J = 6.8 Hz, 1H), 4.06 (t, J = 6.4 Hz, 2H), 3.62 (m, 4H), 2.16 (t, J = 6.8 Hz, 2H), 1.97 (m, 6H), 1.45 (d, J = 6.8 Hz, 6H). HRMS (ESI) m/z [M + H]$^+$ calcd for C$_{24}$H$_{32}$N$_6$O$_{11}$, 424.2343; found, 424.2348. |

TABLE 2-continued

Table showing selected hydroxamate compounds

| EX | Compound | Chemical Structure | Chemical Name and Data |
|---|---|---|---|
| 76 | 12am | 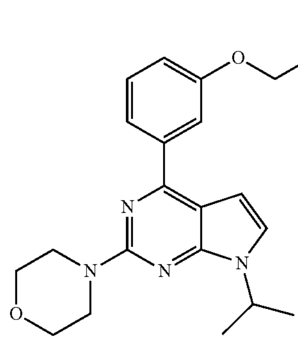 | N-hydroxy-4-(3-(7-isopropyl-2-morpholino-7H-pyrrolo[2,3-d]pyrimidin-4-yl)phenoxy)butanamide. LC-MS m/z 440.1 ([M + H]+). HPLC purity (254 nm): 97.8%; $^1$H NMR (DMSO-d$_6$) δ 10.46 (s, 1H), 7.66 (m, 1H), 7.58 (s, 1H), 7.41-7.48 (m, 2H), 7.10 (dd, J = 8.0, 2.0 Hz, 1H), 6.65 (d, J = 4.0 Hz, 1H), 4.92 (m, J = 6.8 Hz, 1H), 4.04 (t, J = 6.4 Hz, 2H), 3.76 (m, 4H), 3.73 (m, 4H), 2.18 (m, 2H), 1.45 (d, J = 6.8 Hz, 6H), 1.18 (m, 2H); HRMS (ESI) m/z [M + H]+ calcd for C$_{24}$H$_{32}$N$_6$O$_{12}$, 440.2292; found, 440.2314. |
| 77 | 19z | 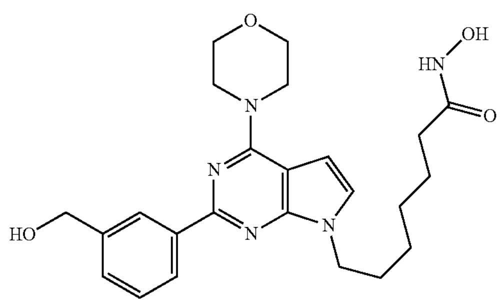 [SMILES: O=C(CCCCCCn1ccc2c(N3CCOCC3)nc(-c3cccc(CO)c3)nc21)NO] | N-hydroxy-7-(2-(3-(hydroxymethyl)phenyl)-4-morpholino-7H-pyrrolo[2,3-d]pyrimidin-7-yl)heptanamide. LC-MS m/z 454 ([M + H]+). $^1$HNMR (DMSO-d$_6$) δ 10.33 (br s, 1H), 8.35 (s, 1H), 8.28 (d, J = 7.6 Hz, 1H), 7.42-7.34 (m, 3H), 6.70 (d, J = 3.6 Hz, 1H), 4.58 (s, 2H), 4.24 (t, J = 7.2 Hz, 2H), 3.97-3.94 (m, 4H), 3.79-3.77 (m, 4H), 1.91 (t, J = 7.2 Hz, 2H), 1.84-1.77 (m, 2H), 1.49-1.42 (m, 2H), 1.33-1.23 (m, 4H). HRMS (ESI) m/z [M + H]+ calcd for C$_{24}$H$_{32}$N$_5$O$_4$, 454.2449; found, 454.2448. |
| 78 | 19aa | 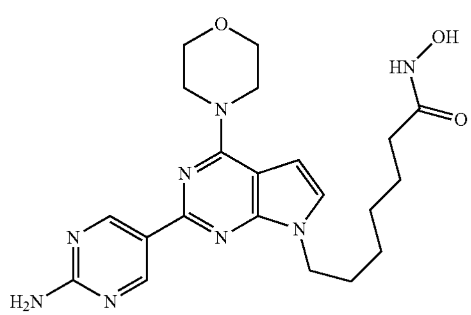 [SMILES: Nc1ncc(-c2nc(N3CCOCC3)c3ccn(CCCCCCC(=O)NO)c3n2)cn1] | 7-(2-(2-aminopyrimidin-5-yl)-4-morpholino-7H-pyrrolo[2,3-d]pyrimidin-7-yl)-N-hydroxyheptanamide. LC-MS m/z 441 ([M + H]+). $^1$HNMR DMSO-d$_6$) δ 10.30 (s, 1H), 9.11 (s, 2H), 8.65 (s, 1H), 7.27 (d, J = 3.6 Hz, 1H), 6.97 (s, 2H), 6.65 (d, J = 3.6 Hz, 1H), 4.19 (t, J = 6.8 Hz, 2H), 3.92-3.90 (m, 4H), 3.77-3.74 (m, 4H), 1.91 (t, J = 7.2 Hz, 2H), 1.78 (quintet, J = 7.2 Hz, 2H), 1.45 (quintet, J = 7.2 Hz, 2H), 1.33-1.22 (m, 4H). |
| 79 | 19ab | 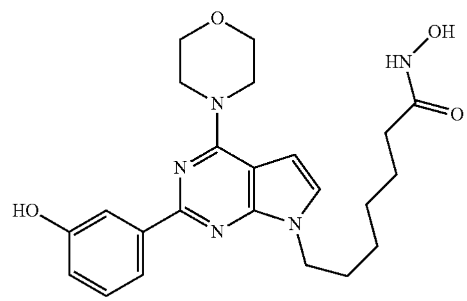 [SMILES: O=C(CCCCCCn1ccc2c(N3CCOCC3)nc(-c3cccc(O)c3)nc21)NO] | N-hydroxy-7-(2-(3-hydroxyphenyl)-4-morpholino-7H-pyrrolo[2,3-d]pyrimidin-7-yl)heptanamide. LC-MS m/z 440 ([M + H]). $^1$HNMR (DMSO-d$_6$) δ 10.33 (br s, 1H), 7.85-7.83 (m, 2H), 7.33 (d, J = 3.6 Hz, 1H), 7.25 (t, J = 8.0 Hz, 1H), 6.83-6.80 (m, 1H), 6.68 (d, J = 3.6 Hz, 1H), 4.23 (t, J = 6.8 Hz, 2H), 3.95-3.93 (m, 4H), 3.79-3.77 (m, 4H), 1.92 (t, J = 7.2 Hz, 2H), 1.83-1.76 (m, 2H), 1.49-1.42 (m, 2H), 1.33-1.26 (m, 4H). HRMS (ESI) m/z [M + H]+ calcd for C$_{23}$H$_{30}$N$_5$O$_4$, 440.2292; found, 440.2306. |

TABLE 2-continued

Table showing selected hydroxamate compounds

| EX | Compound | Chemical Structure | Chemical Name and Data |
|---|---|---|---|
| 80 | 24b | 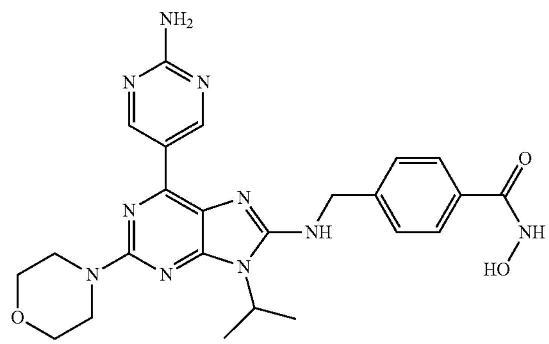 [SMILES: CC(C)n1c(NCc2ccc(C(=O)NO)cc2)nc2c(-c3cnc(N)nc3)nc(N3CCOCC3)nc21] | 4-(((6-(2-aminopyrimidin-5-yl)-9-isopropyl-2-morpholino-9H-purin-8-yl)amino)methyl)-N-hydroxybenzamide. LC-MS m/z 505.2 ([M + H]$^+$). HPLC purity (254 nm): $^1$H NMR (DMSO-d$_6$) δ 11.09 (s, 1H), 9.28 (s, 2H), 7.81 (s, 1H), 7.77 (d, J = 8.0Hz, 2H),7.43 (d, J = 8.4 Hz, 2H), 7.22 (bs, 1H), 4.59 (m, 3H), 3.63 (m, 4H), 3.60 (m, 4H), 1.52 (d, J = 6.8 Hz, 6H). |
| 81 | 21a | 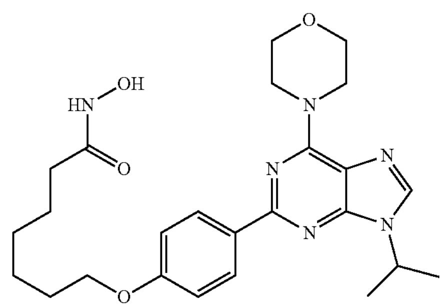 [SMILES: CC(C)n1cnc2c(N3CCOCC3)nc(-c3ccc(OCCCCCCC(=O)NO)cc3)nc21] | N-hydroxy-7-(4-(9-isopropyl-6-morpholino-9H-purin-2-yl)phenoxy)heptanamide. LC-MS m/z 483.1 ([M + H]$^+$). HPLC purity (254 nm): 98.1%. $^1$H NMR (DMSO-d$_6$) δ 10.37 (s, 1H), 8.32 (d, J = 9.2 Hz, 2H), 8.27 (s, 1H), 7.01 (d, J = 8.8 Hz, 2H), 4.87 (m, J = 6.8 Hz, 1H), 4.29 (m, 2H), 4.01 (m, J = 6.4 Hz, 2H), 3.76 (m, 4H), 1.97 (t, J = 7.6 Hz, 2H), 1.73 (m, 2H), 1.57 (d, J = 6.4 Hz, 6H), 1.53 (m, 2H), 1.42 (m, 2H), 1.32 (m, 2H). HRMS (ESI) m/z [M + H]$^+$ calcd for C$_{25}$H$_{34}$N$_6$O$_4$, 483.2715; found, 483.2730. |
| 82 | 21b | 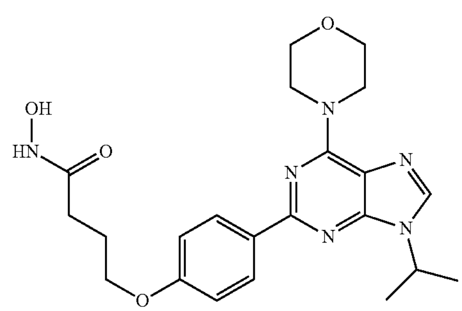 [SMILES: CC(C)n1cnc2c(N3CCOCC3)nc(-c3ccc(OCCCC(=O)NO)cc3)nc21] | N-hydroxy-4-(4-(9-isopropyl-6-morpholino-9H-purin-2-yl)phenoxy)butanamide. LC-MS m/z 441.1 ([M + H]$^+$). HPLC purity (254 nm): 99.1%. $^1$H NMR (DMSO-d$_6$) δ 10.37 (s, 1H), 8.25 (d, J = 8.8 Hz, 2H), 8.20 (s, 1H), 6.94 (d, J = 9.2 Hz, 2H), 4.79 (m, J = 6.8 Hz, 1H), 4.21 (m, 2H), 3.95 (m, J = 6.4 Hz, 2H), 3.70 (m, 4H), 2.10 (t, J = 7.2 Hz, 2H), 1.90 (m, 2H), 1.50 (d, J = 6.8 Hz, 6H). |
| 83 | 21c | 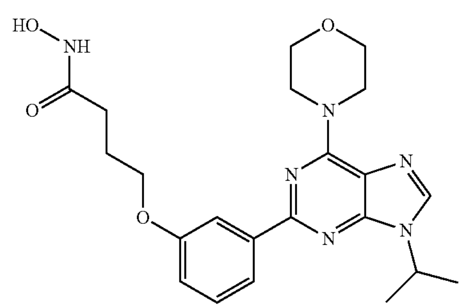 [SMILES: CC(C)n1cnc2c(N3CCOCC3)nc(-c3cccc(OCCCC(=O)NO)c3)nc21] | N-hydroxy-4-(3-(9-isopropyl-6-morpholino-9H-purin-2-yl)phenoxy)butanamide. LC-MS m/z 441.2 ([M + H]$^+$). HPLC purity (254 nm): 99.1%. $^1$H NMR (DMSO-d$_6$) δ 10.46 (s, 1H), 8.33 (s, 1H), 7.98 (d, J = 7.6 Hz, 1H), 7.91 (s, 1H), 7.38 (t, J = 8.0 Hz, 1H), 7.03 (m, 1H), 4.89 (m, J = 6.8 Hz, 1H), 4.31 (m, 4H), 4.04 (m, J = 6.4 Hz, 2H), 3.77 (m, 4H), 2.18 (t, J = 7.2 Hz, 2H), 1.99 (m, 2H), 1.59 (d, J = 6.8 Hz, 6H). |

TABLE 2-continued

Table showing selected hydroxamate compounds

| EX | Compound | Chemical Structure | Chemical Name and Data |
|---|---|---|---|
| 84 | 21d | 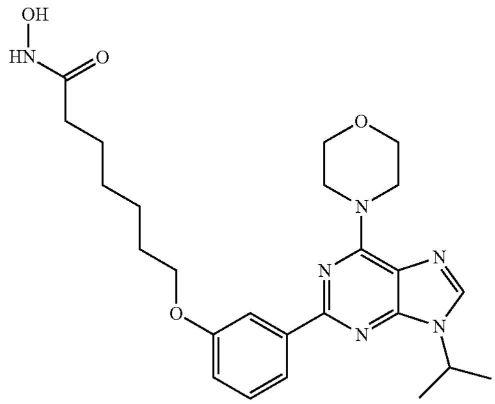 [SMILES: CC(C)n1cnc2c(N3CCOCC3)nc(-c3cccc(OCCCCCCC(=O)NO)c3)nc21] | N-hydroxy-7-(3-(9-isopropyl-6-morpholino-9H-purin-2-yl)phenoxy)heptanamide. LC-MS m/z 483.2 ([M + H]$^+$). HPLC purity (254 nm): 99.3%. $^1$H NMR (DMSO-d$_6$) δ 10.37 (s, 1H), 8.32 (s, 1H), 7.98 (d, J = 7.6 Hz, 1H), 7.91 (s, 1H), 7.38 (t, J = 8.0 Hz, 1H), 7.03 (m, 1H), 4.89 (m, J = 6.8 Hz, 1H), 4.30 (m, 4H), 4.04 (m, J = 6.4 Hz, 2H), 3.77 (m, 4H), 1.97 (t, J = 7.2 Hz, 2H), 1.75 (m, 2H), 1.59 (d, J = 6.8 Hz, 6H), 1.57 (m, 2H), 1.45 (m, 2H), 1.33 (m, 2H). HRMS (ESI) m/z [M + H]$^+$ calcd for C$_{25}$H$_{34}$N$_6$O$_4$, 483.2715; found, 483.2727. |
| 85 | 21e | 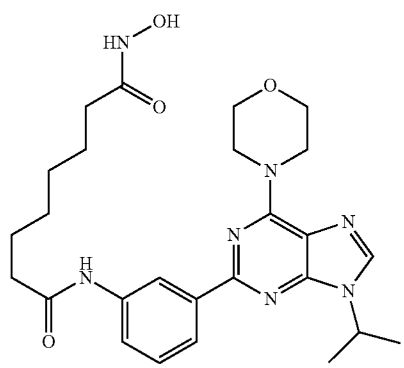 [SMILES: CC(C)n1cnc2c(N3CCOCC3)nc(-c3cccc(NC(=O)CCCCCCC(=O)NO)c3)nc21] | N$^1$-hydroxy-N$^8$-(3-(9-isopropyl-6-morpholino-9H-purin-2-yl)phenyl)octanediamide. LC-MS m/z 510.2 ([M + H]$^+$). HPLC purity (254 nm): 97.5%. $^1$H NMR (DMSO-d$_6$) δ 10.37 (s, 1H), 10.01 (s, 1H), 8.48 (s, 1H), 8.32 (s, 1H), 8.07 (d, J = 8.0 Hz, 1H), 7.87 (d, J = 8.0 Hz, 1H), 7.38 (t, J = 8.0 Hz, 1H), 4.89 (m, J = 6.8 Hz, 1H), 4.32 (m, 4H), 3.78 (m, 4H), 2.34 (t, J = 7.2 Hz, 2H), 1.96 (t, J = 7.2 Hz, 2H), 1.59 (m, 8H), 1.51 (m, 2H), 1.31 (m, 4H). |
| 86 | 27a | 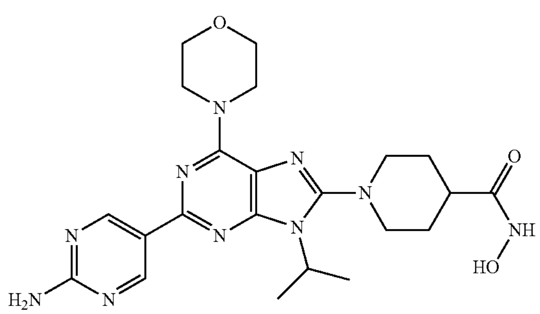 [SMILES: CC(C)n1c(N2CCC(C(=O)NO)CC2)nc2c(N3CCOCC3)nc(-c3cnc(N)nc3)nc21] | 1-(2-(2-aminopyrimidin-5-yl)-9-isopropyl-6-morpholino-9H-purin-8-yl)-N-hydroxypiperidine-4-carboxamide. LC-MS m/z 483.2 ([M + H]$^+$). HPLC purity (254 nm): 80.2%. $^1$H NMR (DMSO-d$_6$) δ 10.26 (s, 1H), 9.09 (s, 2H), 7.24-7.38 (m, 2H), 4.51 (m, J = 6.8 Hz, 1H), 4.19 (m, 4H), 3.73 (m, 4H), 2.90 (m, 2H), 1.76 (m, 4H), 1.64 (m, 6H). |
| 87 | 32a | 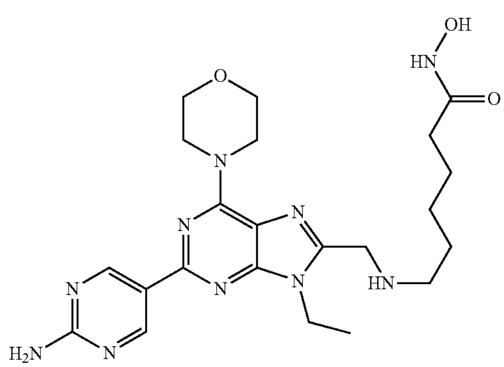 [SMILES: CCn1c(CNCCCCCC(=O)NO)nc2c(N3CCOCC3)nc(-c3cnc(N)nc3)nc21] | 6-(((2-(2-aminopyrimidin-5-yl)-9-ethyl-6-morpholino-9H-purin-8-yl)methyl)amino)-N-hydroxyhexanamide. LC-MS m/z 485 ([M + H]$^+$). $^1$HNMR (DMSO-d$_6$) δ 10.4 (br s, 1H), 9.16 (s, 2H), 7.29 (br s, 2H) 4.60 (t-like, J = 5.2 Hz, 2H), 4.31-4.26 (m, 6H), 3.78 (t-like, J = 4.6 Hz, 4H), 3.15-2.70 (m, 2H), 1.98 (t, J = 7.4 Hz, 2H), 1.74-1.66 (m, 2H), 1.58-1.50 (m, 2H), 1.39-1.30 (m, 5H). HRMS (ESI) m/z [M + H]$^+$ calcd for C$_{22}$H$_{33}$N$_{10}$O$_3$, 485.2732; found, 485.2734. |

TABLE 2-continued

Table showing selected hydroxamate compounds

| EX | Compound | Chemical Structure | Chemical Name and Data |
|---|---|---|---|
| 88 | 32b | 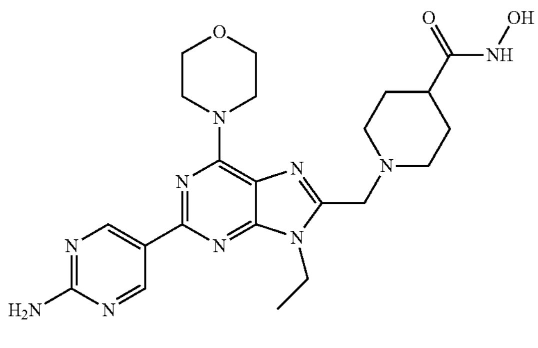 [SMILES: CCn1c(CN2CCC(C(=O)NO)CC2)nc2c(N3CCOCC3)nc(-c3cnc(N)nc3)nc21] | 1-((2-(2-aminopyrimidin-5-yl)-9-ethyl-6-morpholino-9H-purin-8-yl)methyl)-N-hydroxypiperidine-4-carboxamide. LC-MS m/z 483 ([M + H]$^+$). $^1$HNMR (DMSO-d$_6$) δ 10.64 (br s, 1H), 9.17 (s, 2H), 7.35 (br s, 2H), 4.70 (s, 2H), 4.35-4.31 (m, 6H), 3.78 (t-like, J = 4.6 Hz, 4H), 3.68 (d-like, 2H), 3.16 (br s, 2H), 1.95-1.87 (m, 4H), 1.38 (t, J = 7.2 Hz, 3H). |
| 89 | 35a | 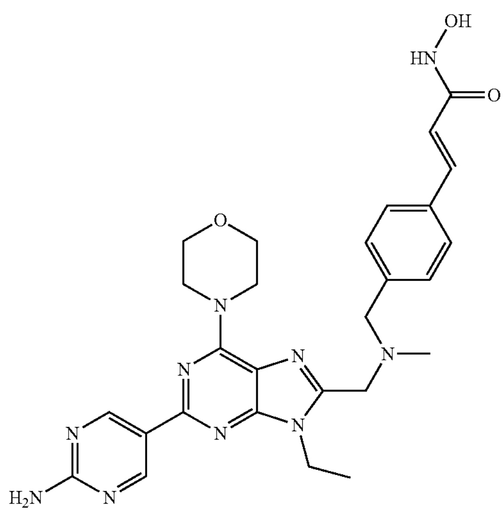 [SMILES: CCn1c(CN(C)Cc2ccc(/C=C/C(=O)NO)cc2)nc2c(N3CCOCC3)nc(-c3cnc(N)nc3)nc21] | (E)-3-(4-((((2-(2-aminopyrimidin-5-yl)-9-ethyl-6-morpholino-9H-purin-8-yl)methyl)(methyl)amino)methyl)phenyl)-N-hydroxyacrylamide. LC-MS m/z 545 ([M + H]$^+$). $^1$HNMR (CD$_3$OD) δ 9.25 (s, 2H), 7.66-7.53 (dd-like, J = 7.6 Hz, 4H), 7.56 (masked peak, 1H), 6.51 (d, J = 16 Hz, 1H), 4.78 (s, 2H), 4.58 (br s, 2H), 4.39-4.29 (m, 6H), 3.87 (t-like, 4H), 3.07 (s, 3H), 1.43 (t, J = 6.8 Hz, 3H). HRMS (ESI) m/z [M + H]$^+$ calcd for C$_{27}$H$_{33}$N$_{10}$O$_3$, 545.2732; found, 545.2742. |
| 90 | 35b | 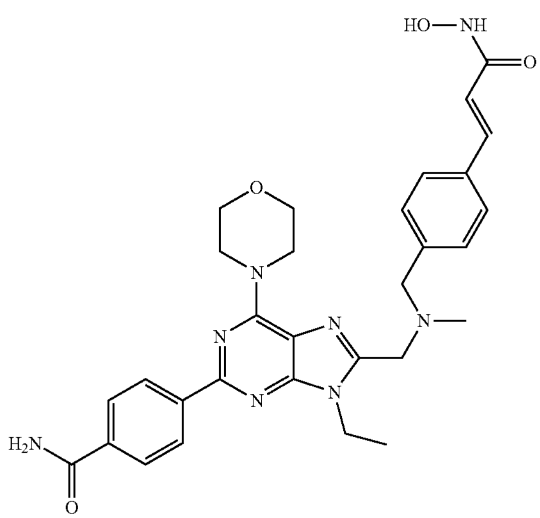 [SMILES: CCn1c(CN(C)Cc2ccc(/C=C/C(=O)NO)cc2)nc2c(N3CCOCC3)nc(-c3ccc(C(N)=O)cc3)nc21] | (E)-4-(9-ethyl-8-(((4-(3-(hydroxyamino)-3-oxoprop-1-en-1-yl)benzyl)(methyl)amino)methyl)-6-morpholino-9H-purin-2-yl)benzamide. LC-MS m/z 531 ([M + H]$^+$). $^1$HNMR (DMSO-d$_6$) δ 10.86 (br s, 1H), 8.45 (d, J = 8.4 Hz, 2H), 8.06 (br s, 1H), 7.98 (d, J = 8.8 Hz, 2H), 7.67 (d, J = 7.6 Hz, 1H), 7.56-7.47 (m, 4H), 6.53 J = 15.6 Hz, 1H), 4.35-4.33 (m 6H), 4.00 (br s, 4H), 3.83 (t-like, J = 4.4 Hz, 4H), 2.83 (br s, 3H), 1.39 (t, J = 7.2 Hz, 3H). HRMS (ESI) m/z [M + H]$^+$ calcd for C$_{30}$H$_{35}$N$_8$O$_4$, 571.2776; found, 531.2799. |

TABLE 2-continued

Table showing selected hydroxamate compounds

| EX | Compound | Chemical Structure | Chemical Name and Data |
|---|---|---|---|
| 91 | 35c | 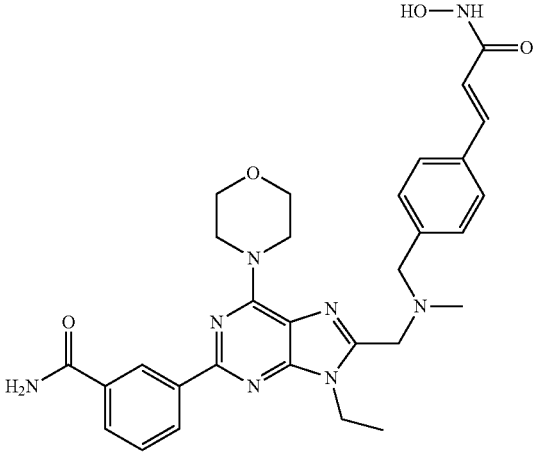 | (E)-3-(9-ethyl-8-(((4-(3-(hydroxyamino)-3-oxoprop-1-en-1-yl)benzyl)(methyl)amino)methyl)-6-morpholino-9H-purin-2-yl)benzamide. LC-MS m/z 571 ([M + H]$^+$). $^1$HNMR (DMSO-d$_6$) δ 10.84 (br s, 1H), 8.86 (t, J = 1.6 Hz, 1H), 8.55 (dt, J = 1.2 Hz, 8.0 Hz, 1H), 8.14 (br s, 1H), 7.97 (dt like, J = 7.6 Hz, 1H), 7.68 (d, J = 7.6 Hz, 1H), 7.60-7.48 (m, 5H), 6.53 (d, J = 16.0 Hz, 1H), 4.35-4.34 (m, 6H), 4.20 (br s, 4H), 3.83 (t, J = 4.4 Hz, 4H), 2.87 (br s, 3H), 1.40 (t, J = 7.2 Hz, 3H). |
| 92 | 35d | 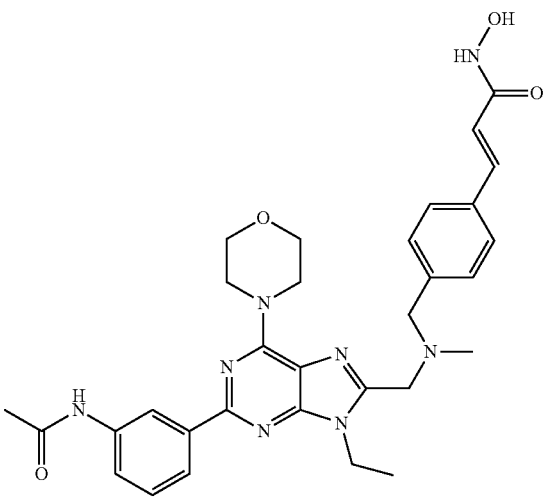 [SMILES: CCn1c(CN(C)Cc2ccc(/C=C/C(=O)NO)cc2)nc2c(N3CCOCC3)nc(-c3cccc(NC(C)=O)c3)nc21] | (E)-3-(4-((((2-(3-acetamidophenyl)-9-ethyl-6-morpholino-9H-purin-8-yl)methyl)(methyl)amino)methyl)phenyl)-N-hydroxyacrylamide. LC-MS m/z 585 ([M + H]$^+$). $^1$HNMR (CD$_3$OD) δ 8.62 (br s, 1H), 8.16 (d, J = 7.6 Hz, 1H), 7.75-7.65 (m, 3H), 7.57-7.50 (m, 4H), 7.38 (t, J = 7.6 Hz, 1H), 4.80 (br s, 2H), 4.61 (br s, 2H), 4.42-4.30 (m, 6H), 3.89 (t-like, 4H), 3.10 (s, 3H), 2.17 (s, 3H), 1.45 (t, J = 7.2 Hz, 3H). |
| 93 | 35e | 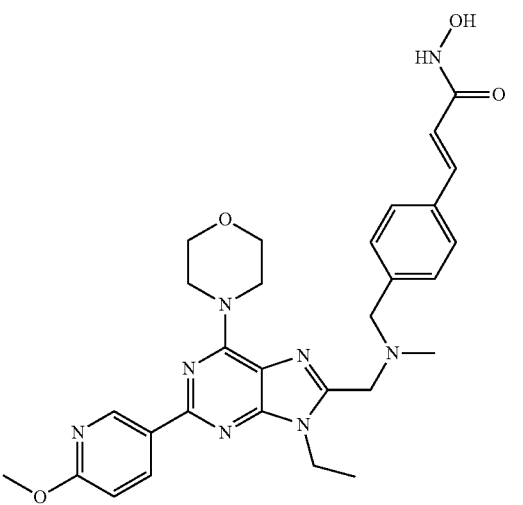 [SMILES: CCn1c(CN(C)Cc2ccc(/C=C/C(=O)NO)cc2)nc2c(N3CCOCC3)nc(-c3ccc(OC)nc3)nc21] | (E)-3-(4-((((9-ethyl-2-(6-methoxypyridin-3-yl)-6-morpholino-9H-purin-8-yl)methyl)(methyl)amino)methyl)phenyl)-N-hydroxyacrylamide. LC-MS m/z 559 ([M + H]$^+$). $^1$HNMR (DMSO-d$_6$) δ 9.18 (d, J = 2.0 Hz, 1H), 8.60 (dd, J = 2.4 Hz, 8.4 Hz, 1H), 7.68 (d, J = 8.0 Hz, 2H), 7.56 (d, J = 8.0 Hz, 2H), 7.49 (d, J = 16.0 Hz, 1H), 6.94 (d, J = 8.8 Hz, 1H), 6.53 (d, J = 15.6 Hz, 1H), 4.33-4.29 (m, 6H), 3.94 (s, 3H), 3.81 (overlapping peaks, 8H), 2.85 (br s, 3H), 1.38 (t, J = 6.8 Hz, 3H). HRMS (ESI) m/z [M + H]$^+$ calcd for C$_{29}$H$_{35}$N$_8$O$_4$, 559.2776; found, 559.2785. |

TABLE 2-continued

Table showing selected hydroxamate compounds

| EX | Compound | Chemical Structure | Chemical Name and Data |
|---|---|---|---|
| 94 | 35f | 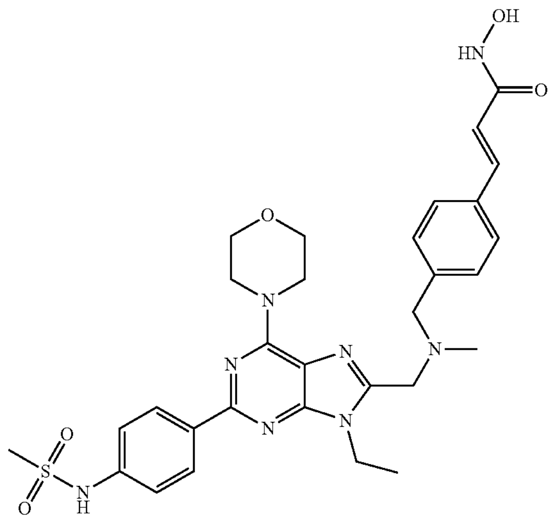 [SMILES: CCn1c(CN(C)Cc2ccc(/C=C/C(=O)NO)cc2)nc2c(N3CCOCC3)nc(-c3ccc(NS(C)(=O)=O)cc3)nc21] | (E)-3-(4-((((9-ethyl-2-(4-(methylsulfonamido)phenyl)-6-morpholino-9H-purin-8-yl)methyl)(methyl)amino)methyl)phenyl)-N-hydroxyacrylamide.<br>LC-MS m/z 621 ([M + H]+). |
| 95 | | 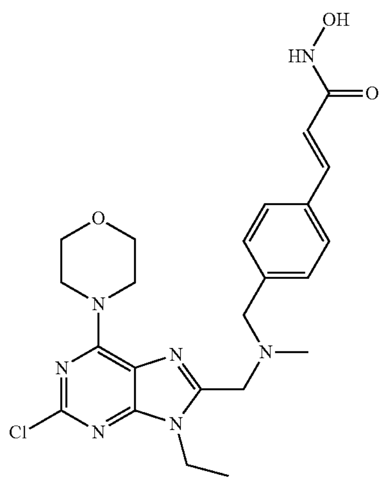 [SMILES: CCn1c(CN(C)Cc2ccc(/C=C/C(=O)NO)cc2)nc2c(N3CCOCC3)nc(Cl)nc21] | (E)-3-(4-((((2-chloro-9-ethyl-6-morpholino-9H-purin-8-yl)methyl)(methyl)amino)methyl)phenyl)-N-hydroxyacrylamide. LC-MS m/z 486 ([M + H]+). $^1$HNMR (DMSO-d$_6$) δ 7.65 (d, J = 8.0 Hz, 2H), 7.52 (d, J = 8.0 Hz, 2H), 7.48 (overlapping, d, J = 15.6 Hz, 1H), 6.52 (d, J = 16.0 Hz, 1H), 4.21-4.16 (m, 10H), 3.77 (t-like, 4H), 2.80 (br s, 3H), 1.29 (t, J = 7.2 Hz, 3H). |
| 96 | 35g | 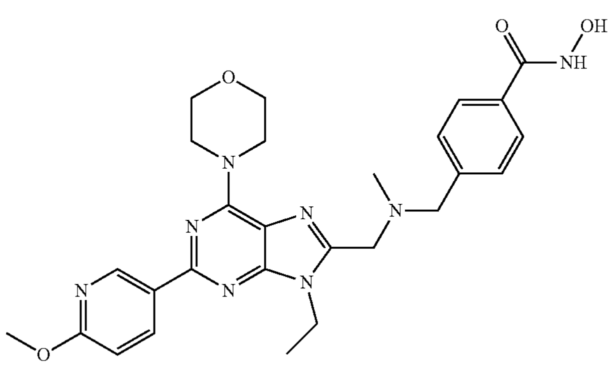 [SMILES: CCn1c(CN(C)Cc2ccc(C(=O)NO)cc2)nc2c(N3CCOCC3)nc(-c3ccc(OC)nc3)nc21] | 4-((((9-ethyl-2-(6-methoxypyridin-3-yl)-6-morpholino-9H-purin-8-yl)methyl)(methyl)amino)methyl)-N-hydroxybenzamide. LC-MS m/z 533 ([M + H]+). $^1$HNMR (DMSO-d$_6$) δ 11.32 (br s, 1H), 9.15 (d, J = 2.0 Hz, 1H), 8.57 (dd, J = 2.4 Hz, 8.8 Hz, 1H), 7.83 (d, J = 8.0 Hz, 2H), 7.59 (d, J = 7.6 Hz, 2H), 6.91 (d, J = 8.8 Hz, 1H), 4.63 (br s, 2H), 4.32-4.26 (m, 8H), 3.91 (s, 3H), 3.78 (t, J = 4.4 Hz, 4H), 2.77 (br s, 3H), 1.35 (t, J = 6.8 Hz, 3H). HRMS (ESI) m/z [M + H]+ calcd for C$_{27}$H$_{33}$N$_8$O$_4$, 533.2619; found, 533.2640. |

TABLE 2-continued

Table showing selected hydroxamate compounds

| EX | Compound | Chemical Structure | Chemical Name and Data |
|---|---|---|---|
| 97 | 35i | 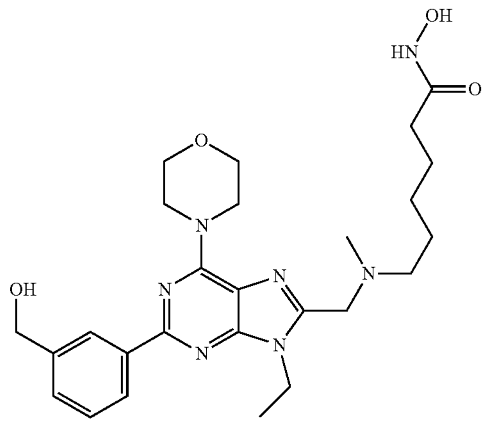 [SMILES: CCn1c(CN(C)CCCCCC(=O)NO)nc2c(N3CCOCC3)nc(-c3cccc(CO)c3)nc21] | 6-(((9-ethyl-2-(3-(hydroxymethyl)phenyl)-6-morpholino-9H-purin-8-yl)methyl)(methypamino)-N-hydroxyhexanamide. LC-MS m/z 512 ([M + H]$^+$). $^1$HNMR (DMSO-d$_6$) δ 10.38 (br s, 1H), 8.36 (s, 1H), 8.29 (dt, J = 1.6 Hz, 7.2 Hz, 1H), 7.46-7.40 (m, 2H), 4.59 (s, 2H), 4.37-4.31 (m, 6H), 3.79 (t, J = 4.8 Hz, 4H), 3.36 (br s, 2H), 3.18 (br s, 2H), 2.96 (s, 3H), 1.82-1.74 (m, 2H), 1.57-1.50 (m, 2H), 1.40 (t, J = 7.2 Hz, 3H), 1.32-1.28 (m, 2H). HRMS (ESI) m/z [M + H]$^+$ calcd for C$_{26}$H$_{38}$N$_7$O$_4$, 512.2980; found, 512.2983. |
| 98 | | 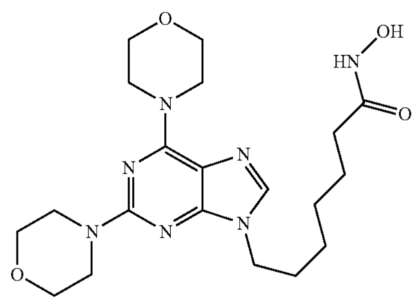 [SMILES: O=C(CCCCCCn1cnc2c(N3CCOCC3)nc(N3CCOCC3)nc21)NO] | 7-(2,6-dimorpholino-9H-purin-9-yl)-N-hydroxyheptanamide. LC-MS m/z 434.2 ([M + H]$^+$). HPLC purity (254 nm): 96.5 %. $^1$H NMR (DMSO-d$_6$) δ 10.33 (s, 1H), 7.89 (s, 1H), 4.12 (m, 4H), 4.02 (m, 2H), 3.70 (m, 4H), 3.64 (m, 4H), 1.92 (m, 2H), 1.76 (m, 2H), 1.46 (m, 2H), 1.23 (m, 4H). |
| 99 | | 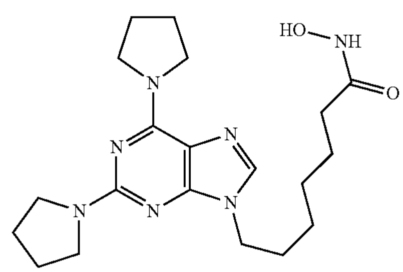 [SMILES: O=C(CCCCCCn1cnc2c(N3CCCC3)nc(N3CCCC3)nc21)NO] | 7-(2,6-di(pyrrolidin-1-yl)-9H-purin-9-yl)-N-hydroxyheptanamide. LC-MS m/z 402.2 ([M + H]$^+$). HPLC purity (254 nm): 97.1%. $^1$H NMR (DMSO-d$_6$) δ 10.37 (s, 1H), 8.31 (s, 1H), 4.15 (m, 2H), 3.94 (m, 2H), 3.67 (m, 2H), 3.53 (m, 4H), 1.95 (m, 10H), 1.77 (m, 2H), 1.47 (m, 2H), 1.25 (m, 2H). |
| 100 | | 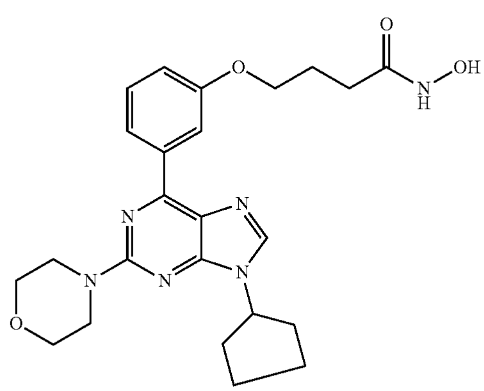 [SMILES: O=C(CCCOc1cccc(-c2nc(N3CCOCC3)nc3c2ncn3C2CCCC2)c1)NO] | 4-(3-(9-cyclopentyl-2-morpholino-9H-purin-6-yl)phenoxy)-N-hydroxybutanamide. LC-MS m/z 467.1 ([M + H]$^+$). HPLC purity (254 nm): 95.6%. $^1$H NMR (DMSO-d$_6$) δ 10.39 (s, 1H), 8.29 (s, 1H), 8.26 ((m, 2H), 7.38 (t, 1H), 7.04 (dd, J = 8.0, 2.4 Hz, 1H), 4.78 (m, 1H), 3.98 (m, 2H), 3.74 (m, 4H), 3.67 (m, 4H), 2.10 (m, 4H), 1.94 (m, 4H), 1.82 (m, 2H), 1.64 (m, 2H). |

TABLE 2-continued

Table showing selected hydroxamate compounds

| EX | Compound | Chemical Structure | Chemical Name and Data |
|---|---|---|---|
| 101 | | 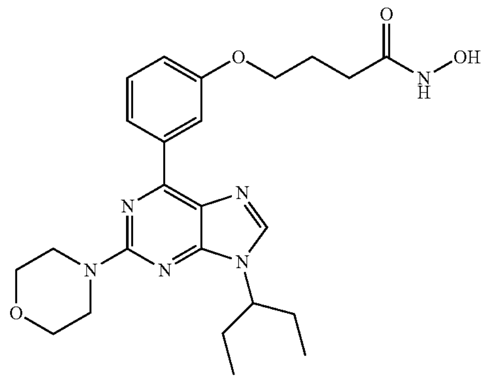 [SMILES: CCC(CC)n1cnc2c(-c3cccc(OCCCC(=O)NO)c3)nc(N3CCOCC3)nc21] | N-hydroxy-4-(3-(2-morpholino-9-(pentan-3-yl)-9H-purin-6-yl)phenoxy)butanamide. LC-MS m/z 469.1 ([M + H]$^+$). HPLC purity (254 nm): 97.8%. $^1$H NMR (DMSO-d$_6$) δ 10.46 (s, 1H), 8.35-8.38 (m, 3H), 7.46 (t, 1H), 7.11 (dd, J = 8.0, 2.2 Hz, 1H), 4.29 (m, 1H), 4.06 (t, J = 6.4 Hz, 2H), 3.79 (m, 4H), 3.75 (m, 4H), 2.18 (m, 2H), 2.01 (m, 4H), 1.91 (m, 2H), 0.74 (t, J = 7.2 Hz, 6H). |
| 102 | | 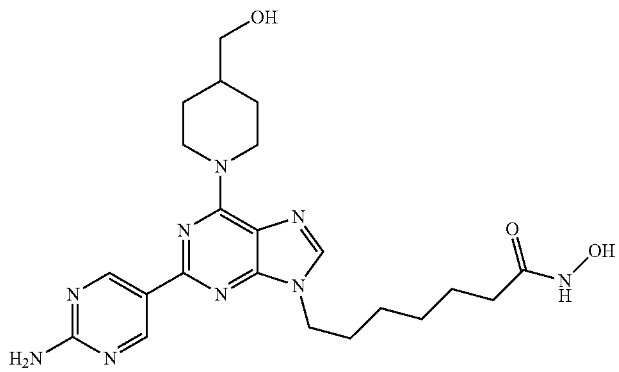 [SMILES: Nc1ncc(-c2nc(N3CCC(CO)CC3)c3ncn(CCCCCCC(=O)NO)c3n2)cn1] | 7-(2-(2-aminopyrimidin-5-yl)-6-(4-(hydroxymethyl)piperidin-1-yl)-9H-purin-9-yl)-N-hydroxyheptanamide. LC-MS m/z 470.1 ([M + H]$^+$). HPLC purity (254 nm): 97.2%. $^1$H NMR (DMSO-d$_6$) δ 9.16 (s, 2H), 8.16 (s, 1H), 4.80 (m, 2H), 4.18 (t, J = 7.2 Hz, 2H), 3.28 (m, 2H), 3.09 (m, 2H), 1.92 (m, 2H), 1.83 (m, 5H), 1.48 (m, 2H), 1.20 (m, 6H). |
| 103 | | 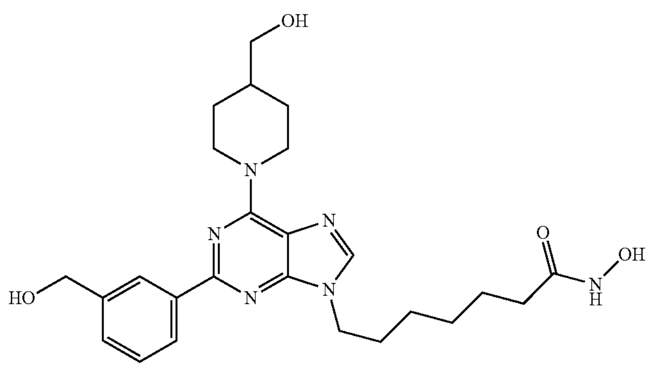 [SMILES: O=C(CCCCCCn1cnc2c(N3CCC(CO)CC3)nc(-c3cccc(CO)c3)nc21)NO] | N-hydroxy-7-(2-(3-(hydroxymethyl)phenyl)-6-(4-(hydroxymethyl)piperidin-1-yl)-9H-purin-9-yl)heptanamide. LC-MS m/z 483.1 ([M + H]$^+$). HPLC purity (254 nm): 86.2%. $^1$H NMR (DMSO-d$_6$) δ 10.33 (s, 1H), 8.34 (s, 1H), 8.26 (d, J = 7.2 Hz, 1H), 8.20 (s, 1H), 7.41 (m, 2H), 5.50 (m, 2H), 4.59 (s, 2H), 4.22 (t, J = 6.8 Hz, 2H), 3.29 (m, 2H), 3.11 (m, 2H), 1.93 (m, 2H), 1.85 (m, 5H), 1.48 (m, 2H), 1.20 (m, 6H). |
| 104 | | 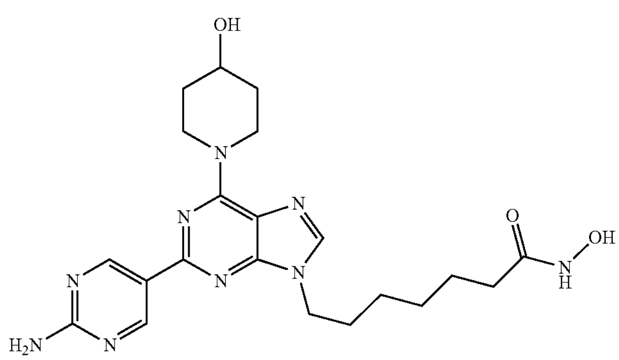 [SMILES: Nc1ncc(-c2nc(N3CCC(O)CC3)c3ncn(CCCCCCC(=O)NO)c3n2)cn1] | 7-(2-(2-aminopyrimidin-5-yl)-6-(4-hydroxypiperidin-1-yl)-9H-purin-9-yl)-N-hydroxyheptanamide. LC-MS m/z 456.1 ([M + H]$^+$). HPLC purity (254 nm): 99.9%. $^1$H NMR (DMSO-d$_6$) δ 10.33 (bs, 1H), 9.13 (s, 2H), 8.15 (s, 1H), 7.26 (bs, 2H), 4.88 (m, 1H), 4.19 (t, J = 6.8 Hz, 2H), 3.81 (m, 2H), 3.67 (m, 2H), 1.93 (m, 2H), 1.84 (m, 4H), 1.48 (m, 4H), 1.28 (m, 4H). |

TABLE 2-continued

Table showing selected hydroxamate compounds

| EX | Compound | Chemical Structure | Chemical Name and Data |
|---|---|---|---|
| 105 | | 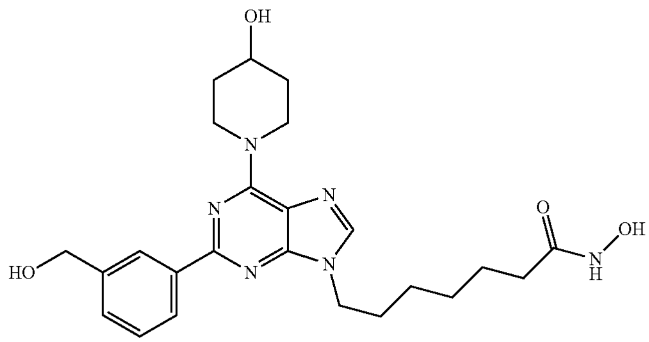 [SMILES: O=C(CCCCCCn1cnc2c(N3CCC(O)CC3)nc(-c3cccc(CO)c3)nc21)NO] | N-hydroxy-7-(2-(3-(hydroxymethyl)phenyl)-6-(4-hydroxypiperidin-l-yl)-9H-purin-9-yl)heptanamide. LC-MS m/z 469.1 ([M + H]$^+$). HPLC purity (254 nm): 93.3%. $^1$H NMR (DMSO-d$_6$) δ 10.34 (s, 1H), 8.35 (s, 1H), 8.27 (m, 1H), 8.21 (s, 1H), 7.42 (m, 2H), 4.95 (m, 1H), 4.60 (s, 2H), 4.23 (m, 2H), 3.82 (m, 2H), 3.70 (m, 2H), 1.93 (m, 2H), 1.91 (m, 4H), 1.48 (m, 4H), 1.30 (m, 4H). |

Example 10: Enzyme Assays

HDAC Enzyme Assay

HeLa nuclear extracts are used as the source of HDACs in routine HDAC inhibition assays. The recombinant HDAC enzymes, HDAC1 (Cat #5005), HDAC3/NcoR2 (Cat #50003), HDAC4 (Cat #50004), HDAC6 (Cat #50006), HDAC8 (Cat #50008) were purchased from BPS Bioscience Inc., United States. HDAC4 (#H86-31G-10), HDAC5 (Cat #H87-31G), HDAC9 (Cat #H91-31G), HDAC10 (Cat #H92-31G), and HDAC11 (Cat #H93-30G) were purchased from SignalChem, Canada. The assay is performed in 96-well format (black NBS half-area 96-well plate, Corning #3993) using a fluorescent-based HDAC activity assay. Substrates Boc-Lys(Ac)-AMC (Cat #1-1875) for HeLa nuclear extracts, HDACs 1, 2, 3, 6, and 10, Boc-Lys(Tfa)-AMC (Cat #1-1985) for HDACs 4, 5, 7, 8, 9 and 11 were purchased from Bachem AG, Switzerland. The reaction mixture (50 µL/well) is composed of assay buffer, containing 25 mM Tris, pH 8.0, 137 mM NaCl, 2.7 mM KCl, 1 mM MgCl, 0.1 mg/mL BSA, test compounds, an appropriate concentration of enzyme, and 50 µM of substrate and incubates at room temperature for 2 h. The reaction is stopped by addition of developer [50 µL/well, containing trypsin (Cat #T4799, Sigma-Aldrich), 2 mg/mL, 50 mM tris pH 8.0, and LAQ824 (CAS 404951-53-7), 4.5 µM] and incubated at 37° C. for 30 min. The fluorescence is detected at the excitation wavelength of 360 nm and emission wavelength of 460 nm using a BioTek Synergy H4 Hybrid Multi-Mode Microplate Reader and raw data are processed using BioTek's Gen5 (v2.03.01) software. The IC$_{50}$s are reported in Table 1, vorinostat (SAHA) is used as positive control which was made as our previously reported (Wang, et al. J. Med. Chem. 2011, 54, 4694-4720).

Kinase Enzyme Assay.

Lipid kinases PI3Kα: Cat # PV4788 from Invitrogen, or Cat #40620 from BPS Bioscience Inc., United States or Cat # P27-18H from SignalChem, Canada; p110α(H1047R)/p85α (Cat #40641) from BPS, p110α(E545K)/p85α(Cat #P27-15H) from SignalChem; PI3Kβ: Cat # P28-10H (SignalChem), Cat #40622 (BPS), PI3Kδ: Cat # P30-10H (SignalChem) were used in the ADP-Glo™ Kinase Assay (Promega). PI3K inhibitors GDC-0941 and wortmannin were purchased from LC Laboratories (165 New Boston Street Woburn, Mass. 01801, United States) as powder and then prepared in DMSO as 10 mM stock. Dual inhibitor of PI3k and mTOR GDC-0980 was purchased from Selleck Chemicals (2626 S Loop W #225, Houston, Tex. 77054, United States) as 10 mM stock in DMSO. Serially diluted compounds solutions (5 µL/well, 3-fold, 8-concentration) was added to a white NBS half-area 96-well plate (Corning #3992). Lipid PIP2:PS (1:3) mixture (0.167 mg/mL: 0.5 mg/mL) in Lipid Dilution Buffer (25 mM HEPES, pH7.5, 0.5 mM EGTA) was diluted (1:1) with Reaction Buffer (3.33×) (159 mM HEPES, pH7.5, 87 mM NaCl, 9.5 mM MgCl$_2$, 0.08 mg/mL BSA) to make a 1.67× working solution, PI3K enzyme was diluted with the 1.67× working solution and 15 µL/well was used for reaction. ATP (125 µM, 5 µL/well) in DI water was added to initiate the reaction. After reaction at room temp for 1 h, the reaction was stopped by addition of ADP-Glo solution (25 µL/well) and incubated at room temp for 40 min, then kinase detection solution (50 µL/well) was added and incubated for 40 min, the luminescence was read on a Biotek Synergy H4 Hybrid Multi-Mode Microplate Reader and raw data are processed using BioTek's Gen5 (v2.03.01) software. The IC50s are reported in Table 1, GDC-0941, GDC-0980 and wortmannin are used as positive controls.

IC$_{50}$ is defined as the concentration of compound required for 50% inhibition of enzyme activity. Definition of the potency: "I": 1 µM<IC$_{50}$≤10 µM. "II": 0.1 µM<IC$_{50}$≤1 µM. "III": 0.01 µM<IC$_{50}$≤0.1 µM. "IV": IC$_{50}$≤0.01 µM

TABLE 3

In Vitro Enzymatic IC$_{50}$ (µM)

| EX | HDAC (HeLa) | HDAC1 | HDAC6 | PI3Kα | PI3Kα (E545K) | PI3Kα (H1047R) | PI3Kβ |
|---|---|---|---|---|---|---|---|
| 1 | III | III | III | I | I | I | |
| 2 | IV | IV | IV | III | III | III | II |
| 3 | III | III | III | III | | | |
| 4 | | III | | | | | |
| 5 | III | | | | | | |
| 6 | II | III | II | III | | | |
| 7 | II | III | III | III | III | III | III |
| 8 | III | | | | | | |
| 9 | II | | | | | | |
| 10 | III | II | | I | | | |
| 11 | III | | | | | | |
| 12 | III | | | | | | |
| 13 | I | | | | | | |
| 14 | II | | | | | | |
| 15 | II | | | | | | |
| 16 | II | | | | | | |
| 17 | I | I | | | | | |

TABLE 3-continued

In Vitro Enzymatic IC$_{50}$ (μM)

| EX | HDAC (HeLa) | HDAC1 | HDAC6 | PI3Kα | PI3Kα (E545K) | PI3Kα (H1047R) | PI3Kβ |
|---|---|---|---|---|---|---|---|
| 18 | | I | | | | | |
| 19 | III | III | | | | | |
| 20 | II | | | | | | |
| 21 | II | | | | | | |
| 22 | I | | | | | | |
| 23 | III | III | | | | | |
| 24 | | I | | I | | | |
| 28 | I | I | | | | | |
| 29 | II | III | | | | | |
| 30 | II | I | | | | | |
| 31 | III | III | | | | | |
| 32 | I | | | | | | |
| 33 | I | | | | | | |
| 34 | I | | | | | | |
| 35 | II | | | | | | |
| 36 | III | | | | | | |
| 37 | II | | | | | | |
| 38 | IV | IV | IV | III | III | III | II |
| 39 | III | | | | | | |
| 40 | I | | | | | | |
| 41 | IV | IV | IV | I | | | |
| 42 | II | | | | | | |
| 43 | III | II | | | | | |
| 44 | III | II | II | I | | | |
| 45 | III | II | | | | | |
| 46 | III | II | | | | | |
| 47 | IV | IV | | | | | |
| 48 | IV | IV | IV | II | | | |
| 49 | IV | IV | IV | II | | | |
| 50 | IV | IV | | I | | | |
| 51 | IV | IV | IV | I | | | |
| 52 | IV | IV | III | I | | | |
| 53 | IV | IV | IV | II | | | |
| 54 | IV | IV | | I | | | |
| 55 | IV | IV | III | II | II | II | |
| 56 | III | | | | | | |
| 57 | III | | | | | | |
| 58 | II | | | | | | |
| 59 | I | | | | | | |
| 60 | IV | IV | IV | II | | | |
| 61 | II | | | | | | |
| 62 | III | | | | | | |
| 63 | III | | | | | | |
| 64 | IV | IV | | II | | | |
| 65 | IV | | | | | | |
| 66 | II | | | | | | |
| 67 | IV | | | | | | |
| 68 | II | | | | | | |
| 69 | II | | | | | | |
| 70 | IV | IV | | II | | | |
| 71 | II | | | | | | |
| 72 | IV | IV | | II | | | |
| 73 | IV | | | | | | |
| 74 | IV | IV | | I | | | |
| 75 | III | | | | | | |
| 76 | III | III | | | | | |
| 77 | IV | IV | IV | III | III | III | |
| 78 | IV | IV | IV | II | II | II | |
| 79 | IV | IV | IV | III | III | III | |
| 80 | | II | | | | | |
| 81 | IV | IV | IV | III | III | III | II |
| 82 | III | | | | | | |
| 83 | II | II | | | | | |
| 84 | III | II | | | | | |
| 85 | IV | III | | | | | |
| 86 | I | I | | III | | | |
| 87 | II | II | II | III | | | |
| 88 | | I | | | | | |
| 89 | II | II | | III | | | |
| 90 | II | II | | II | | | |
| 91 | II | II | II | II | | | |
| 92 | II | II | II | II | | | |
| 93 | I | | | | | | |
| 94 | II | | | | | | |
| 95 | II | | | | | | |
| 96 | II | | | | | | |
| 97 | II | III | II | III | | | |
| 98 | IV | | | | | | |
| 99 | IV | | | | | | |
| 100 | III | | | | | | |
| 101 | III | | | | | | |
| 102 | IV | | | | | | |
| 103 | IV | | | | | | |
| 104 | IV | | | | | | |
| 105 | IV | | | | | | |
| vorinostat | III | III | III | | | | |
| Wortmannin | | | | IV | IV | IV | III |

Example 11: Cell Culture and Anti-Proliferative Assays (Cellular IC$_{50}$)

Representative human tumour cell lines used in the cellular assays are breast cancer (BT-474, MCF7, MDA-MB-231, MDA-MB-436, and MDA-MB-468), colon cancer (COLO 205 and HCT 116), glioblastoma (U87 MG), leukemia (HL-60, K-562, MOLT-4, MV-4-11, RPMI-8226, SUP-B15), lung cancer (A549, NCI-H460, and NCI-H522), melanoma (A-375), ovarian cancer (SK-OV-3), pancreases cancer (BxPC-3 and PANC-1), prostate cancer (PC-3 and DU145), and renal cancer (A-498 and ACHN) cell lines. Cell lines COLO 205, HCT 116, MOLT-4, MV-4-11, K-562, RPMI8226, SUP-B15, U87MG, SK-OV-3, PC-3, DU-145, NCI-H460, NCI-H522, A375, HepG2, SK-HEP1, BxPC-3 and PANC-1 were purchased from ATCC and expanded using ATCC recommended media. Cell lines MCF7, TB474, T-47D, MDA-MB-231, MDA-MB-468, MDA-MB-436, A549, A-498, AHCN, and HeLa were also from ATCC. Cells were cultivated at 37° C., 5% CO$_2$ in media containing 10% FBS and 2 mM glutamine Cells were routinely monitored with MycoAlert™ PLUS Mycoplasma Detection Kit (Lonza Walkersville, Inc.) to make sure they were mycoplasma free. Antibiotics (100 U/mL of penicillin and 100 μg/mL of streptomycin) were only added to the media used for compound dilution and cells in 96-well assay plates. DMEM (4.5 g/L glucose) and RPMI1640 were obtained from Biopolis Shared Facilities (BSF), Singapore. For cellular assays, BxPC-3, PC-3, HCT 116, COLO 205, MV-4-11, RPMI8226, HL-60, SUP-B15, T-47D were cultivated in RPMI1640; A-498, ACHN, DU145, MCF7, PANC-1, U-87MG, NCI-H460, NCI-H522, HeLa, and A-375 were cultivated in DMEM; BT-474, MDA-MB-231, MDA-MB-468, MDA-MB-436 in DMEM/F12 (1:1).

For a typical screening experiment, cells (100 μL/well) are inoculated into 96 well microtiter plates at plating densities ranging from 2,000 to 30,000 cells/well depending on the doubling time of individual cell lines and assay linearity. Clear 96-well tissue culture plates (Corning #3596, or Nunc 167008) are used for colorimetric assay and monitoring cell growth status, while white 96-well tissue culture plates (Corning #3917) are used for luminescent and fluorescent assays. After cell inoculation, the microtiter plates are incubated at 37° C., 5% CO$_2$, 95% air and 100% relative humidity overnight (up to 24 h) prior to addition of compounds for adherent cells. Suspension cells are treated with test compounds immediately after cell inoculation.

Test compounds are serially diluted (3-fold or 4-fold, 8-concentration) using the same media and added to the plates (15 to 25 μL/well). After 72 h of cultivation, the plates are assayed for cell cytotoxicity/viability by using the following two methods. For selected compounds, $IC_{50}$s after 24 h and 48 h of drug treatment were also determined.

Sulforhodamine B (SRB) Method

Cells in plates are fixed with cold trichloroacetic acid (TCA) (50% w/v in DI water, 1/4 volume of the medium in each well), and incubated at 4° C. for 1 h (adherent cells) or 2 h (suspension cells). The plates are washed 5 times (tap water×3, DI water×2) and air-dried. SRB solution 0.4% (w/v) in 1% acetic acid is added to each well (60 μL/well) and the plates are incubated at room temperature for 30 min, then washed with 1% acetic acid solution 4 times, and air-dried. The bound dye is dissolved by addition of Tris base solution (10 mM, 100 μL/well) and the absorbance is read at a wavelength of 515 nm on a BioTek Synergy H4 Hybrid Multi-Mode Microplate Reader.

CellTiter-Glo® Luminescent Cell Viability Assay

The plates are added CellTiter-Glo® Reagent (95 μL/well) and read the luminescence on a BioTek H4 reader per manufacture's protocol.

The raw data are processed using BioTek's Software Gen5 (v2.03.01) to generate inhibitory $IC_{50}$ values. Vorinostat and GDC-0941 are used as positive control.

$IC_{50}$ is defined as the concentration of compound required for 50% inhibition of cell vs non-treated. $IC_{50}$ data are shown in Tables 4 and 5 below.

Definition of the Potency is as follows:

"I":, $IC_{50}$>10 μM. "II": 2 μM>$IC_{50}$≤10 μM. "III": 0.5 μM<$IC_{50}$≤2 μM. "IV": $IC_{50}$≤0.5 μM

TABLE 4

| EX | MV-4-11 | K-562 | MOLT-4 | PC-3 | MCF7 | COLO 205 | HCT 116 | HepG2 |
|---|---|---|---|---|---|---|---|---|
| 1 | IV | III | IV | III | III | III | IV | III |
| 2 | IV | IV | IV | III | III | III | III | III |
| 3 | III | II | II | II | | | III | |
| 4 | | III | | | III | | | |
| 5 | IV | III | | II | III | III | | III |
| 6 | III | II | II | II | II | II | III | |
| 7 | III | III | III | III | IV | III | III | III |
| 10 | IV | III | | II | III | II | | |
| 29 | IV | III | IV | III | III | III | IV | |
| 30 | IV | II | | IV | II | II | | |
| 31 | IV | III | III | II | III | III | | |
| 37 | IV | III | IV | III | III | II | III | III |
| 40 | III | III | III | II | III | II | III | II |
| 41 | IV | IV | IV | II | III | III | III | III |
| 43 | IV | IV | IV | III | III | III | | |
| 44 | IV | III | IV | III | III | III | | III |
| 45 | IV | III | IV | III | III | III | | |
| 46 | IV | IV | IV | III | III | III | | |
| 47 | III | III | IV | II | III | III | | |
| 48 | III | III | IV | II | III | III | | III |
| 49 | III | III | IV | II | III | III | | II |
| 50 | III | III | IV | II | II | III | | II |
| 51 | IV | III | | II | III | III | | III |
| 52 | III | II | | II | III | III | | |
| 53 | IV | III | III | II | III | III | III | III |
| 54 | III | II | | II | II | II | | |
| 55 | IV | III | IV | II | III | III | IV | III |
| 56 | III | II | | | | II | | |
| 57 | I | I | | | | I | | |
| 58 | III | II | | | II | | | |
| 59 | III | I | | | I | | | |
| 60 | IV | III | III | II | II | II | III | II |
| 61 | III | I | | | | I | | |
| 62 | IV | | | II | III | II | | III |
| 63 | III | | | II | | II | | |
| 64 | III | | | I | | I | | |
| 65 | I | | | I | | I | | |
| 66 | III | | | II | | II | | |
| 67 | III | | | II | | II | | |
| 68 | III | | | II | | II | | |
| 69 | III | | | II | | II | | |
| 70 | III | | | II | | II | | |
| 71 | III | | | I | | I | | |
| 72 | III | | | III | | | | III |
| 73 | III | | | II | | | | |
| 74 | III | IV | IV | III | III | | III | III |
| 75 | IV | | | II | III | | III | II |
| 76 | IV | III | IV | III | III | | IV | III |
| 77 | IV | III | IV | II | III | | III | II |
| 78 | IV | IV | IV | III | III | | III | III |
| 79 | IV | III | IV | III | III | | III | II |
| 82 | III | | | I | II | I | | |
| 83 | | II | III | | | II | | |
| 84 | | II | II | | | I | | |
| 85 | III | III | IV | II | III | III | | |
| 86 | | II | III | | | II | | |
| 87 | | I | II | | | I | | |
| 88 | | I | II | | | I | | |
| 89 | | II | III | II | III | II | | |
| 90 | | II | II | | | II | | |
| 91 | | II | II | | | II | | |
| 92 | | II | II | | | II | | |
| 93 | III | II | | II | II | II | | |
| 94 | III | II | | | | II | | |
| 95 | III | II | | | | I | | |
| 96 | III | II | III | II | III | III | III | III |
| 97 | III | | | II | II | | | II |
| 98 | III | III | | II | III | II | | II |
| 99 | III | | | II | | II | | |
| 100 | IV | | IV | | IV | | IV | III |
| 101 | IV | | IV | | IV | | III | III |
| 102 | IV | | III | | III | | | |
| 103 | IV | | IV | | III | | | |
| 104 | IV | | III | | III | | | |
| 105 | IV | | IV | | III | | III | |
| GDC-0941 | III | I | IV | III | IV | III | III | I |
| GDC-0980 | I | II | | | II | IV | | |
| vorinostat | III | III | III | II | II | III | II | II |
| Sorafenib | IV | II | | II | II | | III | II |

TABLE 5

In Vitro Cellular IC$_{50}$ (μM)* for representative compound EX 1, 2, 7, 37, 41, 46, 55, 78, 98, and 100

| Cell Lines | Cancer Panel | 1 | 2 | 7 | 37 | 41 | 46 | 55 | 78 | 98 | 100 | GDC-0941 | Vorinostat | Sorafenib |
|---|---|---|---|---|---|---|---|---|---|---|---|---|---|---|
| BT474 | Breast Cancer | III | III | IV | III | III | III | | | | | IV | II | |
| MCF7 | Breast Cancer | III | III | IV | III | III | III | III | III | III | IV | IV | III | II |
| MDA-MB-231 | Breast Cancer | III | III | II | III | | II | | | | | I | II | |
| MDA-MB-436 | Breast Cancer | III | III | II | III | | II | | | | | III | II | |
| MDA-MB-468 | Breast Cancer | III | III | IV | III | | III | | | | | II | III | |
| 4T1 | Breast cancer (mouse) | III | III | II | | III | | IV | III | | III | II | II | |
| COLO 205 | Colon Cancer | III | III | III | II | III | III | III | | II | | III | III | |
| HCT 116 | Colon Cancer | IV | III | III | III | III | | IV | III | | IV | II | III | II |
| U138MG | Glioblastoma | III | III | | | | | III | III | | III | II | II | II |
| U87 MG | Glioblastoma | III | II | II | II | | II | III | III | | III | II | II | II |
| HuH-7 | HCC | III | IV | | | | | III | III | | IV | III | III | II |
| SK-HEP1 | HCC | III | III | III | III | III | | III | III | | III | II | III | II |
| HCCLM3 | HCC | II | III | | | | | II | II | | II | III | II | II |
| HepG2 | HCC | III | III | III | III | III | | III | III | II | III | I | III | II |
| PLC/PRF/5 | HCC | III | III | | | | | III | II | | III | II | III | II |
| HEL9217 | Leukemia | III | IV | | IV | | IV | | IV | | IV | II | III | |
| HL-60 | Leukemia | IV | IV | IV | III | III | | | | | | III | III | |
| K-562 | Leukemia | III | IV | III | III | IV | IV | III | IV | III | | I | III | II |
| MOLT-4 | Leukemia | IV | IV | III | IV | IV | IV | IV | IV | | IV | IV | III | II |
| MV-4-11 | Leukemia | IV | IV | III | IV | IV | IV | IV | IV | III | IV | III | III | IV |
| RPMI-8226 | Leukemia | IV | III | III | III | IV | | | | | | II | III | |
| SUP-B15 | Leukemia | IV | IV | IV | IV | IV | | | | | | II | III | |
| NCI-H460 | Lung Cancer | III | III | | | | | III | III | | IV | IV | III | II |
| NCI-H522 | Lung Cancer | III | III | II | III | | II | III | III | | III | I | II | II |
| A549 | Lung Cancer | III | III | | | | | III | III | | IV | IV | III | II |
| Pfeiffer | Lymphoma | IV | IV | IV | IV | IV | | III | IV | | IV | IV | III | II |
| Ramos | Lymphoma | IV | IV | III | IV | IV | | IV | IV | | | II | III | |
| Daudi | Lymphoma | IV | IV | | | IV | | IV | | IV | IV | IV | IV | |
| Raji | Lymphoma | III | IV | | | IV | | IV | | IV | II | II | III | II |
| A375 | Melanoma | III | III | II | III | III | | III | | | | III | III | |
| BxPC-3 | Pancreases | III | III | III | III | | III | | | | | III | II | |
| PANC-1 | Pancreases | III | II | II | II | II | | II | | | | III | II | |
| PC-3 | Prostate Cancer | III | III | III | II | II | III | II | III | II | | III | II | II |
| ACHN | Renal Cancer | III | III | II | III | III | III | | | | | III | III | |
| A-431 | Skin cancer | II | III | | | III | | III | | | III | IV | II | |

*"I": IC$_{50}$ > 10 μM.
"II": 2 μM < IC$_{50}$ ≤ 10 μM.
"III": 0.5 μM < IC$_{50}$ ≤ 2 μM.
"IV": IC$_{50}$ ≤ 0.5 μM.
HCC = Hepatocellular carcinoma

Example 12: Western Blot Analysis

Cells are cultivated and treated with test compounds as described in the above Cell Culture and Anti-Proliferative Assays section (Example 11). Cells are washed with cold DPBS twice and cooled on ice and treated with lysis buffer [50 mM Tris (pH7.4), 2.5 mM β-glycerophosphate, 150 mM NaCl, 1% NP-40, 0.5% sodium deoxycholate, 0.1% SDS, 2 mM sodium orthovanadate, 10 mM sodium fluoride, 1 mM EDTA and freshly added protease inhibitor PMSF (0.1 mM) and protease inhibitor cocktail (Cat #03969, Nacalai Tesque, Inc. or Cat. #539134, Calbiochem). Lysates are cleared at 20,000×g 20×2 min, and protein concentrations are determined using BCA Protein Assay K (Cat #71285-3, Novagen, USA). Proteins in cell lysates are resolved by SDS-PAGE and transferred to PVDF and probed with appropriate primary and secondary antibodies. Histone H3 (acetyl K9) (Cat #9649), Histone H3 (Cat #9715), Acetyl-α-Tubulin (Lys40) (Cat #5335), α-Tubulin (Cat #2125), pAkt (Ser473) (Cat #4060), pAkt (Thr308) (Cat #4056, #2965), anti-Akt(pan) (Cat #4685), p56 ribosomal protein (Ser240/244) (Cat #5364), S6 ribosomal protein (Cat #2217), p56 ribosomal protein (S240/244), Phospho-PRAS40 (Thr246) (Cat #2997), p-mTOR (S2448) (Cat #5536), pErk1/2 (T202/y204) (Cat#4376), Phospho-4E-BP1 (Thr37/46) (Cat #2855), p70S6 Kinase (Cat #2708), Phospho-p70 S6 Kinase (Thr389) (Cat #9234), Phospho-p70S6 Kinase (Thr421/5er424) (Cat #9204), Phospho-p70S6 Kinase (Ser371) (Cat #9208), pPDK1 (Ser241) (Cat #3438), and HRP-linked anti-rabbit IgG (Cat #7074) antibodies were purchased from Cell Signaling Technology, Inc., USA. Anti-β-actin (Cat # ab8227) was from Abcam, and anti-GAPDH-HRP (Cat # sc-25778-HRP) was from Santa Cruz Biotechnology, Inc. The protein bands are detected using Pierce ECL Western Blotting Substrate (Cat #3229) and captured using FUJI Super RX-N films which are subsequently scanned and analyzed using ImageJ (1.47V) software. Representative Western blot images are shown in FIG. 15 and analyzed results are presented by FIGS. 17 to 20.

In FIG. 15, the inhibition of HDACs and PI3k-Akt-mTOR pathway in PC-3 cells are shown. PC-3 cells were treated with test compounds at the following concentrations (all contain 0.1% DMSO) for 24 h at 37° C., and then processed according to section of Western Blot Analysis.

| Lane | Sample | Lane | Sample |
|---|---|---|---|
| 1 | DMSO (0.1%) | A | EX3_10 μM |
| 2 | Vorinostat_10 μM | B | EX6_10 μM |
| 3 | GDC-0941_1 uM | C | EX37_10 μM |
| 4 | EX1_1 μM | D | EX40_10 μM |
| 5 | EX1_10 μM | E | EX41_10 μM |
| 6 | EX2_1 μM | F | EX7_10 μM |

| Lane | Sample | Lane | Sample |
|---|---|---|---|
| 7 | EX2_10 µM | G | EX97_10 µM |
| 8 | Insulin (100 µg/mL), 30 min | | |

Hyperacetylation of histone 3 (Lys 9) and α-tubulin were observed for compound examples tested (FIGS. 15A, 15B, 15C and 15D) and the hyperacetylation effect is dose-dependent as demonstrated by both EX1 and EX2 (FIG. 15A). The tested examples also inhibited PI3K-Akt-mTOR pathway with a broad range of activities. Except EX40 and EX41, they all inhibited phosphorylation of Akt (Ser473) or activity of mTORC2 (FIGS. 15A and 15B). They also inhibited phosphorylation of S6(Ser240/244) or activity of mTORC1 (with exception of EX2, EX40 and EX41, FIGS. 15C and 15D). DMSO (0.1%) was used as blank control for protein phosphorylation and normalized as 100% when analyzed by ImageJ. PC-3 cells were also treated with insulin (100 µg/mL) for 30 min and both pAkt and pS6 phosphorylations were significantly enhanced. The gels were digitized and analyzed by ImageJ, see FIGS. 17 to 20 for details.

Figure 16:
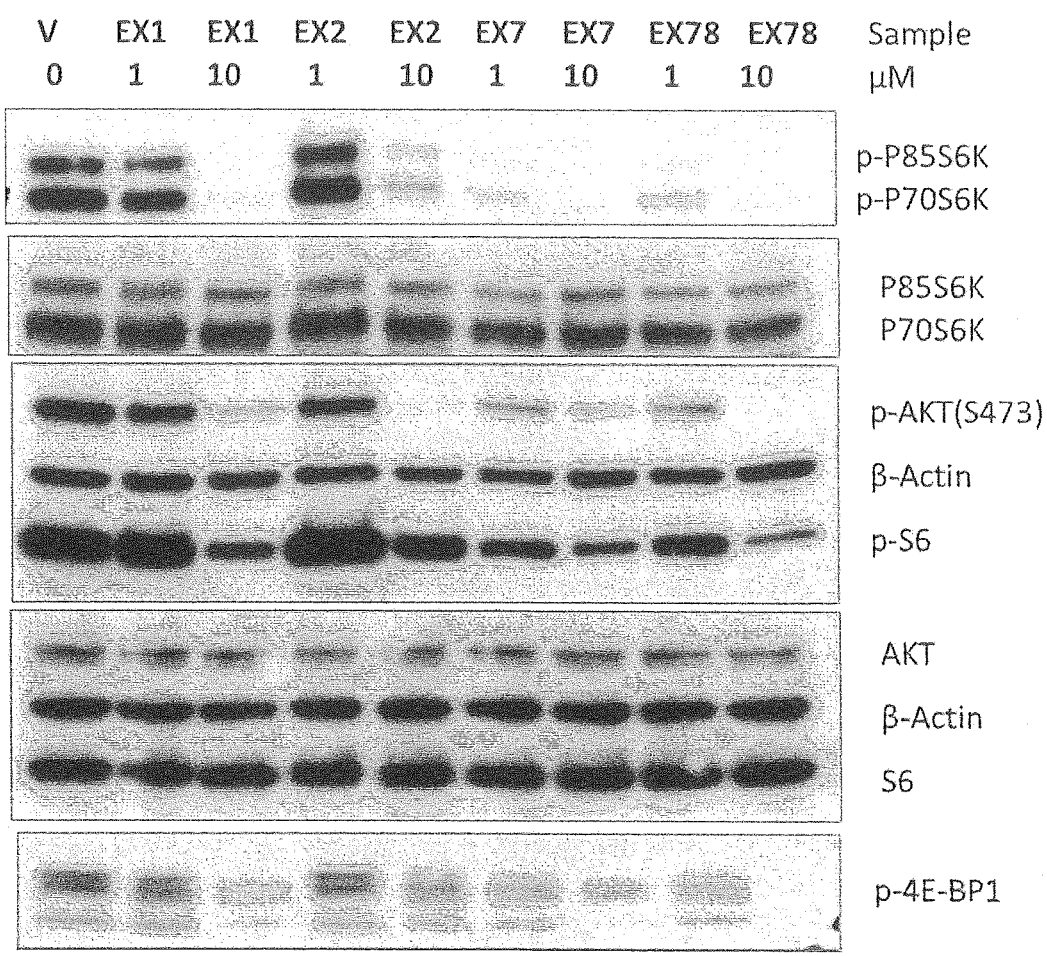
FIG. 16 shows the modulation of the PI3K-AKT-mTOR Pathway in MCF7 cells treated with the compounds.

In FIG. 16, the modulations of PI3K-AKT-mTOR Pathway in MCF7 cells are shown. MCF7 cells were serum starved overnight and treated with test compounds for 2 h including 30 min of insulin stimulation (20 µg/mL). V=vehicle DMSO (0.1%) as blank control, and its phosphorylation level was normalized to 100% in ImageJ analysis. The gels were digitized and analyzed by ImageJ; see FIGS. 17 to 20 for details.

Figure 17A:
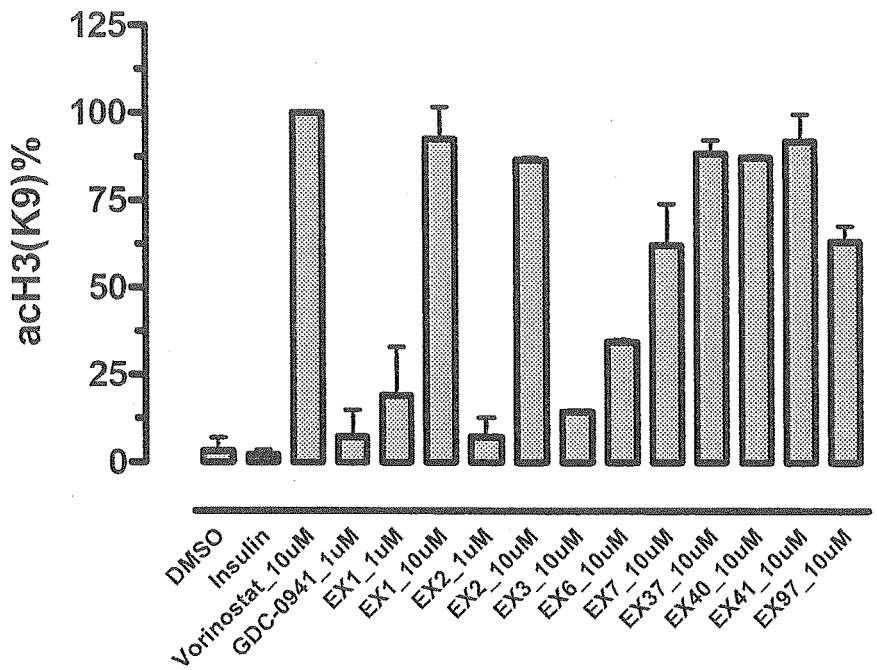
FIG. 17 shows the hyperacetylation of histone 3 (Lys 9) due to inhibition of HDACs in cells treated with the compounds.
Figure 17B:
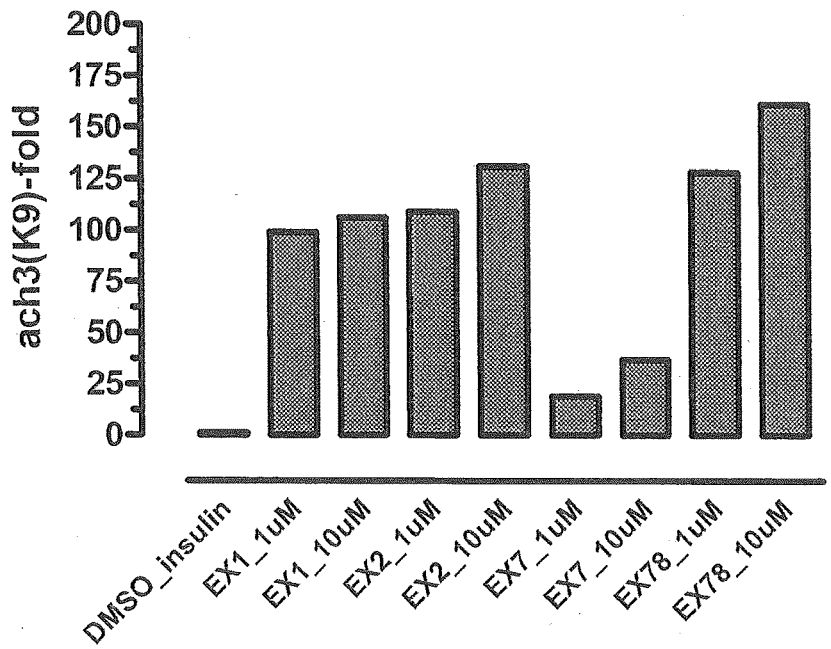

In FIG. 17, the hyperacetylation of histone 3 (Lys 9) due to inhibition of HDACs is shown. FIG. 17A shows PC-3 cells treated with test compounds at above indicated concentrations (FIG. 15) for 24 h. The graph represents results from two Western Blot analyses. Vorinostat (10 µM) was used as positive control, and its acetylation level was normalized to 100% in ImageJ analysis. FIG. 17B shows MCF7 cells that were serum starved overnight and treated with test compounds for 2 h including insulin (20 µg/mL) stimulation in last 30 min for all samples. Vehicle DMSO (0.1%) was used as blank control, and its acH3 level was normalized to 1. Y Axis is expressed as Mean±SD if applicable.

Figure 18A:
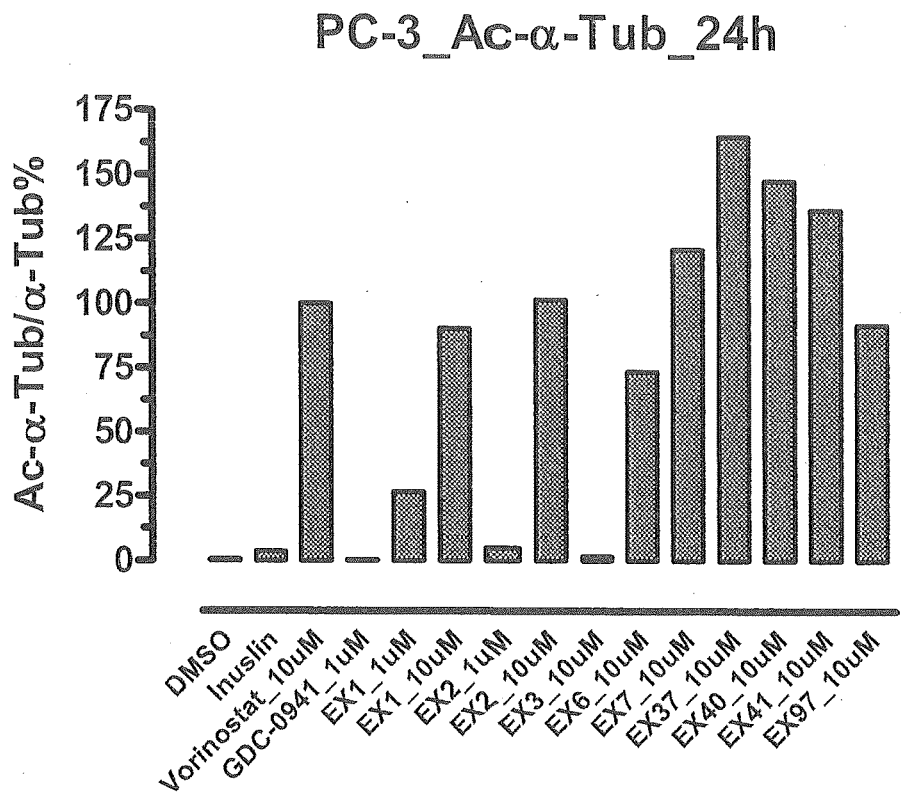
FIG. 18 shows the hyperacetylation of α-tubulin due to inhibition of HDAC6 in cells treated with the compounds.
Figure 18B:
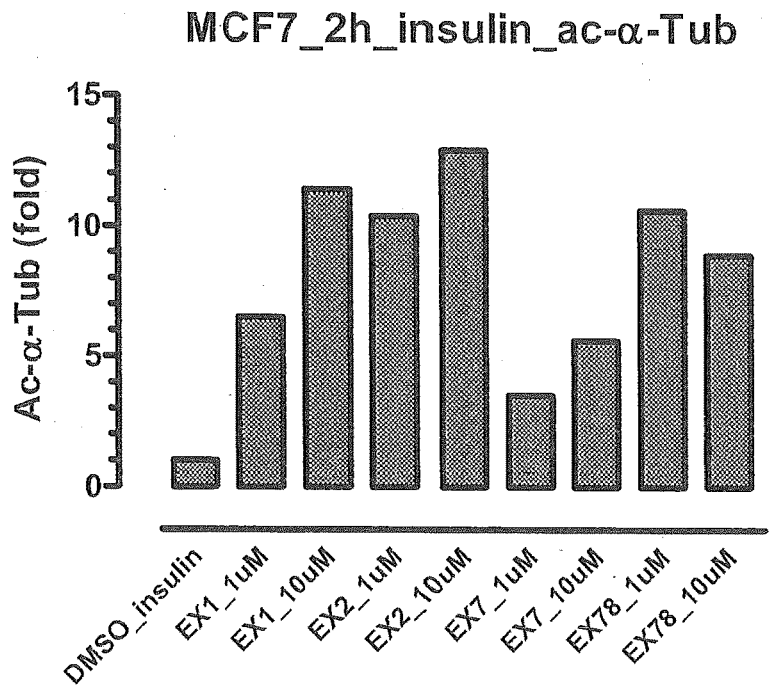

In FIG. 18, hyperacetylation of α-tubulin due to inhibition of HDAC6 is shown. FIG. 18A shows PC-3 cells treated with test compounds at above indicated concentrations (FIG. 15) for 24 h, Figure the graph represents results from two Western Blot analyses. Vorinostat (10 µM) was used as positive control, and its acetylation level was normalized to 100% in ImageJ analysis. FIG. 17B. shows MCF7 cells that were serum starved overnight and treated with test compounds for 2 h including insulin (20 µg/mL) stimulation in last 30 min for all samples. Vehicle DMSO (0.1%) as blank control, and its acetylation level was normalized to 1. Y Axis is expressed as Mean±SD if applicable.

Figure 19A:
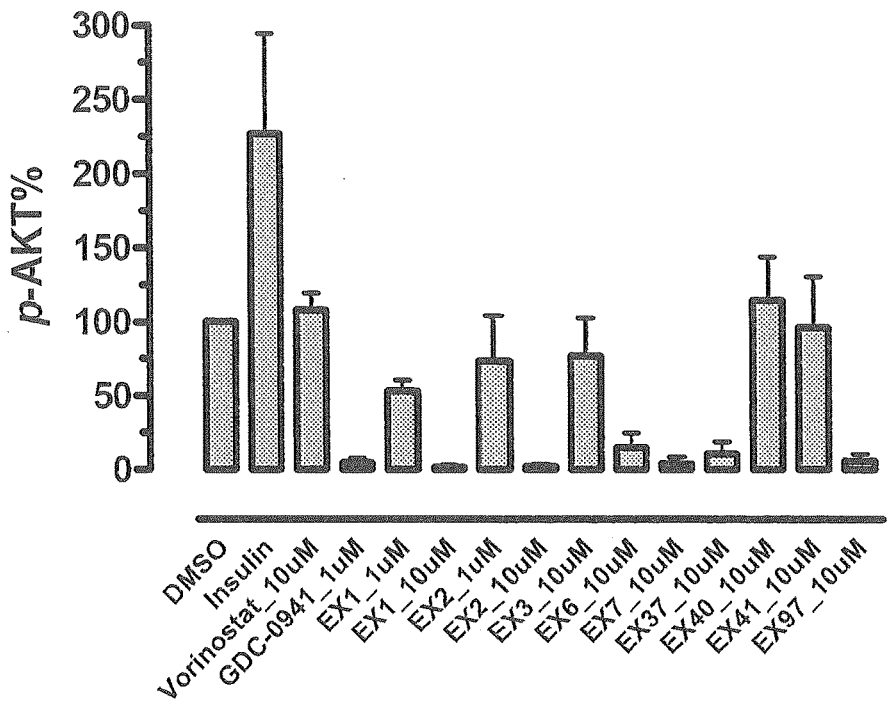
FIG. 19 shows the modulation of the PI3K-AKT-(mTOR) Pathway: p-Akt (Ser473) level and activity of mTORC2 in cells treated with the compounds.
Figure 19B:
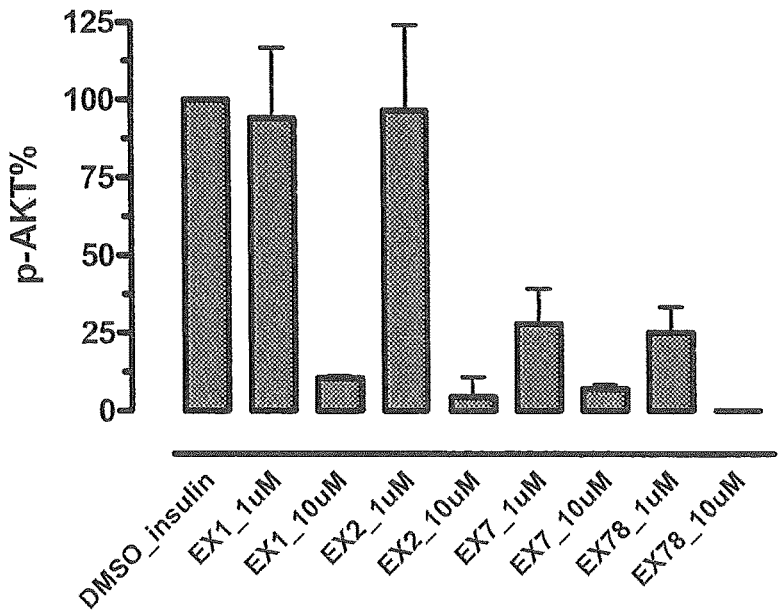
Figure 20A:
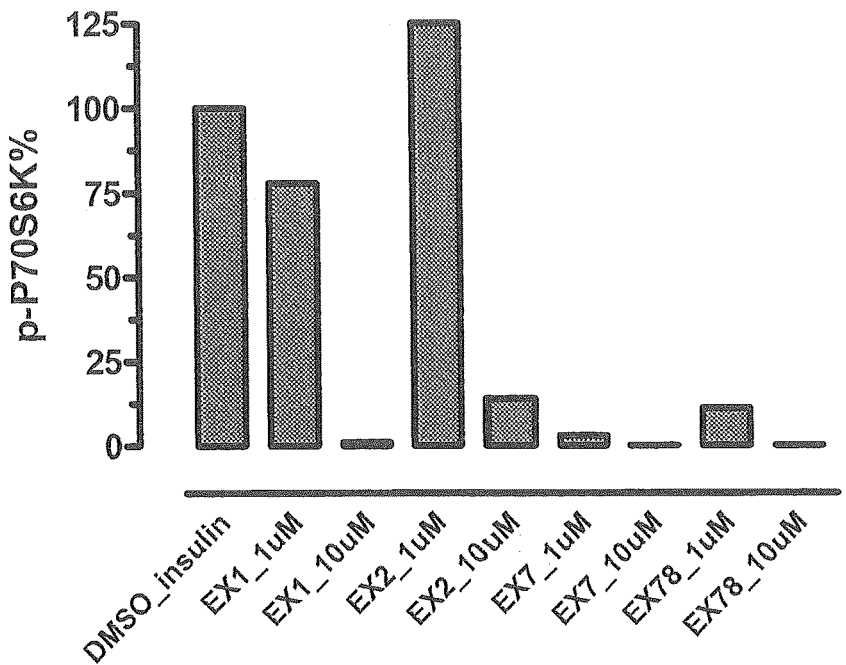
FIG. 20 shows the modulation of the PI3K-AKT-(mTOR) Pathway: mTORC1 activity in cells treated with the compounds.
Figure 20B:
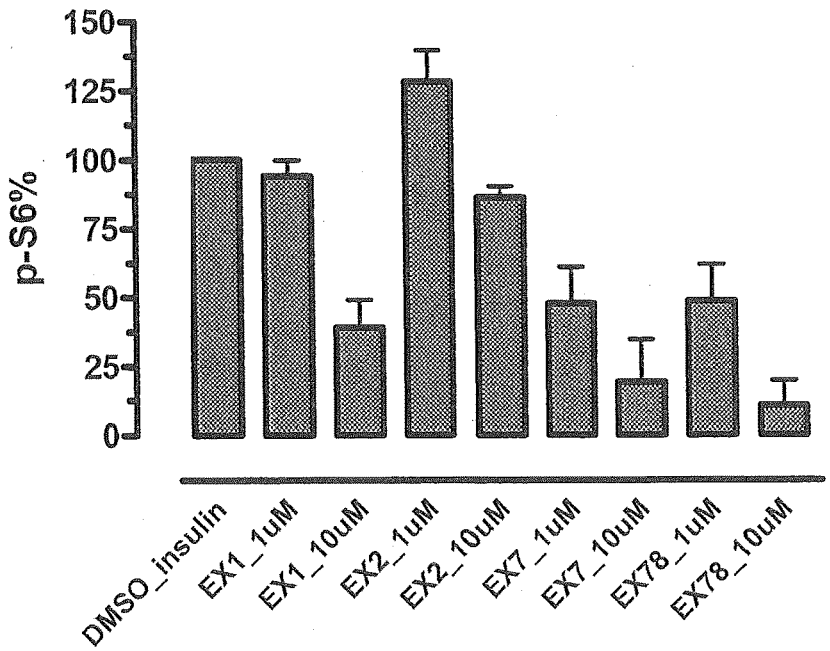
Figure 20C:
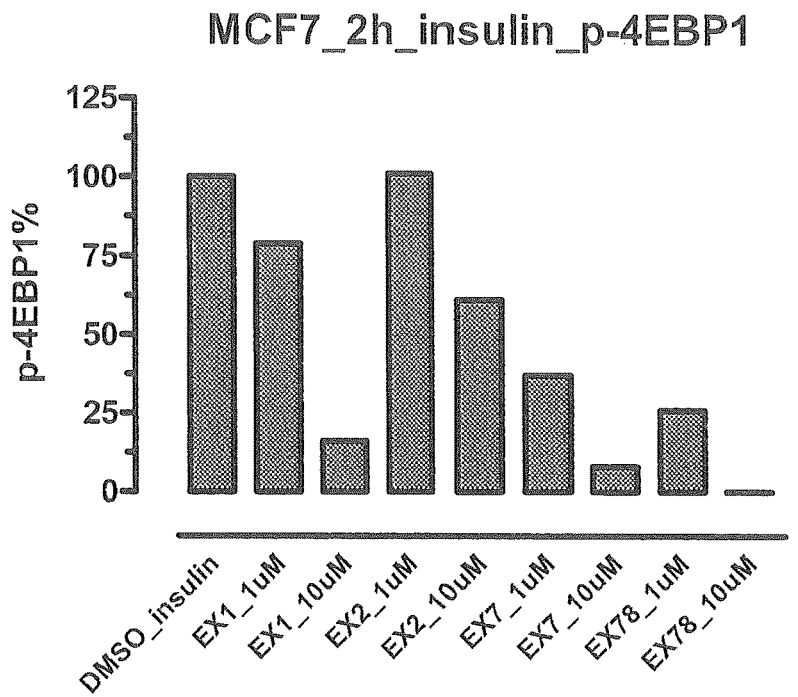
Figure 20D:
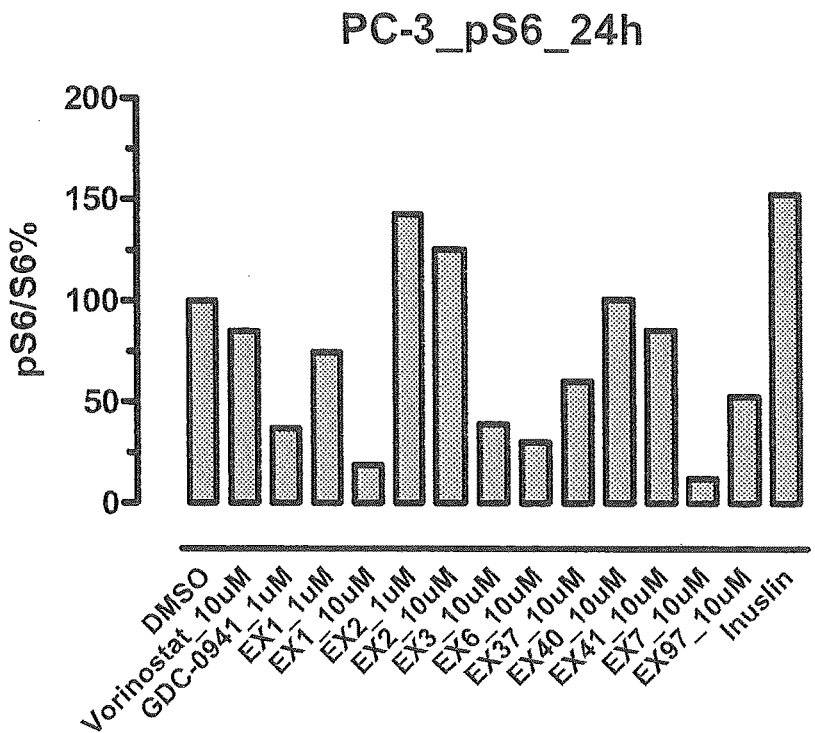

In FIG. 19, the modulation of PI3K-AKT-(mTOR) Pathway: p-Akt (Ser473) level and activity of mTORC2 are shown. FIG. 19A shows PC-3 cells treated with test compounds at above indicated concentrations (FIG. 15) for 24 h, the graph represents results from two Western Blot analyses. Vehicle DMSO (0.1%) was used as blank control, and its phosphorylation level was normalized to 100% in ImageJ analysis. pAkt level was significantly enhanced in insulin (100 µg/mL, 30 min) treated cells. FIG. 19B shows MCF7 cells serum starved overnight and treated with test compounds for 2 h including insulin stimulation (20 µg/mL) in last 30 min for all samples. Vehicle DMSO (0.1%) was used as blank control, its phosphorylation level was normalized to 100%. Y Axis is expressed as Mean±SD if applicable.

In FIG. 20, the modulation of PI3K-AKT-(mTOR) Pathway: mTORC1 activity is shown. MCF7 cells were serum starved overnight and treated with test compounds for 2 h including insulin stimulation (20 µg/mL) in last 30 min for all samples. Vehicle DMSO (0.1%) as blank control, its phosphorylation level was normalized to 100%. In FIG. 20A, p-P70S6K (Thr389)/p-P85S6K (Thr412) level in MCF7 cells is shown. In FIG. 20B, p-S6 (Ser240/244) level in MCF7 cells is shown. In FIG. 20C, the p-4E-BP1 (Thr37/46) level in MCF cells is shown. In FIG. 20D, PC-3 cells were treated with test compounds at above indicated concentrations (FIG. 15) for 24 h. pS6 level was enhanced in insulin (100 µg/mL, 30 min) treated cells. Y Axis is expressed as Mean±SD if applicable.

Example 13: Caspase Activity Assays

Cells are cultivated and treated with test compounds in 96-well plates as described in the above Cell Culture and Anti-Proliferative Assays section. Caspase assay buffer 11100 mM HEPES (pH7.5), 200 mM NaCl, 4 mM EDTA, 0.1% CHAPS, and freshly added 5 mM DTT and 50 µM of Caspase substrate Z-DEVD-R110 or (Z-Asp-Glu-Val-Asp)$_2$-Rhodamine 110 (Cat #M-2615, Bachem, Switzerland)] is added to cells (100 µL/well) and the plates are incubated at room temperature and monitored for the Caspase activity on a BioTek Synergy H4 reader (excitation: 496/9 nm, emission: 521/9 nm). The incubation time can be extended up to overnight (18 h) if the Caspase activity is low. Staurosporine is used as positive control. Representative results are shown in FIG. 21.

Figure 21A:
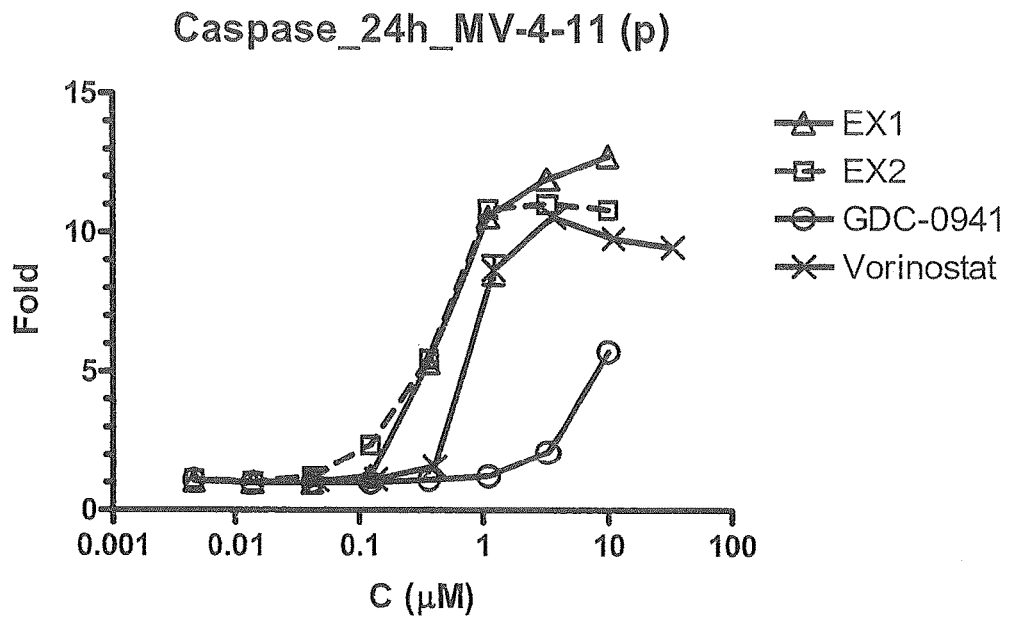
FIG. 21 shows the induction of caspase activity in cells treated with the compounds.
Figure 21B:
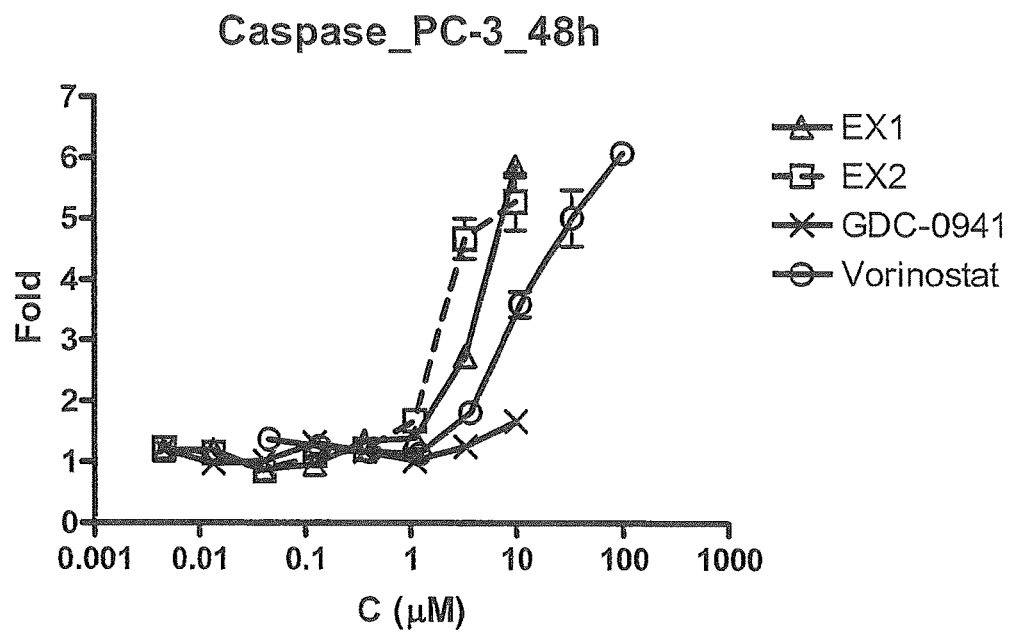
Figure 22A:
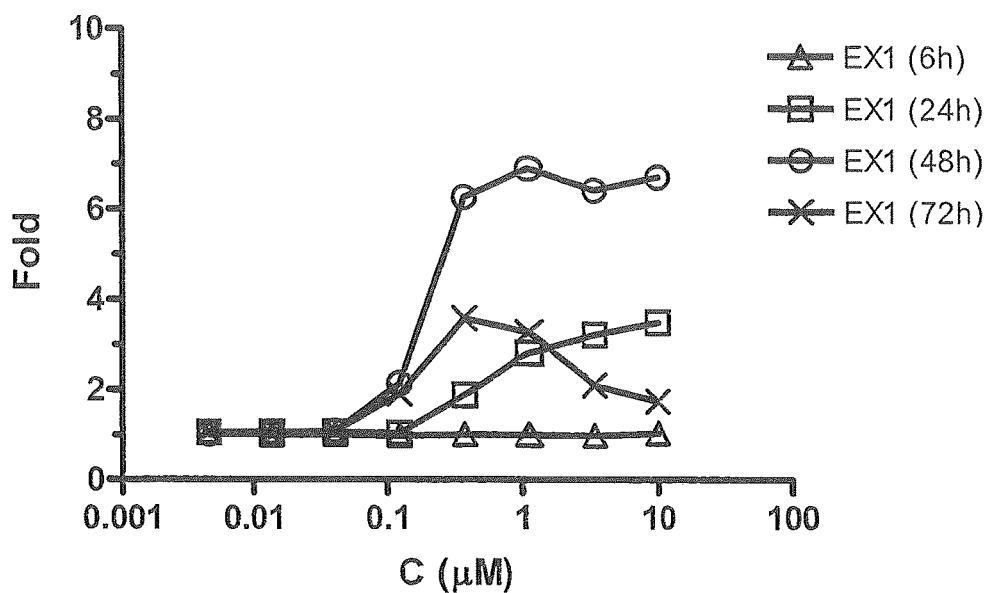
FIG. 22 shows the compound induced death of MV-4-11 cells.
Figure 22B:
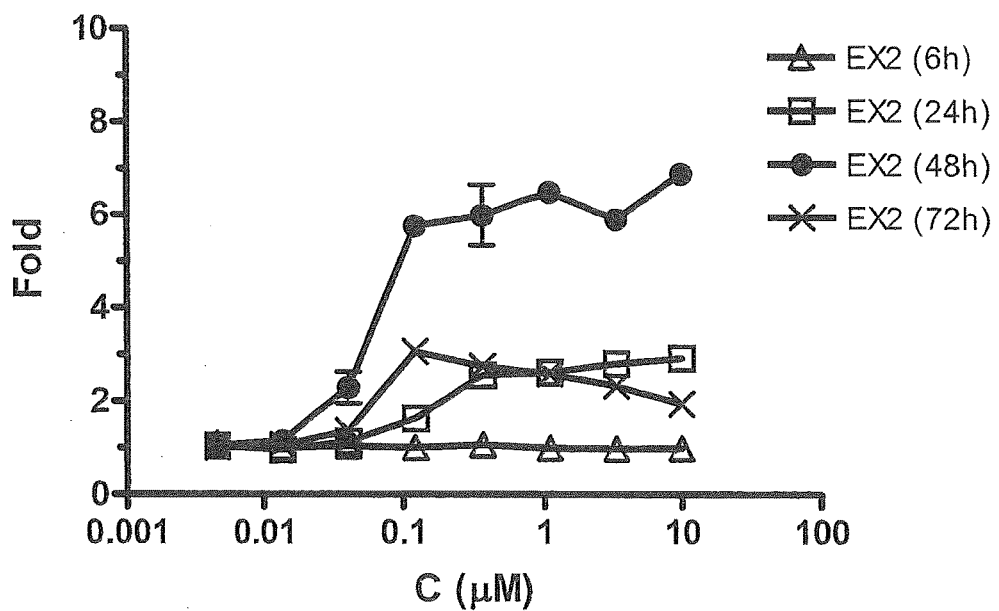
Figure 22C:
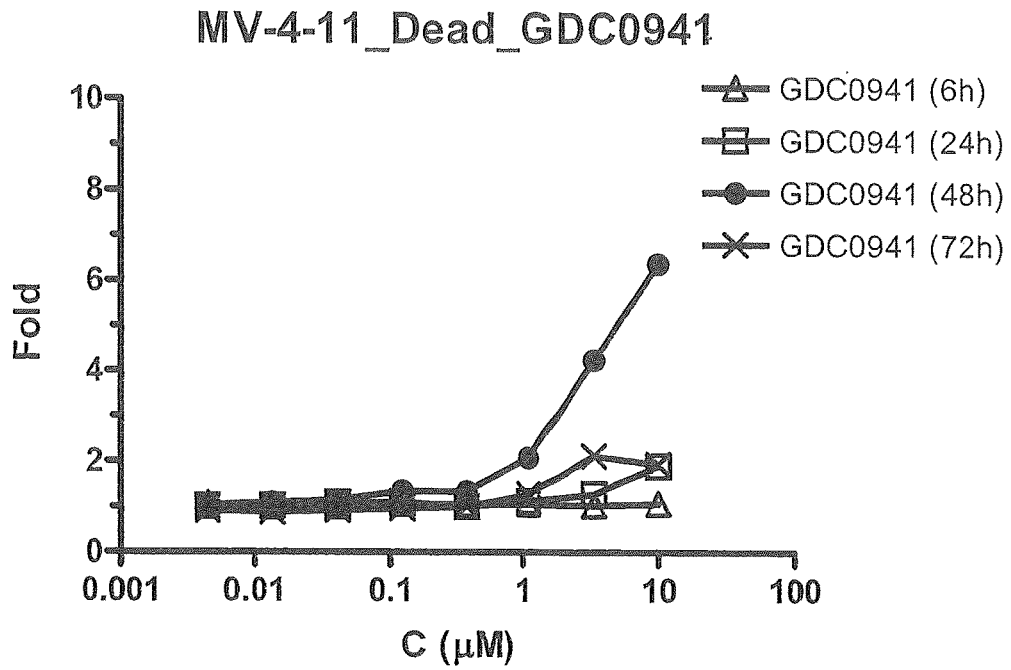
Figure 22D:
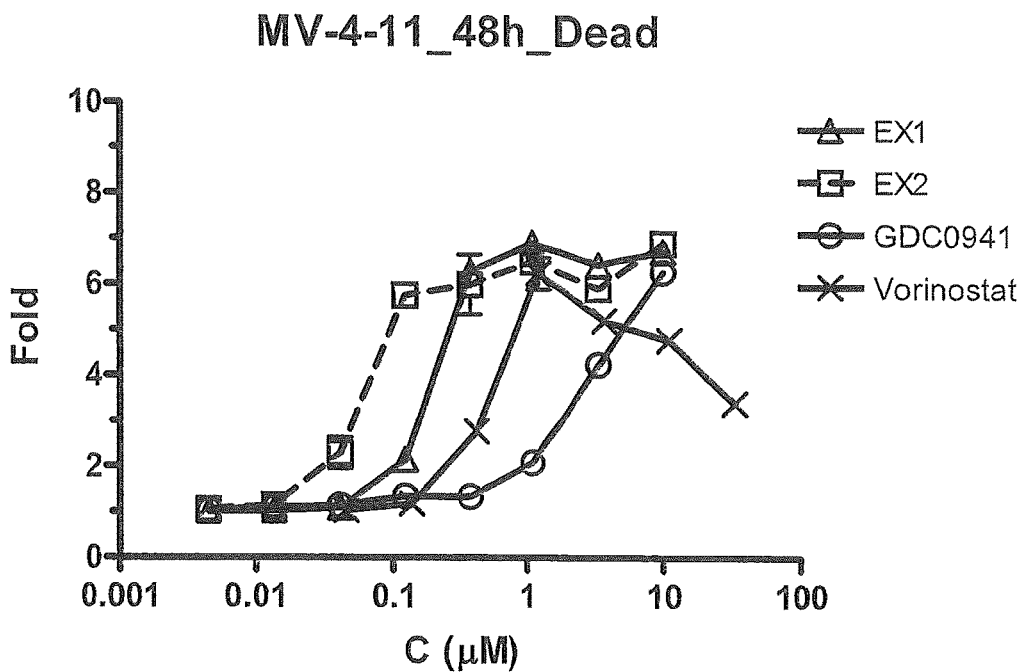

FIG. 21 shows the caspase activity of tested examples. Cells were treated with EX1, EX2, GDC-0941, vorinostat and staurosporine (as positive control) and caspase activity was monitored at different time points. FIG. 21A shows MV-4-11 cells, caspase activity was monitored at 6, 24, 48 and 72 h, and maximal activity was found at 24 h. Both EX2 and EX1 are more potent than vorinostat in terms of induction of caspase activity. GDC0941 showed very weak activity and potency. $EC_{50}$=0.52, 0.50, 1.16, and 12.7 µM for EX1, EX2, vorinostat and GDC-0941, respectively. FIG. 21B shows PC-3 cells monitored at 24, 48 and 72 h time points. Maximal caspase activity was found at 48 h. Both EX1 and EX2 are more potent than vorinostat in terms of induction of caspase activity. GDC-0941 showed very weak activity in both tumor cells. Y Axis is expressed as Mean±SD if applicable.

Example 14: Cell Viability/Cytotoxicity Assay

Cells are cultivated and treated with test compounds in 96-well plates as described in the above Cell Culture and Anti-Proliferative Assays section, the content of dead cells and viable cells are measured using CytoTox-Glo™ Cytotoxicity Assay kit (Promega) per manufacture's protocol. Briefly, CytoTox-Glo™ Cytotoxicity Assay Reagent (48 µL/well) is added to the cells in 96-well plate and the luminescent signals are recorded using a BioTek Synergy H4 reader, then Lysis Reagent (48 µL/well) is added and the luminescent signals derived from both dead and viable cells are recorded. Viability can be calculated by subtracting the luminescent signal resulting from experimental cell death from total luminescent values. Staurosporine is used as positive control. Representative results are shown in FIG. 22.

FIG. 22 shows the compound induced death of MV-4-11 cells. Cells were treated with EX1, EX2, GDC-0941, vorinostat and staurosporine (as positive control) and CytoTox-Glo™ Cytotoxicity Assay kit was used to assess the cell death. Fold of cell death of treated vs untreated was monitored at different time points. Maximal cell death occurred at 48 h after addition of test compounds. FIG. 22A shows EX1, compound example 1. FIG. 22B shows EX2, compound example 2. FIG. 22C shows GDC-0941. FIG. 22D shows cell death at 48 h for EX1, EX2, GDC-0941, and vorinostat. The cell death potency $EC_{50}$ was estimated as 0.19, 0.069, 0.58 and 2.75 μM for EX1, EX2, vorinostat and GDC-0941, respectively. Y Axis is expressed as Mean±SD if applicable.

Example 15: Microsomal Stability

GIBIO pooled human liver microsomes (HLM) (Cat # HMMCPL), mouse liver microsomes (MLM) (Cat # BCM-CPL), and rat liver microsomes (RLM) (Cat # RTMCPL) were purchased from Life Technologies. The incubations consisted of test compound (5 μM) or control compounds (verapamil and dextromethorphan), 0.5 mg/mL of microsomes, 3.3 mM $MgCl_2$, 1.3 mM β-NADPH, and 100 mM potassium phosphate buffer (pH 7.4). Samples are incubated for 30, 45, or 60 min. Reaction is terminated with ice-cold acetonitrile 0.3% formic acid. Samples are subsequently centrifuged at 4° C. for 15 min at 20,000×g. The supernatant is analysed by LC-MS. Representative results are shown in Table 6.

TABLE 6

Microsomal Stability

| EX | HLM | MLM | RLM |
|---|---|---|---|
| 1 | 101% | 96% | 70% |
| 2 | 99% | 99% | 57% |
| 4 | 36% | | 42% |
| 5 | 89% | 133% | 22% |
| 6 | 88% | 89% | 88% |
| 10 | 87% | | 74% |
| 29 | 97% | 75% | 9% |
| 31 | 90% | 53% | 25% |
| 37 | 72% | 73% | 36% |
| 41 | 100% | 93% | 42% |
| 43 | 97% | 96% | 54% |
| 44 | 84% | 84% | 53% |
| 45 | 105% | 78% | 45% |
| 46 | 93% | 89% | 50% |
| 51 | 86% | 9% | 29% |
| 52 | 87% | 102% | 42% |
| 53 | 100% | 84% | 43% |
| 54 | 94% | 48% | 54% |
| 55 | 90% | 83% | 103% |
| 60 | 95% | 71% | 82% |
| 82 | 83% | | 64% |
| 89 | 87% | 70% | 70% |
| 98 | 92% | 83% | 91% |
| Verapamil | 34% | 24% | 12% |
| Dextromethorphan | 65% | 19% | 5% |

Compound in vitro metabolic stability was assayed using liver microsomes (LM) at 0.5 mg/mL of proteins, incubated for 30 min (mouse, MLM), 45 min (rat, RLM), 30 or 45 min (human, HLM). % of remaining parent compound was measured using LC-MS. Both verapamil and dextromethorphan were used as positive controls.

Example 16: Pharmacokinetics (PK)

All animal studies were done as per approved protocols by the Institutional Animal Care and Use Committee at the Biological Resource Centre (BRC) in Singapore. BALB/c mice (8-12 week old, BRC, Biopolis, Singapore) were dosed i.v., p.o. and i.p. with a variety of formulated solutions or suspensions of compound examples. Blood was collected after serial bleeding and centrifuged, and the plasma was frozen at −80° C. Tissues (e.g., livers, lungs, and kidney) were snap frozen in dry ice or liquid nitrogen and kept at −80° C. until analysis. The plasma samples were added internal standard carbamazepine (CBZ) and processed as described previously (Jayaraman, et al. Drug Metab. Dispos. 2011, 39, 2219-2232). Quantitative analysis was carried out on a Waters 2795 separations module equipped with a Waters 2996 Photodiode Array (PDA) detector and micromass Quattro micro mass spectrometer. Sample was resolved on Phenomenex Luna C18(2), 2.0×50 mm column with a SecurityGuard Cartridge (C18 4×2.0 mm) at a flow of 0.5 mL/min with a 6-min gradient (x to 95% of B, solvent A, ultrapure water with 0.1% of formic acid (FA), solvent B, methanol with 0.1% of FA, x is selected from 5 to 50) and data were acquired using multiple reaction monitoring and quantified by QuanLynx in MasLynx software (V 4.1, Waters Inc.). PK parameters were estimated using Microsoft Excel 2010 based on the PK equations defined by Summit PK website (http://www.summitpk.com/equations/equations.htm). Both area under curve calculations and multi-exponential curve stripping were used. The method can deliver comparable results as WinNonlin (Pharsight, Mountain View, Calif.) for our previous data.

Example 17: In Vivo Pharmacodynamics (PD) and Efficacy Studies

All animal studies were done as per approved protocols by the Institutional Animal Care and Use Committee at the Biological Resource Centre (BRC) in Singapore. Female BALB/c nude mice (7 and 10 weeks of age, BRC, Biopolis, Singapore) or female NCr nude mice (5-6 and 7-9 weeks of age, InVivos Pte Ltd, Singapore) were inoculated in the right flank with about $5 \times 10^6$ of tumor cells which were suspended in serum-free DMEM or RPMI1640 growth medium and Matrigel (Cat. No: 354234, Corning Discovery Labware) (1:1) and injected in a total volume of 100 to 150 μL. Tumor were measured using a digital caliper and tumor volumes was estimated by using the formula: tumor volume=length× $width^2 \times 0.5$. Tumor growth inhibition (TGI %)=$[1-(T_t-T_0)/(C_t-C_0)] \times 100$, $C_0$ and $C_t$ are the mean tumor volumes for control group (vehicle) on day 0 and day t, respectively; $T_0$ and $T_t$ are the mean tumor volumes for treatment group on day 0 and day t, respectively. All statistics conducted were done using GraphPad Prism (v4.00 or v6.04, GraphPad Software Inc.), two-tailed unpaired t Test was used for comparing two groups, and one way ANOVA followed by Dunnett's Multiple Comparison Test was used for comparing three and more groups.

Example 18: Target Modulation

In PC-3 Prostate Cancer Xenograft

PC-3 tumor bearing BALB/c nude mice were orally dosed with vehicle, vorinostat (200 mg/kg), EX1 (150 mg/kg) and EX78 (100 mg/kg). Blood samples, tumors and other tissues were collected for PK/PD studies at the indicated time points (two mice each time point). Hyperacetylation of H3 in PC-3 tumors was confirmed by Western blot analyses of tumors of the EX1 and EX78 treated mice, vorinostat was used as positive control (FIG. 23).

Figure 23A:
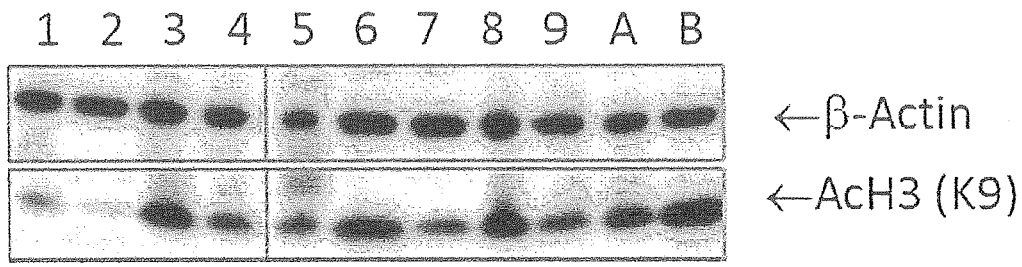
FIG. 23 shows histone hyperacetylation in PC-3 tumors treated with the compounds.

FIG. 23 shows histone hyperacetylation in PC-3 tumors. FIG. 23A shows a Western blot analysis of tumor tissues. The lanes and the concentrations used were as follows:

| Lane | Sample |
| --- | --- |
| 1/2 | Vehicle at 3 h |
| 3/4 | Vorinostat at 3 h |
| 5/6 | EX1 at 1 h |
| 7/8 | EX1 at 2 h |
| 9/A | EX1 at 3 h |
| B | EX78 at 4 h |

Figure 23B:
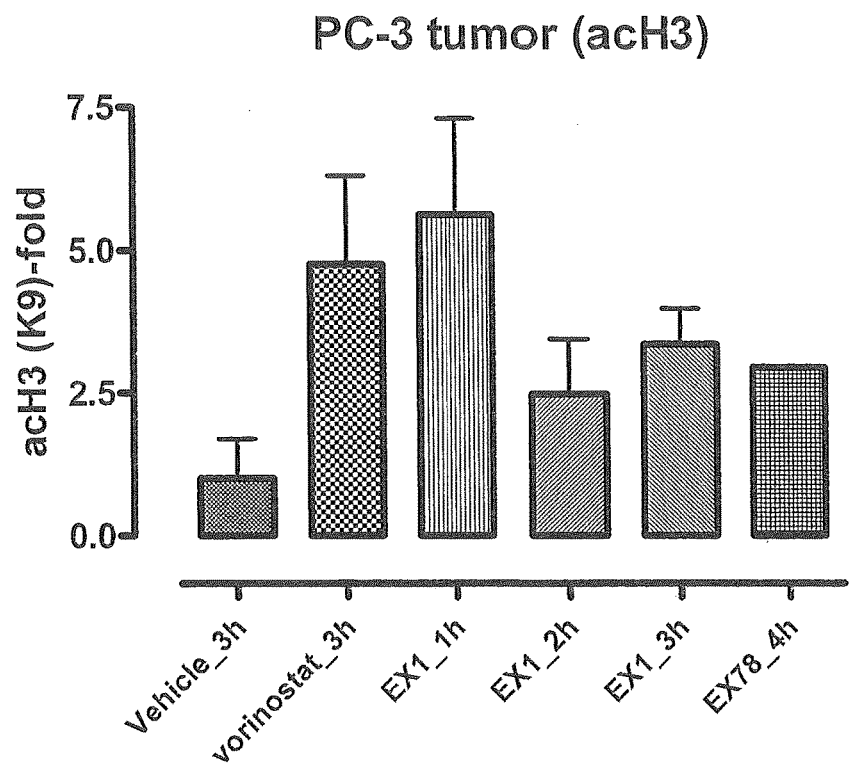

Significant histone hyperacetylation in PC-3 tumor was observed in treated mice. FIG. 23B shows the digitized and normalized Western blot analysis results. Y Axis is expressed as Mean±SEM if applicable.

In MV4-11 Acute Myeloid Leukemia Xenograft

MV4-11 tumor bearing mice were also treated with EX2 via intravenous (IV) (50 mg/kg), intraperitoneal (IP) (100 mg/kg) and per orem (PO) (150 mg/kg) routes, EX78 via both IV (25 mg/kg) and PO (100 mg/kg) routes for Pharmacodynamic (PD) assessment. All three routes of administration of EX2 result in hyperacetylation of H3 in MV4-11 tumors (FIG. 24). EX78 also induced hyperacetylation of H3 via both routes of administration.

Figure 24A:
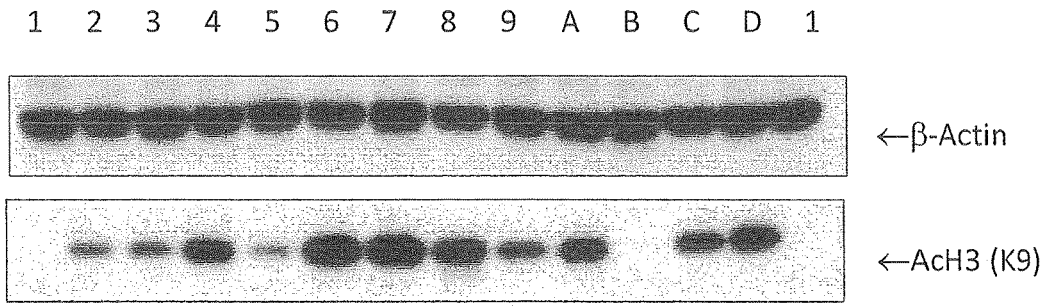
FIG. 24 shows histone hyperacetylation in MV4-11 tumors treated with the compounds.

FIG. 24 shows Histone Hyperacetylation in MV4-11 tumors. BALB/c nude mice bearing MV4-11 tumors which were dosed with vehicle [DMSO/PEG400/sterile water (10:40:50)], EX2 and EX78. Tumors were collected at the indicated time points. FIG. 24A shows Western blot analyses of tumor tissues.

The lanes and the concentrations used were as follows:

| Lane | Sample |
| --- | --- |
| 1 | Vehicle at 3 h, PO |
| 2 | EX2 at 1 h, PO |
| 3 | EX2 at 2 h, PO |
| 4/5/6 | EX2 at 3 h, PO |
| 7 | EX2 at 2 h, IV |
| 8 | EX2 at 3 h, IV |
| 9 | EX2 at 2 h, IP |
| A | EX78 at 1 h, IV |
| B | EX78 at 2 h, PO |
| C | EX78 at 3 h, PO |
| D | EX78 at 4 h, PO |

Figure 24B:
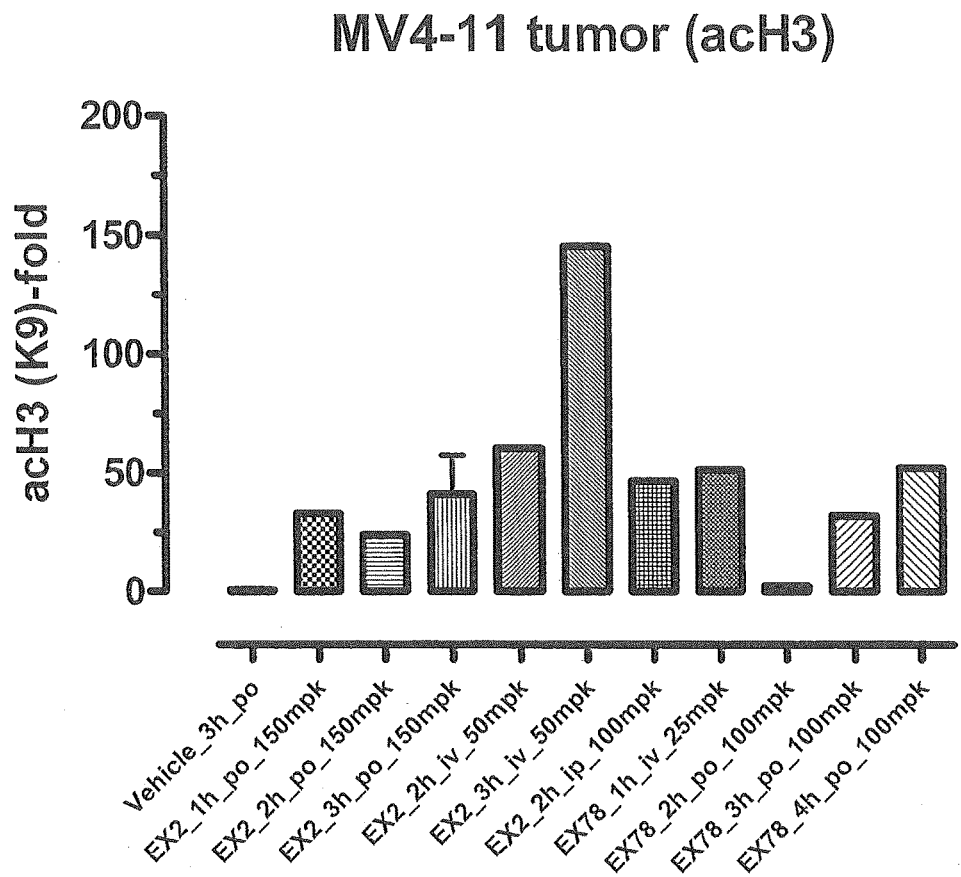

Significant histone hyperacetylation in MV4-11 tumor was observed in treated mice. FIG. 24B shows the digitized and normalized Western blot analysis results. Y Axis is expressed as Mean±SEM if applicable.

Example 19: Efficacy

In NCr Nude Mice HepG2 Xenograft Model

Female NCr nude mice (CrTac:NCr-Foxn1$^{nu}$, 5 weeks of age, InVivos Pte Ltd, Singapore) were inoculated in the right flank with 6×10$^6$ of HepG2 cells. When the HepG2 tumor size was 275 mm$^3$ in average (13 days after implantation), the mice were randomized and dosed orally with vehicle, EX2 (150 mg/kg) and sorafenib tosylate (98 mg/kg) for four weeks (QD×5 per week). The mice of vehicle group were euthanized due to the tumor burden on day 18 after last dose of 3$^{rd}$ cycles. EX2 demonstrated significant tumor inhibition with TGI=96% on day 18 (after last dose) (FIG. 25). Reference sorafenib tosylate (98 mg/kg) was also effective but with TGI=71% (day 18).

Figure 25A:
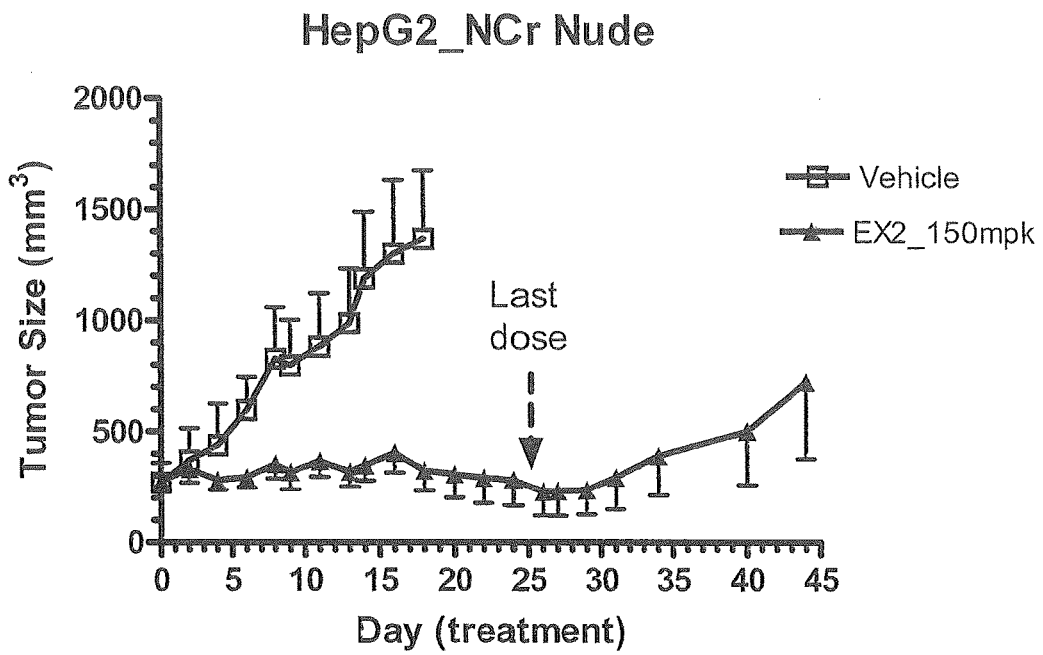
FIG. 25 shows efficacy of the compounds in NCr nude mice HepG2 xenograft model.
Figure 25B:
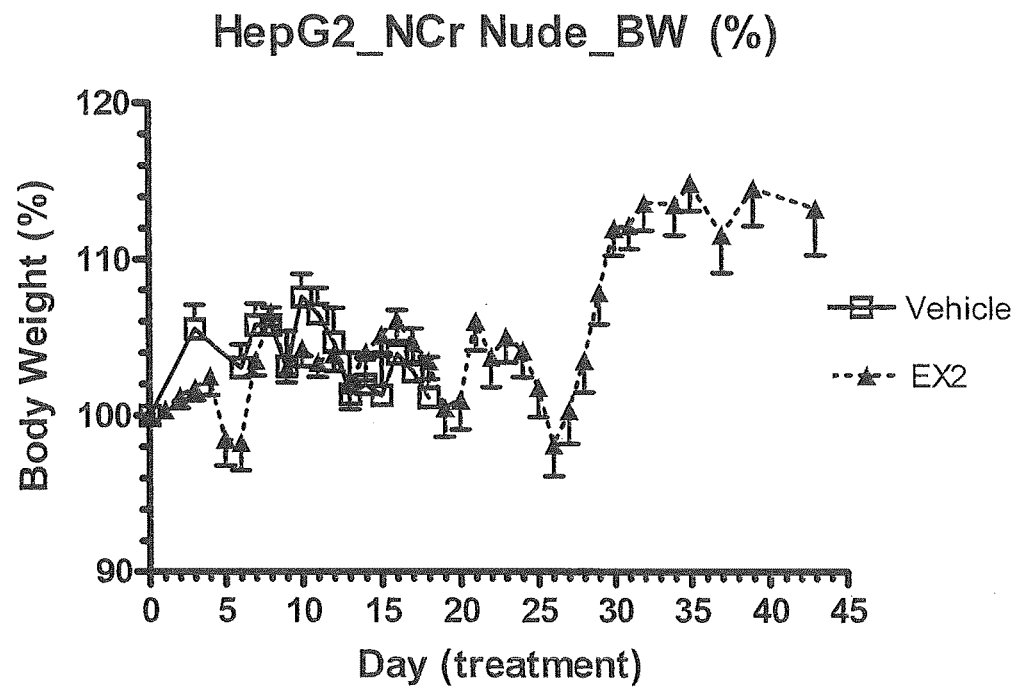
Figure 26A:
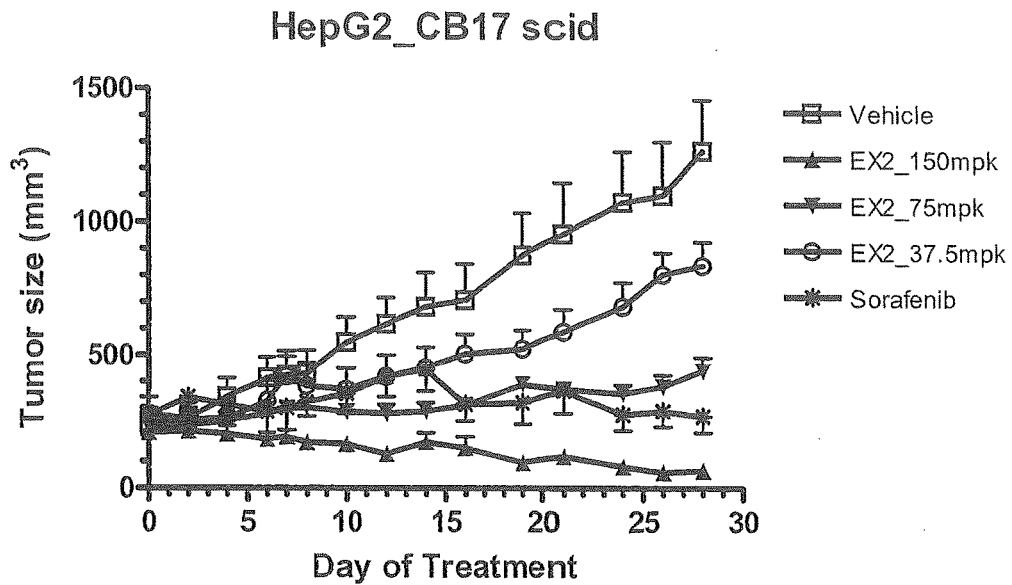
FIG. 26 shows efficacy of the compounds in CB17 scid mice HepG2 xenograft model.
Figure 26B:
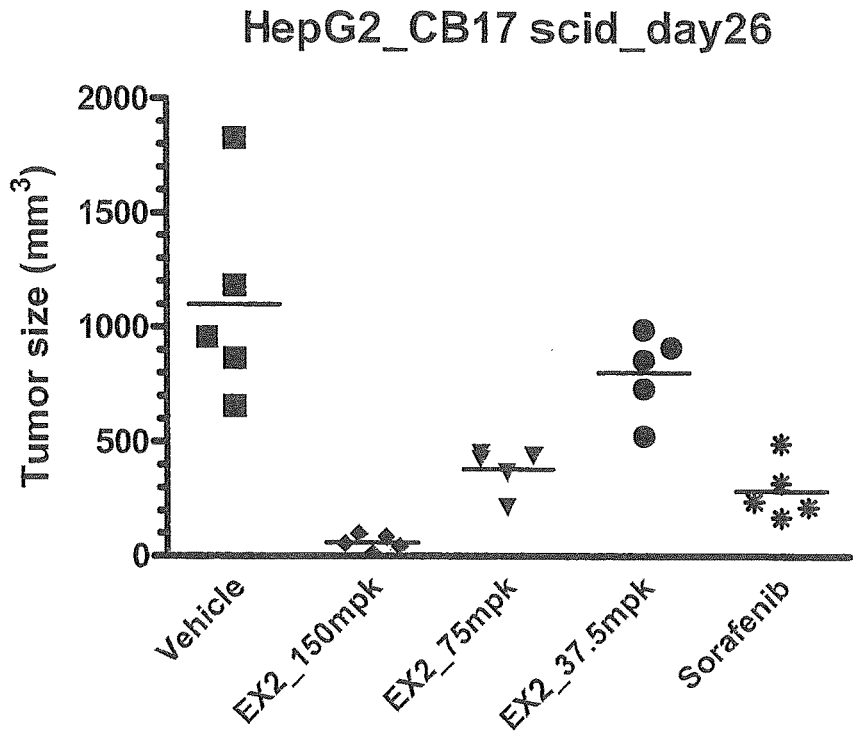
Figure 26C:
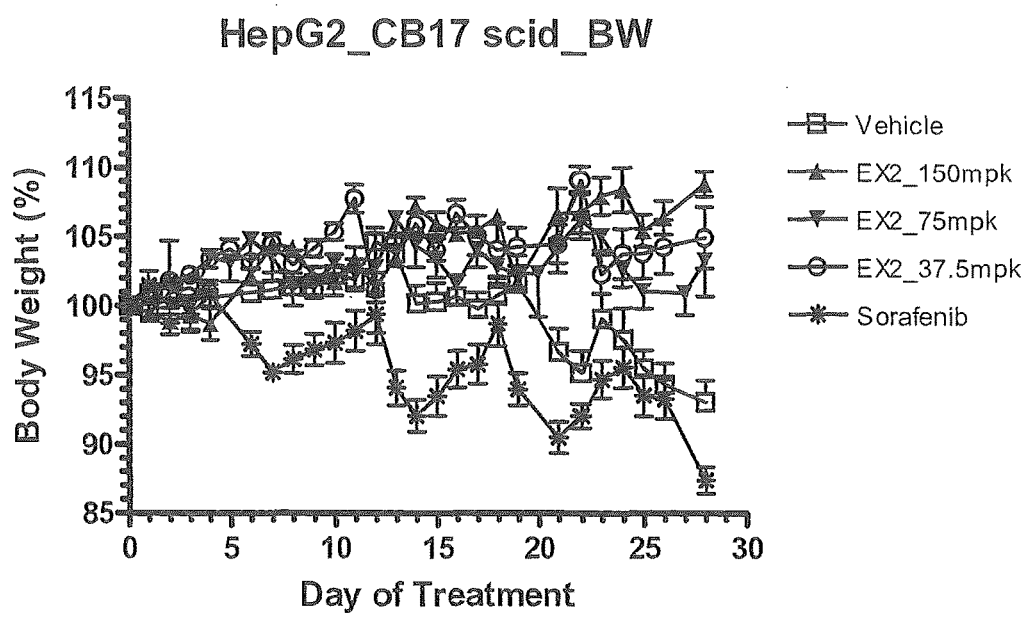
Figure 26D:
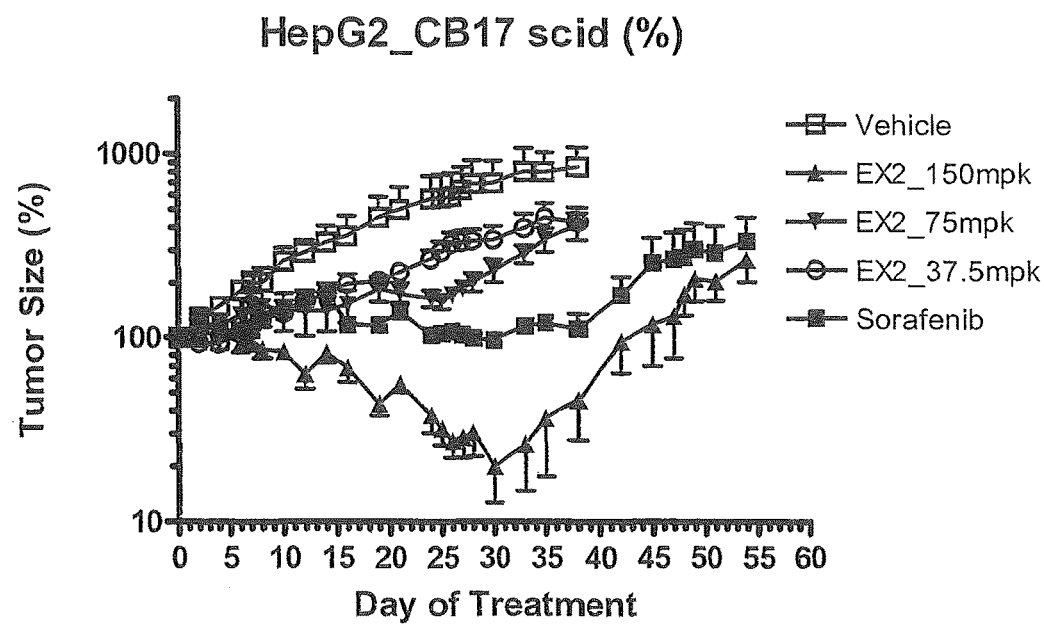

FIG. 25 shows efficacy in NCr nude mice HepG2 xenograft model. HepG2 tumor-bearing female NCr nude mice were treated with either vehicle or EX2 (150 mg/kg) from Day 0 with mean tumor volume about 275 mm$^3$ for four cycles: 5-day-on-2-day-off (QD×5 per week or per cycle). FIG. 25A shows significant tumor growth inhibition (TGI) was achieved from day 4. TGI=96%, p=0.0034 on day 18 after last dose of 3$^{rd}$ cycle. The treatment continued to 4$^{th}$ cycle while the mice of vehicle group were euthanized due to the tumor burden on day 18. FIG. 25B shows that EX2 was well tolerated in NCr nude mice, no significant toxicity was observed at this dose level. Y Axis is expressed as Mean±SEM if applicable.

In CB17 Scid Mice HepG2 Xenograft Model

As EX2 showed excellent antitumor activity in HepG2 tumor bearing NCr nude mice, it was further evaluated with dose repose in CB17 scid mice. Female C.B-17 scid mice (C.B-Igh-1$^b$/IcrTac-Prkdc$^{scid}$, 5 weeks of age, InVivos Pte Ltd, Singapore) were inoculated in the right flank with 5×10$^6$ of HepG2 cells. When the HepG2 tumor size was about 240 mm$^3$ in average, tumor-bearing mice were randomized (5 mice per group) and dosed orally with vehicle, EX2 (150, 75 and 37.5 mg/kg) and sorafenib tosylate for four weeks (QD×5 per week) on day 0. EX2 demonstrated significant tumor inhibition in a dose-dependent manner. All dose levels were well tolerated and significant tumor growth delay was achieved (FIG. 26).

In FIG. 26, Efficacy in CB17 scid mice HepG2 xenograft model is shown. HepG2 tumor-bearing CB17 scid mice were treated with vehicle, EX2 (150, 75 and 37.5 mg/kg) and sorafenib tosylate (100 mg/kg QD×5×2 then 80 mg/kg, QD×5×2) for 4 weeks (QD×5 per week) from Day 0 with mean tumor volume about 240 mm$^3$. FIG. 26A shows that significant tumor growth inhibition (TGI) was achieved from day 4. After last dose of 4$^{th}$ cycles, on day 26, TGI=117%, 82%, 38% and 98% for EX2 (150, 75 and 37.5 mg/kg) and sorafenib tosylate, respectively. FIG. 26B shows that on day 26, tumor size of treated group was significantly smaller than vehicle group, with p<0.01 for EX2 150 and 75 mg/kg groups and sorafenib group, but p>0.05 for 37.5 mg/kg group. FIG. 26C shows that EX2 was well tolerated at all dose levels, no significant body weight (BW) loss. Vehicle group has BW loss due to increasing tumor burden. Sorafenib tosylate (100 mg/kg) was not well tolerated; its dose was reduced to 80 mg/kg in the 3$^{rd}$ and 4$^{th}$ cycles. FIG. 26D shows that tumor size was normalized against the initial value (as 100%). After last dose (day 25), the tumor started re-grow after a long period of growth delay, but EX2 at 150 mg/kg seemed more effective than sorafenib. Y Axis is expressed as Mean±SEM if applicable.

In NCr Nude Mice HuH-7 Xenograft Model

Female NCr nude mice (CrTac:NCr-Foxn1$^{nu}$, 8 weeks of age, InVivos Pte Ltd, Singapore) were inoculated in the right flank with 6.2×10$^6$ of HuH-7 cells. When the HuH-7 tumor size was about 103 mm$^3$ in average, the mice were randomized and dosed orally with vehicle [DMSO/Solutol® HS15/sterile water (10:36:54)] and EX2 (150 mg/kg) for two weeks (QD×5 per week, 5 mice per group), respectively. EX2 demonstrated good tumor growth inhibition with TGI=102% on day 12 (after last dose) and again EX2 was well-tolerated at this dose level (maximum body weight loss was less than 5% vs vehicle group). The experiment was repeated with large and well-established tumors. When the HuH-7 tumor size was about 363 mm$^3$ in average, the mice were randomized (5 mice per group) and dosed orally with vehicle [NMP/Solutol® HS15/sterile water (10:36:54)] and EX2 (150 mg/kg). EX2 demonstrated good tumor growth inhibition with TGI=88% (p=0.0016) after one cycle of treatment (QD×5 per week) on day 6 and TGI=67% (p=0.0082) after two cycles of treatment (QD×5×2) on day 12 (FIG. 27).

Figure 27A:
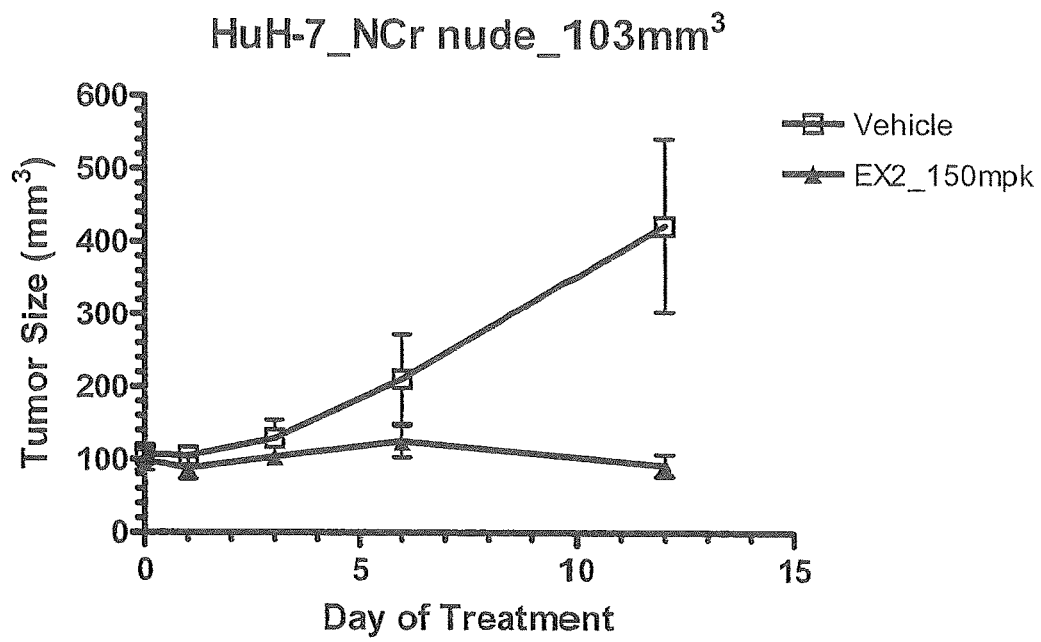
FIG. 27 shows the efficacy of the compounds in NCr nude mice HuH-7 xenograft model.
Figure 27B:
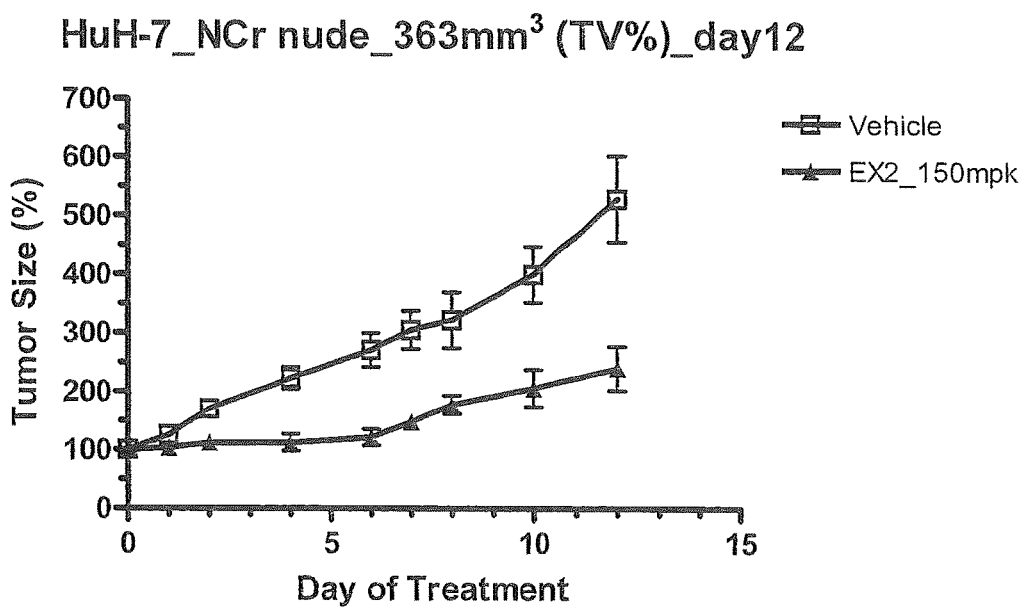

In FIG. 27, the efficacy in NCr nude mice HuH-7 xenograft model is shown. HuH-7 tumor-bearing NCr nude mice were treated with either vehicle or EX2 (150 mg/kg) from Day 0 (QD×5 per week or per cycle, or 5-day-on-2-day-off). FIG. 27A shows good tumor growth inhibition with TGI=102% on day 12 after treatment of mice (mean tumor volume 103 mm$^3$ on day 0) with EX2 (QD×5×2). FIG. 27B shows that EX2 was also effective on well-established tumors (mean tumor size 363 mm$^3$ on day 0) after one cycle of treatment with TGI=88% (p=0.0016) and TGI=67% (p=0.0082) on day 12. The tumor size was normalized against the initial volume (day 0 as 100%) in FIG. 27B. Y Axis is expressed as Mean±SEM if applicable.

In 4T1 Mouse Metastatic Breast Cancer Model

Female NCr nude mice (CrTac:NCr-Foxn1$^{nu}$, 13 weeks of age, InVivos Pte Ltd, Singapore) were implanted 1.1×10$^6$ of 4T1 (ATCC® CRL2539™) cells in fourth mammary fat pad. When 4T1 tumor size was 70-74 mm$^3$ in average (5 days post tumor implantation), tumor-bearing mice were randomized (n=5 per group) and dosed orally with vehicle and EX2 (150 mg/kg) for three cycles (QD×5, 5 day-on-1 day-off per cycle) day 0, day 16 was the last dose of the 3 cycles. EX2 demonstrated significant tumor inhibition with TGI=53% on day 17, p=0.0063 (FIG. 28).

Figure 28A:
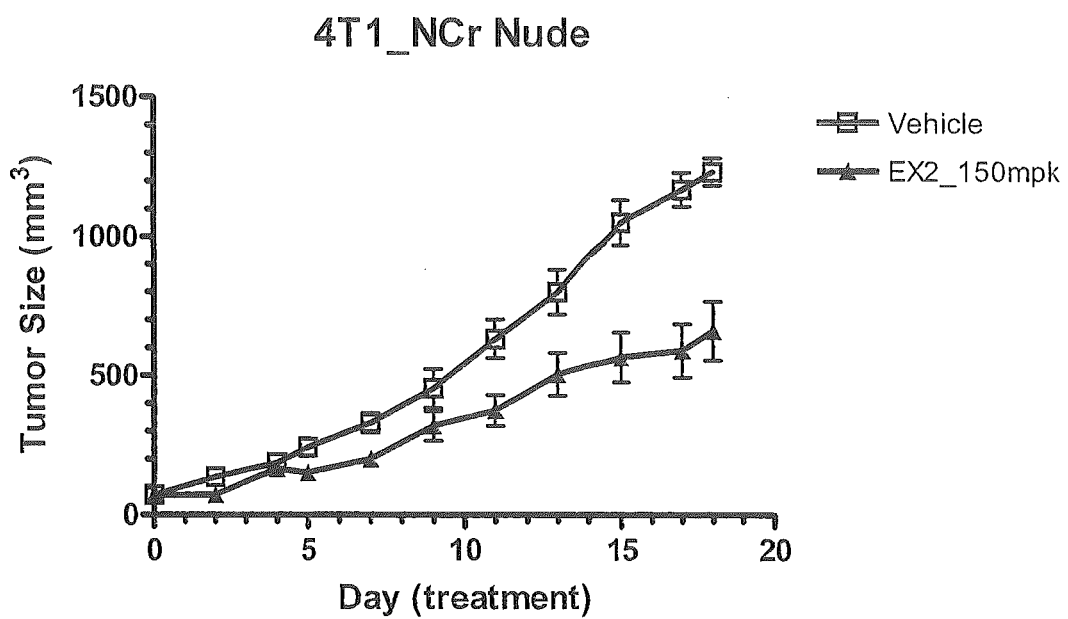
FIG. 28 shows the efficacy of the compounds in 4T1 mouse metastatic breast cancer model.
Figure 28B:
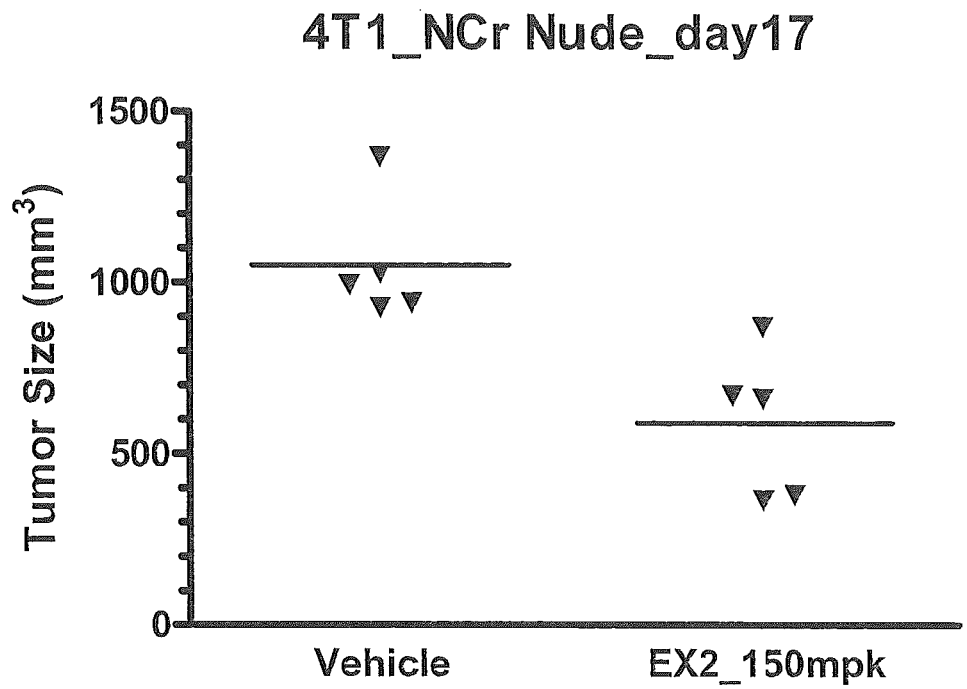

In FIG. 28, the efficacy in 4T1 mouse metastatic breast cancer model is shown. Female NCr nude mice bearing 4T1 tumor was treated with vehicle and EX2 for three cycles (QD×5, 5 day-on-1 day-off per cycle, 5 mice per group). In FIG. 28A, the tumor growth curve is shown. In FIG. 28B the tumor size on day 17 is shown, p=0.0063. Y Axis is expressed as Mean±SEM if applicable.

In NCI-H460 Lung Cancer Xenograft Model

Female C.B-17 scid mice (C.B-Igh-1$^b$/IcrTac-Prkde$^{scid}$, 7 weeks of age, InVivos Pte Ltd, Singapore) were inoculated in the right flank with 6.8×10$^6$ of NCI-H460 cells. When the tumor sizes were between 150 and 160 mm$^3$ in average, the mice were randomized and dosed orally with vehicle and EX2 (150 mg/kg) for two weeks (QD×5 per week) on day 0. EX2 demonstrated significant tumor growth inhibition with TGI=46% (p=0.0292) on day 12 after two cycles of treatment. EX2 was also well tolerated at this dose level (FIG. 29).

Figure 29A:
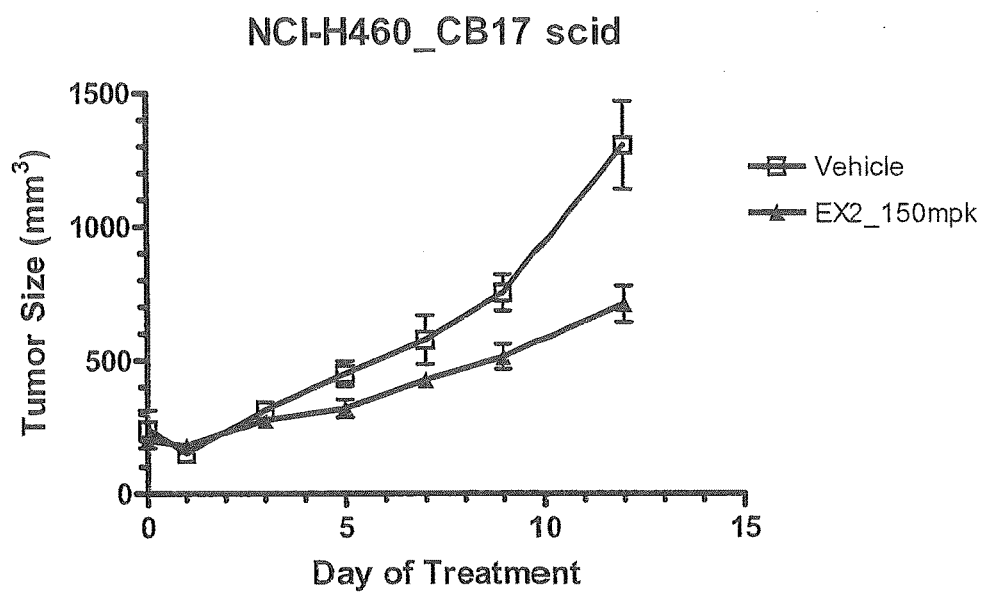
FIG. 29 shows the efficacy of the compounds in NCI-H460 lung cancer xenograft model.
Figure 29B:
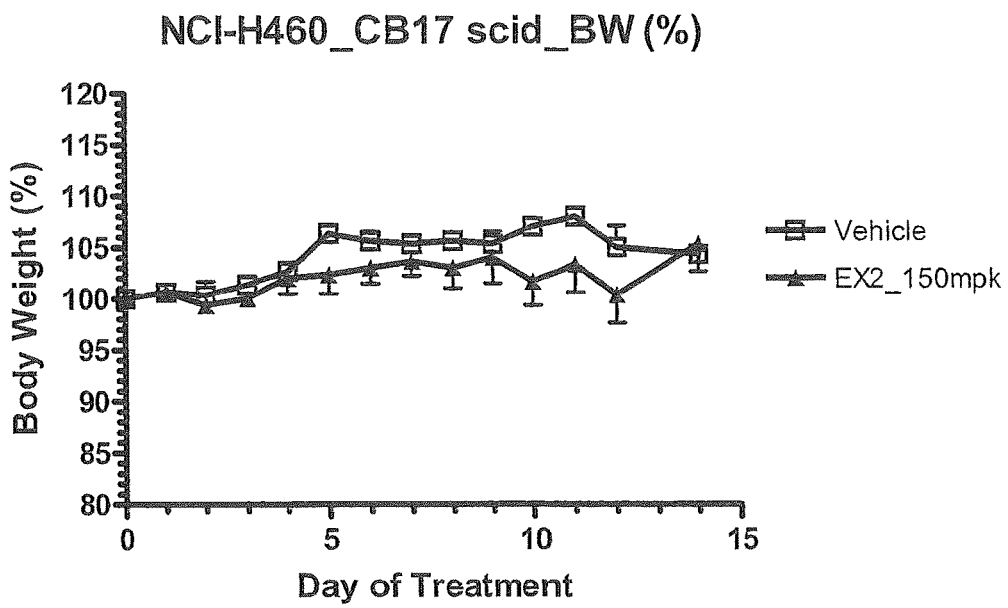

In FIG. 29, the efficacy in NCI-H460 lung cancer xenograft model is shown. Female NCI-H460 tuynor-bearing CB17 scid mice were dosed orally with vehicle and EX2 (150 mg/kg) for two weeks (QD×5 per week). FIG. 29A shows that EX2 demonstrated significant tumor growth inhibition with TGI=46% (p=0.0292) on day 12 after two cycles of treatment. FIG. 29B shows that EX2 was also well tolerated at this dose level. Y Axis is expressed as Mean±SEM if applicable.

In MV4-11 Xenograft Model

Female BALB/c nude (C.Cg/AnNTac-Foxn1$^{nu}$ [cc]NE9, 5 weeks of age, InVivos Pte Ltd, Singapore) were inoculated in the right flank with 11×10$^6$ of MV4-11 cells. When the tumor size was 173 mm$^3$ in average, the mice were randomized (6 mice per group) and dosed orally with vehicle and EX2 (150 and 75 mg/kg) for three weeks (QD×5 per week) on day 0. From day 12 to day 20, EX2 demonstrated average TGI=52% (p<0.05) for 150 mg/kg group (two groups, one non-treatment related death on day 6, final n=11), but TGI=23% (p>0.05) for 75 mg/kg group (FIG. 30).

Figure 30A:
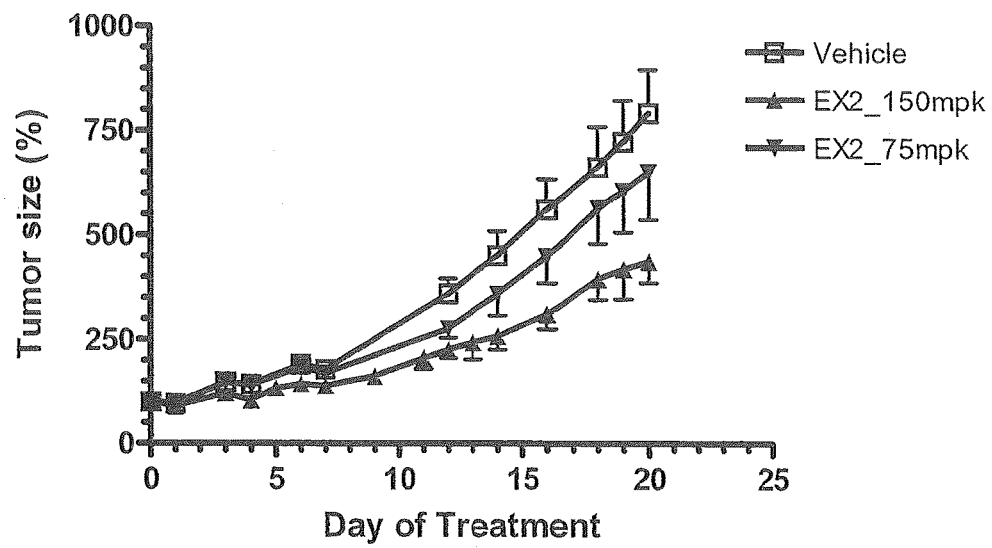
FIG. 30 shows the efficacy of the compounds in MV4-11 xenograft model.
Figure 30B:
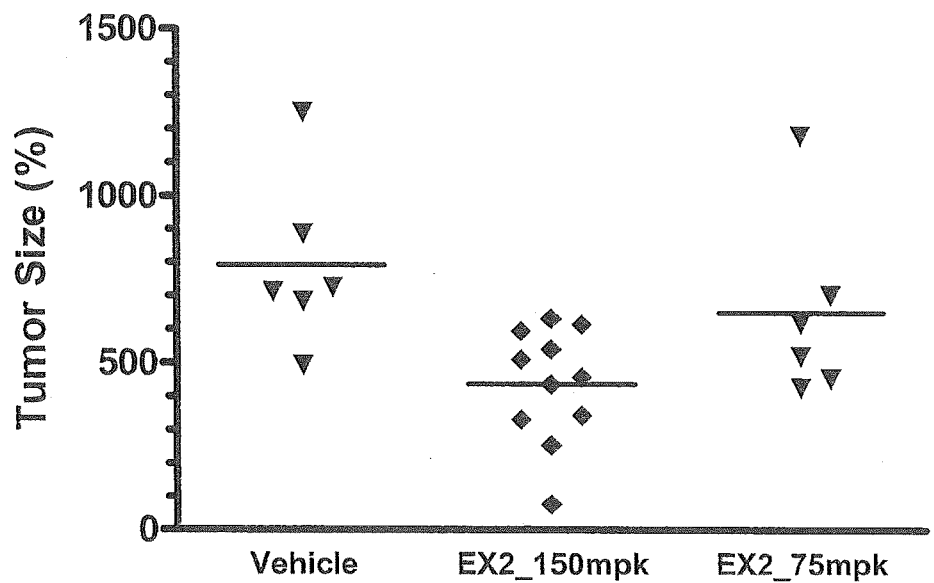
Figure 31:
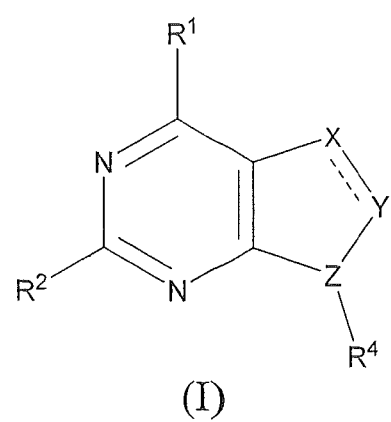
FIG. 31 shows a compound of Formula (I), a family of fused pyrimidine-based hydroxamate compounds.

In FIG. 30, the efficacy in MV4-11 xenograft model is shown. Tumor-bearing female BALB/c nude mice were dosed orally with vehicle and EX2 (150 and 75 mg/kg) for three weeks (QD×5 per week). FIG. 30A shows the tumor growth curve: tumor size was normalized against the initial value (day 0 as 100%), EX2 demonstrated significant tumor inhibition with average TGI=51% between day 12 and day 20 (p<0.05) for 150 mg/kg group, but 75 mg/kg was not significantly effective. FIG. 30B shows the tumor size on day 20, TGI=51% (p<0.05) and 20% (p>0.05) for 150 and 75 mg/kg, respectively. Y Axis is expressed as Mean±SEM if applicable.

Example 19: Summary

The compounds as defined above demonstrated inhibitory activities against HDAC enzymes and PI3K kinases (Table 3) and anti-proliferative activities against a variety of human tumour cell lines (Tables 4 and 5). Most of the compound as defined above demonstrated good drug-like properties, that is, in vitro metabolic stability, solubility and desirable lipophilicity (Table 6). Selected compounds also showed activity against multi-targets in tumor cells (FIG. 15 and FIG. 16), i.e., hyperacetylation of histones (FIG. 17) and α-tubulin (FIG. 18) due to inhibition of HDACs; PI3K-AKT-mTOR pathway: reduction of phosphor-Akt (Ser473) or inhibition the activity of mTORC2 (FIG. 19), and reduction of phospho-P7056K (Thr389)/phospho-P8556K (Thr412), phospho-S6 (Ser240/244) and phospho-4E-BP1 (Thr37/46) or inhibition of the activity of mTOCR1 (FIG. 20). These compounds also induced cell apoptosis in PC-3 cells and MV-4-11 cells (FIG. 21), cell death in MV-4-11 cells (FIG. 22), much more efficiently than PI3k inhibitor GDC-0941 or HDAC inhibitor vorinostat.

These compounds also modulated biological drug targets in tumor models. For example, EX1 and EX78 induced histone hyperacetylation in PC-3 prostate tumors when orally dosed in tumor-bearing mice (FIG. 23), EX2 and EX78 induced histone hyperacetylation in MV4-11 xenograft tumors via different routes of administration (FIG. 24). EX2 also demonstrated excellent antitumor activity in HCC models, e.g., NCr nude mice HepG2 xenograft model (FIG. 25) and CB17 scid mice HepG2 xenograft model (FIG. 26) as well as HuH-7 HCC xenograft model (FIG. 27). Compound EX2 was also demonstrated broad antitumor activity in a number xenograft models when dosed orally: 4T1 mouse metastatic breast cancer model (FIG. 28), NCI-H460 lung cancer xenograft model (FIG. 29) and MV4-11 leukaemia xenograft model (FIG. 30).

INDUSTRIAL APPLICABILITY

The compounds as defined above may find a multiple number of applications in which their ability to inhibit deacetylases, lipid and protein kinases of the type mentioned above can be utilised. For example the compounds as defined above may be used to inhibit deacetylase and kinases, either separately or simultaneously. The compounds may also be used in treating or preventing a condition or disorder in a mammal in which inhibition of a deacetylase and/or a protein kinase and/or co-factor thereof and/or via an unspecified mechanism prevents, inhibits or ameliorates a pathology or a symptomology of the condition. The condition or disorder is cancer, angiogenic disorder or pathological angiogenesis, fibrosis, inflammatory conditions, asthma, neurological disorders, neurodegenerative disorders, muscle degenerative disorders, autoimmune disorders, disorders of the blood or disorders of the bone marrow. The compounds may be particularly useful in treating cancer such as leukemia or myeloma, lymphoma, breast cancer, lung cancer, hepatocellular carcinoma and other hypervascular tumors as well as retinal angiogenic diseases. The compounds as defined above may also have applications in inducing cell reprogramming for generation of iPS cells.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A compound of Formula (I);

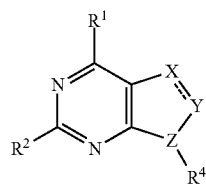
(I)

wherein X, Y and Z are independently selected from N, $CHR^3$ or $CR^3$, wherein at least one of X, Y or Z is N;
----- is a single or double bond, as valency allows;
$R^1$ is selected from the group consisting of optionally substituted amino, optionally substituted cycloalkyl, optionally substituted heterocycloalkyl, optionally substituted aryl and optionally substituted heteroaryl;
$R^2$ is selected from the group consisting of halogen, optionally substituted amino, optionally substituted cycloalkyl, optionally substituted heterocycloalkyl, optionally substituted aryl and optionally substituted heteroaryl;
$R^3$ is selected from the group consisting of hydrogen, optionally substituted alkyl, optionally substituted amino, and optionally substituted heterocycloalkyl;
$R^4$ is optionally substituted alkyl;
at least one of $R^1$, $R^2$, $R^3$ or $R^4$ is further independently substituted by an hydroxamate group $-L^1-R^5-L^2-R^6-L^3-CON(R^a)OR^b$, wherein;
$R^a$ and $R^b$ are hydrogen;
$L^1$, $L^2$ and $L^3$ are independently selected from the group consisting of a bond, optionally substituted alkyl, optionally substituted alkenyl and optionally substituted alkynyl;
$R^5$ and $R^6$ are independently selected from the group consisting of a bond, O, $NR^c$, $S(O)_n$, optionally substituted amide, optionally substituted heterocycloalkyl, optionally substituted aryl and optionally substituted heteroaryl; wherein;
$R^c$ is independently selected from the group consisting of hydrogen or, optionally substituted alkyl; and
n is an integer from 0 to 2;
or a pharmaceutically acceptable form thereof.

2. The compound according to claim 1, wherein X, Y and Z are N; both X and Z are N and Y is $CR^3$; X is CH, Y is $CR^3$ and Z is N; or X is $CH_2$, Y is $CHR^3$ and Z is N.

3. The compound according to claim 1, wherein the compound has the following Formula (Ia), (Ib), (Ic) or (Id):

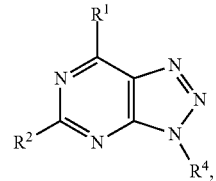
(Ia)

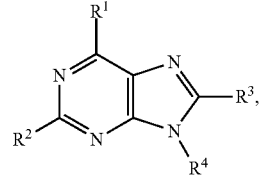
(Ib)

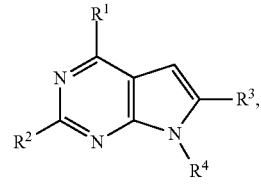
(Ic)

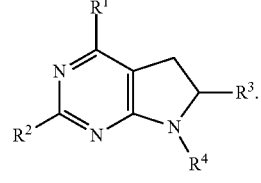
(Id)

4. The compound according to claim 1, wherein $R^1$ is optionally substituted cycloamino, optionally substituted heterocycloamino, optionally substituted alkyl, optionally substituted cycloalkyl, optionally substituted aryl, optionally substituted heteroaryl, optionally substituted arylamino or optionally substituted heteroarylamino; or $R^1$ is an optionally substituted phenyl, optionally substituted pyrimidinyl, optionally substituted pyridinyl, optionally substituted pyrazinyl, optionally substituted thiomorpholino or optionally substituted morphilino, or $R^2$ is a halogen, optionally substituted cycloalkyl, optionally substituted arylamino, optionally substituted heteroarylamino, optionally substituted amino, optionally substituted alkylamino, optionally substituted cycloamino, optionally substituted heterocycloamino, optionally substituted aryl or optionally substituted heteroaryl; or $R^2$ is a Cl, Br, F, $NH_2$, dimethylamino, diethylamino, optionally substituted pyrrolidinyl, optionally substituted piperidinyl, optionally substituted morpholino, optionally substituted phenyl, optionally substituted pyridinyl, optionally substituted pyrimidinyl, optionally substituted pyrazinyl, or optionally substituted benzimidazolyl.

5. The compound according to claim 1, wherein $R^3$ is hydrogen, optionally substituted alkyl, optionally substituted amino, optionally substituted alkylamino, optionally substituted cycloamino, optionally substituted heterocycloamino; or $R^3$ is $NH_2$, diethylamino, optionally substituted pyrrolidinyl or optionally substituted piperidinyl; or $R^4$ is optionally substituted alkyl; or $R^4$ is ethyl, 1-propyl, 2-propyl, 2-butyl, 3-pentyl or cyclopentyl.

6. The compound according to claim 1, wherein $R^a$ and $R^b$ are hydrogen; $L^1$, $L^2$ and $L^3$ are independently a bond, optionally substituted alkyl or optionally substituted alkenyl; or $R^5$ and $R^6$ are independently a bond, —O—, —S—, —NH—, —N(Me)-, —N(Ac)—, —S(O)—, —S(O)$_2$—, —CONH—, —NHCO, optionally substituted heterocycloalkyl or optionally substituted aryl; or R$^5$ and R$^6$ are independently a bond, —O—, —NH—, —N(Me)-, —NHCO—, 1,3-piperidinylene, 1,4-piperidinylene, 2,4-pyrimidinylene, 2,5-pyrimidinylene, 1,2-phenylene, 1,3-phenylene or 1,4-phenylene.

7. The compound according to claim 1, wherein the hydroxamate group -L$^1$-R$^5$-L$^2$-R$^6$-L$^3$-CON(R$^a$)OR$^b$ is selected from the following structures;

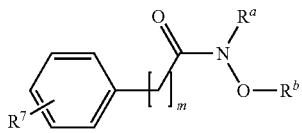

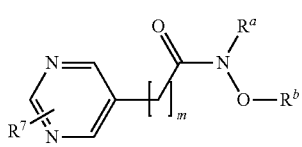

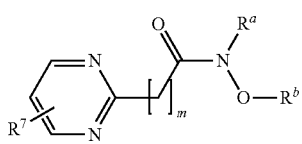

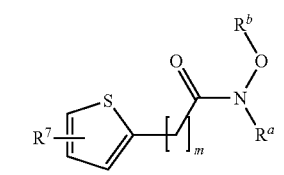

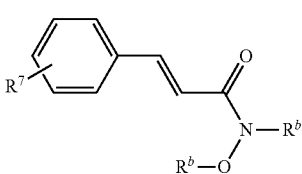

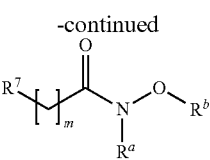

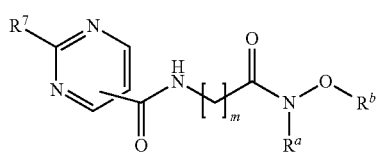

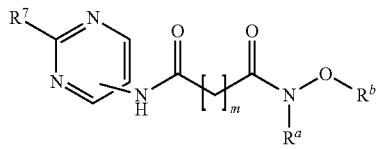

wherein R$^7$ is selected from the group consisting of a bond, optionally substituted alkyl, optionally substituted aryl, optionally substituted heteroaryl, O, S, optionally substituted amino, —CH$_2$O—, —OCH$_2$—, —CH$_2$S(O)$_n$—, —S(O)$_n$—, —CH$_2$N(R$^c$)—, —N(R$^c$)CH$_2$—, —N(R$^c$)—, —CO—, —C(=NOR$^a$)—, —CON(R$^a$)—, and —N(R$^c$)CO—; and m is an integer from 0 to 10.

8. The compound according to claim 1, wherein R$^2$ or R$^4$ contains the hydroxamate group -L$^1$-R$^5$-L$^2$-R$^6$-L$^3$-CON(R$^a$)OR$^b$.

9. The compound according to claim 1, wherein R$^1$ is not a morpholine when R$^2$ or R$^3$ contains the hydroxamate group.

10. The compound according to claim 1, wherein R$^1$ is a substituted amino when R$^2$ or R$^3$ contains the hydroxamate group.

11. A compound according to claim 1, wherein the compound is selected from the group consisting of;

| EX | Chemical Structure and Name |
|---|---|
| 1 | ![structure] N-hydroxy-4-(3-(9-isopropyl-2-morpholino-9H-purin-6-yl)phenoxy)butanamide |

| EX | Chemical Structure and Name |
|---|---|
| 2 | 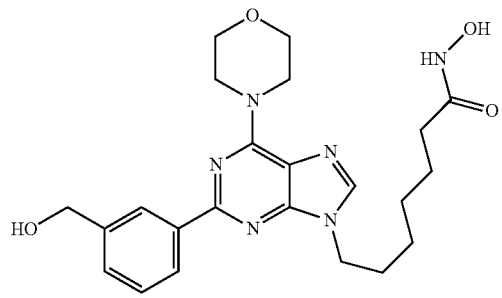 [SMILES: O=C(CCCCCCn1cnc2c(N3CCOCC3)nc(-c3cccc(CO)c3)nc21)NO]
N-hydroxy-7-(2-(3-(hydroxymethyl)phenyl)-6-morpholino-9H-purin-9-yl)heptanamide |
| 3 | 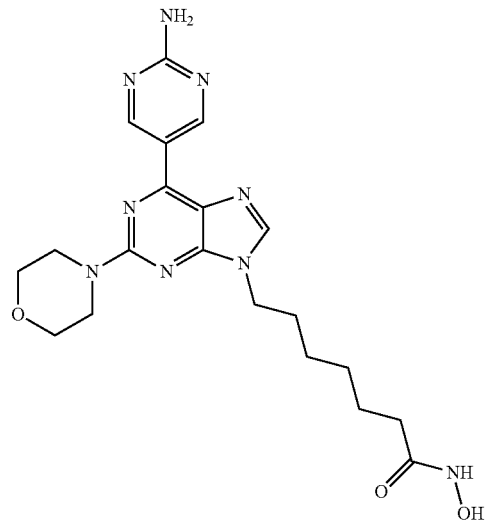
7-(6-(2-aminopyrimidin-5-yl)-2-morpholino-9H-purin-9-yl)-N-hydroxyheptanamide |
| 4 | 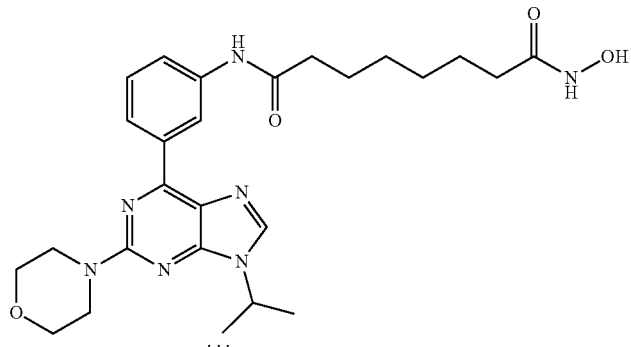
$N^1$-hydroxy-$N^8$-(3-(9-isopropyl-2-morpholino-9H-purin-6-yl)phenyl)octanediamide |

| EX | Chemical Structure and Name |
|---|---|
| 5 | 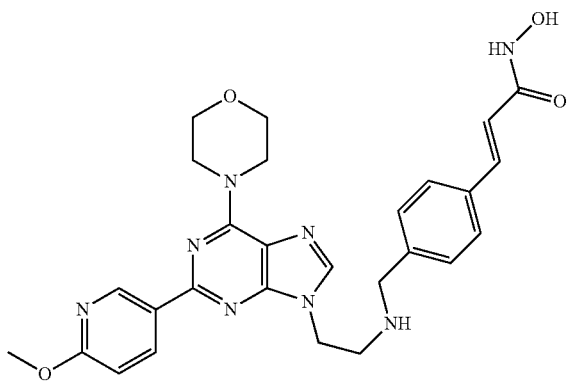<br>$N^1$-hydroxy-$N^8$-(3-(9-isopropyl-2-morpholino-9H-purin-6-yl)phenyl)octanediamide |
| 6 | 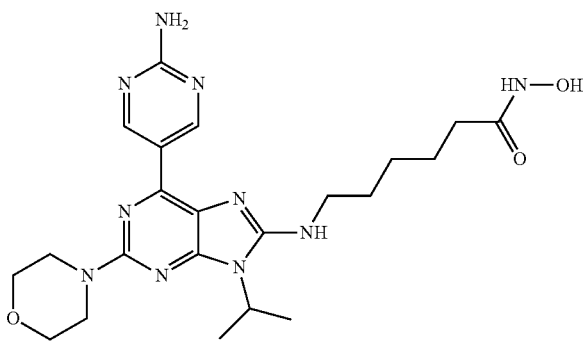<br>6-((6-(2-aminopyrimidin-5-yl)-9-isopropyl-2-morpholino-9H-purin-8-yl)amino)-N-hydroxyhexanamide |
| 7 | 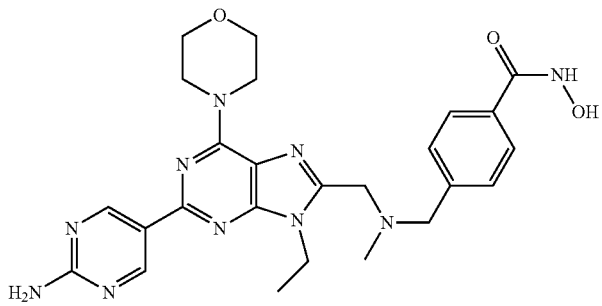<br>4-((((2-(2-aminopyrimidin-5-yl)-9-ethyl-6-morpholino-9H-purin-8-yl)methyl)(methyl)amino)methyl)-N-hydroxybenzamide |

| EX | Chemical Structure and Name |
|----|------------------------------|
| 8 | 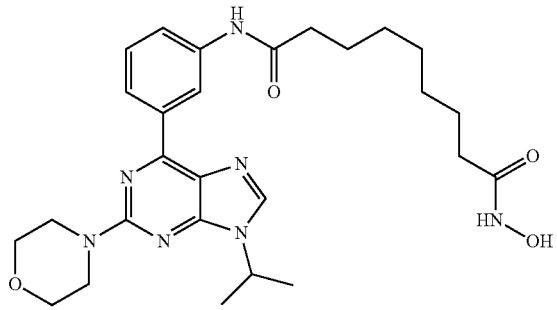 [SMILES: CC(C)n1cnc2c(-c3cccc(NC(=O)CCCCCCCC(=O)NO)c3)nc(N3CCOCC3)nc21]<br>N$^1$-hydroxy-N$^9$-(3-(9-isopropyl-2-morpholino-9H-purin-6-yl)phenyl)nonanediamide. |
| 9 | 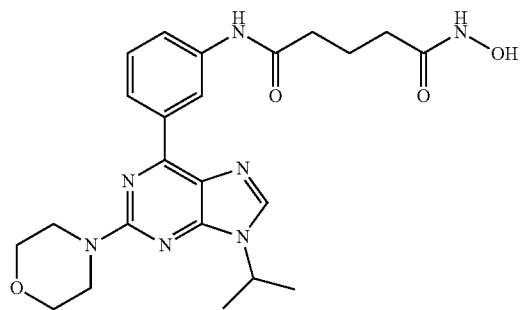<br>N$^1$-hydroxy-N$^5$-(3-(9-isopropyl-2-morpholino-9H-purin-6-yl)phenyl)glutaramide. |
| 10 | 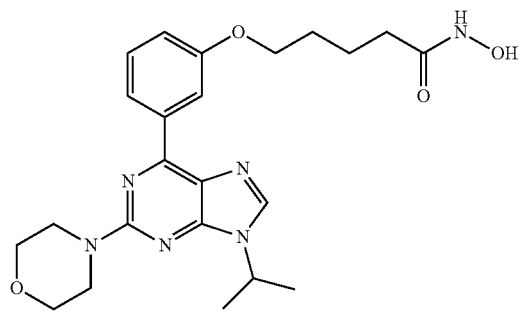<br>N-hydroxy-5-(3-(9-isopropyl-2-morpholino-9H-purin-6-yl)phenoxy)pentanamide. |

| EX | Chemical Structure and Name |
|---|---|
| 11 | 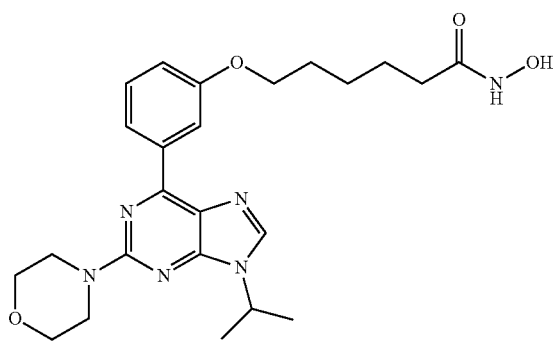<br>N-hydroxy-6-(3-(9-isopropyl-2-morpholino-9H-purin-6-yl)phenoxy)hexanamide. |
| 12 | 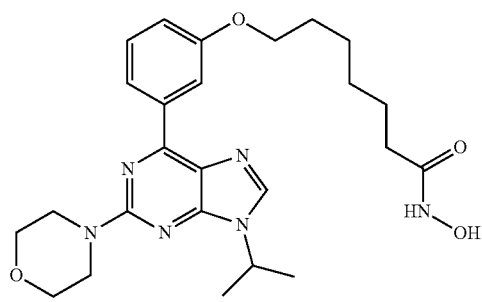<br>N-hydroxy-7-(3-(9-isopropyl-2-morpholino-9H-purin-6-yl)phenoxy)heptanamide. |
| 13 | 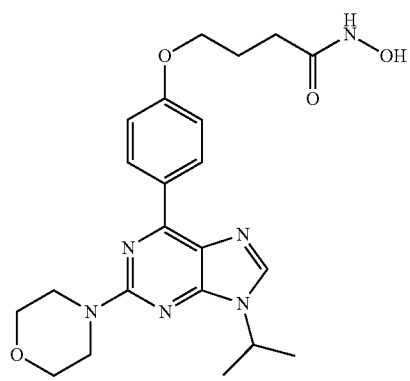<br>N-hydroxy-4-(4-(9-isopropyl-2-morpholino-9H-purin-6-yl)phenoxy)butanamide. |

| EX | Chemical Structure and Name |
|----|-----------------------------|
| 14 | 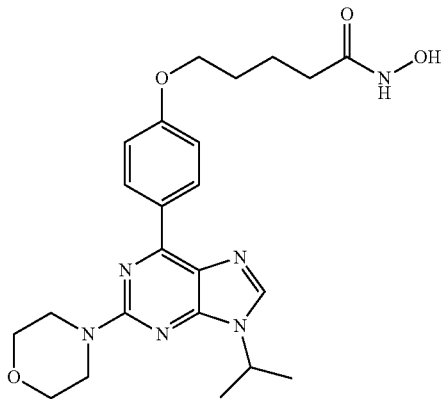  N-hydroxy-5-(4-(9-isopropyl-2-morpholino-9H-purin-6-yl)phenoxy)pentanamide. |
| 15 | 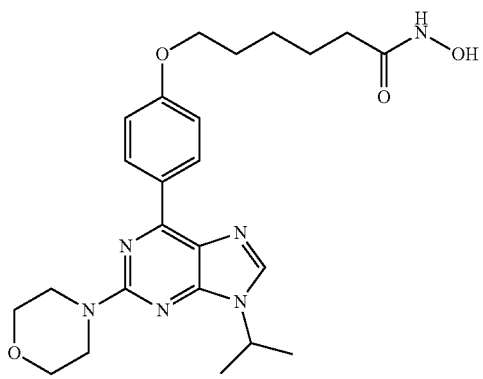  N-hydroxy-6-(4-(9-isopropyl-2-morpholino-9H-purin-6-yl)phenoxy)hexanamide. |
| 16 | 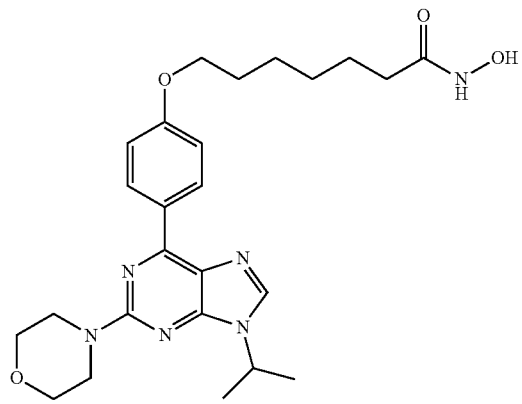  N-hydroxy-7-(4-(9-isopropyl-2-morpholino-9H-purin-6-yl)phenoxy)heptanamide. |

| EX | Chemical Structure and Name |
|---|---|
| 17 | 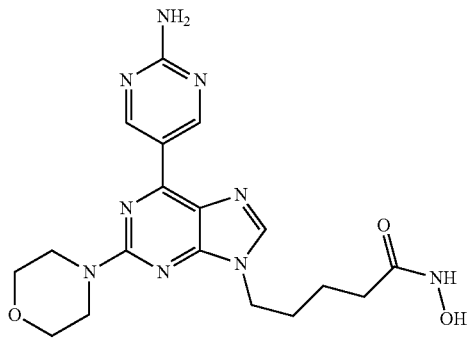<br>5-(6-(2-aminopyrimidin-5-yl)-2-morpholino-9H-purin-9-yl)-N-hydroxypentanamide. |
| 18 | 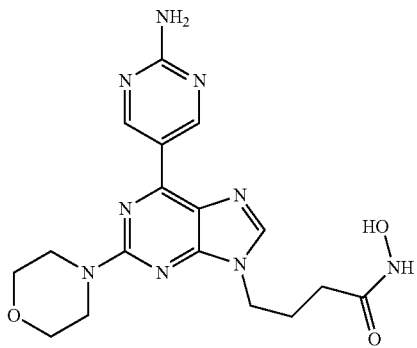<br>4-(6-(2-aminopyrimidin-5-yl)-2-morpholino-9H-purin-9-yl)-N-hydroxybutanamide. |
| 19 | 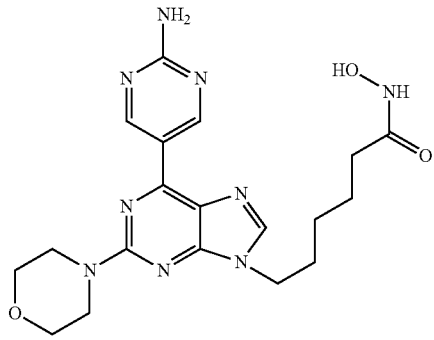<br>6-(6-(2-aminopyrimidin-5-yl)-2-morpholino-9H-purin-9-yl)-N-hydroxyhexanamide. |

| EX | Chemical Structure and Name |
|---|---|
| 20 | 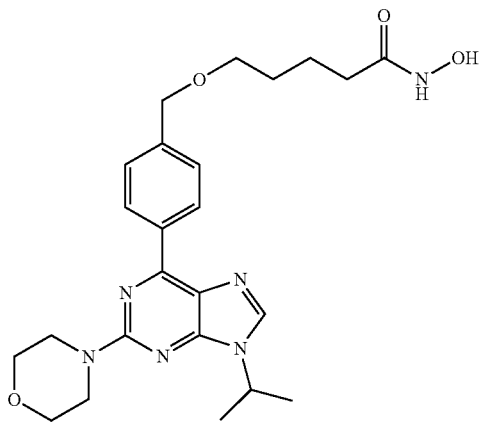<br>N-hydroxy-5-((4-(9-isopropyl-2-morpholino-9H-purin-6-yl)benzyl)oxy)pentanamide. |
| 21 | 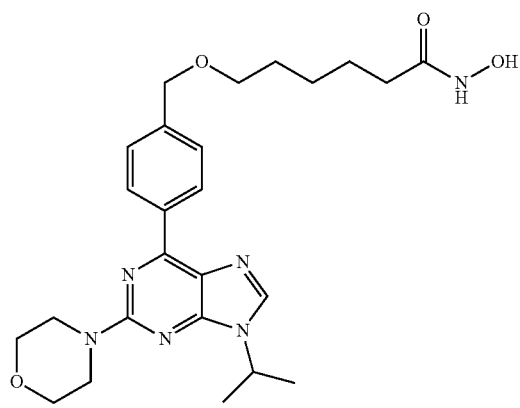<br>N-hydroxy-6-((4-(9-isopropyl-2-morpholino-9H-purin-6-yl)benzyl)oxy)hexanamide. |
| 22 | 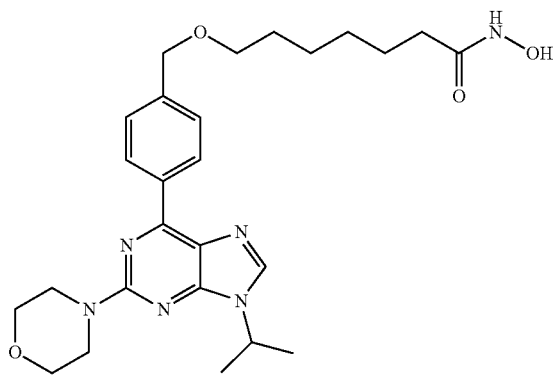<br>N-hydroxy-7-((4-(9-isopropyl-2-morpholino-9H-purin-6-yl)benzyl)oxy)heptanamide. |

| EX | Chemical Structure and Name |
|---|---|
| 23 | 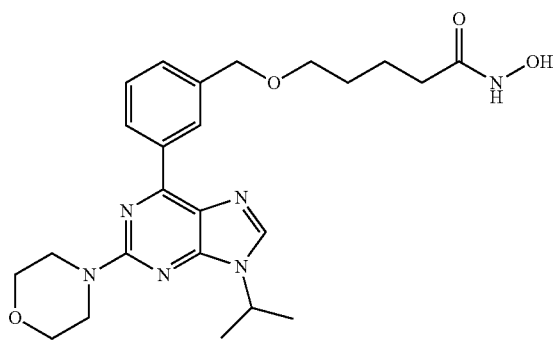
N-hydroxy-5-((3-(9-isopropyl-2-morpholino-9H-purin-6-yl)benzyl)oxy)pentanamide. |
| 24 | 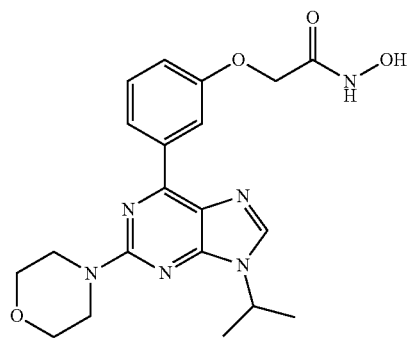
N-hydroxy-2-(3-(9-isopropyl-2-morpholino-9H-purin-6-yl)phenoxy)acetamide. |
| 25 | 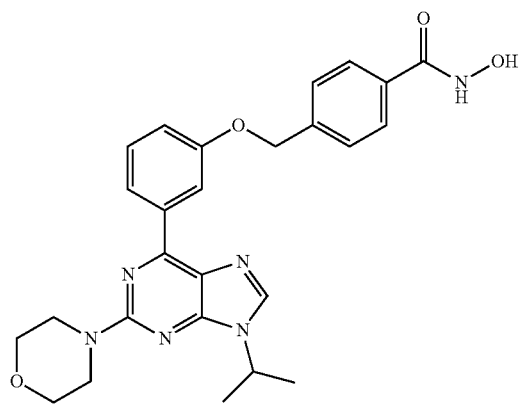
N-hydroxy-4-((3-(9-isopropyl-2-morpholino-9H-purin-6-yl)phenoxy)methyl)benzamide. |

| EX | Chemical Structure and Name |
|---|---|
| 26 | 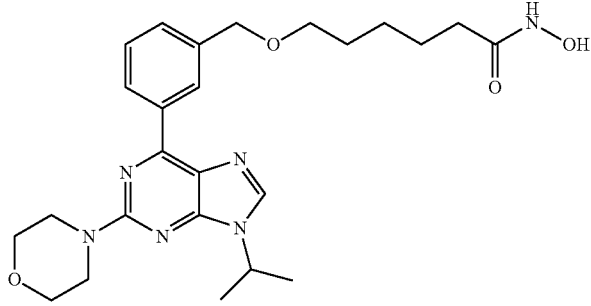<br>N-hydroxy-6-((3-(9-isopropyl-2-morpholino-9H-purin-6-yl)benzyl)oxy)hexanamide. |
| 27 | 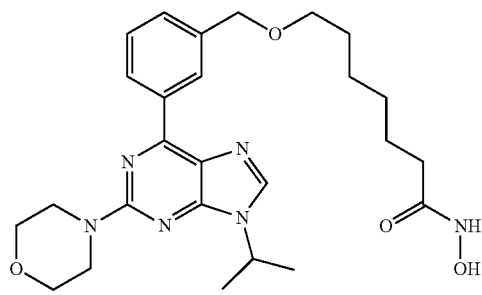<br>N-hydroxy-7-((3-(9-isopropyl-2-morpholino-9H-purin-6-yl)benzyl)oxy)heptanamide. |
| 28 | 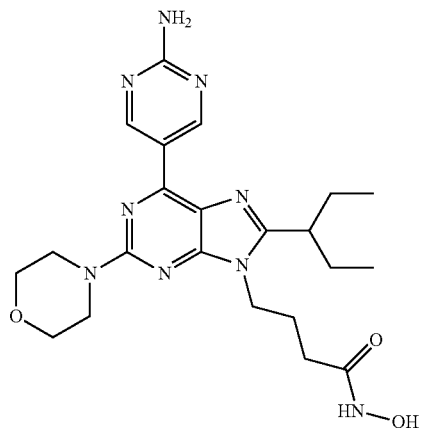<br>4-(6-(2-aminopyrimidin-5-yl)-8-(diethylamino)-2-morpholino-9H-purin-9-yl)-N-hydroxybutanamide. |

| EX | Chemical Structure and Name |
|---|---|
| 29 | 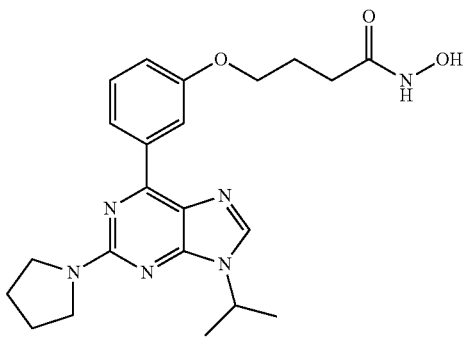<br>N-hydroxy-4-(3-(9-isopropyl-2-(pyrrolidin-1-yl)-9H-purin-6-yl)phenoxy)butanamide. |
| 30 | 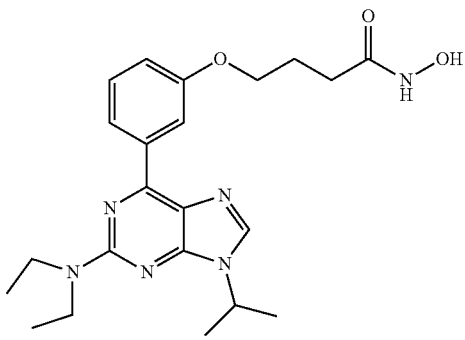<br>4-(3-(2-(diethylamino)-9-isopropyl-9H-purin-6-yl)phenoxy)-N-hydroxybutanamide. |
| 31 | 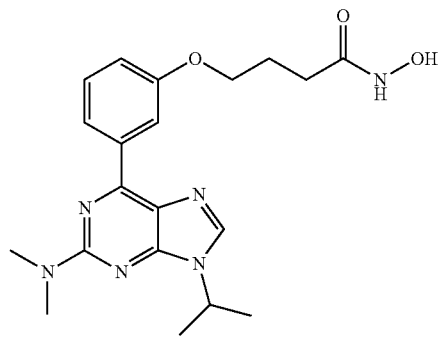<br>4-(3-(2-(dimethylamino)-9-isopropyl-9H-purin-6-yl)phenoxy)-N-hydroxybutanamide. |

| EX | Chemical Structure and Name |
|---|---|
| 32 | 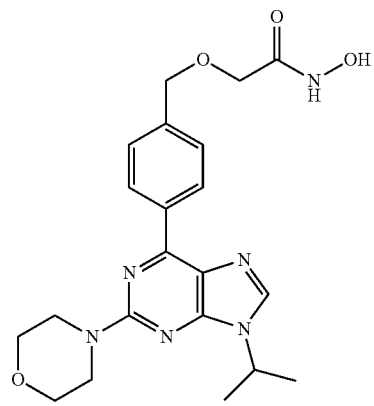<br>N-hydroxy-2-((4-(9-isopropyl-2-morpholino-9H-purin-6-yl)benzyl)oxy)acetamide. |
| 33 | 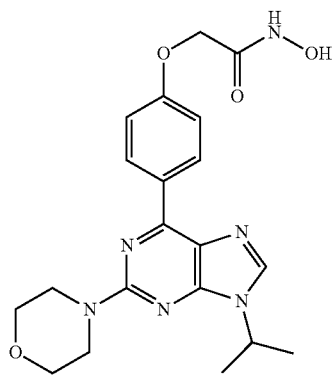<br>N-hydroxy-2-(4-(9-isopropyl-2-morpholin-9H-purin-6-yl)phenoxy)acetamide. |
| 34 | 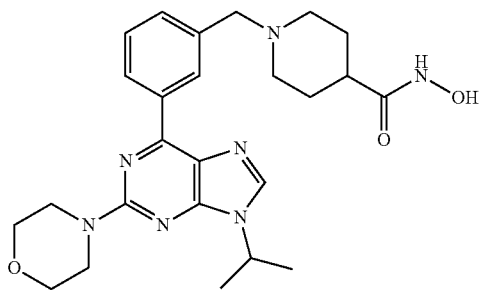<br>N-hydroxy-1-(3-(9-isopropyl-2-morpholino-9H-purin-6-yl)benzyl)piperidine-4-carboxamide. |

| EX | Chemical Structure and Name |
|---|---|
| 35 | 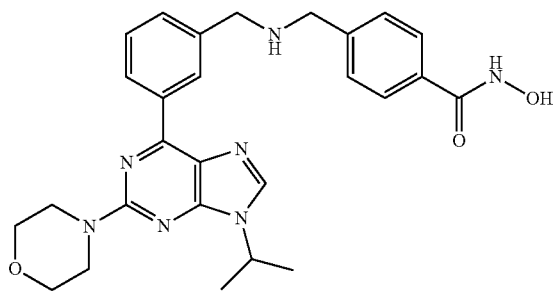<br>N-hydroxy-4-(((3-(9-isopropyl-2-morpholino-9H-purin-6-yl)benzyl)amino)methyl)benzamide. |
| 36 | 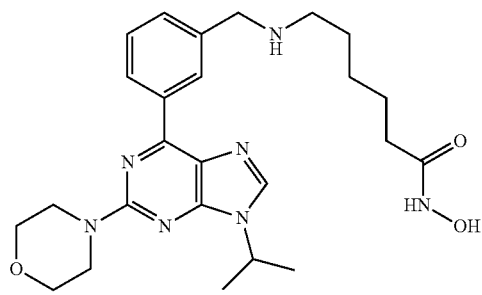<br>N-hydroxy-6-((3-(9-isopropyl-2-morpholino-9H-purin-6-yl)benzyl)amino)hexanamide. |
| 37 | 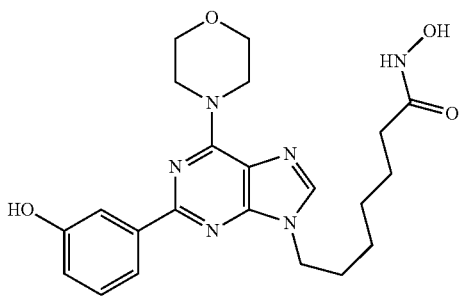<br>N-hydroxy-7-(2-(3-hydroxyphenyl)-6-morpholino-9H-purin-9-yl)heptanamide. |
| 38 | 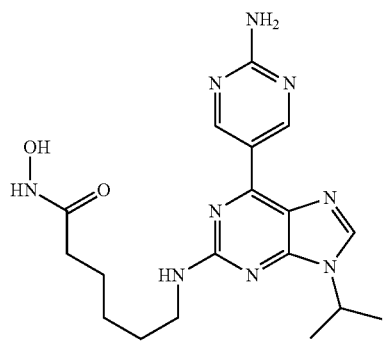<br>6-((6-(2-aminopyrimidin-5-yl)-9-isopropyl-9H-purin-2-yl)amino)-N-hydroxyhexanamide |

| EX | Chemical Structure and Name |
|----|-----------------------------|
| 39 | 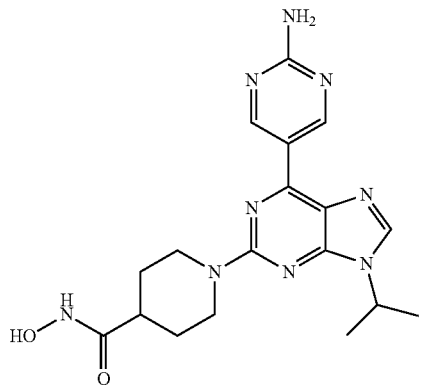<br>1-(6-(2-aminopyrimidin-5-yl)-9-isopropyl-9H-purin-2-yl)-N-hydroxypiperidine-4-carboxamide. |
| 40 | 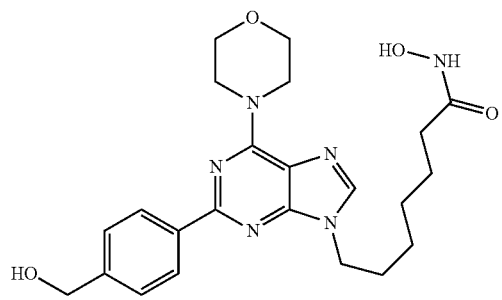<br>N-hydroxy-7-(2-(4-(hydroxymethyl)phenyl)-6-morpholino-9H-purin-9-yl)heptanamide. |
| 41 | 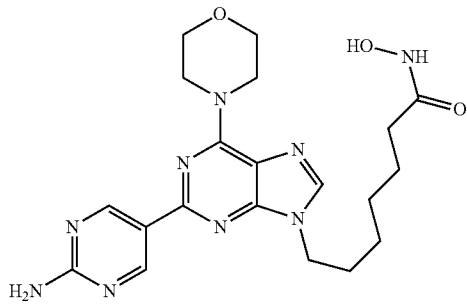<br>7-(2-(2-aminopyrimidin-5-yl)-6-morpholino-9H-purin-9-yl)-N-hydroxyheptanamide. |

| EX | Chemical Structure and Name |
|---|---|
| 42 | 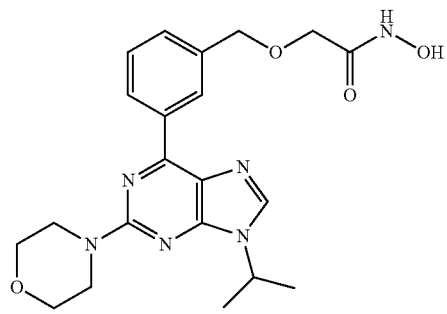<br>N-hydroxy-2-((3-(9-isopropyl-2-morpholino-9H-purin-6-yl)benzyl)oxy)acetamide. |
| 43 | 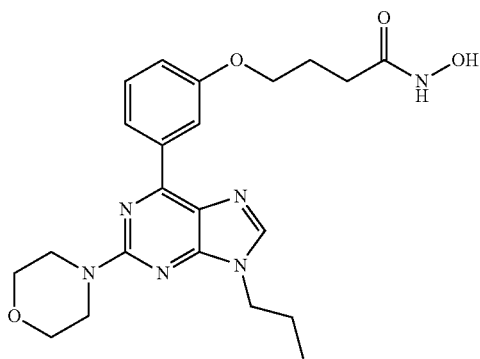<br>N-hydroxy-4-(3-(2-morpholino-9-propyl-9H-purin-6-yl)phenoxy)butanamide. |
| 44 | 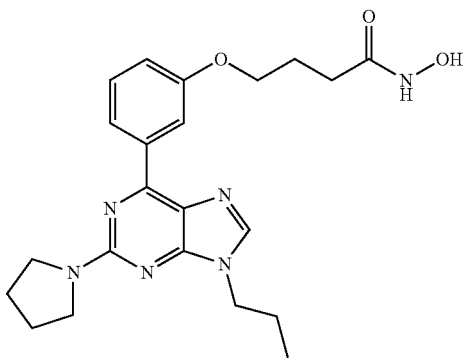<br>N-hydroxy-4-(3-(9-propyl-2-(pyrrolidin-1-yl)-9H-purin-6-yl)phenoxy)butanamide. |

| EX | Chemical Structure and Name |
|---|---|
| 45 | 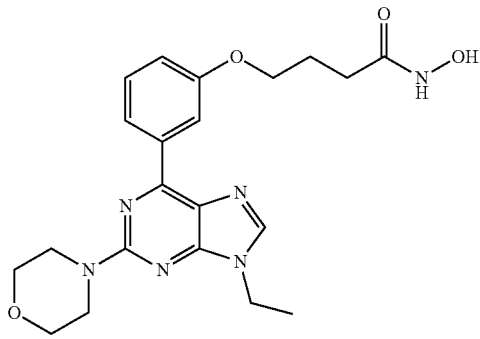<br>4-(3-(9-ethyl-2-morpholino-9H-purin-6-yl)phenoxy)-N-hydroxybutanamide. |
| 46 | 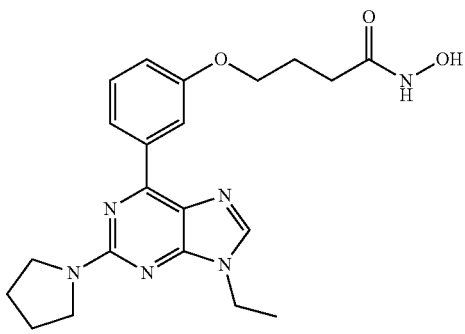<br>4-(3-(9-ethyl-2-(pyrrolidin-1-yl)-9H-purin-6-yl)phenoxy)-N-hydroxybutanamide. |
| 47 | 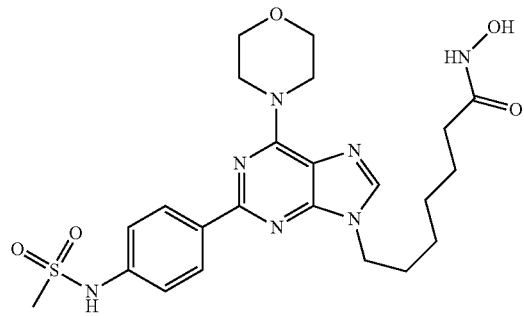<br>N-hydroxy-7-(2-(4-(methylsulfonamideo)phenyl)-6-morpholino-9H-purin-9-yl)heptanamide. |

| EX | Chemical Structure and Name |
|---|---|
| 48 | 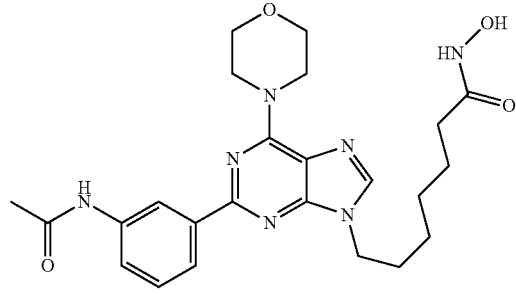
7-(2-(3-acetamidophenyl)-6-morpholino-9H-purin-9-yl)-N-hydroxyheptanamide. |
| 49 | 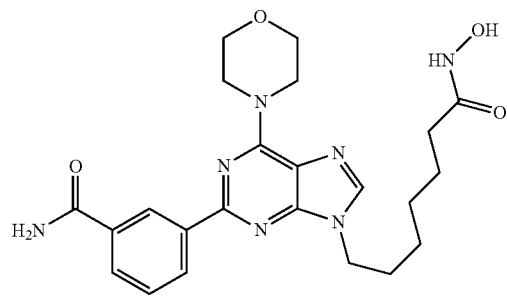
3-(9-(7-(hydroxyamino)-7-oxoheptyl)-6-morpholino-9H-purin-2-yl)benzamide. |
| 50 | 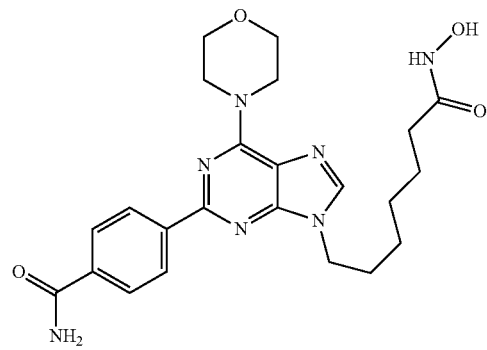
4-(9-(7-(hydroxyamino)-7-oxoheptyl)-6-morpholin-9H-purin-2-yl)benzamide. |

| EX | Chemical Structure and Name |
|---|---|
| 51 | 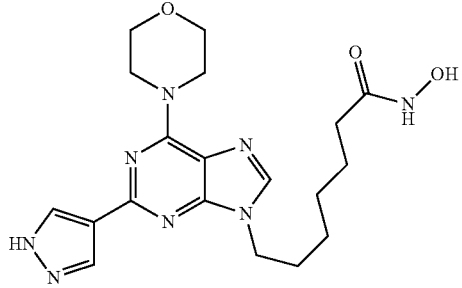<br>N-hydroxy-7-(6-morpholino-2-(1H-pyrazol-4-yl)-9H-purin-9-yl)heptanamide. |
| 52 | 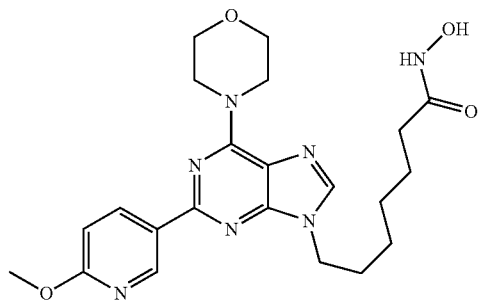<br>N-hydroxy-7-(2-(6-methoxypyridin-3-yl)-6-morpholino-9H-purin-9-yl)heptanamide. |
| 53 | 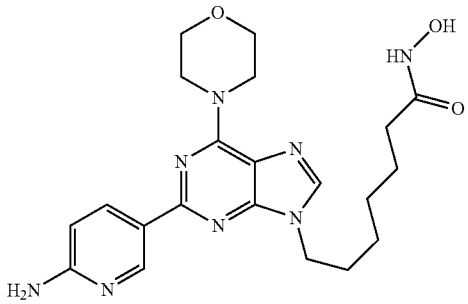<br>7-(2-(6-aminopyridin-3-yl)-6-morpholino-9H-purin-9-yl)-N-hydroxyheptanamide. |
| 54 | 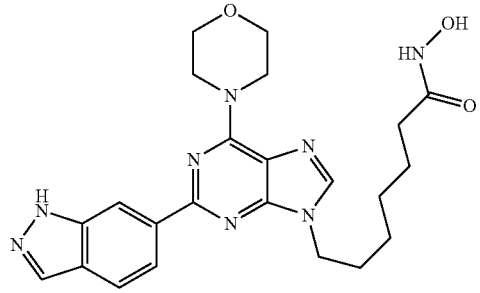<br>7-(2-(1H-indazol-6-yl)-6-morpholino-9H-purin-9-yl)-N-hydroxyheptanamide. |

| EX | Chemical Structure and Name |
|---|---|
| 55 | 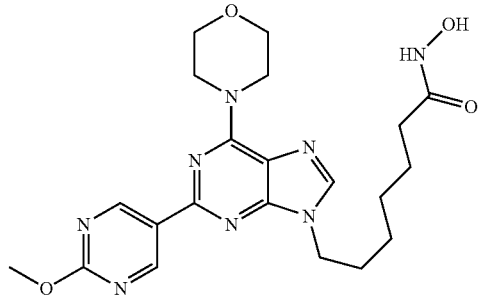<br>N-hydroxy-7-(2-(2-methoxypyrimidin-5-yl)-6-morpholino-9H-purin-9-yl)heptanamide. |
| 56 | 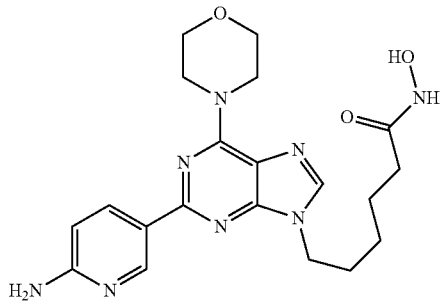<br>6-(2-(6-aminopyridin-3-yl)-6-morpholino-9H-purin-9-yl)-N-hydroxyhexanamide. |
| 57 | 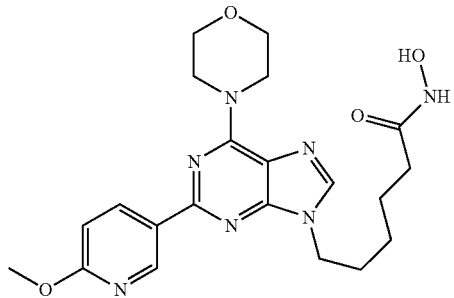<br>N-hydroxy-6-(2-(6-methoxypyridin-3-yl)-6-morpholino-9H-purin-9-yl)hexanamide. |
| 58 | 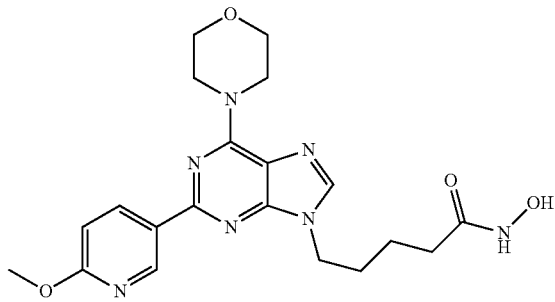<br>N-hydroxy-5-(2-(6-methoxypyridin-3-yl)-6-morpholino-9H-purin-9-yl)pentanamide. |

| EX | Chemical Structure and Name |
|---|---|
| 59 | 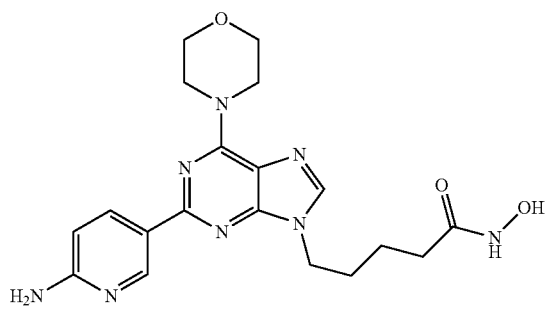<br>5-(2-(6-aminopyridin-3-yl)-6-morpholino-9H-purin-9-yl)-N-hydroxypentanamide |
| 60 | 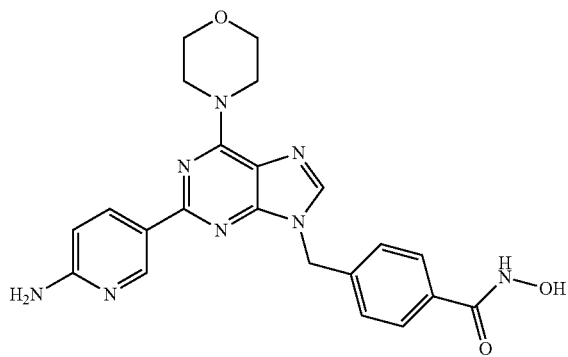<br>4-((2-(6-aminopyridin-3-yl)-6-morpholino-9H-purin-9-yl)methyl)-N-hydroxybenzamide. |
| 61 | 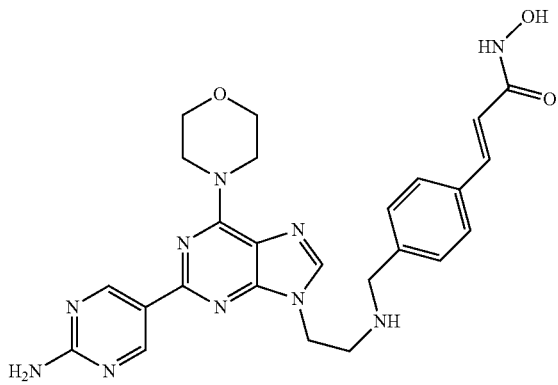<br>(E)-3-(4-(((2-(2-(2-aminopyrimidin-5-yl)-6-morpholino-9H-purin-9-yl)ethyl)amino)methyl)phenyl)-N-hydroxyacrylamide. |

| EX | Chemical Structure and Name |
|----|------------------------------|
| 62 | 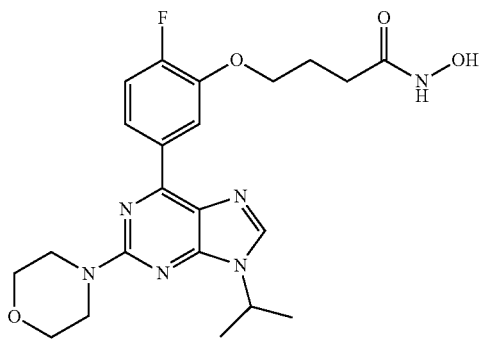<br>4-(2-fluoro-5-(9-isopropyl-2-morpholino-9H-purin-6-yl)phenoxy)-N-hydroxybutanamide. |
| 63 | 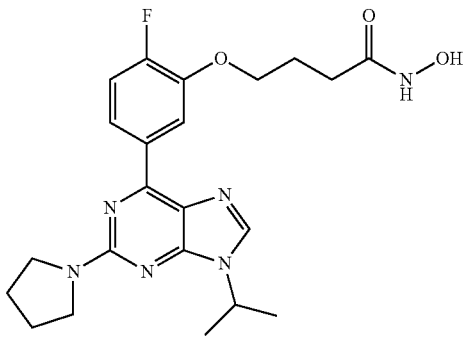<br>4-(2-fluoro-5-(9-isopropyl-2-(pyrrolidin-1-yl)-9H-purin-6-yl)phenoxy)-N-hydroxybutanamide. |
| 64 | 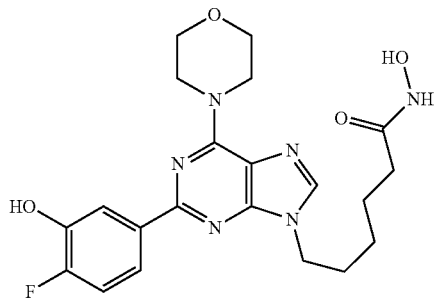<br>6-(2-(4-fluoro-3-hydroxyphenyl)-6-morpholino-9H-purin-9-yl)-N-hydroxyhexanamide. |

| EX | Chemical Structure and Name |
|----|------------------------------|
| 65 | 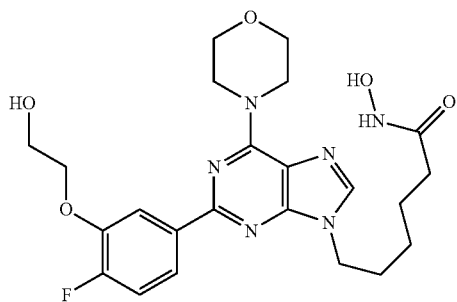<br>6-(2-(4-fluoro-3-(2-hydroxyethoxy)phenyl)-6-morpholino-9H-purin-9-yl)-N-hydroxyhexanamide |
| 66 | 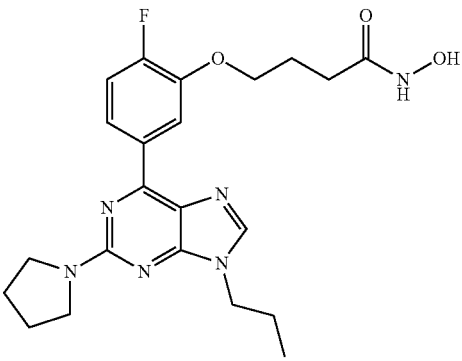<br>4-(2-fluoro-5-(9-propyl-2-(pyrrolidin-1-yl)-9H-purin-6-yl)phenoxy)-N-hydroxybutanamide. |
| 67 | 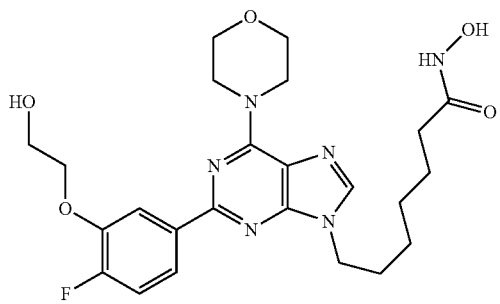<br>7-(2-(4-fluoro-3-(2-hydroxyethoxy)phenyl)-6-morpholino-9H-purin-9-yl)-N-hydroxyheptanamide. |

| EX | Chemical Structure and Name |
|----|------------------------------|
| 68 | 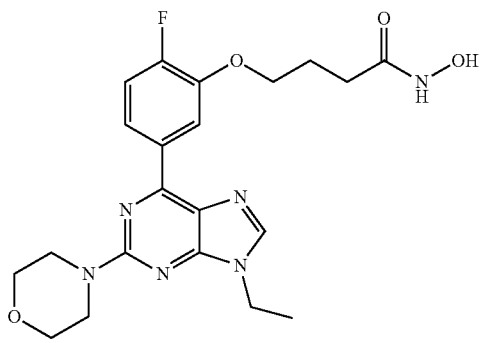<br>4-(5-(9-ethyl-2-morpholino-9H-purin-6-yl)-2-fluorophenoxy)-N-hydroxybutanamide. |
| 69 | 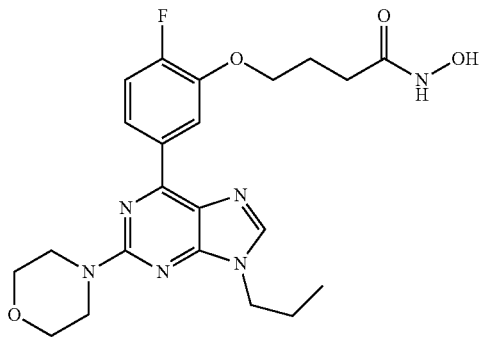<br>4-(2-fluoro-5-(2-morpholino-9-propyl-9H-purin-6-yl)phenoxy)-N-hydroxybutanamide. |
| 70 | 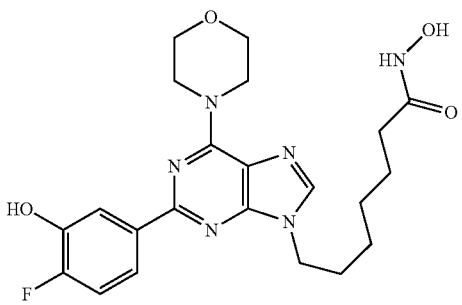<br>7-(2-(4-fluoro-3-hydroxyphenyl)-6-morpholino-9H-purin-9-yl)-N-hydroxyheptanamide. |

| EX | Chemical Structure and Name |
|---|---|
| 71 | 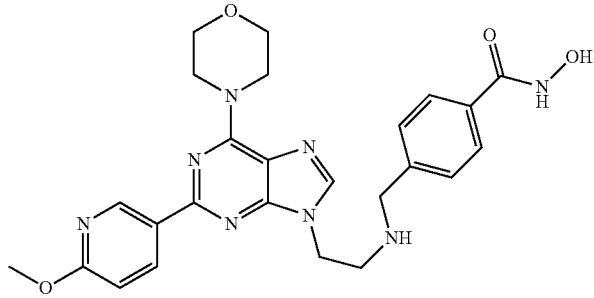<br>N-hydroxy-4-(((2-(2-(6-methoxypyridin-3-yl)-6-morpholino-9H-purin-9-yl)ethyl)amino)methyl)benzamide. |
| 72 | 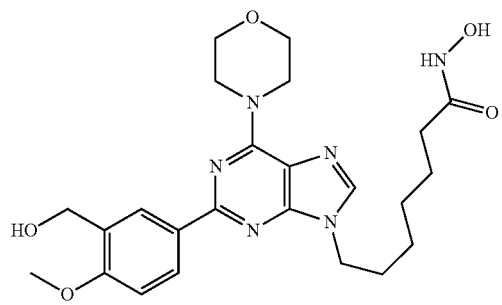<br>N-hydroxy-7-(2-(3-(hydroxymethyl)-4-methoxyphenyl)-6-morpholino-9H-purin-9-yl)heptanamide. |
| 73 | 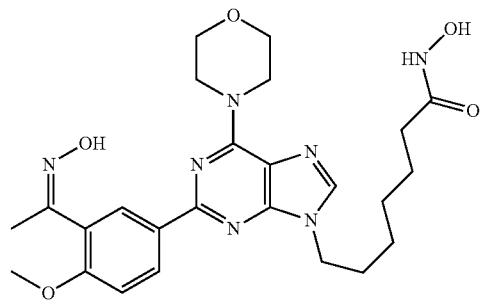<br>(Z)-N-hydroxy-7-(2-(3-(1-(hydroxyimino)ethyl)-4-methoxyphenyl)-6-morpholino-9H-purin-9-yl)heptanamide. |

| EX | Chemical Structure and Name |
|----|------------------------------|
| 74 | 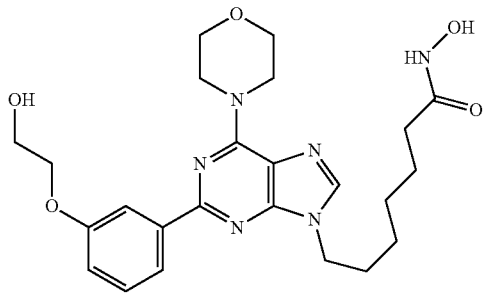<br>N-hydroxy-7-(2-(3-(2-hydroxyethoxy)phenyl)-6-morpholino-9H-purin-9-yl)heptanamide. |
| 75 | 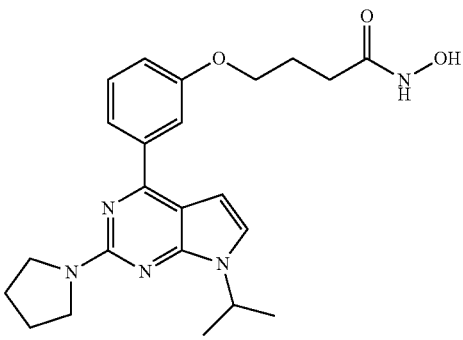<br>N-hydroxy-4-(3-(7-isopropyl-2-(pyrrolidin-1-yl)-7H-pyrrolo[2,3-d]pyrimidin-4-yl)phenoxy)butanamide |
| 76 | 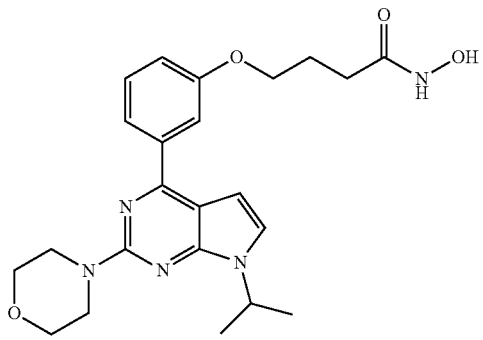<br>N-hydroxy-4-(3-(7-isopropyl-2-morpholino-7H-pyrrolo[2,3-d]pyrimidin-4-yl)phenoxy)butanamide |

| EX | Chemical Structure and Name |
|---|---|
| 77 | 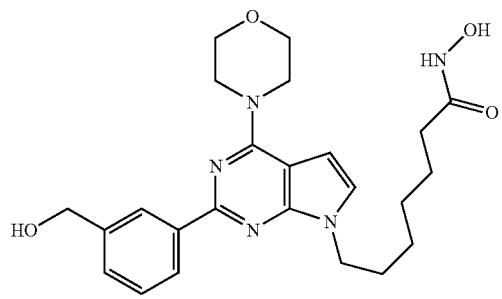<br>N-hydroxy-7-(2-(3-(hydroxymethyl)phenyl)-4-morpholino-7H-pyrrolo[2,3-d]pyrimidin-7-yl)heptanamide. |
| 78 | 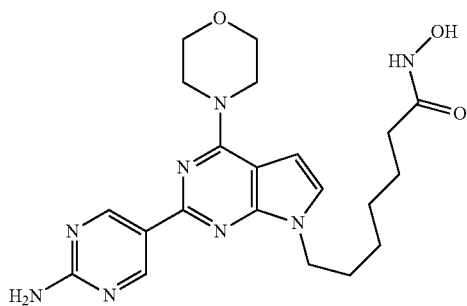<br>7-(2-(2-aminopyrimidin-5-yl)-4-morpholin-7H-pyrrolo[2,3-d]pyrimidin-7-yl)-N-hydroxyheptanamide. |
| 79 | 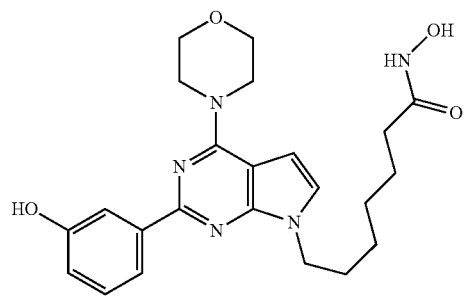<br>N-hydroxy-7-(2-(3-hydroxyphenyl)-4-morpholino-7H-pyrrolo[2,3-d]pyrimidin-7-yl)heptanamide. |

| EX | Chemical Structure and Name |
|---|---|
| 80 | 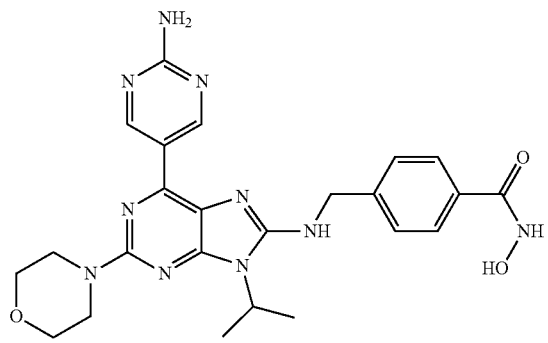
4-(((6-(2-aminopyrimidin-5-yl)-9-isopropyl-2-morpholino-9H-purin-8-yl)amino)methyl)-N-hydroxybenzamide. |
| 81 | 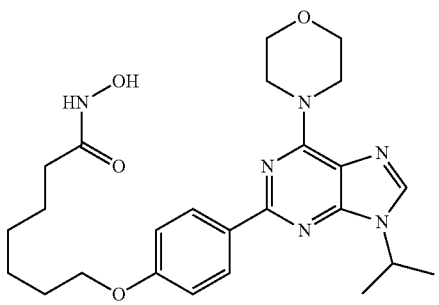
N-hydroxy-7-(4-(9-isopropyl-6-morpholino-9H-purin-2-yl)phenoxy)heptanamide. |
| 82 | 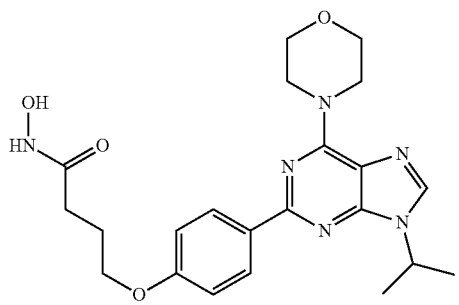
N-hydroxy-4-(4-(9-isopropyl-6-morpholino-9H-purin-2-yl)phenoxy)butanamide. |

| EX | Chemical Structure and Name |
|---|---|
| 83 | 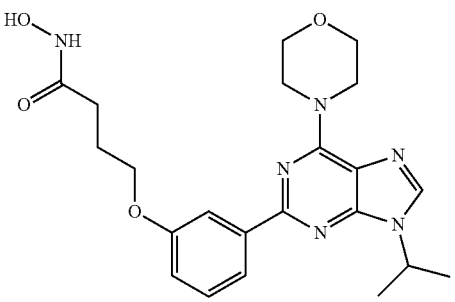
N-hydroxy-4-(3-(9-isopropyl-6-morpholino-9H-purin-2-yl)phenoxy)butanamide. |
| 84 | 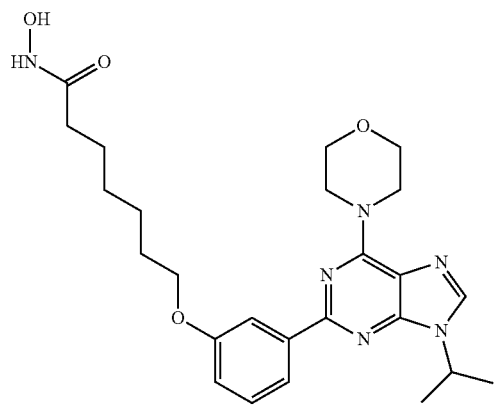
N-hydroxy-7-(3-(9-isopropyl-6-morpholino-9H-purin-2-yl)phenoxy)heptanamide. |
| 85 | 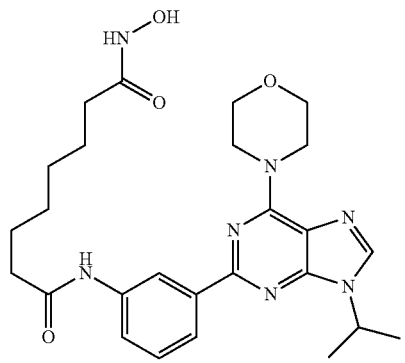
$N^1$-hydroxy-$N^8$-(3-(9-isopropyl-6-morpholino-9H-purin-2-yl)phenyl)octanediamide. |

| EX | Chemical Structure and Name |
|---|---|
| 86 | 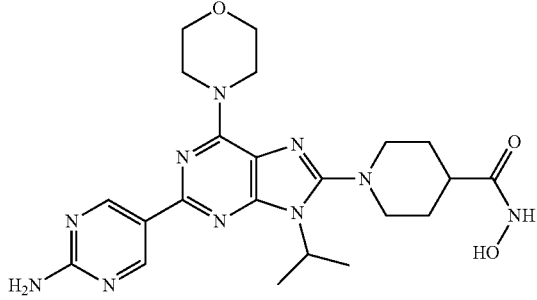<br>1-(2-(2-aminopyrimidin-5-yl)-9-isopropyl-6-morpholino-9H-purin-8-yl)-N-hydroxypiperidine-4-carboxamide. |
| 87 | 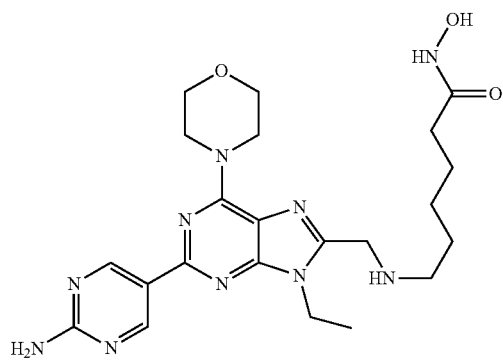<br>6-(((2-(2-aminopyrimidin-5-yl)-9-ethyl-6-morpholino-9H-purin-8-yl)methyl)amino)-N-hydroxyhexanamide. |
| 88 | 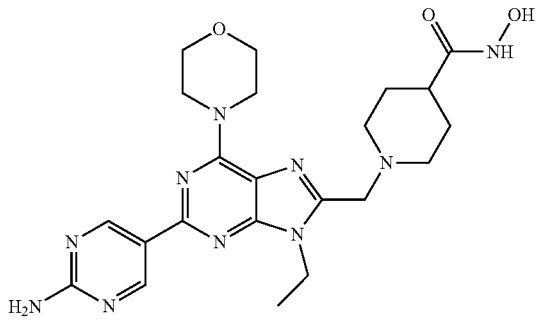<br>1-((2-(2-aminopyrimidin-5-yl)-9-ethyl-6-morpholino-9H-purin-8-yl)methyl)-N-hydroxypiperidine-4-carboxamide. |

| EX | Chemical Structure and Name |
|----|------------------------------|
| 89 | 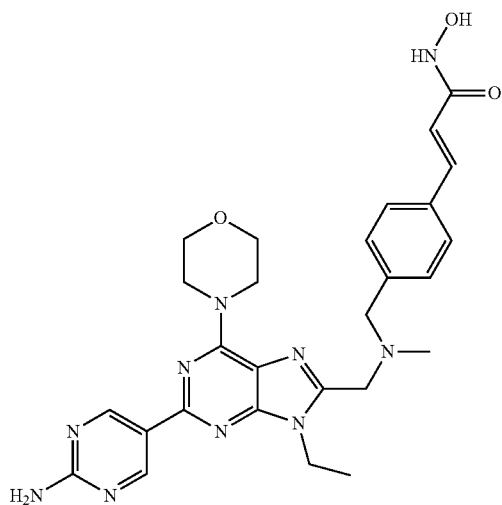<br>(E)-3-(4-(((((2-(2-aminopyrimidin-5-yl)-9-ethyl-6-morpholino-9H-purin-8-yl)methyl)(methyl)amino)methyl)phenyl)-N-hydroxyacrylamide. |
| 90 | 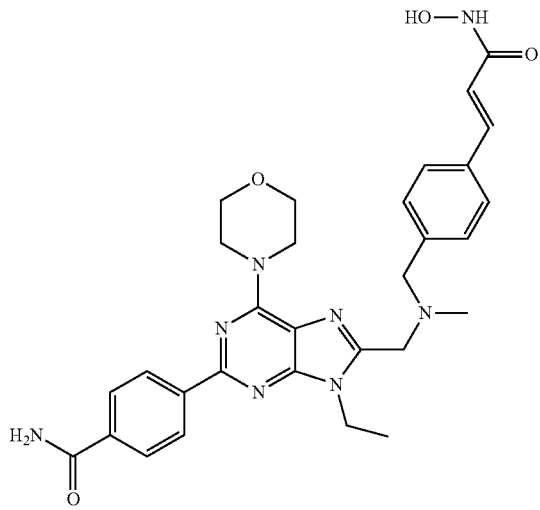<br>(E)-4-(9-ethyl-8-(((4-(3-(hydroxyamino)-3-oxoprop-1-en-1-yl)benzyl)(methyl)amino)methyl)-6-morpholino-9H-purin-2-yl)benzamide. |

| EX | Chemical Structure and Name |
|---|---|
| 91 | 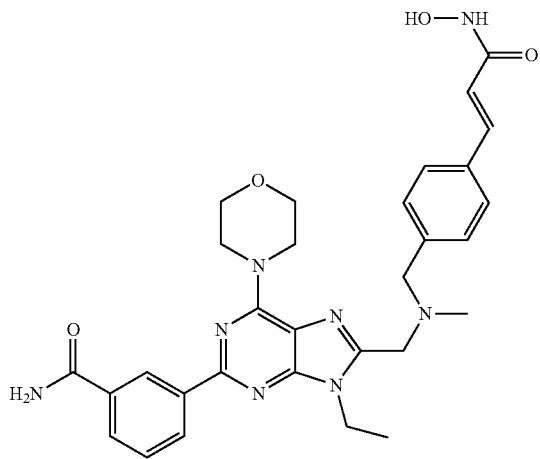<br>(E)-3-(9-ethyl-8-((((4-(3-(hydroxyamino)-3-oxoprop-1-en-1-yl)benzyl)(methyl)amino)methyl)-6-morpholino-9H-purin-2-yl)benzamide. |
| 92 | 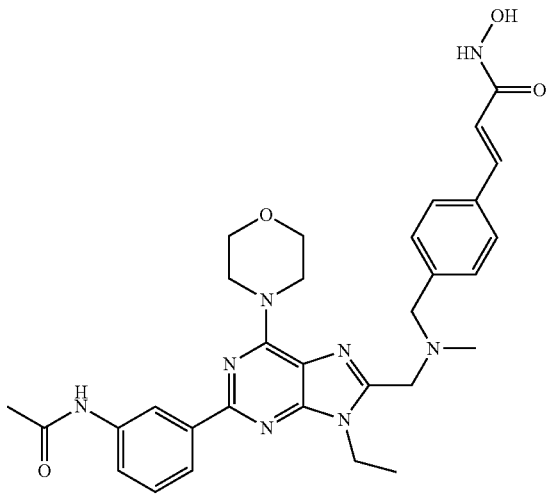<br>(E)-3-(4-((((2-(3-acetamidophenyl)-9-ethyl-6-morpholino-9H-purin-8-yl)methyl)(methyl)amino)methyl)phenyl)-N-hydroxyacrylamide. |

| EX | Chemical Structure and Name |
|---|---|
| 93 | 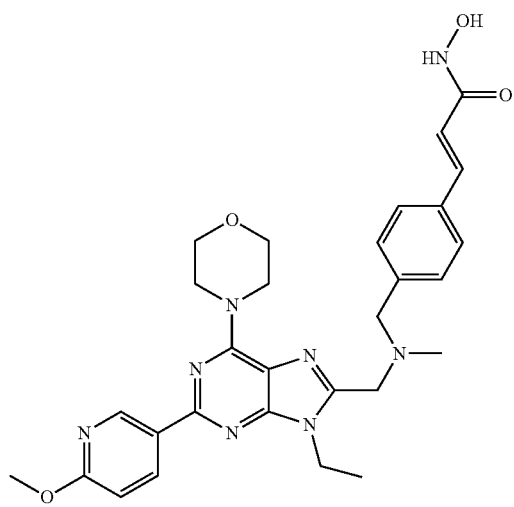<br>(E)-3-(4-((((9-ethyl-2-(6-methoxypyridin-3-yl)-6-morpholino-9H-purin-8-yl)methyl)(methyl)amino)methyl)phenyl)-N-hydroxyacrylamide. |
| 94 | 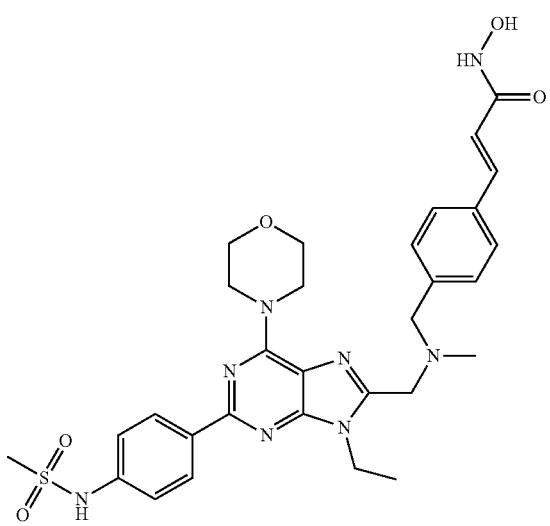<br>(E)-3-(4-((((9-ethyl-2-(4-(methylsulfonamido)phenyl)-6-morpholino-9H-purin-8-yl)methyl)(methyl)amino)methyl)phenyl)-N-hydroxyacrylamide |

| EX | Chemical Structure and Name |
|---|---|
| 95 | 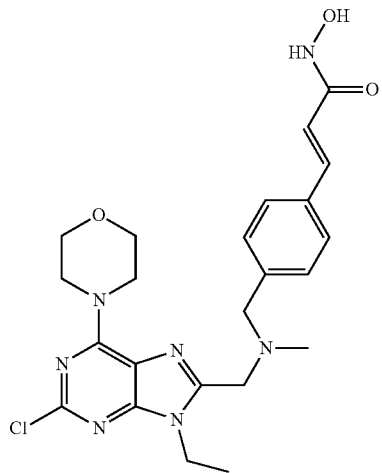
(E)-3-(4-(((((2-chloro-9-ethyl-6-morpholino-9H-purin-8-yl)methyl)(methyl)amino)methyl)phenyl)-N-hydroxyacrylamide. |
| 96 | 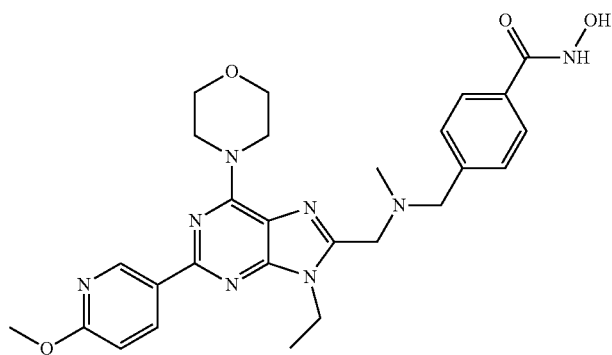
4-(((((9-ethyl-2-(6-methoxypyridin-3-yl)-6-morpholino-9H-purin-8-yl)methyl)(methyl)amino)methyl)-N-hydroxybenzamide. |
| 97 | 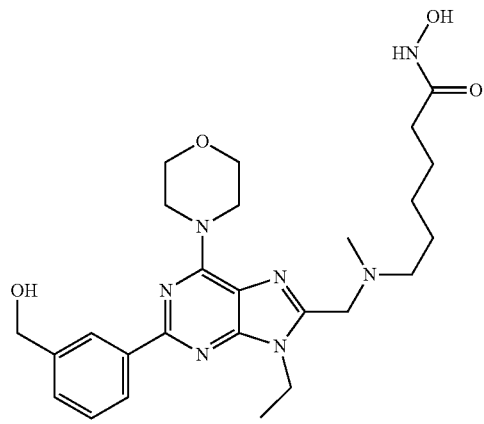
6-(((9-ethyl-2-(3-(hydroxymethyl)phenyl)-6-morpholino-9H-purin-8-yl)methyl)(methyl)amino)-N-hydroxyhexanamide. |

| EX | Chemical Structure and Name |
|---|---|
| 98 | 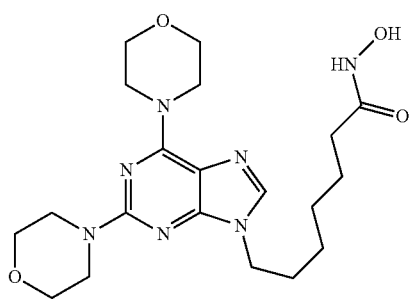
7-(2,6-dimorpholino-9H-purin-9-yl)-N-hydroxyheptanamide. |
| 99 | 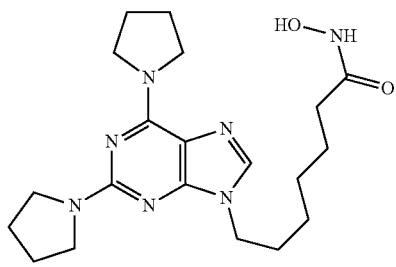
7-(2,6-di(pyrrolidin-1-yl)-9H-purin-9-yl)-N-hydroxyheptanamide. |
| 100 | 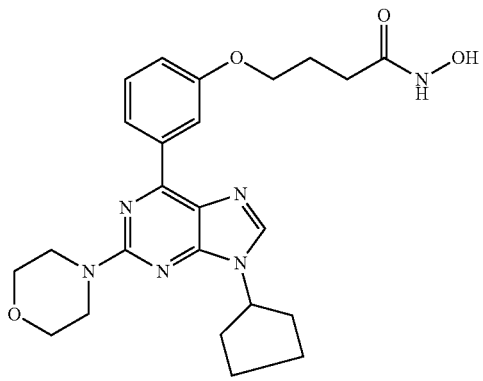
4-(3-(9-cyclopentyl-2-morpholino-9H-purin-6-yl)phenoxy)-N-hydroxybutanamide |

| EX | Chemical Structure and Name |
|---|---|
| 101 | 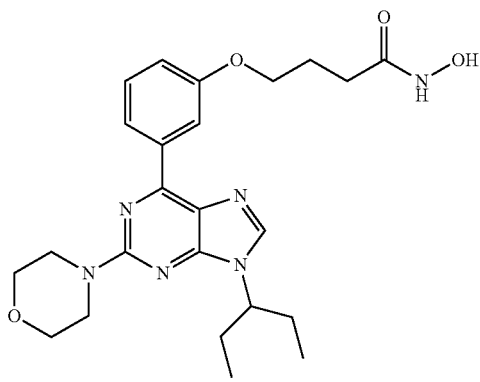<br>N-hydroxy-4-(3-(2-morpholino-9-(pentan-3-yl)-9H-purin-6-yl)phenoxy)butanamide |
| 102 | 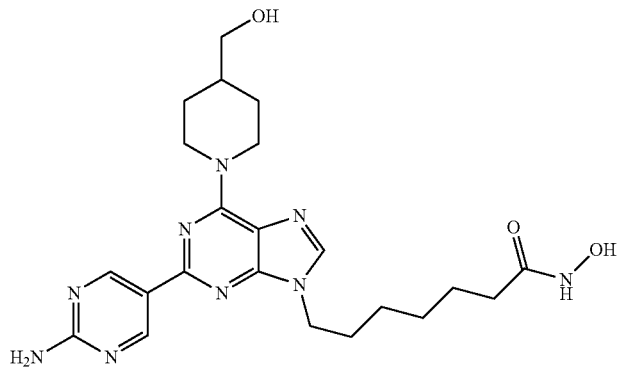<br>7-(2-(2-aminopyrimidin-5-yl)-6-(4-(hydroxymethyl)piperidin-1-yl)-9H-purin-9-yl)-N-hydroxyheptanamide |
| 103 | 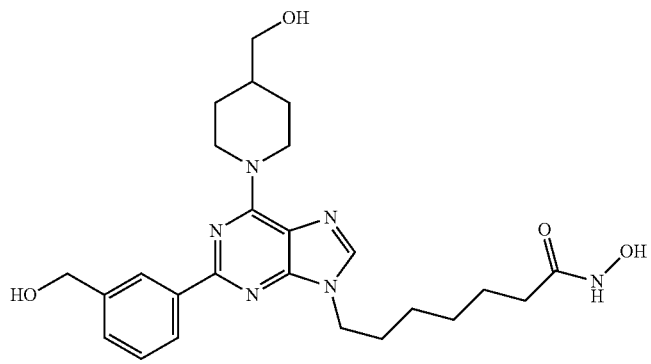<br>N-hydroxy-7-(2-(3-(hydroxymethyl)phenyl)-6-(4-(hydroxymethyl)piperidin-1-yl)-9H-purin-9-yl)heptanamide |

| EX | Chemical Structure and Name |
|---|---|
| 104 | 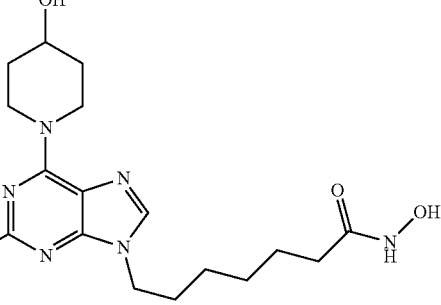<br>7-(2-(2-aminopyrimidin-5-yl)-6-(4-hydroxypiperidin-1-yl)-9H-purin-9-yl)-N-hydroxyheptanamide |
| 105 | 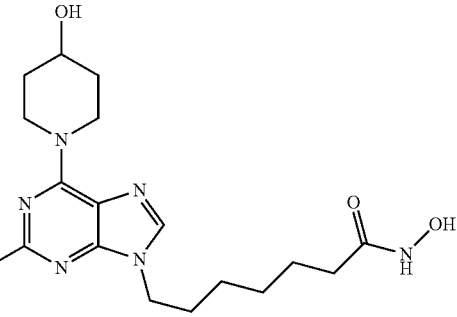<br>N-hydroxy-7-(2-(3-(hydroxymethyl)phenyl)-6-(4-hydroxypiperidin-1-yl)-9H-purin-9-yl)heptanamide | or a pharmaceutically acceptable salt thereof.

12. A pharmaceutical composition comprising a compound of claim 1, or a pharmaceutically acceptable form thereof, and a pharmaceutically acceptable excipient.

13. A process for synthesizing the compound of formula (I) according to claim 1, comprising the steps of:
(a) providing a halogen-disubstituted purine-based or halogen di-substituted fused pyrimidine-based compound;
(b) alkylating the amine (—NH— group) in the compound of step (a);
(c) selectively or sequentially displacing the halide atoms of the intermediary compound of step (b) with an optionally substituted boronic ester or an optionally substituted amine to form a substituted aromatic or a substituted amine, respectively;
(d) selectively coupling the intermediary compound of step (c) with a protected hydroxamic acid group having the structure -L$^1$-R$^5$-L$^2$-R$^6$-L$^3$-CON(R$^a$)OR$^b$ or an ester (hydroxamic acid precursor); and
(e) converting the protected hydroxamate or the ester of the intermediary compound of step (d) to a hydroxamic acid under reaction conditions to form the compound of formula (I), or comprising the steps of;
(a) providing a halogen-disubstituted purine-based or halogen di-substituted fused pyrimidine-based compound;
(b) alkylating the amine (—NH— group) in the compound of step (a);
(c) selectively displacing one of the halide atoms of said compound with an optionally substituted boronic ester or an optionally substituted amine to form a substituted aromatic or a substituted amine, respectively;
(c) alkylating the amine (—NH— group) in the intermediary compound of step (b);
(d) selectively displacing the remaining halide atom of the intermediary compound of step (c) with an optionally substituted boronic ester or an optionally substituted amine to form a substituted aromatic or a substituted amine, respectively;
(e) selectively coupling the intermediary compound of step (d) with a protected hydroxamic acid group having the structure -L$^1$-R$^5$-L$^2$-R$^6$-L$^3$-CON(R$^a$)OR$^b$ or an ester (hydroxamic acid precursor); and
(f) converting the protected hydroxamate or the ester of the intermediary compound of step (e) to a hydroxamic acid under reaction conditions to form the compound of formula (I), or comprising the steps of;
(a) providing a halogen-disubstituted purine-based or halogen di-substituted fused pyrimidine-based compound;
(b) alkylating the amine in the compound of step (a);
(c) selectively or sequentially displacing the halide atoms of the intermediary compound of step (b) with an optionally substituted boronic ester or an optionally substituted amine to form a substituted aromatic or a substituted amine, respectively;

(d) alkylating, in the intermediary compound of step (c), the carbon atom that corresponds to the Y-position of formula (I);
(e) selectively coupling the intermediary compound of step (d) with a protected hydroxamic acid group having the structure -$L^1$-$R^5$-$L^2$-$R^6$-$L^3$-CON($R^a$)O$R^b$ or an ester (hydroxamic ester precursor); and
(f) converting the protected hydroxamate or the ester of the intermediary compound of step (e) to a hydroxamic acid under reaction conditions to form the compound of formula (I), or comprising the steps of;
(a) providing a halogen-disubstituted purine-based or halogen di-substituted fused pyrimidine-based compound;
(b) selectively displacing one of the halide atoms of said compound with an optionally substituted boronic ester or an optionally substituted amine to form a substituted aromatic or a substituted amine, respectively;
(c) alkylating the amine (—NH— group) in the intermediary compound of step (b);
(d) alkylating, in the intermediary compound of step (c), the carbon atom that corresponds to the Y-position of formula (I);
(e) selectively displacing the remaining halide atom of the intermediary compound of step (d) with an optionally substituted boronic ester or an optionally substituted amine to form a substituted aromatic or a substituted amine, respectively;
(f) selectively coupling the compound of step (e) with a protected hydroxamic acid group having the structure -$L^1$-$R^5$-$L^2$-$R^6$-$L^3$-CON($R^a$)O$R^b$ or an ester (hydroxamic acid precursor); and
(g) converting the protected hydroxamate or the ester of the intermediary compound of step (f) to a hydroxamic acid under reaction conditions to form the compound of formula (I).

* * * * *